United States Patent
Ismagilov et al.

(10) Patent No.: US 10,207,269 B2
(45) Date of Patent: Feb. 19, 2019

(54) SYSTEM AND METHOD FOR MOVEMENT AND TIMING CONTROL

(71) Applicants: CALIFORNIA INSTITUTE OF TECHNOLOGY, Pasadena, CA (US); SLIPCHIP CORPORATION, Chicago, IL (US)

(72) Inventors: Rustem F. Ismagilov, Altadena, CA (US); Feng Shen, Pasadena, CA (US); Liang Li, Pasadena, CA (US); David Selck, Alhambra, CA (US); Joe Baker, Fallbrook, CA (US); Espir Kahatt, Carlsbad, CA (US); Chris Da Costa, Vista, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 15/022,879

(22) PCT Filed: Sep. 18, 2014

(86) PCT No.: PCT/US2014/056401
§ 371 (c)(1),
(2) Date: Mar. 17, 2016

(87) PCT Pub. No.: WO2015/084458
PCT Pub. Date: Jun. 11, 2015

(65) Prior Publication Data
US 2016/0263577 A1    Sep. 15, 2016

Related U.S. Application Data

(60) Provisional application No. 62/035,857, filed on Aug. 11, 2014, provisional application No. 61/936,275, (Continued)

(51) Int. Cl.
*B01L 99/00* (2010.01)
*B01L 3/00* (2006.01)
(Continued)

(52) U.S. Cl.
CPC .......... *B01L 3/527* (2013.01); *B01L 3/50273* (2013.01); *B01L 3/502715* (2013.01);
(Continued)

(58) Field of Classification Search
CPC ....... B01L 2300/0861; B01L 2300/045; B01L 2200/0642
See application file for complete search history.

(56) References Cited

U.S. PATENT DOCUMENTS 4,266,681 A    5/1981 Fredericks
5,804,141 A    9/1998 Chianese
(Continued)

FOREIGN PATENT DOCUMENTS

CN    102439717    5/2012
EP    2 633 911 A1    9/2013
(Continued)

OTHER PUBLICATIONS

European Patent Office, Extended European Search Report and Opinion, European Patent Application No. EP 15780401.4, dated Aug. 28, 2017, 9 pages.
(Continued)

*Primary Examiner* — Paul S Hyun
(74) *Attorney, Agent, or Firm* — Fenwick & West LLP

(57) ABSTRACT

The present invention relates to fluidic systems for controlling one or more fluids and/or one or more reagents. These systems can be used in combination with one or more devices for assaying, processing, and/or storing samples. In particular, the systems and related methods can allow for
(Continued)

dispensing fluid in a controlled manner and/or introducing pause(s) when implementing assays or processes.

18 Claims, 81 Drawing Sheets

Related U.S. Application Data filed on Feb. 5, 2014, provisional application No. 61/917,300, filed on Dec. 17, 2013, provisional application No. 61/879,487, filed on Sep. 18, 2013.

(51) Int. Cl.
  *G01N 1/40* (2006.01)
  *B01L 7/00* (2006.01)

(52) U.S. Cl.
  CPC ......... *B01L 3/502738* (2013.01); *B01L 3/523* (2013.01); *G01N 1/4077* (2013.01); *B01L 3/502753* (2013.01); *B01L 7/52* (2013.01); *B01L 2200/027* (2013.01); *B01L 2200/0605* (2013.01); *B01L 2200/0642* (2013.01); *B01L 2200/0684* (2013.01); *B01L 2200/0689* (2013.01); *B01L 2200/16* (2013.01); *B01L 2300/041* (2013.01); *B01L 2300/042* (2013.01); *B01L 2300/044* (2013.01); *B01L 2300/045* (2013.01); *B01L 2300/046* (2013.01); *B01L 2300/047* (2013.01); *B01L 2300/069* (2013.01); *B01L 2300/0672* (2013.01); *B01L 2300/0861* (2013.01); *B01L 2300/0867* (2013.01); *B01L 2300/0874* (2013.01); *B01L 2300/123* (2013.01); *B01L 2300/161* (2013.01); *B01L 2300/1855* (2013.01); *B01L 2300/1877* (2013.01); *B01L 2400/043* (2013.01); *B01L 2400/0409* (2013.01); *B01L 2400/0457* (2013.01); *B01L 2400/0478* (2013.01); *B01L 2400/0481* (2013.01); *B01L 2400/0487* (2013.01); *B01L 2400/0493* (2013.01); *B01L 2400/0644* (2013.01); *B01L 2400/0677* (2013.01); *B01L 2400/0683* (2013.01)

(56) References Cited

U.S. PATENT DOCUMENTS

| | | | |
|---|---|---|---|
| 5,947,167 A | 9/1999 | Bogen et al. | |
| 6,319,476 B1 | 11/2001 | Victor, Jr. et al. | |
| 6,656,428 B1 | 12/2003 | Clark et al. | |
| 2004/0132218 A1 | 7/2004 | Ho | |
| 2006/0216212 A1 | 9/2006 | Lum et al. | |
| 2007/0026439 A1 | 2/2007 | Faulstich et al. | |
| 2008/0125704 A1* | 5/2008 | Anderson | A61J 1/1412 604/87 |
| 2008/0217246 A1 | 9/2008 | Benn et al. | |
| 2009/0253566 A1 | 10/2009 | Chavarria | |
| 2010/0129898 A1 | 5/2010 | Squirrell | |
| 2010/0331522 A1 | 12/2010 | Irvine et al. | |
| 2011/0244466 A1 | 10/2011 | Juncosa et al. | |
| 2012/0028342 A1 | 2/2012 | Ismagilov et al. | |
| 2012/0107811 A1 | 5/2012 | Kelso et al. | |
| 2012/0201726 A1 | 8/2012 | Pearcy et al. | |
| 2013/0280725 A1 | 10/2013 | Ismagilov et al. | |
| 2013/0309679 A1 | 11/2013 | Ismagilov et al. | |
| 2013/0331298 A1 | 12/2013 | Rea | |
| 2014/0045275 A1 | 2/2014 | Rothacher et al. | |

FOREIGN PATENT DOCUMENTS

| | | |
|---|---|---|
| JP | 2004077476 | 3/2004 |
| JP | 2011524313 | 9/2011 |
| JP | 2012521219 | 9/2012 |
| JP | 2015514997 | 5/2015 |
| WO | WO-2006/032853 A2 | 3/2006 |
| WO | WO2006060195 | 6/2006 |
| WO | WO 2007/016692 A1 | 2/2007 |
| WO | WO2008115626 | 9/2008 |
| WO | WO 2012/110159 A1 | 8/2012 |

OTHER PUBLICATIONS

European Patent Office, Extended European Search Report and Opinion, EP Patent Application No. 14867907.9, dated Apr. 28, 2017, eight pages.
Singapore Invitation to Respond to Written Opinion, Singapore Application No. 11201602064S, dated May 19, 2017, one page.
Singapore Written Opinion, Singapore Application No. 11201602064S, dated May 19, 2017, nine pages.
PCT International Search Report and Written Opinion, International Application No. PCT/US2014/056401, dated Jun. 25, 2015, 17 Pages.
Office Action for Chinese Patent Application No. CN 201480063127. 6, dated Jun. 13, 2017, 53 Pages (With English Translation).
Communication Pursuant to Article 94(3) EPC for European Patent Application No. EP 15780401.4, dated Apr. 3, 2018, 4 Pages.
Examination Report No. 1 for Australian Patent Application No. 2014357716 dated Jan. 16, 2018, 3 Pages.

* cited by examiner

SYSTEM AND METHOD FOR MOVEMENT AND TIMING CONTROL

STATEMENT AS TO FEDERALLY SPONSORED RESEARCH

This invention was made with the support of the United States government under Contract number HR0011-11-2-0006 by the Defense Advanced Research Projects Agency. The government has certain rights in the invention.

CROSS-REFERENCE

This application is a U.S. National Phase patent application of PCT/US2014/056401, filed Sep. 18, 2014, which claims the benefit of U.S. Provisional Application No. 61/879,487, filed Sep. 18, 2013, U.S. Provisional Application No. 61/917,300, filed Dec. 17, 2013, U.S. Provisional Application No. 61/936,275, filed Feb. 5, 2014, and U.S. Provisional Application No. 62/035,857, filed Aug. 11, 2014, which applications are incorporated herein by reference.

BACKGROUND

Modern biological techniques, including nucleic acid analysis, offer powerful tools for the analysis of samples. Samples from subjects and environmental sources can be analyzed for the presence of various compounds and organisms. Patients can be diagnosed for diseases, including infectious diseases and genetic diseases.

However, many analysis techniques require centralized laboratory facilities, trained technicians, sample preparation, refrigeration, and other resources. Such requirements can limit the utility of these techniques in point-of-care settings, limited resource settings, and other environments with difficult or no access to necessary resources.

SUMMARY

In some aspects, this disclosure provides a reagent dispensing device comprising: (a) a first substrate having a first surface, wherein the first substrate comprises one or more first chambers situated within the first substrate; (b) a first resistant unit disposed adjacent to the surface of the first substrate and fluidically connected to at least one of the one or more first chambers, wherein the first resistant unit comprises a first reagent; and (c) a first pushing unit configured to move along a circular path within a plane parallel or about parallel to the first surface of the first substrate, wherein a first relative movement of the first pushing unit along the circular path within the plane parallel or about parallel to the first surface of the first substrate causes the first reagent to enter at least one of the one or more first chambers.

In some aspects, this disclosure provides a reagent dispensing device comprising: (a) a first substrate having a first surface and comprising one or more first chambers situated within the first substrate, wherein the one or more first chambers comprise a first process chamber; (b) a first resistant unit disposed adjacent to the surface of the first substrate, wherein the first resistant unit comprises a first reagent and wherein the first resistant unit is in fluidic connection with at least one of the one or more first chambers; and (c) a first pushing unit, wherein the first pushing unit is configured to provide direct or indirect contact with the first resistant unit and wherein a first relative movement of the first pushing unit in a rotation around an axis perpendicular to the first surface of the first substrate causes the first reagent in the first resistant unit to enter the first process chamber.

In some aspects, this disclosure provides a reagent dispensing device comprising: (a) a first substrate having a surface and comprising one or more first chambers situated within the first substrate; (b) a first resistant unit disposed adjacent to the surface of the first substrate, wherein the first resistant unit comprises a first reagent and wherein the first resistant unit is in fluidic communication with at least one of the one or more first chambers; and (c) a first pushing unit comprising at least one protrusion, wherein the first pushing unit is configured to provide direct or indirect contact with the first resistant unit, wherein a first relative movement of the first pushing unit in a direction parallel or about parallel to the surface of the first substrate causes at least one protrusion to contact the first resistant unit, thereby releasing the first reagent in the first resistant unit into at least one of the one or more first chambers.

In some aspects, this disclosure provides a reagent dispensing device comprising: (a) a first substrate having a surface and comprising one or more first chambers situated within the first substrate, wherein at least one of the one or more first chambers is a first process chamber; (b) a first resistant unit disposed adjacent to the surface of the first substrate, wherein the first resistant unit comprises a first reagent; and (c) a first pushing unit, wherein a first relative movement of the first pushing unit causes the first reagent in the first resistant unit to enter the first process chamber and wherein the device is not powered electrically.

In some aspects, this disclosure provides a reagent dispensing device comprising: (a) a first substrate having a surface and comprising one or more first chambers situated within the first substrate, wherein at least one of the one or more first chambers is a first process chamber; (b) a first resistant unit comprising a first reagent and a second resistant unit comprising a second reagent, wherein the first and second resistant units are disposed adjacent to the surface of the first substrate and are fluidly connected to at least one of the one or more first chambers; and (c) a first pushing unit, wherein a first relative movement of the first pushing unit in a direction relative to the surface of the first substrate causes the first reagent in the first resistant unit to enter the first process chamber and wherein the height or length of the first resistant unit is designed to control relative timing or sequence of release of the first reagent from the first resistant unit relative to release of the second reagent from the second resistant unit.

In some aspects, this disclosure provides a reagent dispensing device comprising: (a) a first substrate having a first surface and comprising one or more first chambers situated within the first substrate; (b) a first resistant unit comprising a first reagent and a second resistant unit comprising a second reagent, wherein the first and second resistant units are disposed adjacent to the first surface of the first substrate and are fluidly connected to at least one of the one or more first chambers; and (c) a third resistant unit located between the first and second resistant units, wherein the third resistant unit is configured to control relative timing of release of the first reagent relative to the second reagent into at least one of the one or more first chambers.

In some aspects, this disclosure provides a reagent dispensing device comprising: (a) a first substrate having a first surface and comprising one or more first chambers situated within the first substrate; (b) a first resistant unit comprising a first reagent and a second resistant unit comprising a second reagent, wherein the first and second resistant units are disposed adjacent to the first surface of the first substrate and are fluidly connected to at least one of the one or more first chambers; and (c) a first pushing unit, wherein a first relative movement of the first pushing unit in a direction relative to the surface of the first substrate causes the first reagent to enter at least one of the one or more first chambers, wherein the first relative movement does not comprise axial rotation.

In some aspects, this disclosure provides a fluid dispensing system comprising: (i) a device comprising one or more first chambers in a first substrate having a first surface, wherein at least one first chamber is a process chamber; (ii) one or more resistant units disposed above the first substrate along the first surface, wherein at least one resistant unit comprises a reagent and one or more resistant units are configured to comprise one or more fluids; and (iii) a first pushing unit configured to provide direct or indirect contact with at least one resistant unit, wherein a first relative movement of the first pushing unit in a direction parallel to the first surface of the first substrate causes fluid in one of the one or more resistant units to enter the process chamber.

In some aspects, this disclosure provides a fluid dispensing system comprising: (i) a device comprising one or more first chambers in a first substrate having a first surface; (ii) one or more resistant units disposed above the first substrate along the first surface, wherein the one or more resistant units are configured to control relative timing in adding one or more fluids and/or to control a sequential addition of one or more fluids; and (iii) a first pushing unit configured to provide direct or indirect contact with at least one resistant unit, wherein a first relative movement of the first pushing unit causes fluid in the one or more resistant units to enter at least one first chamber.

In some aspects, this disclosure provides a method of using a reagent dispensing device, comprising: providing a reagent dispensing device comprising (a) a first substrate having a first surface, wherein the first substrate comprises one or more first chambers situated within the first substrate, (b) a first resistant unit disposed adjacent to the surface of the first substrate and fluidically connected to at least one of the one or more first chambers, wherein the first resistant unit comprises a first reagent, and (c) a first pushing unit; and moving the first pushing unit along a circular path within a plane parallel or about parallel to the first surface of the first substrate, wherein a first relative movement of the first pushing unit along the circular path within the plane parallel or about parallel to the first surface of the first substrate causes the first reagent to enter at least one of the one or more first chambers.

In some aspects, this disclosure provides a method of using a reagent dispensing device, comprising: providing a reagent dispensing device comprising (a) a first substrate having a first surface and comprising one or more first chambers situated within the first substrate, wherein the one or more first chambers comprise a first process chamber, (b) a first resistant unit disposed adjacent to the surface of the first substrate, wherein the first resistant unit comprises a first reagent and wherein the first resistant unit is in fluidic connection with at least one of the one or more first chambers, and (c) a first pushing unit; and moving the first pushing unit into direct or indirect contact with the first resistant unit, wherein a first relative movement of the first pushing unit in a rotation around an axis perpendicular to the first surface of the first substrate causes the first reagent in the first resistant unit to enter the first process chamber.

In some aspects, this disclosure provides a method of using a reagent dispensing device, comprising: providing a reagent dispensing device comprising (a) a first substrate having a surface and comprising one or more first chambers situated within the first substrate, (b) a first resistant unit disposed adjacent to the surface of the first substrate, wherein the first resistant unit comprises a first reagent and wherein the first resistant unit is in fluidic communication with at least one of the one or more first chambers, and (c) a first pushing unit comprising at least one protrusion; and moving the first pushing unit to provide direct or indirect contact with the first resistant unit, wherein a first relative movement of the first pushing unit in a direction parallel or about parallel to the surface of the first substrate causes at least one protrusion to contact the first resistant unit, thereby releasing the first reagent in the first resistant unit into at least one of the one or more first chambers.

In some aspects, this disclosure provides a method of using a reagent dispensing device, comprising: providing a reagent dispensing device comprising (a) a first substrate having a first surface and comprising one or more first chambers situated within the first substrate, (b) a first resistant unit comprising a first reagent and a second resistant unit comprising a second reagent, wherein the first and second resistant units are disposed adjacent to the first surface of the first substrate and are fluidly connected to at least one of the one or more first chambers, and (c) a third resistant unit located between the first and second resistant units; and using the third resistant unit to control relative timing of release of the first reagent relative to the second reagent into at least one of the one or more first chambers.

In some aspects, this disclosure provides a method of using a reagent dispensing device, comprising: providing a reagent dispensing device comprising (i) a device comprising one or more first chambers in a first substrate having a first surface, wherein at least one first chamber is a process chamber, (ii) one or more resistant units disposed above the first substrate along the first surface, wherein at least one resistant unit comprises a reagent and one or more resistant units comprise one or more fluids, and (iii) a first pushing unit; moving the first pushing unit to provide direct or indirect contact with at least one resistant unit, wherein a first relative movement of the first pushing unit in a direction parallel to the first surface of the first substrate causes fluid in one of the one or more resistant units to enter the process chamber.

In some aspects, this disclosure provides a method of using a reagent dispensing device, comprising: providing a reagent dispensing device comprising (i) a device comprising one or more first chambers in a first substrate having a first surface, (ii) one or more resistant units disposed above the first substrate along the first surface, and (iii) a first pushing unit; moving the first pushing unit to provide direct or indirect contact with at least one resistant unit, wherein a first relative movement of the first pushing unit causes fluid in the one or more resistant units to enter at least one first chamber; and using the one or more resistant units to control relative timing in adding one or more fluids and/or to control a sequential addition of one or more fluids.

In some embodiments of aspects provided herein, the reagent dispensing device further comprises: (d) a first pushing unit, wherein a first relative movement of the first pushing unit in a direction relative to the first surface of the first substrate causes the first reagent to enter at least one of the one or more first chambers. In some embodiments of aspects provided herein, the device further comprises a second resistant unit comprising a second reagent, wherein the volume, shape, or length of the first resistant unit relative to the second resistant unit is configured to control relative timing of release of the first reagent relative to the second reagent into at least one of the one or more first chambers. In some embodiments of aspects provided herein, the device further comprises a second resistant unit comprising a second reagent and wherein the distance between the first resistant unit and the second resistant unit is configured to control relative timing of release of the first reagent relative to the second reagent into the one or more first chambers. In some embodiments of aspects provided herein, the relative timing is provided by at least one resistant unit configured to provide resistance to the first relative movement, thereby modifying the speed of the first relative movement. In some embodiments of aspects provided herein, the relative timing is provided by a combination of one or more resistant units and one or more first chambers configured to provide resistance to the first relative movement. In some embodiments of aspects provided herein, the device further comprises a second resistant unit comprising a second reagent, wherein viscosity of the first reagent is configured to control relative timing of release of the first reagent relative to the second reagent into at least one of the one or more first chambers. In some embodiments of aspects provided herein, the one or more first chambers further comprise a delay chamber, wherein the delay chamber is not in fluidic communication with the first process chamber. In some embodiments of aspects provided herein, the third resistant unit comprises a sacrificial reagent. In some embodiments of aspects provided herein, the third resistant unit comprises a solid material that is solid at operating temperatures. In some embodiments of aspects provided herein, the device further comprises a heating unit configured to melt the solid material. In some embodiments of aspects provided herein, the third resistant unit is in fluidic communication with the delay chamber. In some embodiments of aspects provided herein, the third resistant unit is in fluidic communication with the delay chamber and the first relative movement causes the sacrificial reagent in the third resistant unit to enter the delay chamber. In some embodiments of aspects provided herein, the third resistant unit has a length, shape or volume configured to create a specific delay time. In some embodiments of aspects provided herein, the sacrificial reagent comprises an aqueous solution, a lubricant, an oil, an aqueous-immiscible liquid, a gel, a gas, a fluorocarbon oil, a surfactant, gas, air, or any combination thereof. In some embodiments of aspects provided herein, the first reagent is air. In some embodiments of aspects provided herein, the first reagent comprises a lysis buffer, a wash buffer, an elution buffer, a liquid, a powder, a gel, microbeads, probes, primers, nucleic acids, DNA, RNA, polypeptides, antibodies, or any combination thereof. In some embodiments of aspects provided herein, the reagent dispensing device further comprises a barrier unit situated between the pushing unit and the first resistant unit. In some embodiments of aspects provided herein, the pushing unit is spring-loaded or motorized; or a first relative movement of the first pushing unit parallel or about parallel to the first substrate causes the first reagent in the first resistant unit to enter at least one of the first chambers. In some embodiments of aspects provided herein, the first resistant unit is further fluidically connected to a fourth resistant unit comprising a fourth reagent, and wherein the first relative movement causes the first reagent to enter the fourth resistant unit, thereby combining the first and fourth reagents and causing the combination to enter at least one of the one or more first chambers. In some embodiments of aspects provided herein, the first reagent is a first fluid and the fourth reagent is a dry reagent. In some embodiments of aspects provided herein, the first resistant unit encloses a fifth resistant unit comprising a fifth reagent and wherein the first reagent is disposed within the first resistant unit and outside of the fifth resistant unit. In some embodiments of aspects provided herein, the fifth resistant unit encloses a sixth resistant unit comprising a sixth reagent and wherein the fifth reagent is disposed within the fifth resistant unit and outside of the sixth resistant unit. In some embodiments of aspects provided herein, the first relative movement directly causes a change in pressure within the first substrate. In some embodiments of aspects provided herein, the first relative movement arises from change in pressure, change in force, or change in temperature. In some embodiments of aspects provided herein, the pushing unit, if present, is situated within a chamber. In some embodiments of aspects provided herein, the chamber further comprises a chemical capable of generating an exothermic reaction. In some embodiments of aspects provided herein, at least one of the one or more first chambers comprises a fluid and the first resistant unit comprises an immiscible fluid that generally forms a different phase from the fluid in the first chamber. In some embodiments of aspects provided herein, the first pushing unit provides constant force or non-constant force. In some embodiments of aspects provided herein, the first pushing unit and the first resistant unit are configured to provide feedback for the first relative movement that results in decelerating, accelerating, maintaining, or stopping of the first relative movement. In some embodiments of aspects provided herein, the first resistant unit comprises one or more structures selected from the group consisting of the first chamber, a chamber, a channel, a capture agent, a capture region, a filter, a matrix, a membrane, a channel, a blister, and a deformable substrate. In some embodiments of aspects provided herein, the first resistant unit comprises a deformable substrate or a blister. In some embodiments of aspects provided herein, at least one of the one or more chambers is a channel, a compartment, a sample chamber, an elution chamber, a wash chamber, a process chamber, or a heating chamber. In some embodiments of aspects provided herein, the first resistant unit comprises a first wall bordering an aperture within the first surface, wherein the aperture is in fluid communication with one or more of the one or more first chambers. In some embodiments of aspects provided herein, the first relative movement causes the first wall to rupture, thereby causing the first reagent in the first resistant unit to enter at least one of the one or more first chambers. In some embodiments of aspects provided herein, the reagent dispensing device further comprises one or more barrier units configured to control relative timing in adding one or more fluids, wherein the one or more barrier units are disposed between the first pushing unit and the first resistant unit and adjacent to the first surface of the first substrate. In some embodiments of aspects provided herein, the first resistant unit is disposed in a second substrate and the second substrate is disposed adjacent to the first surface of the first substrate. In some embodiments of aspects provided herein, the second substrate comprises at least two resistant units. In some embodiments of aspects provided herein, the second substrate comprises a molded substrate. In some embodiments of aspects provided herein, the second substrate comprises a sample inlet aperture. In some embodiments of aspects provided herein, wherein the second substrate comprises a resistant unit comprising lysis buffer. In some embodiments of aspects provided herein, the second substrate comprises a lysis dispense nozzle. In some embodiments of aspects provided herein, the pushing unit is configured to move along a circular path. In some embodiments of aspects provided herein, the pushing unit is configured to move along a helical path. In some embodiments of aspects provided herein, the device further comprises a fourth substrate configured to engage the pushing unit. In some embodiments of aspects provided herein, the fourth substrate comprises a key way configured to engage the pushing unit. In some embodiments of aspects provided herein, the fourth substrate comprises a threaded region configured to engage the pushing unit. In some embodiments of aspects provided herein, the pushing unit comprises a threaded region configured to engage the threaded region of the fourth substrate. In some embodiments of aspects provided herein, the fourth substrate is configured to rotate around an axis. In some embodiments of aspects provided herein, the pushing unit comprises protrusions configured to engage the fourth substrate. In some embodiments of aspects provided herein, the pushing unit is configured to rotate when engaged by the fourth substrate. In some embodiments of aspects provided herein, the pushing unit is configured to engage the first substrate. In some embodiments of aspects provided herein, the pushing unit comprises exterior threads. In some embodiments of aspects provided herein, the pushing unit comprises interior threads. In some embodiments of aspects provided herein, the first substrate comprises threads configured to engage the exterior threads of the pushing unit. In some embodiments of aspects provided herein, the pushing unit comprises interior threads and exterior threads, wherein a thread pitch of the interior threads is different from a thread pitch of the exterior threads. In some embodiments of aspects provided herein, the one or more first chambers comprise a sample chamber configured to contain a sample and an elution chamber configured to contain the sample after elution, and wherein the sample chamber and the elution chamber are disposed within the first substrate and are fluidically connected to the first resistant unit. In some embodiments of aspects provided herein, the device further comprises one or more capture regions disposed within the first substrate, and wherein the one or more capture regions are in fluidic communication with at least one of the one or more first chambers or, if present, with the process chamber, sample chamber, or elution chamber. In some embodiments of aspects provided herein, at least one of the one or more first chambers is designed to hold a set amount of reagent. In some embodiments of aspects provided herein, the at least one of the one or more first chambers designed to hold a set amount of reagent is fluidly connected to an overflow chamber, wherein the overflow chamber is configured to capture reagent that overflows from the at least one of the one or more of the first chambers. In some embodiments of aspects provided herein, the device further comprises a third substrate having a third surface, wherein the third substrate comprises one or more third chambers and is disposed adjacent to the first substrate, and wherein at least one first chamber and at least one third chamber are configured to be connected by a second relative movement. In some embodiments of aspects provided herein, the first relative movement causes the second relative movement. In some embodiments of aspects provided herein, the device further comprises one or more capture regions disposed within first substrate, within the third substrate, or between the first and third substrates, and wherein the one or more capture regions, at least one first chamber, and at least one third chamber are able to be connected by a third relative movement. In some embodiments of aspects provided herein, the first or second relative movement causes the third relative movement. In some embodiments of aspects provided herein, the one or more capture regions comprises one or more capture agents. In some embodiments of aspects provided herein, the one or more capture agents is a column, a filter, a matrix, a polymer, a charge switch material, a membrane, an antibody, a nucleic acid probe, or a combination thereof. In some embodiments of aspects provided herein, the device comprises two first chambers and the one or more capture regions are configured to connect the two first chambers. In some embodiments of aspects provided herein, one or more capture regions are configured to connect two or more of the first chambers.

In some embodiments of aspects provided herein, at least two first chambers and the membrane or at least one bridge are able to be connected by the fourth relative movement. In some embodiments of aspects provided herein, the device comprises an intermediate substrate disposed adjacent to the first substrate, and wherein the intermediate substrate comprises a membrane or one or more bridges. In some embodiments of aspects provided herein, at least one first chamber and the membrane or at least one bridge are able to be connected by a fourth relative movement. In some embodiments of aspects provided herein, the device further comprises a fourth substrate comprising one or more fourth chambers, wherein the intermediate substrate is between the first and fourth substrates, and wherein at least one first chamber, at least one fourth chamber, and the membrane or at least one bridge are able to be connected by a fifth relative movement. In some embodiments of aspects provided herein, the device further comprises a fifth substrate comprising one or more fifth chambers, wherein the fifth substrate is beneath the fourth substrate, and wherein at least one first chamber, at least one third chamber, at least one fourth chamber, at least one fifth chamber, and the membrane or at least one bridge are able to be connected by a sixth relative movement. In some embodiments of aspects provided herein, the intermediate substrate comprises a continuous membrane. In some embodiments of aspects provided herein, the device further comprises a deformable substrate between the first substrate and the intermediate substrate and/or between the intermediate substrate and the fourth substrate, if the fourth substrate is present. In some embodiments of aspects provided herein, the first substrate or, if present, the intermediate, second, third, fourth, or fifth substrates, or a portion thereof, is differentially wetted. In some embodiments of aspects provided herein, the first substrate or, if present, the intermediate, second, third, fourth, and/or fifth substrates translates longitudinally. In some embodiments of aspects provided herein, the first substrate and/or, if present, the intermediate, second, third, fourth, or fifth substrates rotates axially. In some embodiments of aspects provided herein, the device further comprises a lid that encloses a cavity having volume $V_1$ and surrounds a through-hole in the device, wherein the through-hole connects to at least one first chamber, wherein closure of the lid encloses the cavity and exerts a pressure commensurate with a volume difference between the volume $V_1$ and an open system having volume $V_0$. In some embodiments of aspects provided herein, the device further comprises a housing system surrounding the device having a through-hole that connects to at least one first chamber, wherein the housing system comprises an access port that connects to the through-hole for inserting a sample; and a cap for enclosing the housing system, wherein closing the cap results in introducing the sample into the through-hole or results in relatively moving the first substrate. In some embodiments of aspects provided herein, the device is a microfluidic device. In some embodiments of aspects provided herein, the device further comprises one or more air vents fluidically connected to one or more first chambers. In some embodiments of aspects provided herein, the device further comprises a second pushing unit configured to provide direct or indirect contact with at least one resistant unit, wherein a relative movement of the second pushing unit in a direction parallel or about parallel to the first surface of the first substrate causes fluid in one of the one or more resistant units to enter the first chamber. In some embodiments of aspects provided herein, the first pushing unit or, if present, the second pushing unit are configured to slidably engage along the first surface or with the resistant unit disposed above the first substrate along the first surface. In some embodiments of aspects provided herein, the surface of the first or second pushing unit is non-planar or non-uniform along the long axis of the pushing unit. In some embodiments of aspects provided herein, the device further comprises one or more heating or cooling elements disposed in thermal contact with at least one of the first chambers, or at least one of the resistant units. In some embodiments of aspects provided herein, the reagent dispensing device comprises one or more heating elements and wherein at least one of the one or more heating elements comprise an exothermic chemical reagent. In some embodiments of aspects provided herein, at least one of the one or more heating or cooling elements is situated within a chamber that is in fluid communication with a source of oxygen. In some embodiments of aspects provided herein, the conductive material is phase change material, a metal, a metallic powder, an electrolyte, a polymer, or a combination thereof. In some embodiments of aspects provided herein, the first relative movement dispenses the conductive material, thereby resulting in electrical contact between the conductive material and a conductive structure. In some embodiments of aspects provided herein, the electrical contact increases or decreases the current or voltage in an electrical circuit. In some embodiments of aspects provided herein, the first substrate further comprises at least one valve configured to control the flow of the first reagent. In some embodiments of aspects provided herein, the pushing unit, if present, is attached to the first substrate. In some embodiments of aspects provided herein, the pushing unit, if present, is detachable from the first substrate. In some embodiments of aspects provided herein, the first substrate comprises at least one first indentation. In some embodiments of aspects provided herein, the pushing unit, if present, comprises a ridge configured to fit within the at least one first indentation. In some embodiments of aspects provided herein, the first substrate comprises at least one first ridge configured to contain the at least one first indentation. In some embodiments of aspects provided herein, the first pushing unit, if present, is configured to slide along the length of the first substrate. In some embodiments of aspects provided herein, the first substrate comprises at least one valve configured to control the flow of the first reagent within the first substrate. In some embodiments of aspects provided herein, the first pushing unit is configured to directly or indirectly contact the valve in order to control the flow of the first reagent within the first substrate. In some embodiments of aspects provided herein, the reagent dispensing device further comprises a sample inlet port or sample input well. In some embodiments of aspects provided herein, the reagent dispensing device further comprises controller to the control the movement of the first pushing unit, if present. In some embodiments of aspects provided herein, this disclosure provides an integrated device comprising: (a) the reagent dispensing device of aspects or embodiments provided herein, wherein a sample input port is fluidly connected to at least one of the one or more chambers; and (b) a detector attached to the reagent dispensing device; wherein the integrated device is configured to detect at least one biological molecule within forty minutes or less after a biological sample is loaded into the sample input port.

In some aspects, this disclosure provides a sample preparation device comprising: (a) a first substrate comprising a sample input port and comprising one or more chambers situated within the first substrate, wherein the one or more chambers comprise a reaction chamber fluidly connected with the sample input port; and (b) at least one resistant unit adjacent to a surface of the first substrate, wherein the at least one resistant unit: (i) comprises a reagent and (ii) is in fluidic connection with at least one of the one or more chambers; wherein the sample preparation device is configured to extract a set of biological molecules from a biological sample comprising inhibitors of a reaction within ten minutes after the biological sample is loaded into the sample input port and wherein the extracted set of biological molecules comprises less than 75% of the inhibitors of the reaction.

In some embodiments of aspects provided herein, the extracted set of biological molecules comprises less than 50% of the inhibitors of the reaction. In some embodiments of aspects provided herein, the biological molecule is extracted from the biological sample in five minutes or less. In some embodiments of aspects provided herein, the biological sample comprises at least one intact cell comprising the biological molecule. In some embodiments of aspects provided herein, the biological sample comprises or is suspected of comprising molecules associated with chlamydia or gonorrhea. In some embodiments of aspects provided herein, the biological molecule is a nucleic acid. In some embodiments of aspects provided herein, the biological molecule is DNA. In some embodiments of aspects provided herein, the biological molecule is RNA. In some embodiments of aspects provided herein, the biological molecule is a polypeptide. In some embodiments of aspects provided herein, the reaction is an amplification reaction. In some embodiments of aspects provided herein, an integrated device comprises: (a) the sample preparation device of aspects or embodiments provided herein; and (b) a detector attached to the sample preparation device; wherein the integrated device is configured to detect the at least one biological molecule within forty minutes or less after the biological sample is loaded into the sample input port. In some embodiments of aspects provided herein, the integrated device weighs less than five pounds. In some embodiments of aspects provided herein, the detector produces a qualitative result. In some embodiments of aspects provided herein, the detector produces a quantitative result.

In some aspects, this disclosure provides a reagent dispensing system comprising: (a) a device comprising: (i) a first substrate comprising one or more chambers, a first surface and a first through-hole, wherein at least one of the one or more chambers is a process chamber comprising a matrix and at least one or more of the chambers is in fluidic communication with the first through-hole; and (ii) a threaded post that is attached to a surface of the device; and (b) a cap for the device, wherein the cap comprises a hollow region configured to engage the threaded post such that, after engagement of the cap with the threaded post and rotation of the cap, the cap moves closer to the surface of the device, thereby increasing pressure within the process chamber.

In some aspects, this disclosure provides a reagent dispensing system comprising: (a) a device comprising: (i) a first substrate comprising: one or more chambers, a first surface and a first through-hole, wherein at least one of the one or more chambers is a process chamber comprising a matrix and at least one or more of the chambers is in fluidic communication with the first through-hole; and (ii) a threaded hollow region within a surface of the device; and (b) a cap for the device, wherein the cap comprises a threaded post configured to engage the threaded hollow region such that, after engagement of the threaded post with the threaded hollow region and rotation of the cap, the cap moves closer to the first surface of the first substrate, thereby increasing pressure within the process chamber.

In some embodiments of aspects provided herein, the cap moves closer to the first substrate in a step-wise fashion when rotated, thereby causing an incremental increase in the pressure within the process chamber. In some embodiments of aspects provided herein, the reagent system further comprises a first resistant unit comprising a first reagent. In some embodiments of aspects provided herein, the resistant unit is configured to release the first reagent into the process chamber after the cap is engaged and rotated. In some embodiments of aspects provided herein, the resistant unit is configured to release the first reagent through the first through-hole into at least one of the one or more chambers after the cap is engaged and rotated. In some embodiments of aspects provided herein, the resistant unit is located within the cap. In some embodiments of aspects provided herein, the resistant unit is located on the surface of the first substrate. In some embodiments of aspects provided herein, the first substrate comprises only one through-hole. In some embodiments of aspects provided herein, the first substrate comprises a second through-hole. In some embodiments of aspects provided herein, the first reagent comprises air, lysis buffer, wash buffer, elution buffer, antibodies, primers, or probes. In some embodiments of aspects provided herein, the device further comprises a pushing unit configured to rupture the resistant unit. In some embodiments of aspects provided herein, the at least one of the one or more chambers is a sample chamber fluidically connected to the first through-hole and fluidically connected to the process chamber. In some embodiments of aspects provided herein, the at least one of the one or more chambers is fluidically connected to the exterior of the device by an air vent. In some embodiments of aspects provided herein, the matrix comprises a filter capable of binding a biological molecule.

In some aspects, this disclosure provides a reagent dispensing system comprising: (a) a first substrate comprising (i) a first surface comprising at least one first well; and (ii) one or more first chambers, wherein at least one of the one or more first chambers is fluidly connected to the at least one first well; (b) a second substrate comprising a first resistant unit configured to fit within the first well, wherein the first resistant unit comprises a first reagent; (c) a pushing unit comprising a prong capable of piercing the first resistant unit; and (d) a lid for the device, wherein the lid causes the pushing unit to pierce the first resistant unit when the lid is manually rotated or pushed.

In some embodiments of aspects provided herein, wherein the lid causes the pushing. In some embodiments of aspects provided herein, the lid comprises a threaded region capable of engaging the first substrate. In some embodiments of aspects provided herein, the first substrate comprises a threaded region capable of engaging the threaded region of the lid. In some embodiments of aspects provided herein, the first resistant unit comprises a first membrane configured to be pierced by the prong of the pushing unit. In some embodiments of aspects provided herein, the first resistant unit comprises a second membrane configured to be pierced by first substrate. In some embodiments of aspects provided herein, the first membrane comprises foil, laminate or plastic. In some embodiments of aspects provided herein, the second membrane comprises foil, laminate or plastic.

In some embodiments of any of the above aspects, the one or more resistant units are configured to control relative timing in adding one or more fluids and/or to control a sequential addition of one or more fluids. In some embodiments, the first relative movement of the pushing unit comprises translation and/or rotation in a direction parallel to a first surface of the first substrate, wherein the first chambers are along the first surface. In some embodiments of any of the above aspects, the relative timing is provided by at least one resistant unit configured to provide resistance to the first relative movement. In some embodiments of any of the above aspects, the relative timing is provided by a combination of one or more resistant units and one or more first chambers configured to provide resistance to the first relative movement. In some embodiments where resistance is provided to the first relative movement, the resistance is caused by the resistant unit modifying the speed of the first relative movement. In some embodiments of any of the above aspects, the rate of the first relative movement is constant, decelerating, or accelerating. In some embodiments of any of the above aspects, the relative timing is provided by at least one resistant unit comprising a fluid, wherein the at least one resistant unit is in fluid communication with a second chamber in the device, and wherein the first relative movement causes the fluid in the at least one resistant unit to enter the second chamber. In some embodiments of any of the above aspects, the second chamber, if present, is not in fluidic communication with the reagent chamber. In some embodiments of aspects provided herein, the first substrate is planar or non-planar.

In some embodiments of the aspects provided herein, the fluid or reagent within the at least one resistant unit is an immiscible fluid that forms a different phase as compared to one or more fluids in the process chamber. In some embodiments, the immiscible fluid is an oil, a lubricant, a solid material, or a phase change material.

In some embodiments of any of aspects involving sequential addition of fluid and/or reagent, the sequential addition is provided by at least one resistant unit configured to comprise one or more fluids, and wherein the first relative movement causes the one or more fluids to enter the process chamber. In some embodiments, the sequential addition is provided by a first resistant unit comprising a first fluid and a second resistant unit comprising a second fluid, wherein the first and second resistant units are fluidically connected to the process chamber, and wherein the first relative movement causes the first fluid and the second fluid to enter the process chamber. In some embodiments of aspects provided herein, the first resistant unit is further fluidically connected to the second resistant unit, and wherein the first relative movement causes the first fluid to enter the second resistant unit, thereby combining the first and second fluids and causing the combination to enter the process chamber. In some embodiments of aspects provided herein, the sequential addition is provided by a first resistant unit comprising a first fluid and a second resistant unit comprising a dry reagent, wherein the first and second resistant units are fluidically connected to the process chamber, and wherein the first relative movement causes the first fluid and the dry reagent to enter the process chamber. In some embodiments of aspects provided herein, the first resistant unit is further fluidically connected to the second resistant unit, and wherein the first relative movement causes the first fluid to enter the second resistant unit comprising the dry reagent, thereby combining the first fluid with the dry reagent and causing the combination to enter the process chamber. In some embodiments of aspects provided herein, at least one resistant unit comprises an immiscible fluid that generally forms a different phase as compared to one or more fluids in the first chamber. In some embodiments of aspects provided herein, the system or device further comprises two or more resistant units, wherein a first resistant unit comprises a reagent and a second resistant unit comprises an aqueous liquid, and wherein the first relative movement causes the aqueous liquid in the second resistant unit to enter the first resistant unit. In some embodiments of aspects provided herein, the first relative movement of the pushing unit causes the combined reagent and aqueous fluid to enter the first chamber. In some embodiments of aspects provided herein, the first pushing unit and at least one resistant unit are configured to control relative timing in adding one or more fluids. In some embodiments of aspects provided herein, at least one resistant unit having a top surface and a bottom surface is disposed above the first substrate along the first surface, wherein the bottom surface of the resistant unit is contacting the first chamber, and wherein the first relative movement causes the bottom surface to rupture, thereby causing fluid in the at least one resistant unit to enter the first chamber.

In some aspects, this disclosure provides a method of isolating a biological molecule comprising: (i) providing the device or system of aspects or embodiments provided herein; (ii) introducing a test sample into the device or system, wherein the test sample comprises one or more biological molecules; (iii) sequentially contacting the test sample with a set of different reagents; and (iv) eluting the one or more biological molecules, thereby obtaining an eluted sample.

In some aspects, this disclosure provides a method of testing a sample for a target, the method comprising: (i) providing the fluid dispensing system, wherein at least one fluid comprises a detection agent for the target; (ii) introducing a test sample into the device; (iii) contacting the one or more resistant units with the first and/or second pushing unit, thereby introducing the detection agent with the sample to produce a reaction mixture; and (iv) measuring a signal from the detection agent to determine the presence or absence of the target in the test sample.

In some embodiments of aspects provided herein, the test sample comprises whole blood, a nucleic acid, a bodily fluid, blood, plasma, serum, sputum, urine, fecal matter, sweat, spinal fluid, amniotic fluid, interstitial fluid, tear fluid, bone marrow, a swab, a tissue sample, a buccal mouthwash sample, an aerosol, a cell, a protein, and/or an enzyme. In some embodiments of aspects provided herein, the method further comprises capturing one or more analytes from the test sample with the one or more capture regions. In some embodiments of aspects provided herein, the method further comprises washing the one or more analytes into at least one first chamber using a washing buffer or, if present, into at least one third chamber, fourth chamber, fifth chamber, process chamber, sample chamber, waste chamber, and/or elution chamber using a washing buffer. In some embodiments of aspects provided herein, the method further comprises eluting the one or more analytes into at least one of first chamber using an elution buffer or, if present, into at least one third chamber, fourth chamber, fifth chamber, process chamber, sample chamber, and/or elution chamber using an elution buffer. In some embodiments of aspects provided herein, the method further comprises one or more of the following steps at any time and in any order after step (ii): partitioning the test sample into separate aliquots, drying one or more of the aliquots, recovering one or more of the aliquots, and/or quantifying the volume of the one or more aliquots after partitioning, before drying, after drying, or after recovering. In some embodiments of aspects provided herein, the method further comprises one or more of the following steps at any time and in any order after step (i): filtering, lysing, dehydrating, rehydrating, binding, washing, eluting, assaying, incubating, and/or detecting the test sample. In some embodiments of aspects provided herein, the method comprises nucleic acid extraction, nucleic acid purification, nucleic acid enrichment, concentrating of a nucleic acid, protein extraction, protein purification, protein enrichment, concentrating of a protein, cell separation, sample enrichment, nucleic acid amplification, nucleic acid detection, or protein detection. In some embodiments of aspects provided herein, the eluted sample has a volume that is not larger than the volume of the test sample. In some embodiments of aspects provided herein, the concentration of the biological molecule within the eluted sample is at least two-fold higher than the concentration of the biological molecule in the test sample. In some embodiments of aspects provided herein, the time between the introducing of the sample to the device and the eluting of the biological molecule from the device is less than ten minutes. In some embodiments of aspects provided herein, the test sample comprises inhibitors of a reaction. In some embodiments of aspects provided herein, the reaction is an amplification reaction. In some embodiments of aspects provided herein, the reaction is a polymerase chain reaction. In some embodiments of aspects provided herein, the eluted sample comprises greater than 40% of the biological molecules within the test sample. In some embodiments of aspects provided herein, wherein the one or more biological molecules comprise a target biological molecule that is present in a ratio of less than one target biological molecules per $10^{10}$ biological molecules and wherein the eluted sample comprises greater than 40% of the target biological molecules.

In some aspects, this disclosure provides a kit comprising: (i) the device or system; and (ii) a collector for collecting a sample for use with the device.

In some embodiments of the kit aspect, the system or device further comprises one or more of a sample, a washing buffer, an elution buffer, a lysis agent, a reagent, a dye, a desiccant, a stabilizer, a protein, a nucleic acid, a filter, a membrane, or a marker.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 34A shows an exemplary schematic of a base station.

FIG. 34B shows exemplary motors.

FIG. 34C shows exemplary schematics of spring configurations.

FIG. 34D shows exemplary position sensors.

FIG. 35A shows an exemplary sample preparation device with autonomous control in a starting position.

FIG. 35B shows an exemplary sample preparation device with autonomous control undergoing automatic rotation.

FIG. 35C shows an exemplary sample preparation device with autonomous control in a second position.

FIG. 35D shows an exemplary schematic of a disc layer from a sample preparation device.

FIG. 35E shows an exemplary schematic of a disc layer from a sample preparation device.

FIG. 35F shows an exemplary schematic of a bottom layer from a sample preparation device with a push button or pin.

FIG. 36 shows an electronic device being used to take a picture of results from an exemplary sample preparation device.

FIG. 37A shows an exemplary sample preparation device undergoing sample loading.

FIG. 37B shows an exemplary sample preparation device closed and rotated from a first position to a second position.

FIG. 37C shows an exemplary sample preparation device rotated to a third position.

FIG. 37D shows an exemplary sample preparation device rotated to a fourth position.

FIG. 37E shows an exemplary sample preparation device with completed sample preparation.

FIG. 37F shows an exemplary sample preparation device undergoing incubation.

FIG. 37G shows an exemplary sample preparation device displaying results.

Figure 38:
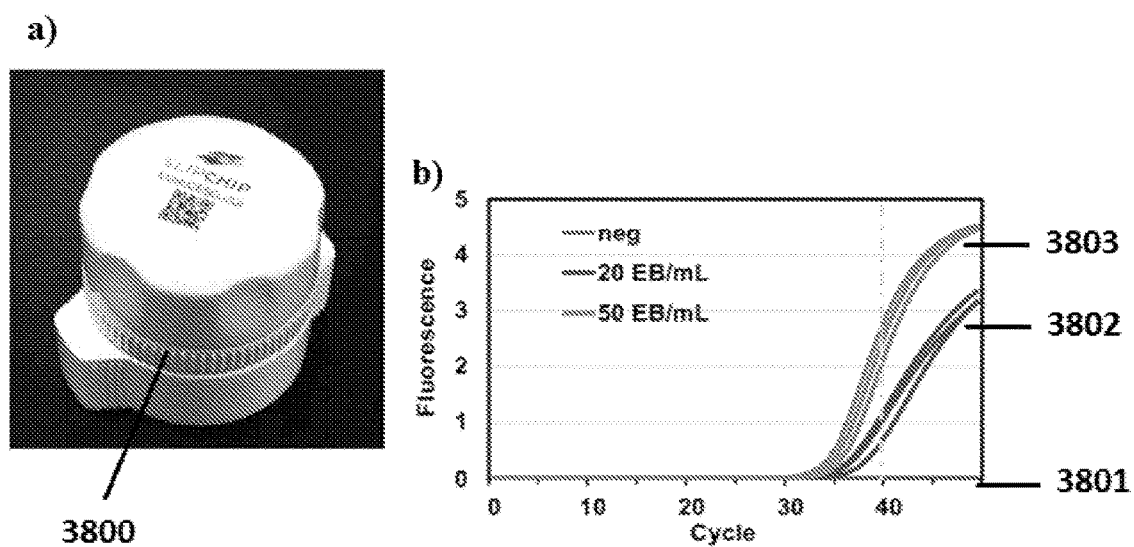

FIG. 38A shows an exemplary sample preparation device.

FIG. 38B shows results from a sample in an exemplary sample preparation device

Figure 39:
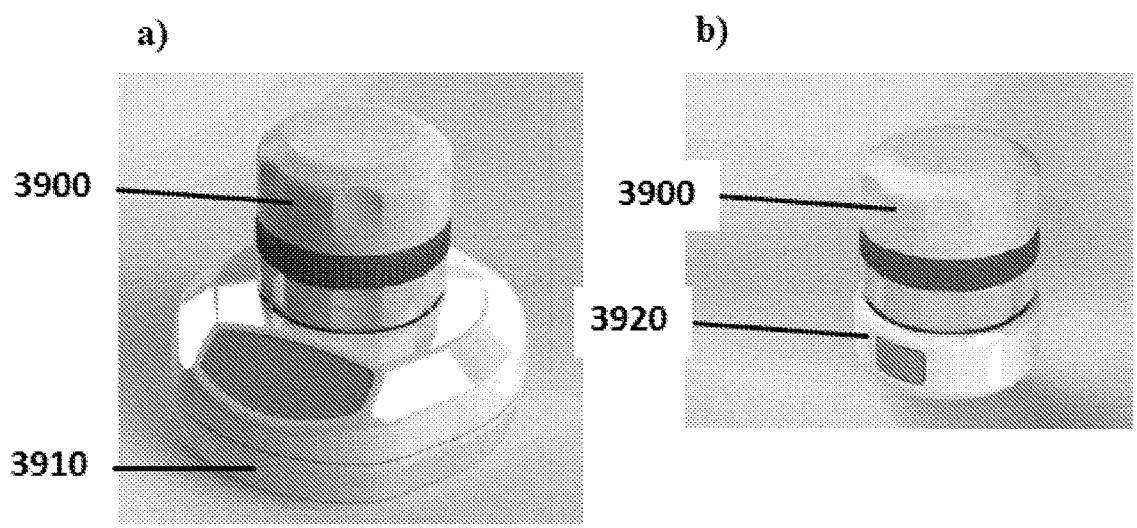

FIG. 39A shows an exemplary sample preparation device with a base station.

FIG. 39B shows an exemplary sample preparation device with a base layer.

Figure 40:
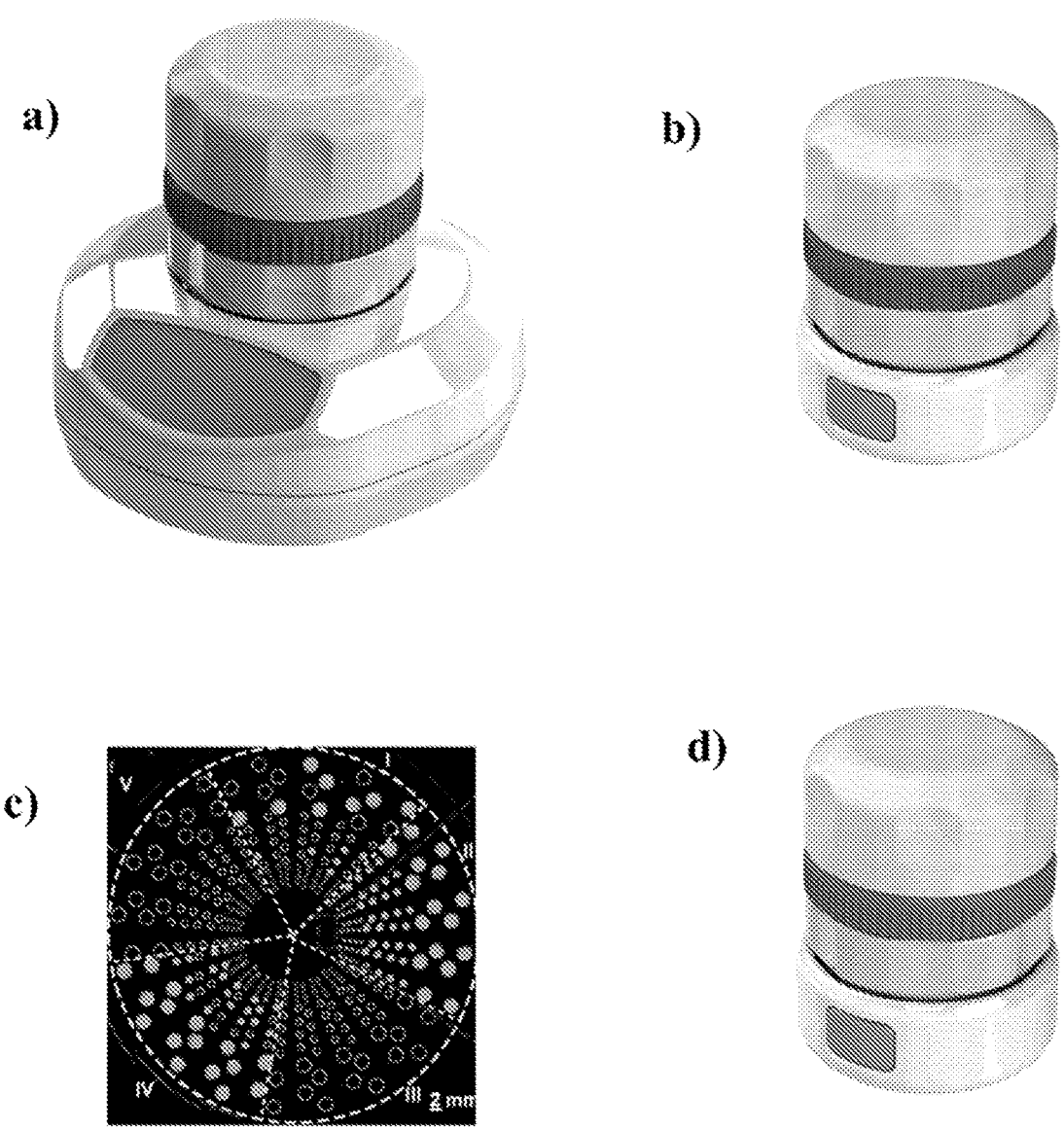

FIG. 40A shows an exemplary sample preparation device with a base station for a qualitative point-of-care or low resource setting test.

FIG. 40B shows exemplary sample preparation device with a disposable base layer for a qualitative low resource setting test.

FIG. 40C shows an exemplary digital PCR chip.

FIG. 40D shows exemplary sample preparation device with a disposable base layer for a quantitative low resource setting test.

FIG. 41A shows an exemplary sample preparation device with an exemplary temperature control unit.

Figure 41:
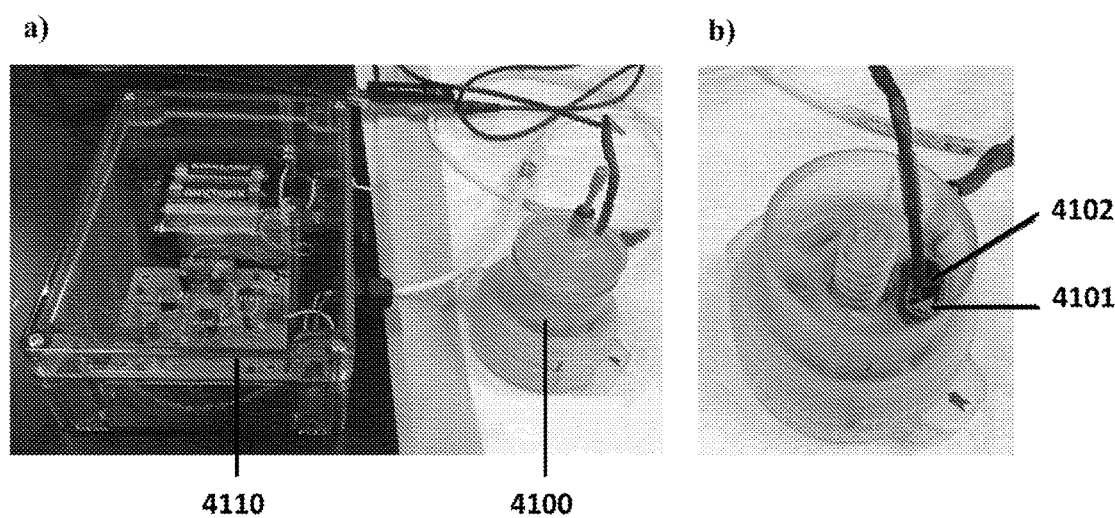
Figure 42A:
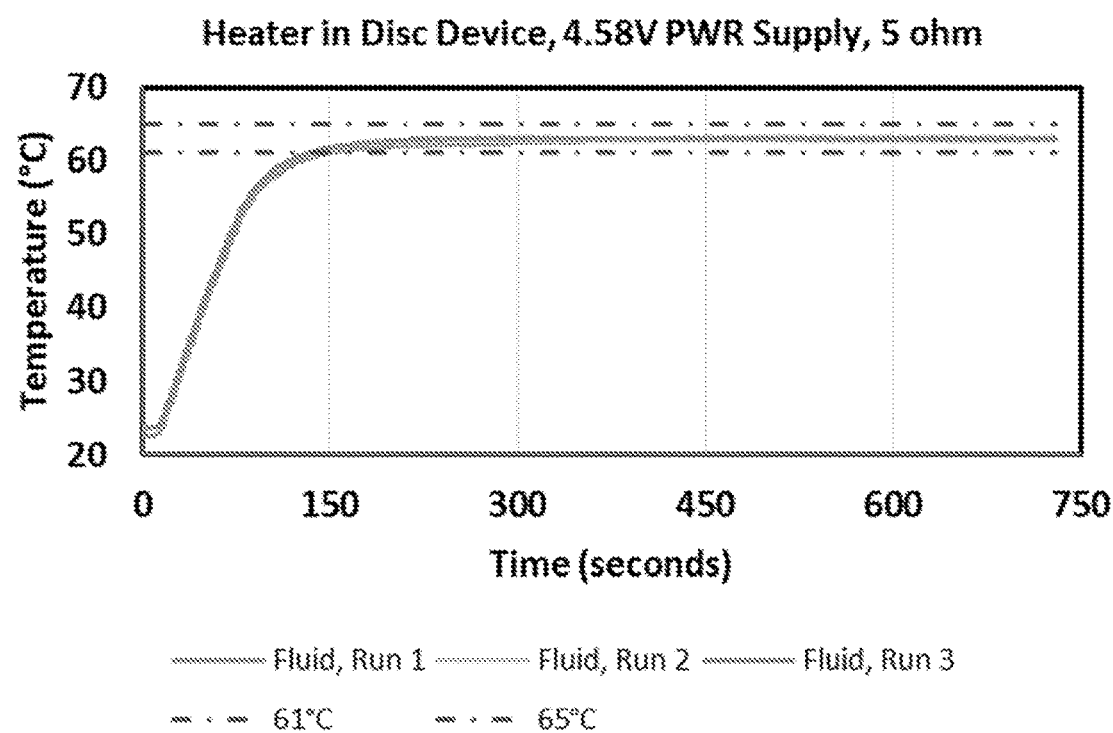

FIG. 41B shows an interior view of an exemplary sample preparation device with an exemplary temperature control unit FIG. 42A shows exemplary results from a temperature controller.

Figure 42B:
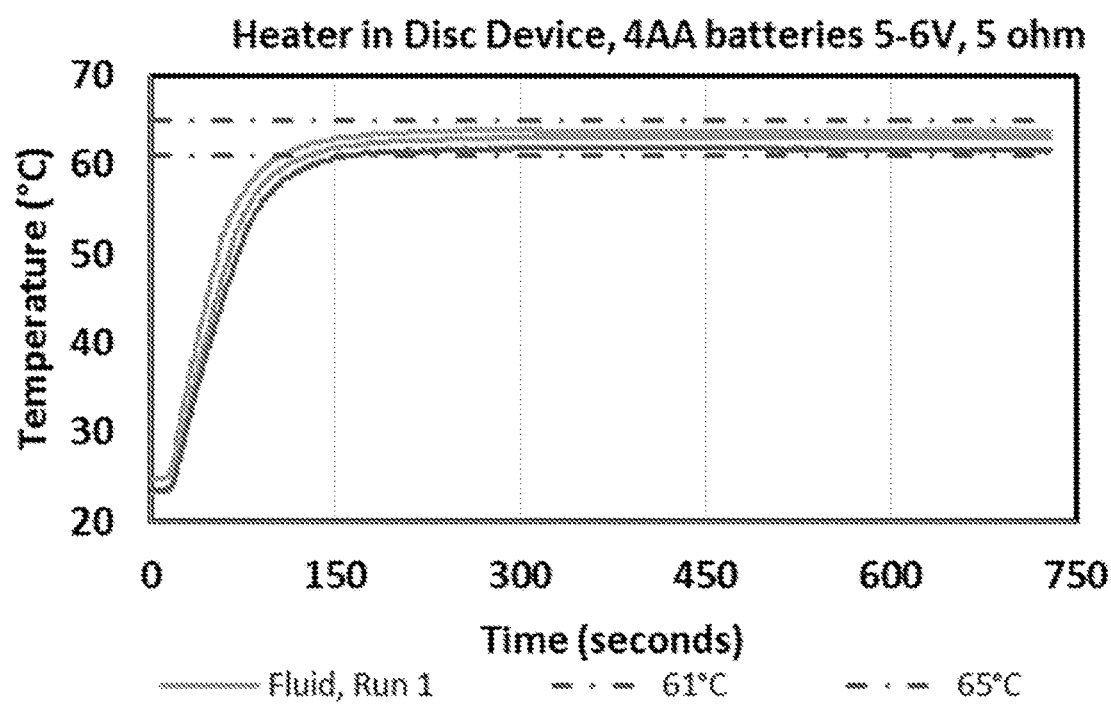

FIG. 42B shows exemplary results from a temperature controller.

Figure 42C:
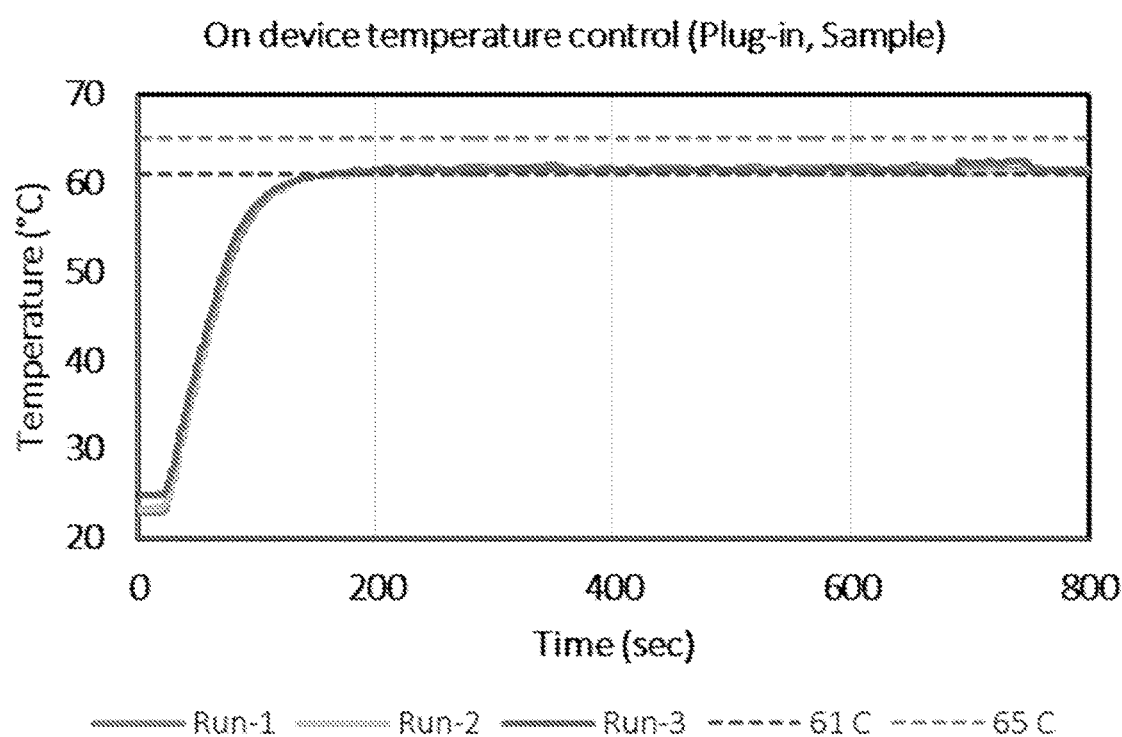

FIG. 42C shows exemplary results from a temperature controller.

Figure 42D:
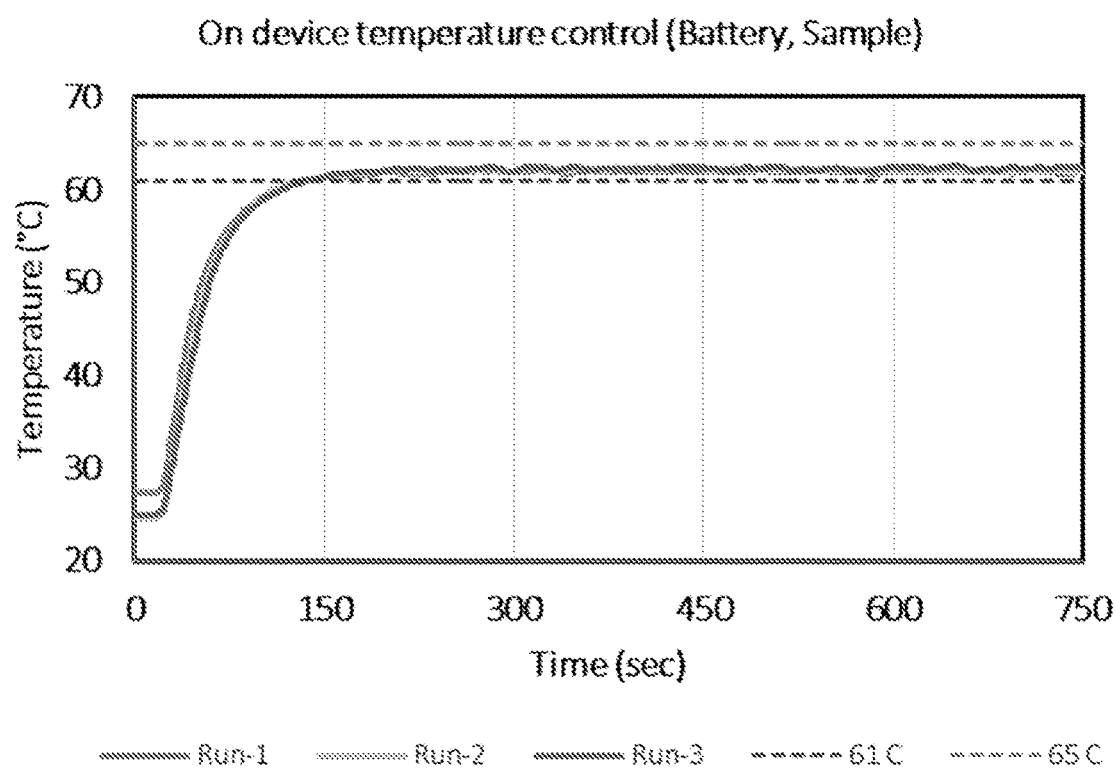

FIG. 42D shows exemplary results from a temperature controller.

DETAILED DESCRIPTION OF THE INVENTION

We describe devices and methods in this disclosure that may be used individually or in various combinations for applications including but not limited to those listed herein. Furthermore, they can be used in various combinations with previously disclosed devices and methods for previously-described applications. The present application incorporates the following applications by reference in their entireties for any and all purposes: U.S. Application 61/516,628, "Digital Isothermal Quantification of Nucleic Acids Via Simultaneous Chemical Initiation of Recombinase Polymerase Amplification (RPA) Reactions on Slip Chip," filed on Apr. 5, 2011, and also to U.S. Application 61/518,601, "Quantification of Nucleic Acids With Large Dynamic Range Using Multivolume Digital Reverse Transcription PCR (RT-PCR) On A Rotational Slip Chip Tested With Viral Load," filed on May 9, 2011; U.S. application Ser. No. 13/257,811, "Slip Chip Device and Methods," filed on Sep. 20, 2011 (U.S. Pub. No. 2012-0028342); that United States application is a national stage entry of international application PCT/US2010/028316, "Slip Chip Device and Methods," filed on Mar. 23, 2010 (Int. Pub. No. WO 2010/111265), which international application claimed priority to U.S. Application 61/262,375, "Slip Chip Device and Methods," filed on Nov. 18, 2009, to U.S. Application 61/162,922, "Slip Chip Device and Methods," filed on Mar. 24, 2009, to U.S. Application 61/340,872, "Slip Chip Device and Methods," filed on Mar. 22, 2010, to U.S. application Ser. No. 13/440,371, "Analysis Devices, Kits, And Related Methods For Digital Quantification Of Nucleic Acids And Other Analytes," filed on Apr. 5, 2012 (U.S. Pub. No. 2012-0264132), and to U.S. application Ser. No. 13/467,482, "Multivolume Devices, Kits, and Related Methods for Quantification and Detection of Nucleic Acids and Other Analytes," filed on May 9, 2012 (U.S. Pub. No. 2012-0329038); U.S. application Ser. No. 13/868,009 and International Application PCT/US2013/037658, both of which are entitled "Fluidic Devices for Biospecimen Preservation" and filed on Apr. 22, 2013, each of which claims priority to U.S. Application 61/636,426, "On-Chip Drying of Samples," filed on Apr. 20, 2012; U.S. application Ser. No. 13/868,028 and International Application PCT/US2013/037660, both of which are entitled "Fluidic Devices and Systems for Sample Preparation or Autonomous Analysis" and filed on Apr. 22, 2013, each of which claims priority to U.S. Application 61/636,426, "On-Chip Drying of Samples," filed on Apr. 20, 2012, and to U.S. Application 61/726,089, "Loading apparatus for controlling pressure and filling fluids in channels," filed on Nov. 14, 2012; and U.S. application Ser. No. 13/869,856, "Slip-Induced Compartmentalization," filed on Apr. 24, 2013, which claims priority to U.S. Application 61/637,661, "Slip-Induced Compartmentalization," filed on Apr. 24, 2012.

This disclosure describes systems and methods for time control during movement. The described systems and methods can be used to provide desired time delay in a series of movements. This desired time delay can be used in a variety of applications, including but not limited to fluid or reagent dispensing, reactions, extraction, purification, isolation, incubation, mixing, dissolution, precipitation, crystallization, cell growth, heating, cooling, rehydration, and reconstitution of reagents, samples, or analytes. The systems and methods can allow activation of resistant units and can dispense fluids in a particular desired order, such as sequentially, simultaneously, or in combination. Resistant units can be activated by pushing units, which can move linearly, rotationally, or a combination thereof. Time control and fluid dispensing systems can be integrated into devices, including but not limited to devices for sample preparation, sample preservation, and sample analysis.

Numerous benefits can be associated with the present invention. For instance, the present systems and methods can be used to dispense fluid in a controlled or automated manner, in which the order of fluid addition and/or the timing between fluid additions is controlled. This can provide straightforward and reproducible results with a minimum of user input or user error. In some cases, the controlled or automated operation can be conducted without external power, or without electrical power, allowing portable operation even in remote or low-resource settings. In another instance, the present system and methods allow for storage of reagents and/or samples in a stable, sterile environment. Such storage can be beneficial in, for example, point-of-care diagnostics, where further testing can be conducted off-site on a stored sample, as well as in conducting assays at remote locations such that reagents and samples may require long-term storage. Another benefit includes the introduction of pauses or time delays when conducting assays within the device. Typically, introducing such pauses (e.g., in an automated manner) can be challenging. For instance, complicated feedback interactions may be required to determine the extent of delay needed to heat a particular portion of the system, such as feedback between temperature gauges located near the area of interest, the extent of heat dispersed from a heating element, the dispensing system to control fluid flow and reagent addition, and, of course, a system with integrated circuitry and sensors to effect the feedback. In contrast, the present system and methods can allow for a more simplified approach. In the present approach, a time delay mechanism and dispensing mechanism can be integrated into structures of pushing unit(s) and resistant unit(s), as well as the barrier unit(s) if present, as described herein. In this manner, feedback can occur between the pushing unit and resistant unit to control timing or order. For example, a resistant unit can comprise a blister or blister pack connected to a channel, and a pushing unit can comprise a cam; the hydrodynamic resistance of a fluid within the blister or blister pack flowing through the channel can control the timing of the cam motion. Additionally, these systems and methods can provide rapid sample processing and analysis, such as short times from input to preparation, extraction, or detection.

Figure 1:
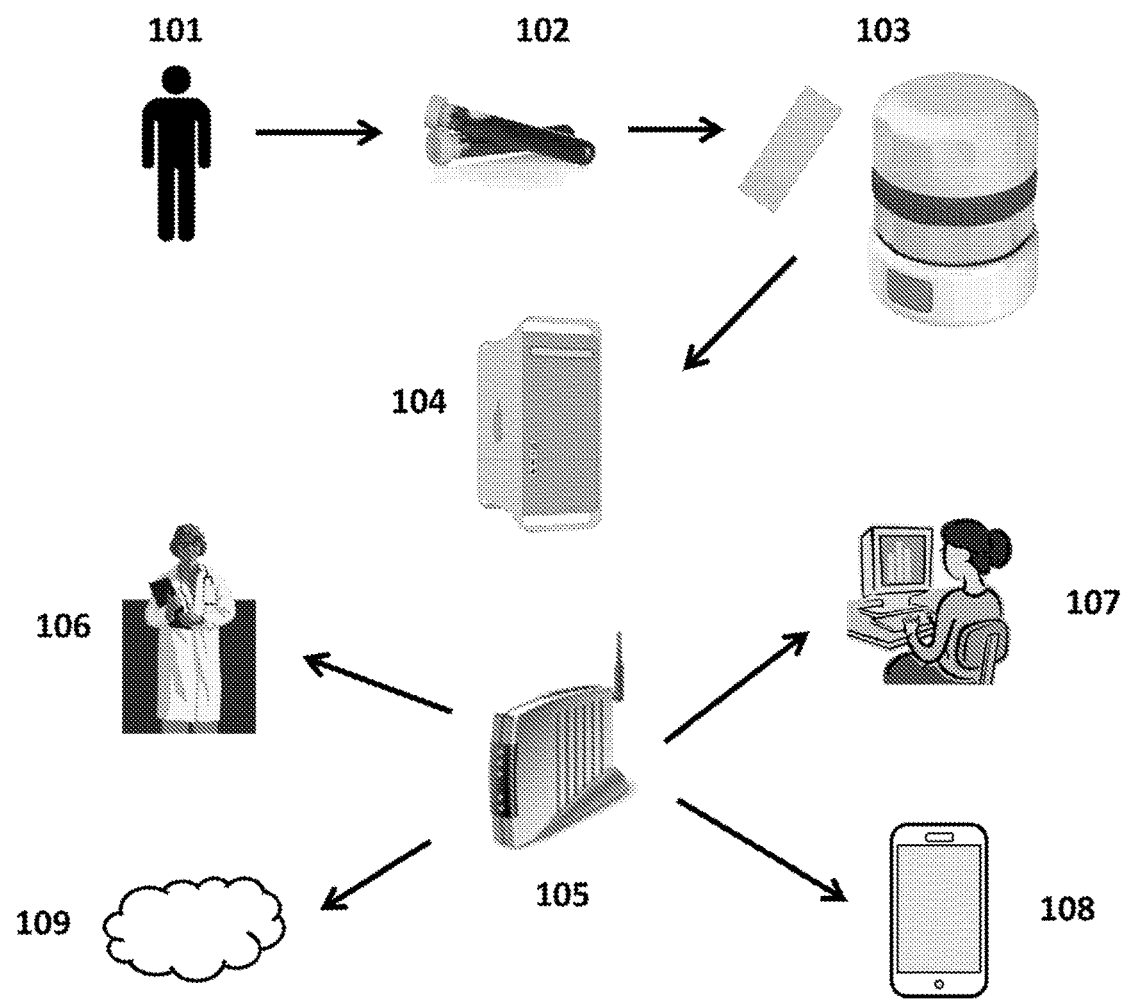
FIG. 1 shows an exemplary schematic of assaying a sample from a subject.

For example, FIG. 1 shows an exemplary schematic of assaying a sample from a subject 101. A sample 102 from the subject can be received and loaded into a sample preparation device 103. Results from the sample preparation device can be analyzed 104. Prepared sample from the sample preparation device can also be stored, transported, or further analyzed. Results can be transmitted, for example over a network 105 (e.g., the internet), to a medical professional 106, a subject or patient 107, to a mobile device 108 or an app, or to other locations 109.

Fluid or Reagent Dispensing System

This disclosure provides a fluid dispensing system, which can include one or more components to allow for time-controlled dispensing of one or more reagents or fluids. These components can include any useful configuration. One non-limiting example is provided in FIG. 2A-C. For example, in FIG. 2A a pushing unit 210 is located above a substrate 201 in a channel 202 and contacts a resistant unit 220; in FIG. 2B the resistant unit blocks the pushing unit and force from the pushing unit moves fluid or reagent out through the resistant unit; in FIG. 2C the pushing unit overcomes the resistance and moves forward. Another non-limiting example is provided in FIG. 2D-F, which further includes a barrier unit 230 in addition to a resistant unit 220 and a pushing unit 210 located above a substrate 201 in a channel 202. The barrier unit can stop or slow down the movement of the pushing unit at certain conditions, and it can allow pushing unit to pass at certain conditions.

Pushing Units

A pushing unit can comprise elements including but not limited to pistons, levers, arms, rods, springs, elastic elements, plungers, spheres, discs, tips, barbs, protrusions, rollers, drums, and combinations thereof. In some cases, a pushing unit does not comprise a roller.

The pushing unit can be made from soft material, hard material or combination of both. The movement of the pushing unit can have various directions (e.g., along a first surface), such as linear, circular, oval, sinusoidal, wavy, or a combination of different directions. This relative movement (i.e., between a first position of the pushing unit and a second position of the pushing unit) can include a sliding movement, a translating movement, a rolling movement, or combinations thereof. As shown in non-limiting FIG. 2, the pushing unit can have any useful configuration. For instance, the pushing unit 210 can be disposed above a first surface of a first substrate 201. In other examples, the pushing unit can be disposed within a channel 202 and above the first surface. The relative movement can be in any useful direction. In particular cases, the relative movement can be in a direction that is parallel to a surface of the device, thereby causing fluid or reagent to enter one or more chambers within the device. In some cases, the relative movement can be in a direction that is about parallel to a surface of the device, or is less than about 90°, 80°, 70°, 60°, 50°, 40°, 30°, 20°, or 10° from the surface. The relative movement can be linear. The relative movement can be not linear. The relative movement can be translational. The relative movement can be not translational. The relative movement can be rotational. The relative movement can be not rotational. Rotation can be around an axis perpendicular to a surface of the device or substrate. Rotation can be in a path, such as a circular path, within a plane parallel to a surface of the device or substrate. Rotation can be in a path within a plane about parallel to a surface of the device or substrate, or is less than about 90°, 80°, 70°, 60°, 50°, 40°, 30°, 20°, or 10° from the surface.

Figure 3:
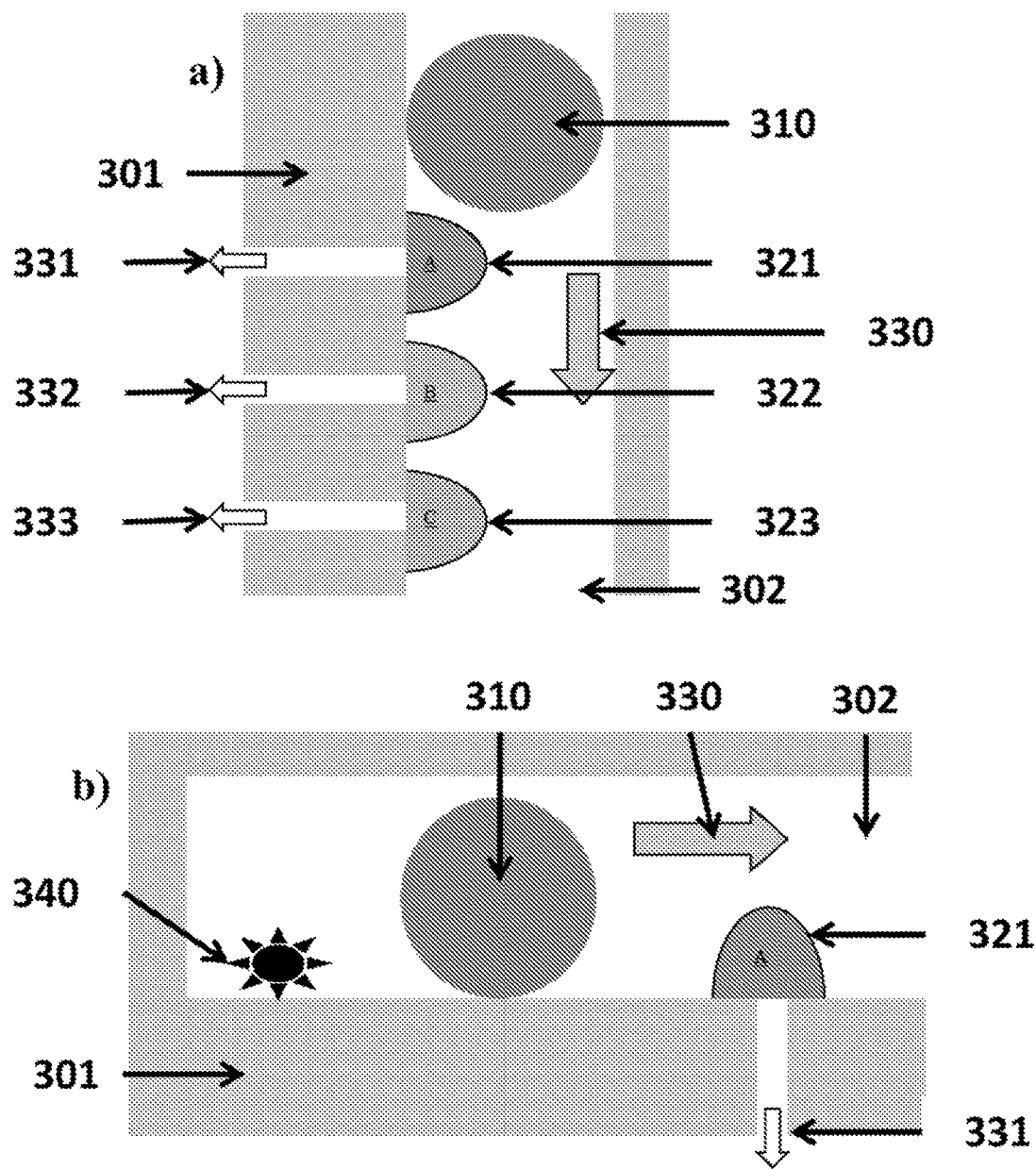
FIG. 3A shows an exemplary schematic of a pushing unit moving via gravitational force.
FIG. 3B shows an exemplary schematic of a pushing unit moving via a reaction.

The pushing unit can exert any useful force. For example, the force can be a mechanical force, such as that arising from a spring, a piston, or a motor. In another example, the force can arise from gravity, magnetic force, or changes in temperature. In a non-limiting example, the relative movement of the pushing unit arises from gravity (e.g., FIG. 3A). As can be seen, the pushing unit 310 travels by relative movement 330 through a channel 302 over a substrate 301, thereby causing fluid or reagents in resistant units 321, 322, 323 to enter a first chamber 331, 332, 333.

A pushing unit can be driven by a force and can relatively move in a certain direction following a certain path. The applied force can be constant over time or can change over time, and this force can include acceleration and/or deceleration. Force can be applied to a pushing unit by direct or indirect contact, such as for example, by contact with solid, liquid, or gas, or by use of a spring or piston. Force can be provided, generated, or triggered by various sources, including but not limited to springs, elastic elements, mechanical movement, pressure, chemical reactions, physical changes, biological reactions, light, sound waves, compression, changes in orientation of the pushing unit (e.g., allowing for use of gravity). Exemplary, non-limiting forces and gradients include use of centrifugal force; a surface tension gradient; osmotic pressure; capillary pressure, such as by including arrays of channels and/or chambers to create gradients of capillary pressure; positive or negative pressure that can be generated externally, (e.g., by using pumps or syringes); slipping, such as by relative movement of one or more layers; pressure generated by compressing or expanding a chamber containing a fluid or reagent; an electric force; an electroosmotic force; gravity; a magnetic force; or a chemical reaction or process (e.g., by using reagents to produce a gaseous product, thereby generating pressure, such as the combination of sulfuric acid with a carbonate salt or the combination of sodium bicarbonate with a solid acid, for example tartaric acid, activated by addition of water; or by using reagents that consume gas, thereby causing a decrease in pressure, such as the combination of sodium hydroxide with carbon dioxide), which may be initiated externally or initiated by relative movement (e.g., by slipping). In some cases, the relative movement of the pushing unit can arise from a change in pressure. This change in pressure can be induced by any physical phenomenon, including but not limited to changes in temperature, changes in physical matter, changes in volume, chemical reactions, phase changes, or combinations thereof. In one non-limiting example, for example as shown in FIG. 3B, a reaction 340 causes expansion of gas/liquid to increase pressure, thereby moving the pushing unit 310 above a substrate 301 in a channel 302 in the direction of the expanding gas/liquid 330 and causing fluid or reagent from a resistant unit 321 to enter a first chamber 331. In some cases, a reaction can cause shrinkage of gas or liquid to decrease pressure, thereby moving the pushing unit in the direction of the shrinking gas or liquid. In other cases, the relative movement of the pushing unit can arise by use of vacuum causing a pressure gradient. In some cases, the force for a given pushing unit can be different depending on the position along the path of the pushing unit, or, for some movements, position along the radius of movement(s).

The pushing unit(s) and device(s) can include the use of one or more forces or gradients to move one or more substances within the device. A pressure gradient can be created by any component described herein, such as the capping system described herein. The devices herein can optionally include posts or other three-dimensional structures that partially or completely block a chamber and/or channel. For example, a post member can be provided in a first layer, which can block a chamber in a second layer upon moving the first layer relative to the second layer. In this manner, positive pressure can be generated in front of the post member and negative pressure can be generated behind. This approach can be used to load, dispose, or move a substance within the device. Flow can also be generated by the pressure gradient created by the relative movement.

In some cases, the pushing unit can include a plunger (e.g., a syringe plunger) that can be moved, for example manually or by a motor. In particular cases, the plunger can be configured to slidably engage along a first surface of a first substrate. In further cases, a channel can be disposed above the first surface, or the first surface can be contiguous and can form a channel, and the plunger can slidably engage within the channel and along the first surface of the first substrate. The plunger can include a tip configured to contact one or more resistant units, where the tip can include a head or seal (e.g., rubber) to form an airtight seal against the surface of the channel or the first surface. A motor can be attached to the distal end of the plunger in any useful manner. For instance, the plunger can include one or more flanges that interface with a locking mechanism (e.g., a bracket, a clamp, etc.), where the locking mechanism is further attached to a drive shaft that is driven by a motor or a pump. Exemplary drive shafts, drive heads, pumps, drivers, and plungers are provided in U.S. Pat. Nos. 6,932,242 and 5,545,140, each of which is incorporated herein by reference in its entirety.

In further cases, one or more resistant units can be arranged in the interior of a channel (e.g., disposed above the first surface of the first substrate), where the channel has a cylindrical or other cross-sections (e.g., a square, rectangle, semicircle, triangle, etc. cross-sections). The one or more resistant units can be actuated by one or more pushing units (e.g., one or more plungers) traveling through the channel.

A system can comprise one or more pushing units. In some non-limiting examples, multiple pushing units may be preferred for multiple operations (e.g., processing, analyzing, mixing, reacting, incubating, filtering, extracting, and/or detecting) to be activated at different time points. For instance, a first pushing unit can interact with one or more first resistant units that provide particular first reagents, and a second pushing unit can interact with one or more second resistant units that provide other reagents. Furthermore, the configuration of the first resistant unit(s) can provide a first relative timing in adding one or more reagents, and this configuration may be distinct from that of the second resistant unit(s). In yet another example, a first pushing unit can interact with an array of first resistant units (e.g., including one or more reagents for sample preparation) configured for a process (e.g. nucleic acid extraction), where the first pushing unit then activates a second pushing unit. Then, the second pushing unit can interact with an array of second resistant units (e.g., including one or more reagents for sample detection and/or analysis) configured for another process (e.g., amplifying and/or detecting target nucleic acid from the sample). In this manner, time delays can be added between various processes, for example, preparing and analyzing a target nucleic acid from a sample. Additional pushing units and/or resistant units (including arrays of such resistant units) can be configured for the particular purpose or use of the system or device.

Figure 4:
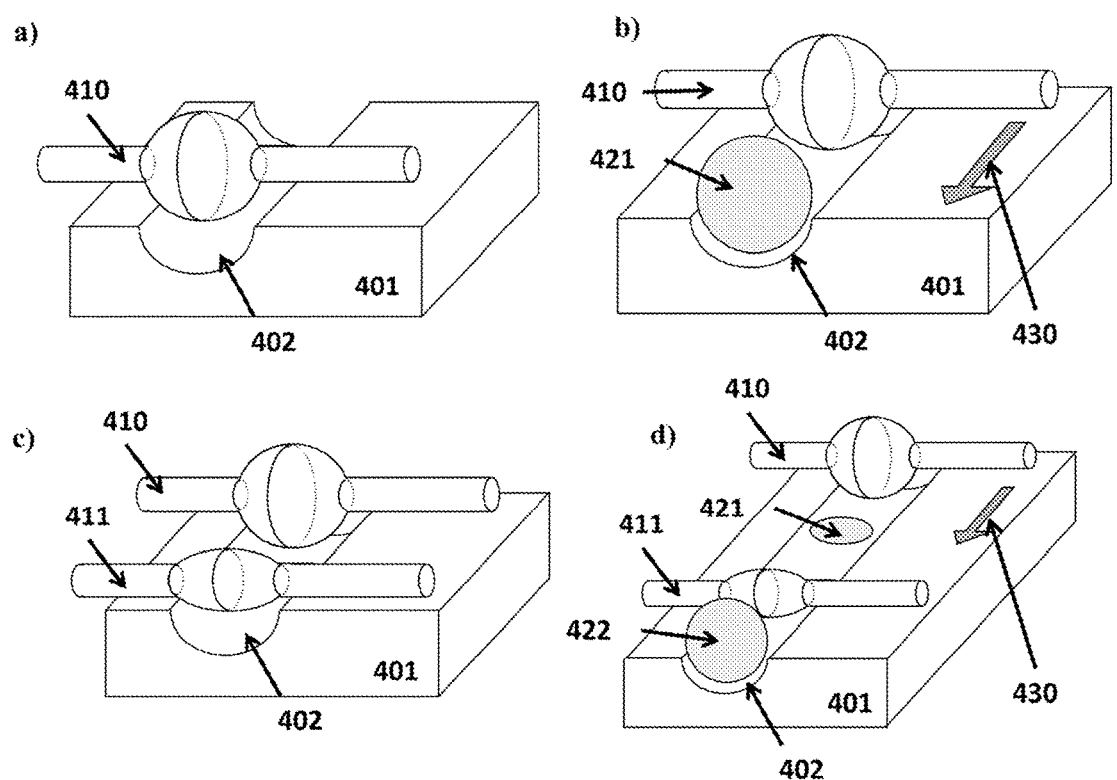
FIG. 4A shows an exemplary schematic of a pushing unit engaged with a channel.
FIG. 4B shows an exemplary schematic of a pushing unit moving linearly toward a resistant unit.
FIG. 4C shows an exemplary schematic of two pushing units with different geometries.
FIG. 4D shows an exemplary schematic of two pushing units with different geometries moving linearly toward resistant units.

The pushing unit can have any useful geometry that allows for pushing against the resistant unit and/or barrier unit (see, e.g., FIG. 4A-D). For instance, the pushing unit can be configured to slidably engage along the first surface. A pushing unit can move linearly 430 (e.g., FIG. 4B, FIG. 4D) or rotationally 530 (e.g., FIG. 5A). In one non-limiting example, the first substrate 401 can comprise a first surface 402 which includes a channel having a semicircular cross-section, and the pushing unit 410 is geometrically configured to slidably engage with the channel (see, e.g., FIG. 4A). In another non-limiting example, the system includes two or more pushing units, where each pushing unit can have the same or different geometry. In yet another example, the system can include two or more pushing units 410, 411, where each pushing unit can have the same or different geometry (see, e.g., FIG. 4C); as can be seen in FIG. 4C, two pushing units are present, and while both units are configured to slidably engage with the first surface 402 of the first substrate 401, the actual configuration of each pushing unit is different. In use, the pushing unit(s) can be used to push out the same fluid/reagent multiple times and/or to bypass a resistant unit by certain pushing units while activating the resistant with another pushing unit.

The pushing unit and resistant unit can be configured to interact with each other (as well as the first surface) to allow for direct or indirect contact. In a non-limiting example, the pushing unit 410 and resistant unit 421 can be configured to contact when a first relative movement 430 of the pushing unit occurs in a direction parallel to the first surface of the substrate (see, e.g., FIG. 4B). In another non-limiting example, two or more pushing units 410, 411 and two or more resistant units 421, 422 are configured to contact with a first relative movement 430 (see, e.g., FIG. 4D). For instance, the system can include two or more pushing units, where each unit can have the same or different configuration. In yet another instance, the system can include two or more resistant units, where each unit can have the same or different configuration. As can be seen in FIG. 4D, two pushing units of different configurations 410, 411 slidably engage with the first surface and encounter a relative movement 430 in a direction parallel to the first surface 402 of the first substrate 401. The two resistant units are configured differently, where the first resistant unit 411 has a smaller cross-sectional dimension than the second resistant unit 410. These different configurations allow the first pushing unit 411 to bypass the first resistant unit 421 and interact with the second resistant unit 422 (see FIG. 4D). The second resistant unit 410 has a large cross-section that allows it to interact with both the first 421 and second 422 resistant units. In a similar manner, a skilled artisan would be able to adapt the configurations of the pushing unit(s) and resistant unit(s) to dispense fluid or reagent and/or introduce delays in a time-dependent manner.

Resistant and Barrier Units

A resistant unit can provide a certain resistance to stop or slow a pushing unit. A barrier unit can stop or slow down the movement of the pushing unit at certain conditions, and it can allow pushing unit to pass at certain conditions. A resistant unit can comprise various materials and geometries, including but not limited to deformable materials, blisters, blister packs, gels, compressible liquids or gases, sponges, springs, channels, chambers, and combinations thereof. In some cases, a channel or multiple channels of different geometries can be used to provide a fluidic path for the content of a resistant unit. In some cases, the channel(s) can have dead-end filling structures. Resistance can also be provided by additional structures, such as a filter (e.g., a filter for solid phase extraction of nucleic acids), a membrane (e.g., a membrane for separation of blood components), or a channel. Furthermore, resistance can be provided by any useful combination of structures, such as by use of a blister pack in combination with a channel and a filter.

A pushing unit can contact a resistant unit directly or indirectly. For indirect contact, a structure or component can be included between the pushing unit and the resistant unit, such as a barrier unit or a volume of fluid (e.g., air).

Figure 2:
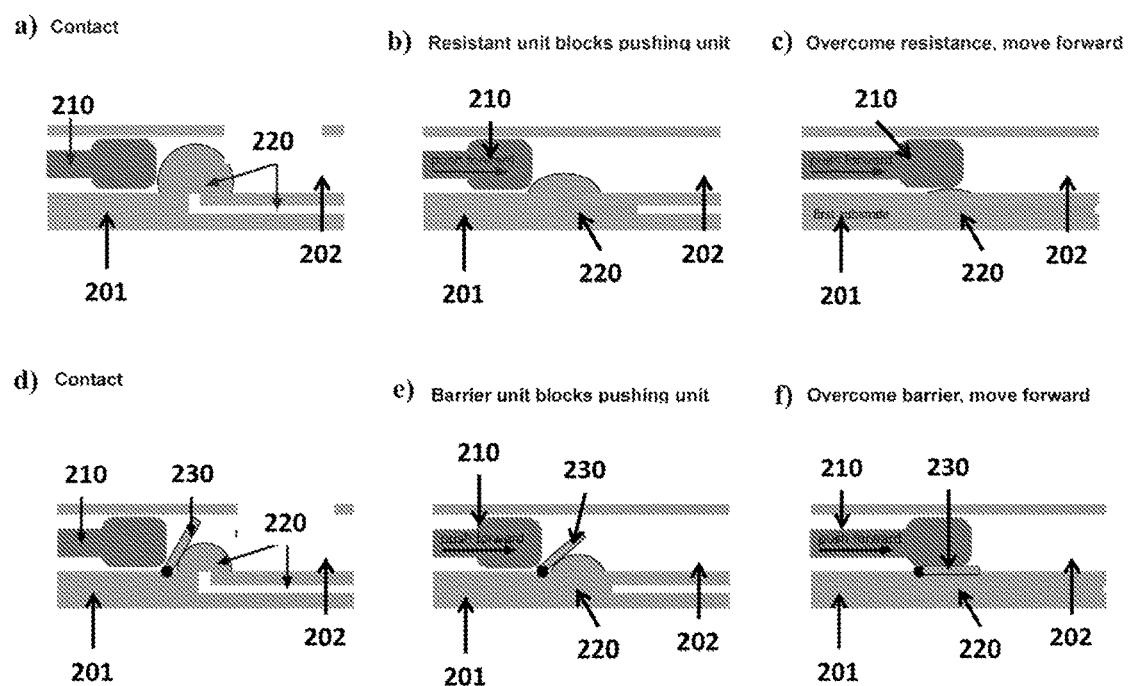
FIG. 2A shows an exemplary schematic of a pushing unit contacting a resistant unit.
FIG. 2B shows an exemplary schematic of a resistant unit blocking a pushing unit.
FIG. 2C shows an exemplary schematic of a pushing unit overcoming a resistant unit.
FIG. 2D shows an exemplary schematic of a pushing unit contacting a barrier unit.
FIG. 2E shows an exemplary schematic of a barrier unit blocking a pushing unit.
FIG. 2F shows an exemplary schematic of a pushing unit overcoming a barrier unit.

Another non-limiting example is provided in FIG. 2, which further includes a barrier unit 230 in addition to a resistant unit 220 and a pushing unit 210 located above a substrate 201 in a channel 202. The barrier unit can stop or slow down the movement of the pushing unit at certain conditions, and it can allow pushing unit to pass at certain conditions. It can be moved certain distance, such as up to about 1 µm, 10 µm, 100 µm, 1 mm, 10 mm, 100 mm, 1 cm, or 10 cm. It can be rotated at certain angles, such as up to about 1°, 5°, 10°, 20°, 60°, 90°, 180°, 270°, or 360°. A barrier unit is optional. In some cases, a barrier unit can be combined with a resistant unit into a single component, such as a blister pack. A barrier unit can require a certain force or pressure for the pushing unit to reach before the pushing unit can overcome the barrier unit. In some examples, the pushing unit can be driven by a spring; the spring can be wound by a mechanism until the spring force is sufficient to overcome the pushing unit.

In one example, a resistant unit comprising a blister pack blocks movement of a pushing unit. The pushing unit pushes against the blister pack, applying a force and increasing the pressure inside the blister pack. At a certain pressure, a seal separating the blister pack from a channel ruptures, and fluid or reagent begins to flow through the channel into a chamber. The geometry of the channel and the viscosity of the fluid or reagent contribute to the resistance of the resistant unit. Once a sufficient volume of fluid or reagent has been evacuated from the resistant unit into the chamber, the resistant unit no longer blocks the pushing unit, and the pushing unit proceeds to a second resistant unit. The volume of fluid or reagent, seal rupturing pressure, and channel geometry can be optimized to provide a desired fluid or reagent dispensing time.

Figure 6:
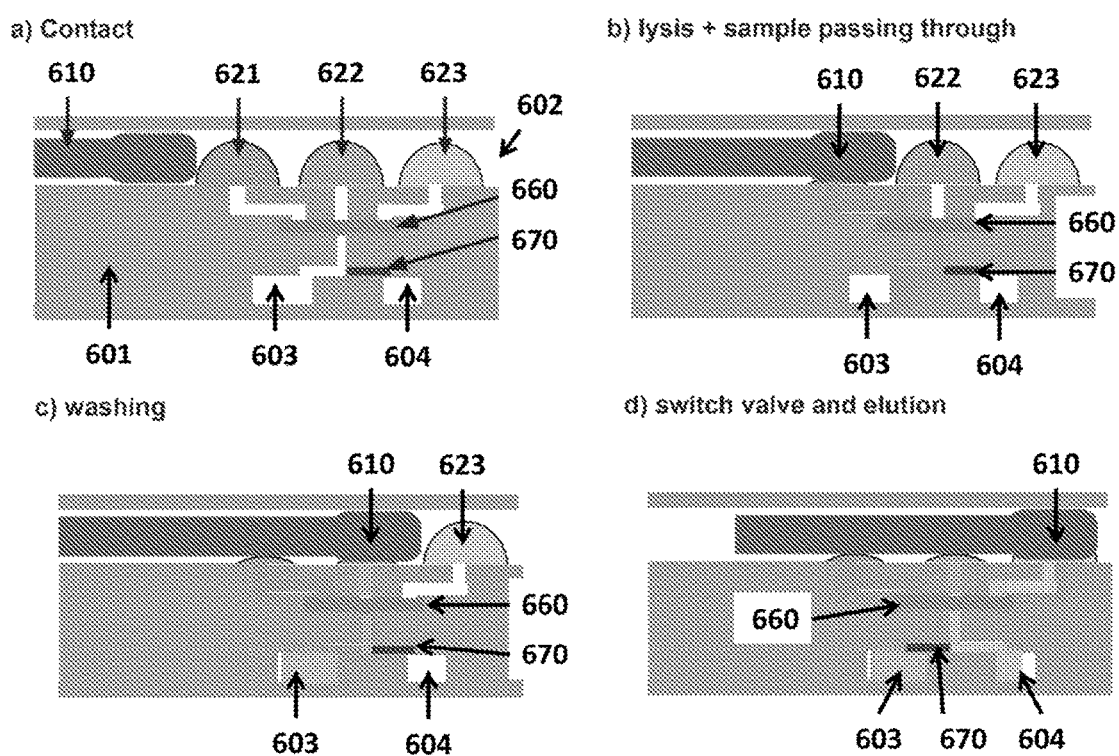
FIG. 6A shows an exemplary schematic of a pushing unit contacting a first resistant unit.
FIG. 6B shows an exemplary schematic of a pushing unit contacting a second resistant unit while fluid from a first resistant unit flows into a first chamber.
FIG. 6C shows an exemplary schematic of a pushing unit contacting a third resistant unit while fluid from a second resistant unit flows into a first chamber.
FIG. 6D shows an exemplary schematic of fluid from a third resistant unit flowing into a second chamber.
Figure 7A:
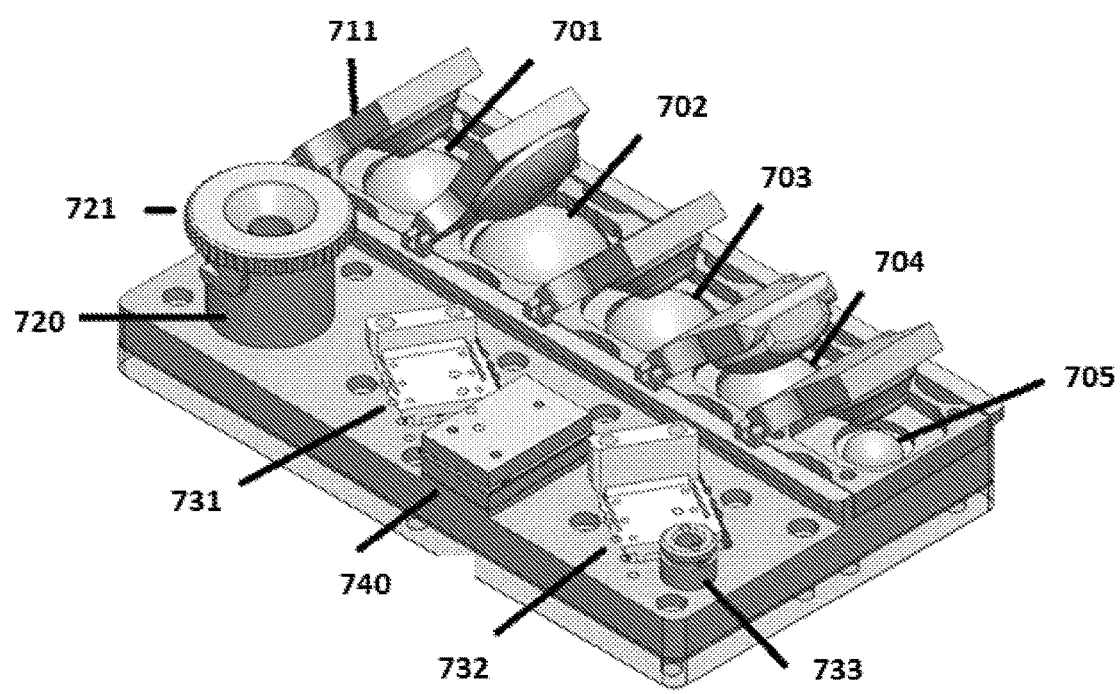
FIG. 7A shows an exemplary schematic of a linear sample preparation device from a three-quarters view.
Figure 7B:
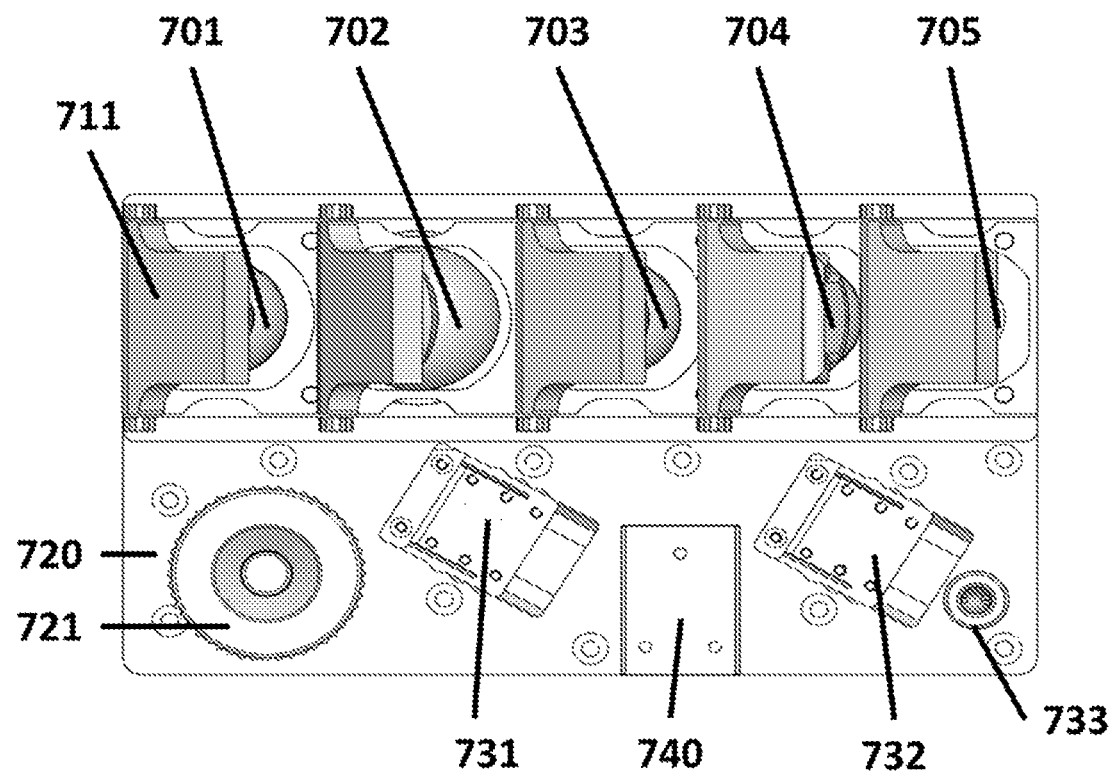
FIG. 7B shows an exemplary schematic of a linear sample preparation device from a top view.
Figure 7C:
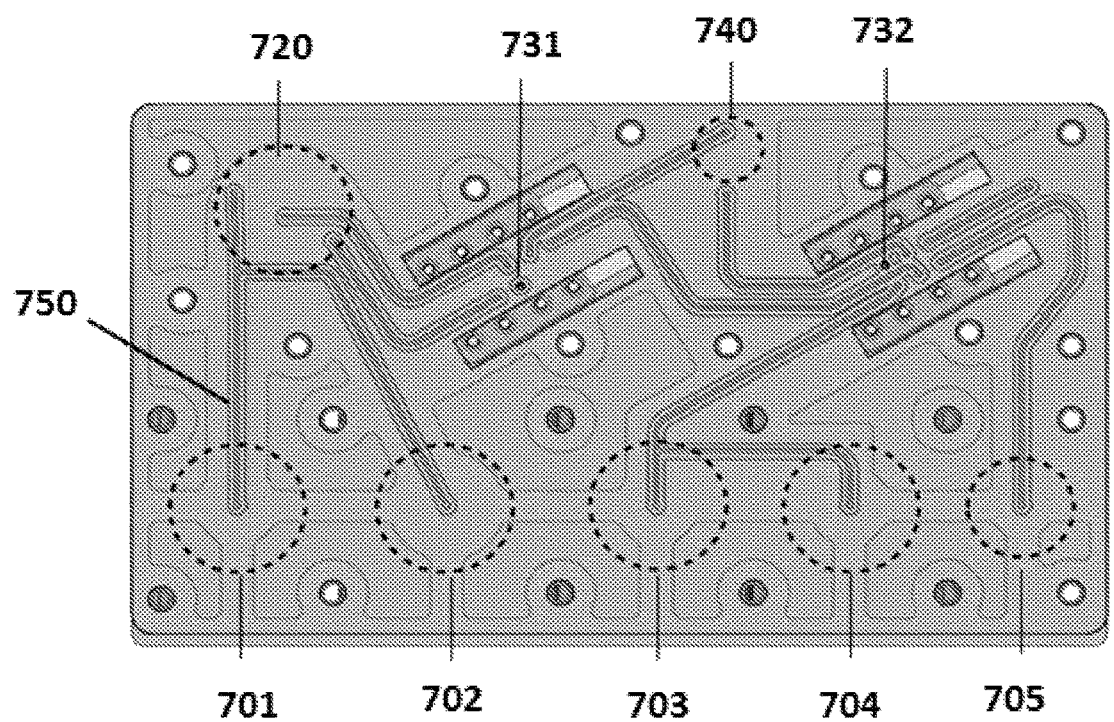
FIG. 7C shows an exemplary schematic of a linear sample preparation device from a bottom view.
Figure 7D:
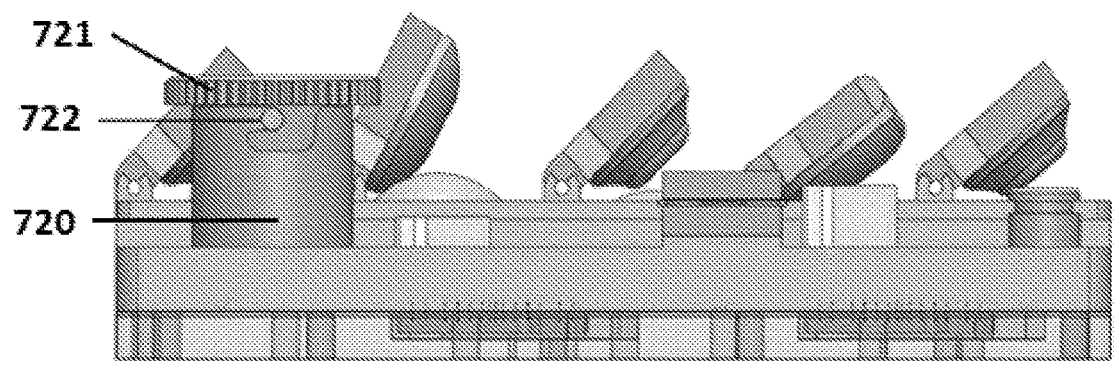
FIG. 7D shows an exemplary schematic of a linear sample preparation device from a side view.
Figure 7E:
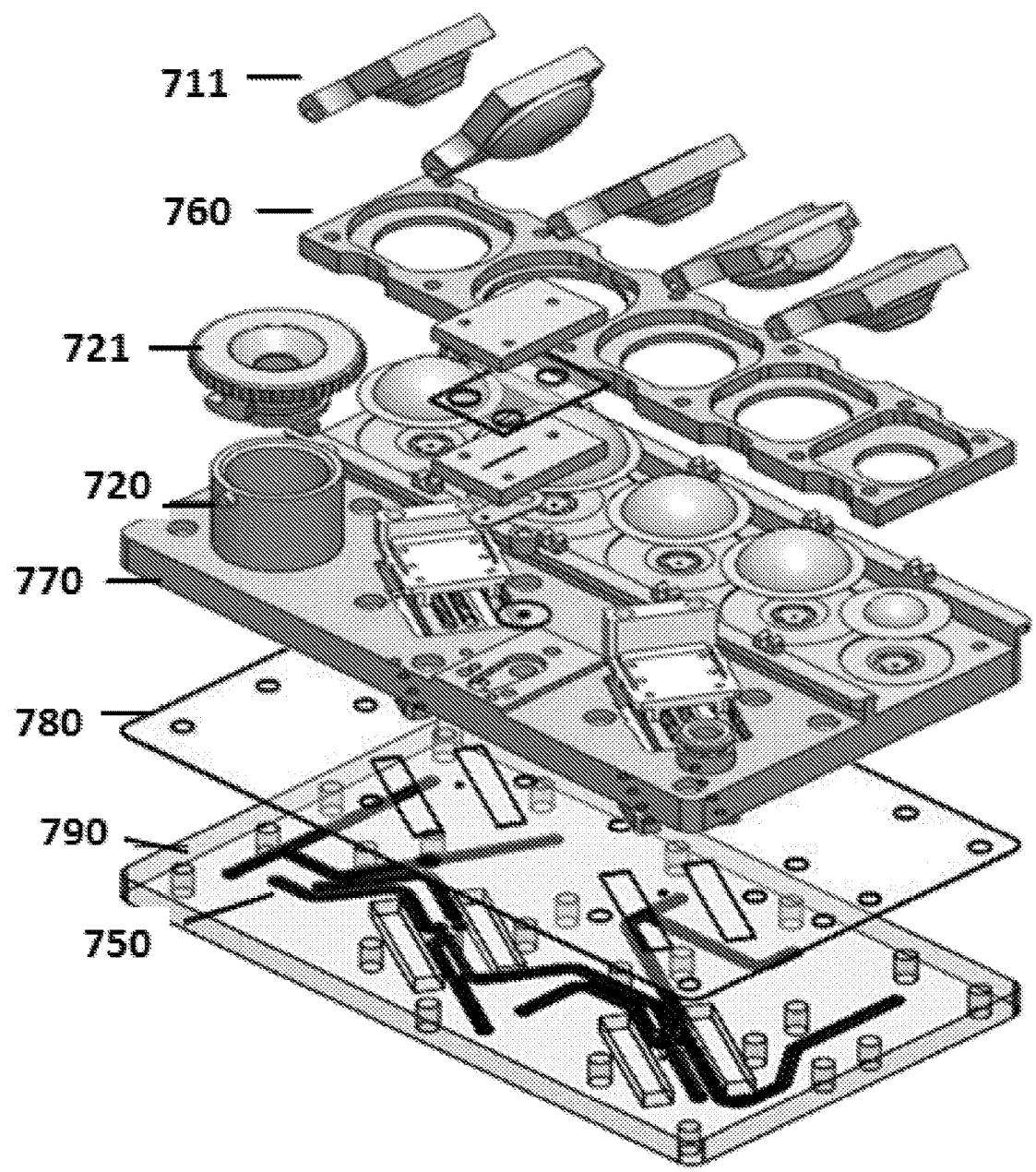
FIG. 7E shows an exemplary schematic of a linear sample preparation device from an exploded view.
Figure 7F:
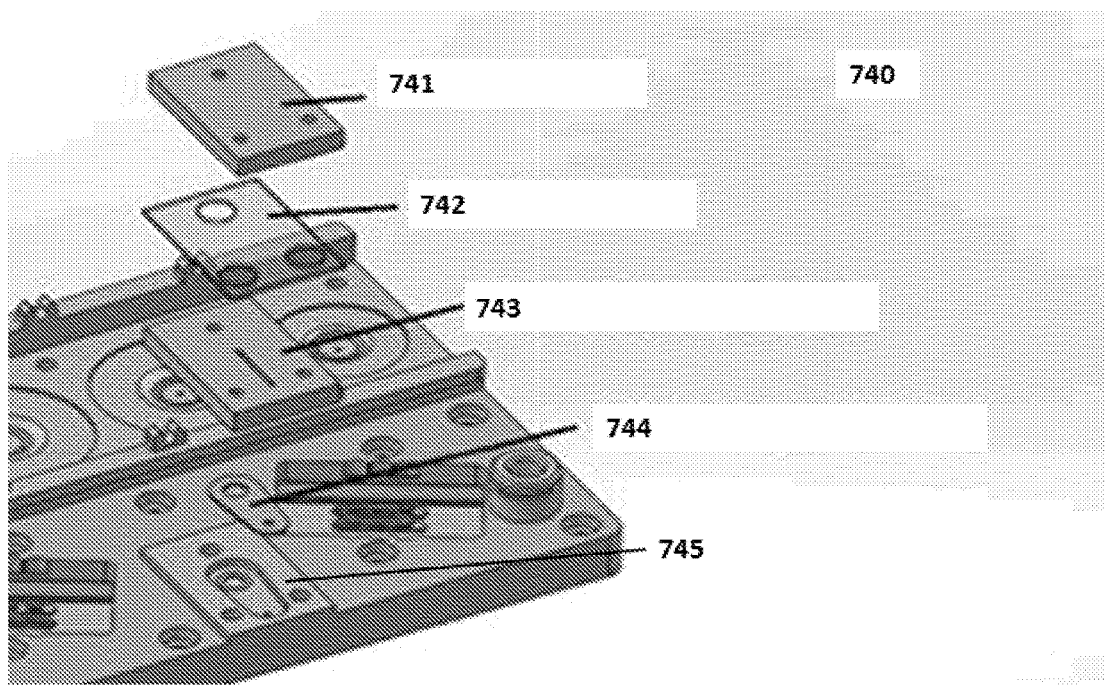
FIG. 7F shows an exemplary schematic of a matrix and matrix housing from an exploded view.
Figure 7G:
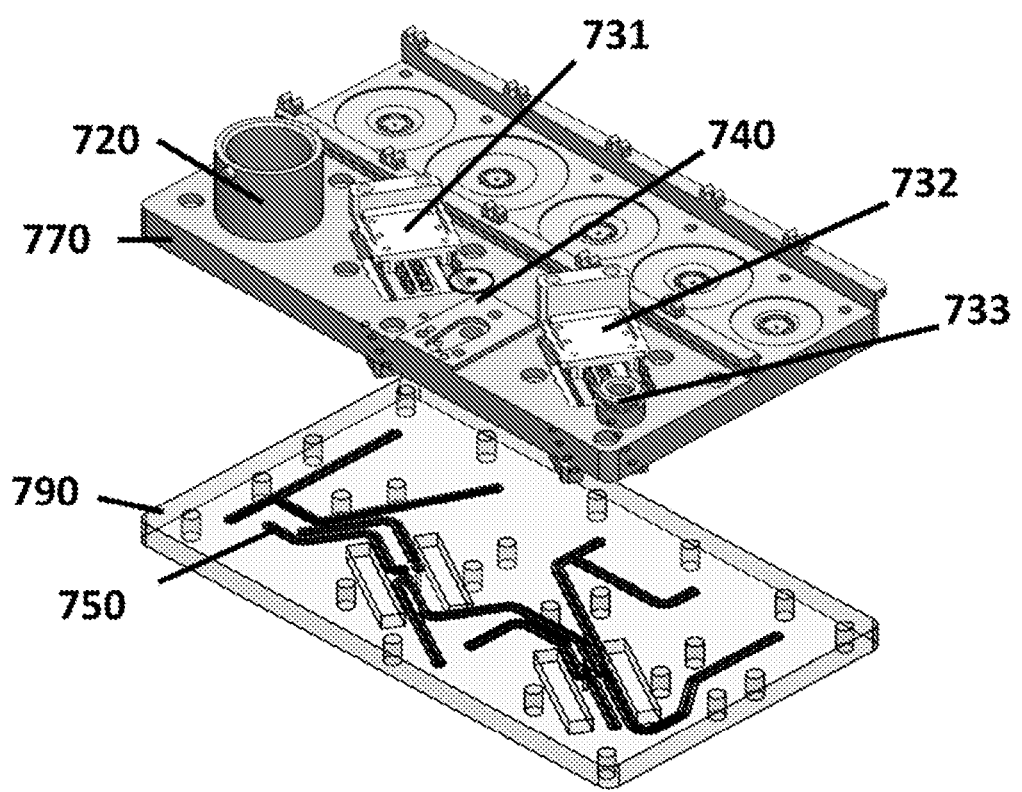
FIG. 7G shows an exemplary schematic of a top layer and a bottom layer of a linear sample preparation device from an exploded view.
Figure 7H:
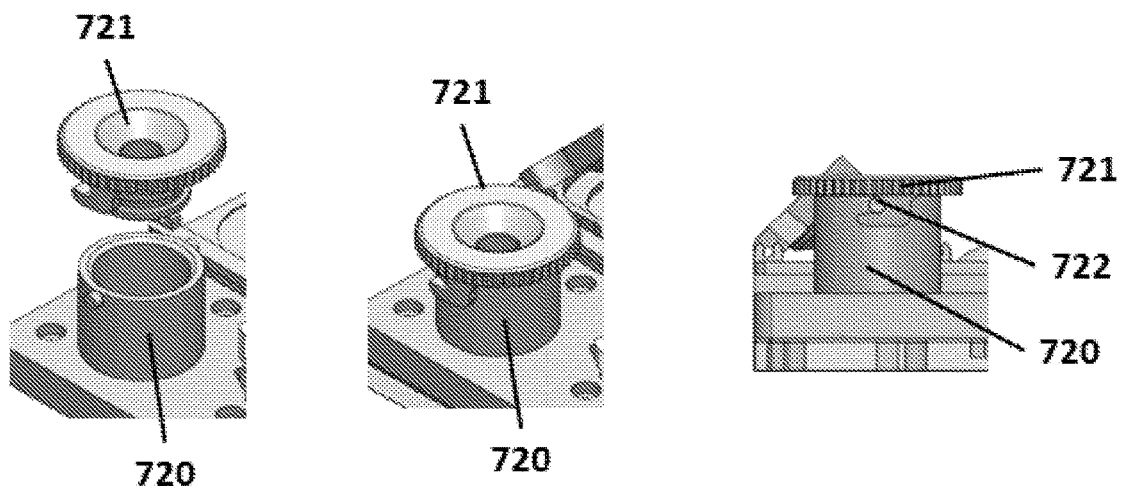
FIG. 7H shows an exemplary schematic of a sample well and cap.

Resistant units can comprise reagents or other fluids and can be configured for a particular assay, reaction, or analysis of a sample (e.g., FIG. 6). Resistant units and barrier units can each comprise any useful fluid or reagent, as described herein. For instance, a fluid or reagent can be useful for any assay, test, diagnostic, or other operation to be executed by the device.

A resistant unit (e.g., a blister or a blister pack) can include one or more burstable seals, which can allow for fluid or reagent flow from the resistant unit into a chamber, channel, or other structure. Exemplary non-limiting seals include a valve, a weakened heat seal, a pressure seal, and combinations thereof. A resistant unit can retain fluid or reagent without a seal, for example by capillary pressure or surface tension.

A certain amount of fluid or reagent within a resistant unit can be dispensed (e.g. by activation or actuation with a pushing unit). The amount of fluid or reagent dispensed can be at least about 10%, 20%, 30%, 40%, 50%, 60%, 70%, 80%, 90%, 95%, 96%, 97%, 98%, 99%, or 100% of the fluid within the resistant unit. The amount of fluid or reagent dispensed can be at most about 10%, 20%, 30%, 40%, 50%, 60%, 70%, 80%, 90%, 95%, 96%, 97%, 98%, 99%, or 100% of the fluid within the resistant unit. The amount of fluid or reagent dispensed can be about 10%, 20%, 30%, 40%, 50%, 60%, 70%, 80%, 90%, 95%, 96%, 97%, 98%, 99%, or 100% of the fluid within the resistant unit.

Fluid or reagent within a resistant unit can be dispensed at a certain pressure. The fluid or reagent can be dispensed from a resistant unit at a pressure of at least about 1 pascal (Pa), 10 Pa, 100 Pa, 1 kilopascal (kPa), 10 kPa, 100 kPa, 1 megapascal (MPa), 10 MPa, 100 MPa, or 1 gigapascal (GPa). The fluid or reagent can be dispensed from a resistant unit at a pressure of at most about 1 pascal (Pa), 10 Pa, 100 Pa, 1 kilopascal (kPa), 10 kPa, 100 kPa, 1 megapascal (MPa), 10 MPa, 100 MPa, or 1 gigapascal (GPa). The fluid or reagent can be dispensed from a resistant unit at a pressure of about 1 pascal (Pa), 10 Pa, 100 Pa, 1 kilopascal (kPa), 10 kPa, 100 kPa, 1 megapascal (MPa), 10 MPa, 100 MPa, or 1 gigapascal (GPa).

One or more resistant or barrier units can be included within a single substrate (e.g., a uniform substrate). In some cases, the resistant units can be provided as an array in a single substrate. In further cases, the geometric configuration of the array can allow for controlling the relative timing in adding one or more fluids or reagents.

Resistant units or barrier units can comprise one or more substances to assist in timing control. One or more resistant units can be configured to control relative timing in adding one or more fluids or reagents, or to control a sequential addition of one or more fluids or reagents. In some cases, these units can comprise a solid substance (e.g., a phase change material, such as wax or any other phase change material described herein) that further provides resistance to the pushing. In some cases, these units can comprise substances or reagents for a chemical reaction or a phase change, such as for example the dissolution of a salt barrier in an aqueous solution. In one non-limiting example, a resistant or barrier unit can include a solid state substance having a particular melting point temperature $T_m$, where upon reaching $T_m$ the substance melts and provides decreased resistance to the pushing unit; in this manner, the pushing unit can proceed to travel in a desired direction and/or at a desired speed across the device, resistant units, and/or barrier units. The timing provided by such an approach can be controlled by the composition of the substance, the amount of the substance, the shape or geometry of the substance, the heating profile applied to the substance, or any combination thereof. This example could be useful for, without limitation, confirming the working status of a heater integrated with the device, or to compensate for environmental variation in temperature that may affect an incubation time or reaction rate. In a similar manner, a barrier unit can comprise a solid state substance (e.g., a phase change material, such as wax or any other phase change material described herein), which blocks the pushing unit until the barrier unit is heated to temperature $T_m$. In any of these examples, the resistant unit(s) and/or barrier unit(s) can be provided in a substrate (e.g., a layer, film, or deformable layer). In some examples, a substrate including one or more resistant units or barrier units serves to contain a solid state substance (e.g., phase change material).

Resistance from a resistant unit can change over time, linearly or nonlinearly. The change rate of the resistance can also be dependent on the force from the pushing unit (e.g., such that feedback occurs between the resistant unit and the pushing unit). In some non-limiting examples, feedback arises from an interaction (e.g., a physical interaction) between the pushing unit and the resistant unit, such as a resistant unit comprising a non-Newtonian fluid where the fluid viscosity is dependent on the applied shear rate, or such as a resistant unit comprising a channel made of deformable material where the size of the channel is dependent on the applied pressure. In some cases, the resistant unit can respond to temperature. Change of temperature can be used to increase or decrease the resistance. For example, the viscosity of a fluid in a resistant unit (e.g., blister pack) can be decreased with higher temperatures, which can also decrease the time to displace fluid from the resistant unit.

In some cases, a physical and/or chemical change of a resistant unit can be applied in various applications, such as, mixing, dissolution, or washing. In one non-limiting example, a multi-cavity blister pack can be used as a resistant unit, and different contents, such as liquid, gas, or solid can be in the cavities; the deformation of the blister pack can introduce mixing and/or reactions in the multi-cavity blister pack.

In use, a pushing unit can interact with one or more resistant units on a first surface of a first substrate. For example, the relative movement of a pushing unit (e.g., in a direction parallel, about parallel, or less than about 90° to the first surface) can cause fluid or reagent in one or more resistant units to enter a first chamber (e.g., a process chamber). The fluid can be a reagent fluid to be added to a sample, or can be a sacrificial fluid which does not interact with the sample. For example and without limitation, in a system having three resistant units 521, 522, 523 (e.g., FIG. 5B), the first resistant unit 521 can include a first fluid, the second resistant unit 522 can include a sacrificial fluid, and the third resistant unit 523 can include a second fluid. When the pushing unit 511 contacts the first resistant unit, the first fluid can enter a process chamber 550. Upon pushing past the first resistant unit 521, the pushing unit can approach the second resistant unit 522 having the sacrificial fluid. In order to divert the sacrificial fluid away from the process chamber, the second resistant unit can be configured so that the sacrificial fluid enters another chamber.

As shown for example in FIG. 6, a valve 670 can be used to control fluidic communication between resistant units 621, 622, 623 and chambers 603, 604. A pushing unit 610 located in a channel 602 above a substrate 601 can contact a first resistant unit 621 (e.g., FIG. 6A). The pushing unit can push fluid from the first resistant unit through a filter 660 and can be directed by a valve 670 into a first chamber 603. Once the fluid is dispensed, the pushing unit can pass the first resistant unit and can contact the second resistant unit 622 (e.g., FIG. 6B). Similarly, the pushing unit can push fluid from the second resistant unit through the filter into the first chamber, and once the fluid is dispensed the pushing unit can contact a third resistant unit 623 (e.g., FIG. 6C). The valve can be used to direct flow into a second chamber 604, and the pushing unit can push fluid from the third resistant unit through the filter into the second chamber (e.g., FIG. 6D). In this manner, two factors can be controlled: first, the order of addition can be controlled, where the first fluid or reagent from a first resistant unit 621 is added to the first chamber 603 prior to the second fluid or reagent from the second resistant unit 622; second, the time between adding the first and second fluid or reagent can be controlled. For instance, the distance between the first and second resistant units can be used to control the time between additions. In another instance, the rate of moving the pushing unit 610 can be used to control this time. For example, this rate can be controlled by changing the speed of a motor or an unwinding/winding of a spring attached to the pushing unit. In another example, there can be feedback between the resistant unit and the pushing unit, where the pushing unit travels at a constant force that encounters resistance provided by the resistant unit. In yet another instance, the viscosity of a fluid or reagent inside a resistant unit can result in speeding up or slowing down of the pushing unit.

The system and method can contain various geometries of relative position of a pushing unit, optional barrier unit and resistant unit. In some cases, the barrier unit and resistant unit can be integrated at one unit. The barrier unit can stop the pushing unit from moving in a particular direction, with the resistance provided by the resistant unit for a specified time period. The barrier unit can completely stop the movement of pushing unit or reduce the speed of the movement of pushing unit. The resistance from the resistant unit can change over time, and the position of the barrier unit can change accordingly. After a specified time period, the barrier unit can no longer stop/withhold the pushing unit, and the pushing unit can move forward. The time period can be a desired time to conduct an operation, reaction, or other application, including but not limited to reactions, incubation, mixing, heating, cooling, dissolution, precipitation, crystallization, cell growth, filtration, elution, or any other operation described herein. The specified time period can be at least about 1 millisecond, 10 milliseconds, 100 milliseconds, 1 second, 10 seconds, 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours 5 hours, 6 hours, 7 hours, 8 hours, 9 hours, 10 hours, 11 hours, 12 hours, 1 day, 5 days, 10 days, or 1 month. The specified time period can be at most about 1 millisecond, 10 milliseconds, 100 milliseconds, 1 second, 10 seconds, 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours 5 hours, 6 hours, 7 hours, 8 hours, 9 hours, 10 hours, 11 hours, 12 hours, 1 day, 5 days, 10 days, or 1 month. The specified time period can be about 1 millisecond, 10 milliseconds, 100 milliseconds, 1 second, 10 seconds, 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours 5 hours, 6 hours, 7 hours, 8 hours, 9 hours, 10 hours, 11 hours, 12 hours, 1 day, 5 days, 10 days, or 1 month.

In some cases, a combination of different resistant unit(s) and barrier unit(s) can be applied and the total time period can be well controlled. A series of blister packs can have the same or different shapes, volumes, and contents. One or more pushing units can be used, wherein the resistant unit(s) and/or barrier unit(s) are configured to interact with the pushing unit.

Blister Packs

Resistant units or barrier units can comprise blisters or blister packs. A blister pack can comprise variety of materials, including but not limited to metal, plastic, thermoplastic, elastomer, paper, foil, film, membranes, and combinations thereof. A blister pack can comprise one or more cavities or pockets. A blister pack can contain at least 1, 2, 3, 4, 5, 6, 7, 8, 9, or 10 cavities or pockets. A cavity or pocket in a blister pack can comprise a variety of materials, including gas, liquid, solid or a combination thereof.

Resistant units, such as blisters or blister packs, can be activated to dispense fluid or reagents. Fluid or reagents can be introduced into fluid conduits (e.g. channels). Fluid or reagent dispensing can be used for a various applications, including but not limited to reactions, assays, mixing, incubation, washing, heating, dissolution, rehydration, and reconstitution of reagents. The time for a fluid or reagent to be dispensed and/or travel through a channel can be determined by the flow resistance, channel length, cross-sectional dimensions, surface properties, and the fluids present in the channel, as well as the properties of the fluid or reagent being dispensed (e.g., viscosity).

A blister or blister pack can be formed using any useful method, including but not limited to laminating, folding, feeding, and/or cutting of one or more films, sheets, substrates, or layers. In some cases, a blister pack can include a top film and a bottom film, where the top and bottom films enclose one or more predetermined volumes. In other cases, a blister pack can include a semi-rigid material (e.g., a sheet of a semi-rigid material, such as cardboard, plastic or the like) and an article receiving member having a plurality of blisters (e.g., a sheet of some suitable plastic material such as polystyrene, acetate, polyvinyl chloride, polyethylene or the like, having a plurality of blisters) attached to the semi-rigid material. The blister pack can optionally include a plurality of spaced windows within the semi-rigid material (e.g., by stamping the sheet with a suitable die), where the spaced windows and blisters are aligned and then the semi-rigid material and article receiving member are secured together. Exemplary blister packs are provided in U.S. Pat. Nos. 3,856,144 and 3,399,763, each of which is incorporated herein in its entirety.

In use, the cavity enclosing a predetermined volume can rupture when a pushing unit contacts the cavity. The time at which the cavity ruptures can depend on the force exerted by the pushing unit, as well as the resistance provided (in part) by the cavity. This resistance can depend on the geometric structure of the cavity, as well as the material used to form the blister pack.

A blister pack can include multiple cavities that can be fluidically connected by a relative movement. For instance, a blister pack can include resistant units 525 and 526, as shown in FIG. 5B, which become fluidically connected when the pushing unit overcomes the resistance provided by unit 525. In this manner, reagents can be stored (e.g., as in resistant unit 526) in a dried state and then reconstituted only upon activating the pushing unit. Storage in a dried state may be desired for increasing the shelf life of particular reagents (e.g., one or more buffers, proteins, reagents, etc.). Such multiple cavities may also be useful if a particular reagent must be pre-activated before introduction of a sample. For example, when the reagent includes one or more protecting groups, pre-activation of the reagent with deprotecting agents may be required. Thus, the reagent can be stored in resistant unit 526, and then the deprotecting agent can be stored in resistant unit 525. Upon activation of the pushing unit, the deprotecting agent will enter resistant unit 526, thereby activating the reagent, and the activated reagent can then be introduced to the sample within process chamber 550.

Timing Control

Various attributes of the system and its components, including pushing units, resistant units, barrier units, driving forces, associated channels, and others, can be designed to result in specifically controlled times for operations (e.g., fluid dispensing) or between operations.

The volume of fluid or reagent within a resistant unit or a barrier unit can be designed or selected to control the operation time. For example, a larger fluid or reagent volume can take more time to dispense from a resistant unit or barrier unit, and therefore can prevent a pushing unit from proceeding for a longer amount of time. On the other hand, a smaller fluid or reagent volume can take less time to dispense from a resistant unit or barrier unit, and therefore can prevent a pushing unit from proceeding for a shorter amount of time. The fluid or reagent volume within a resistant unit or barrier unit can be about 1 femtoliter (fL), 10 fL, 100 fL, 1 picoliter (pL), 10 pL, 100 pL, 1 nanoliter (nL), 10 nL, 100 nL, 1 microliter (μL), 10 μL, 100 μL, 1 milliliter (mL), 10 mL, or 100 mL. The volume of fluid or reagent within a resistant unit or barrier unit can be at least about 1 femtoliter (fL), 10 fL, 100 fL, 1 picoliter (pL), 10 pL, 100 pL, 1 nanoliter (nL), 10 nL, 100 nL, 1 microliter (μL), 10 μL, 100 μL, 1 milliliter (mL), 10 mL, or 100 mL. The fluid or reagent volume within a resistant unit or barrier unit can be at most about 1 femtoliter (fL), 10 fL, 100 fL, 1 picoliter (pL), 10 pL, 100 pL, 1 nanoliter (nL), 10 nL, 100 nL, 1 microliter (μL), 10 μL, 100 μL, 1 milliliter (mL), 10 mL, or 100 mL. Different resistant units or barrier units can comprise fluid or reagents of the same volume or fluid or reagents of different volumes.

The viscosity of fluid within a resistant unit or barrier unit can be designed or selected to control the operation time. For example, a fluid with higher viscosity can take more time to dispense from a resistant unit or barrier unit, and therefore can prevent a pushing unit from proceeding for a longer amount of time. On the other hand, a fluid with a lower viscosity can take less time to dispense from a resistant unit or barrier unit, and therefore can prevent a pushing unit from proceeding for a shorter amount of time. The viscosity of a fluid within a resistant unit or barrier unit can be about 1 micropascal-second (μPa·s), 10 μPa·s, 20 μPa·s, 30 μPa·s, 40 μPa·s, 50 μPa·s, 60 μPa·s, 70 μPa·s, 80 μPa·s, 90 μPa·s, 100 μPa·s, 200 μPa·s, 300 μPa·s, 400 μPa·s, 500 μPa·s, 600 μPa·s, 700 μPa·s, 800 μPa·s, 900 Pa·s, 1 millipascal-second (mPa·s), 2 mPa·s, 3 mPa·s, 4 mPa·s, 5 mPa·s, 6 mPa·s, 7 mPa·s, 8 mPa·s, 9 mPa·s, 10 mPa·s, 20 mPa·s, 30 mPa·s, 40 mPa·s, 50 mPa·s, 60 mPa·s, 70 mPa·s, 80 mPa·s, 90 mPa·s, 100 mPa·s, 200 mPa·s, 300 mPa·s, 400 mPa·s, 500 mPa·s, 600 mPa·s, 700 mPa·s, 800 mPa·s, 900 mPa·s, 1 pascal-second (Pa·s), 2 Pa·s, 3 Pa·s, 4 Pa·s, 5 Pa·s, 6 Pa·s, 7 Pa·s, 8 Pa·s, 9 Pa·s, 10 Pa·s, 20 Pa·s, 30 Pa·s, 40 Pa·s, 50 Pa·s, 60 Pa·s, 70 Pa·s, 80 Pa·s, 90 Pa·s, or 100 Pa·s. The viscosity of a fluid within a resistant unit or barrier unit can be at least about 1 micropascal-second (μPa·s), 10 μPa·s, 20 μPa·s, 30 μPa·s, 40 μPa·s, 50 μPa·s, 60 μPa·s, 70 μPa·s, 80 μPa·s, 90 μPa·s, 100 μPa·s, 200 μPa·s, 300 μPa·s, 400 μPa·s, 500 μPa·s, 600 μPa·s, 700 μPa·s, 800 μPa·s, 900 μPa·s, 1 millipascal-second (mPa·s), 2 mPa·s, 3 mPa·s, 4 mPa·s, 5 mPa·s, 6 mPa·s, 7 mPa·s, 8 mPa·s, 9 mPa·s, 10 mPa·s, 20 mPa·s, 30 mPa·s, 40 mPa·s, 50 mPa·s, 60 mPa·s, 70 mPa·s, 80 mPa·s, 90 mPa·s, 100 mPa·s, 200 mPa·s, 300 mPa·s, 400 mPa·s, 500 mPa·s, 600 mPa·s, 700 mPa·s, 800 mPa·s, 900 mPa·s, 1 pascal-second (Pa·s), 2 Pa·s, 3 Pa·s, 4 Pa·s, 5 Pa·s, 6 Pa·s, 7 Pa·s, 8 Pa·s, 9 Pa·s, 10 Pa·s, 20 Pa·s, 30 Pa·s, 40 Pa·s, 50 Pa·s, 60 Pa·s, 70 Pa·s, 80 Pa·s, 90 Pa·s, or 100 Pa·s. The viscosity of a fluid within a resistant unit or barrier unit can be at most about 1 micropascal-second (μPa·s), 10 μPa·s, 20 μPa·s, 30 μPa·s, 40 μPa·s, 50 μPa·s, 60 μPa·s, 70 μPa·s, 80 μPa·s, 90 μPa·s, 100 μPa·s, 200 μPa·s, 300 μPa·s, 400 μPa·s, 500 μPa·s, 600 μPa·s, 700 μPa·s, 800 μPa·s, 900 μPa·s, 1 millipascal-second (mPa·s), 2 mPa·s, 3 mPa·s, 4 mPa·s, 5 mPa·s, 6 mPa·s, 7 mPa·s, 8 mPa·s, 9 mPa·s, 10 mPa·s, 20 mPa·s, 30 mPa·s, 40 mPa·s, 50 mPa·s, 60 mPa·s, 70 mPa·s, 80 mPa·s, 90 mPa·s, 100 mPa·s, 200 mPa·s, 300 mPa·s, 400 mPa·s, 500 mPa·s, 600 mPa·s, 700 mPa·s, 800 mPa·s, 900 mPa·s, 1 pascal-second (Pa·s), 2 Pa·s, 3 Pa·s, 4 Pa·s, 5 Pa·s, 6 Pa·s, 7 Pa·s, 8 Pa·s, 9 Pa·s, 10 Pa·s, 20 Pa·s, 30 Pa·s, 40 Pa·s, 50 Pa·s, 60 Pa·s, 70 Pa·s, 80 Pa·s, 90 Pa·s, or 100 Pa·s. Different resistant units or barrier units can comprise fluids of the same viscosity or fluids of different viscosities.

The temperature dependence of the viscosity of a fluid within a resistant unit or barrier unit can be used to control the operation time. For example, many fluids exhibit decreasing viscosities with increasing temperatures. A fluid can be heated or cooled to decrease or increase its viscosity, respectively. A fluid with higher viscosity can take more time to dispense from a resistant unit or barrier unit and therefore can prevent a pushing unit from proceeding for a longer amount of time, while a fluid with a lower viscosity can take less time to dispense from a resistant unit or barrier unit and therefore can prevent a pushing unit from proceeding for a shorter amount of time. Specific temperatures can be set to produce specific viscosities for a fluid.

A resistant unit or a barrier unit can comprise a solid with a given melting point. The resistant unit or barrier unit can prevent a pushing unit from proceeding until a desired or specified amount of time. Once the desired or specified time has elapsed, the solid can be heated to melt into a liquid. The resulting liquid can then be flowed out from the resistant unit or barrier unit and the pushing unit can be allowed to proceed. The solid can have a melting point of about 0° C., 5° C., 10° C., 15° C., 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., or 200° C. The solid can have a melting point of at least about 0° C., 5° C., 10° C., 15° C., 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., or 200° C. The solid can have a melting point of at most about 0° C., 5° C., 10° C., 15° C., 20° C., 25° C., 30° C., 35° C., 40° C., 45° C., 50° C., 55° C., 60° C., 65° C., 70° C., 75° C., 80° C., 85° C., 90° C., 95° C., 100° C., 105° C., 110° C., 115° C., 120° C., 125° C., 130° C., 135° C., 140° C., 145° C., 150° C., 155° C., 160° C., 165° C., 170° C., 175° C., 180° C., 185° C., 190° C., 195° C., or 200° C.

A resistant unit or a barrier unit can comprise a sacrificial fluid, that is, a fluid which is not used as a reagent, buffer, or other component of a sample preparation or reaction. A resistant unit or a barrier unit comprising a sacrificial fluid can be used to provide timing control between steps of a procedure, for example between fluid dispensing steps. A sacrificial fluid can be flowed out of a resistant unit or barrier unit to a chamber, well, vent, waste port, outside environment, or other destination. A sacrificial fluid can be flowed through a channel or other conduit. A sacrificial fluid can be characterized by any of the attributes of fluids described herein, including but not limited to volume, viscosity, and melting point.

The distance or separation between resistant units or barrier unit can be designed or selected to control the operation time. For example, a longer distance between resistant units or barrier units can increase the amount of time for a pushing unit to encounter a resistant unit or to move from one resistant unit to a subsequent resistant unit or barrier unit. On the other hand, a shorter distance between resistant units or barrier units can decrease the amount of time for a pushing unit to encounter a resistant unit or barrier unit, or to move from one resistant unit to a subsequent resistant unit or barrier unit. The distance between resistant units or barrier units can be about 1 micrometer (μm), 2 μm, 3 μm, 4 μm, 5 μm, 6 μm, 7 μm, 8 μm, 9 μm, 10 μm, 20 μm, 30 μm, 40 μm, 50 μm, 60 μm, 70 μm, 80 μm, 90 μm, 100 μm, 200 μm, 300 μm, 400 μm, 500 μm, 600 μm, 700 μm, 800 μm, 900 μm, 1 millimeter (mm), 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, or 100 mm. The distance between resistant units or barrier units can be at least about 1 micrometer (μm), 2 μm, 3 μm, 4 μm, 5 μm, 6 μm, 7 μm, 8 μm, 9 μm, 10 μm, 20 μm, 30 μm, 40 μm, 50 μm, 60 μm, 70 μm, 80 μm, 90 μm, 100 μm, 200 μm, 300 μm, 400 μm, 500 μm, 600 μm, 700 μm, 800 μm, 900 μm, 1 millimeter (mm), 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, or 100 mm. The distance between resistant units or barrier units can be at most about 1 micrometer (μm), 2 μm, 3 μm, 4 μm, 5 μm, 6 μm, 7 μm, 8 μm, 9 μm, 10 μm, 20 μm, 30 μm, 40 μm, 50 μm, 60 μm, 70 μm, 80 μm, 90 μm, 100 μm, 200 μm, 300 μm, 400 μm, 500 μm, 600 μm, 700 μm, 800 μm, 900 μm, 1 millimeter (mm), 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, or 100 mm. The distance between different resistant units or barrier units can be the same distance or can be different distances.

Fluid or reagent from a resistant unit or barrier unit can be flowed through or dispensed via a channel or other conduit. The geometric parameters (e.g. length, width, height, diameter) of a channel can be designed to control the operation time. For example, a longer channel or a narrower channel can be characterized by a larger hydrodynamic resistance and can increase the amount of time for a fluid or reagent to dispense from a resistant unit or barrier unit, and can therefore prevent a pushing unit from proceeding for a longer amount of time. On the other hand, a shorter channel or wider channel can be characterized by a smaller hydrodynamic resistance and can decrease the amount of time for a fluid or reagent to dispense from a resistant unit or barrier unit, and can therefore prevent a pushing unit from proceeding for a shorter amount of time. The length of a channel or other conduit through which a fluid or reagent flows can be about 1 micrometer ($\mu m$), 2 $\mu m$, 3 $\mu m$, 4 $\mu m$, 5 $\mu m$, 6 $\mu m$, 7 $\mu m$, 8 $\mu m$, 9 $\mu m$, 10 $\mu m$, 20 $\mu m$, 30 $\mu m$, 40 $\mu m$, 50 $\mu m$, 60 $\mu m$, 70 $\mu m$, 80 $\mu m$, 90 $\mu m$, 100 $\mu m$, 200 $\mu m$, 300 $\mu m$, 400 $\mu m$, 500 $\mu m$, 600 $\mu m$, 700 $\mu m$, 800 $\mu m$, 900 $\mu m$, 1 millimeter (mm), 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, or 100 mm. The length of a channel or other conduit through which a fluid or reagent flows can be at least about 1 micrometer ($\mu m$), 2 $\mu m$, 3 $\mu m$, 4 $\mu m$, 5 $\mu m$, 6 $\mu m$, 7 $\mu m$, 8 $\mu m$, 9 $\mu m$, 10 $\mu m$, 20 $\mu m$, 30 $\mu m$, 40 $\mu m$, 50 $\mu m$, 60 $\mu m$, 70 $\mu m$, 80 $\mu m$, 90 $\mu m$, 100 $\mu m$, 200 $\mu m$, 300 $\mu m$, 400 $\mu m$, 500 $\mu m$, 600 $\mu m$, 700 $\mu m$, 800 $\mu m$, 900 $\mu m$, 1 millimeter (mm), 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, or 100 mm. The length of a channel or other conduit through which a fluid or reagent flows can be at most about 1 micrometer ($\mu m$), 2 $\mu m$, 3 $\mu m$, 4 $\mu m$, 5 $\mu m$, 6 $\mu m$, 7 $\mu m$, 8 $\mu m$, 9 $\mu m$, 10 $\mu m$, 20 $\mu m$, 30 $\mu m$, 40 $\mu m$, 50 $\mu m$, 60 $\mu m$, 70 $\mu m$, 80 $\mu m$, 90 $\mu m$, 100 $\mu m$, 200 $\mu m$, 300 $\mu m$, 400 $\mu m$, 500 $\mu m$, 600 $\mu m$, 700 $\mu m$, 800 $\mu m$, 900 $\mu m$, 1 millimeter (mm), 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, or 100 mm. The height, width, or diameter of a channel or other conduit through which a fluid or reagent flows can be about 1 micrometer ($\mu m$), 2 $\mu m$, 3 $\mu m$, 4 $\mu m$, 5 $\mu m$, 6 $\mu m$, 7 $\mu m$, 8 $\mu m$, 9 $\mu m$, 10 $\mu m$, 20 $\mu m$, 30 $\mu m$, 40 $\mu m$, 50 $\mu m$, 60 $\mu m$, 70 $\mu m$, 80 $\mu m$, 90 $\mu m$, 100 $\mu m$, 200 $\mu m$, 300 $\mu m$, 400 $\mu m$, 500 $\mu m$, 600 $\mu m$, 700 $\mu m$, 800 $\mu m$, 900 $\mu m$, 1 millimeter (mm), 2 mm, 3 mm, 4 mm, 5 mm, 6 mm, 7 mm, 8 mm, 9 mm, or 10 mm. The height, width, or diameter of a channel or other conduit through which a fluid or reagent flows can be at least about 1 micrometer ($\mu m$), 2 $\mu m$, 3 $\mu m$, 4 $\mu m$, 5 $\mu m$, 6 $\mu m$, 7 $\mu m$, 8 $\mu m$, 9 $\mu m$, 10 $\mu m$, 20 $\mu m$, 30 $\mu m$, 40 $\mu m$, 50 $\mu m$, 60 $\mu m$, 70 $\mu m$, 80 $\mu m$, 90 $\mu m$, 100 $\mu m$, 200 $\mu m$, 300 $\mu m$, 400 $\mu m$, 500 $\mu m$, 600 $\mu m$, 700 $\mu m$, 800 $\mu m$, 900 $\mu m$, 1 millimeter (mm), 2 mm, 3 mm, 4 mm, 5 mm, 6 mm, 7 mm, 8 mm, 9 mm, or 10 mm. The height, width, or diameter of a channel or other conduit through which a fluid or reagent flows can be at most about 1 micrometer ($\mu m$), 2 $\mu m$, 3 $\mu m$, 4 $\mu m$, 5 $\mu m$, 6 $\mu m$, 7 $\mu m$, 8 $\mu m$, 9 $\mu m$, 10 $\mu m$, 20 $\mu m$, 30 $\mu m$, 40 $\mu m$, 50 $\mu m$, 60 $\mu m$, 70 $\mu m$, 80 $\mu m$, 90 $\mu m$, 100 $\mu m$, 200 $\mu m$, 300 $\mu m$, 400 $\mu m$, 500 $\mu m$, 600 $\mu m$, 700 $\mu m$, 800 $\mu m$, 900 $\mu m$, 1 millimeter (mm), 2 mm, 3 mm, 4 mm, 5 mm, 6 mm, 7 mm, 8 mm, 9 mm, or 10 mm. The geometric parameters of different channels or other conduits can be the same or can be different.

Channels or other conduits can comprise different surface characteristics. Surface characteristics of a channel or other conduit can include but are not limited to wettability or hydrophobicity, binding affinity, or electrical charge. Channel or conduit surface characteristics can be designed to control the operation time. For example, a hydrophobic channel can provide increased resistance to flow to an aqueous fluid or reagent and can increase the amount of time for such a fluid or reagent to dispense from a resistant unit or barrier unit. On the other hand, a hydrophilic channel can provide decreased resistance to flow to an aqueous fluid or reagent and can decrease the amount of time for such a fluid or reagent to dispense from a resistant unit or barrier unit.

Systems and devices described herein can comprise filters, membranes, gels, and other separation materials. The presence of a separation material in a channel, conduit, or other flow conduit can increase the resistance to flow through that flow conduit. Parameters of a separation material can be chosen to provide a specific resistance to control the operation time. Parameters of a separation material can include thickness, porosity, pore size, wettability or hydrophobicity, binding affinity, or electrical charge of the material. For example, a separation material with greater thickness or smaller pore size can be characterized by a larger resistance to flow and can increase the amount of time for a fluid or reagent to dispense from a resistant unit or barrier unit, and can therefore prevent a pushing unit from proceeding for a longer amount of time. On the other hand, a separation material with lesser thickness or larger pore size can be characterized by a smaller resistance to flow and can decrease the amount of time for a fluid or reagent to dispense from a resistant unit or barrier unit, and can therefore prevent a pushing unit from proceeding for a shorter amount of time.

Various attributes of the system and its components, including pushing units, resistant units, barrier units, driving forces, associated channels, and others, can be designed to result in specifically controlled times for operations (e.g., fluid or reagent dispensing) or between operations. The specified time period can be at least about 1 millisecond, 10 milliseconds, 100 milliseconds, 1 second, 10 seconds, 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours 5 hours, 6 hours, 7 hours, 8 hours, 9 hours, 10 hours, 11 hours, 12 hours, 1 day, 5 days, 10 days, or 1 month. The specified time period can be at most about 1 millisecond, 10 milliseconds, 100 milliseconds, 1 second, 10 seconds, 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours 5 hours, 6 hours, 7 hours, 8 hours, 9 hours, 10 hours, 11 hours, 12 hours, 1 day, 5 days, 10 days, or 1 month. The specified time period can be about 1 millisecond, 10 milliseconds, 100 milliseconds, 1 second, 10 seconds, 1 minute, 2 minutes, 3 minutes, 4 minutes, 5 minutes, 6 minutes, 7 minutes, 8 minutes, 9 minutes, 10 minutes, 20 minutes, 30 minutes, 40 minutes, 50 minutes, 1 hour, 2 hours, 3 hours, 4 hours 5 hours, 6 hours, 7 hours, 8 hours, 9 hours, 10 hours, 11 hours, 12 hours, 18 hours, 1 day, 5 days, 10 days, 15 days, 20 days, 25 days, or 1 month.

Time Control in Activating Resistant Units and/or Barrier Units

Applications of described devices and methods include processes that benefit, for example, from timing control, from temperature control, or from handling of multiple reagents. Examples include processing of samples to isolate or enrich nucleic acids; separation of components of whole blood; performing detection of analytes including nucleic acids, cells, proteins; performing quantification reactions of analytes; as well as any other described herein.

In some cases, the system and method can allow activation of resistant units/barrier units/dispense fluids or reagents in a particular/desired order, such as sequentially, simultaneously, or in combination. The pushing unit can have complex shapes and activate multiple resistant units/barrier units in parallel or sequentially. The barrier units can have various shapes or geometries that allow the pushing unit(s) to activate multiple barrier units sequentially, simultaneously, or in combination. In some examples, the resistant unit(s) can have various shapes or geometries that allow the pushing unit(s) to activate multiple barrier units sequentially, simultaneously, in parallel, or in combination. In one non-limiting example, a part of a multi-layer device with one pushing unit can activate several barrier and/or resistant units (e.g., as in blister packs) in a pre-determined sequence is shown in FIG. 5A-B.

Figure 5A:
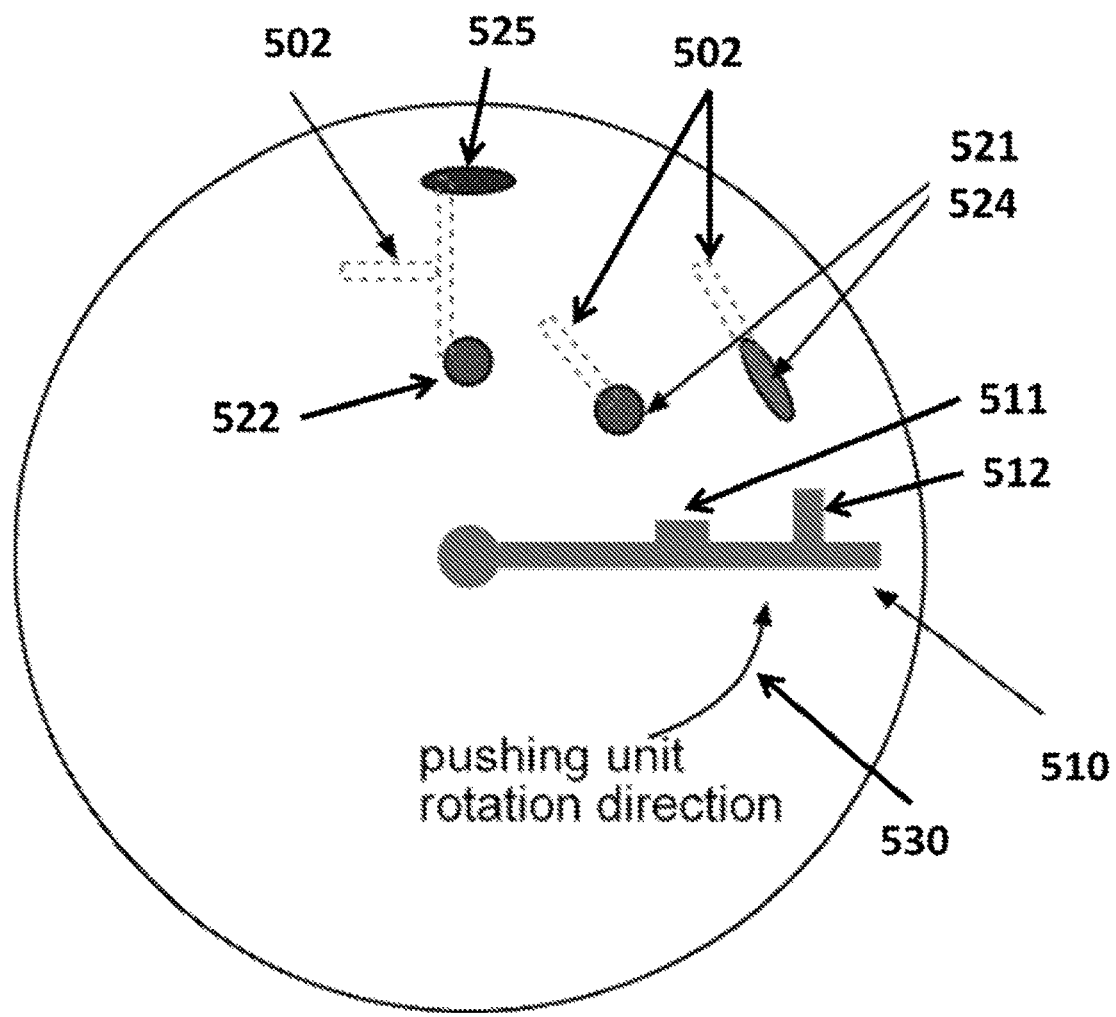
FIG. 5A shows an exemplary schematic of a pushing unit moving rotationally toward multiple resistant units.
Figure 5B:
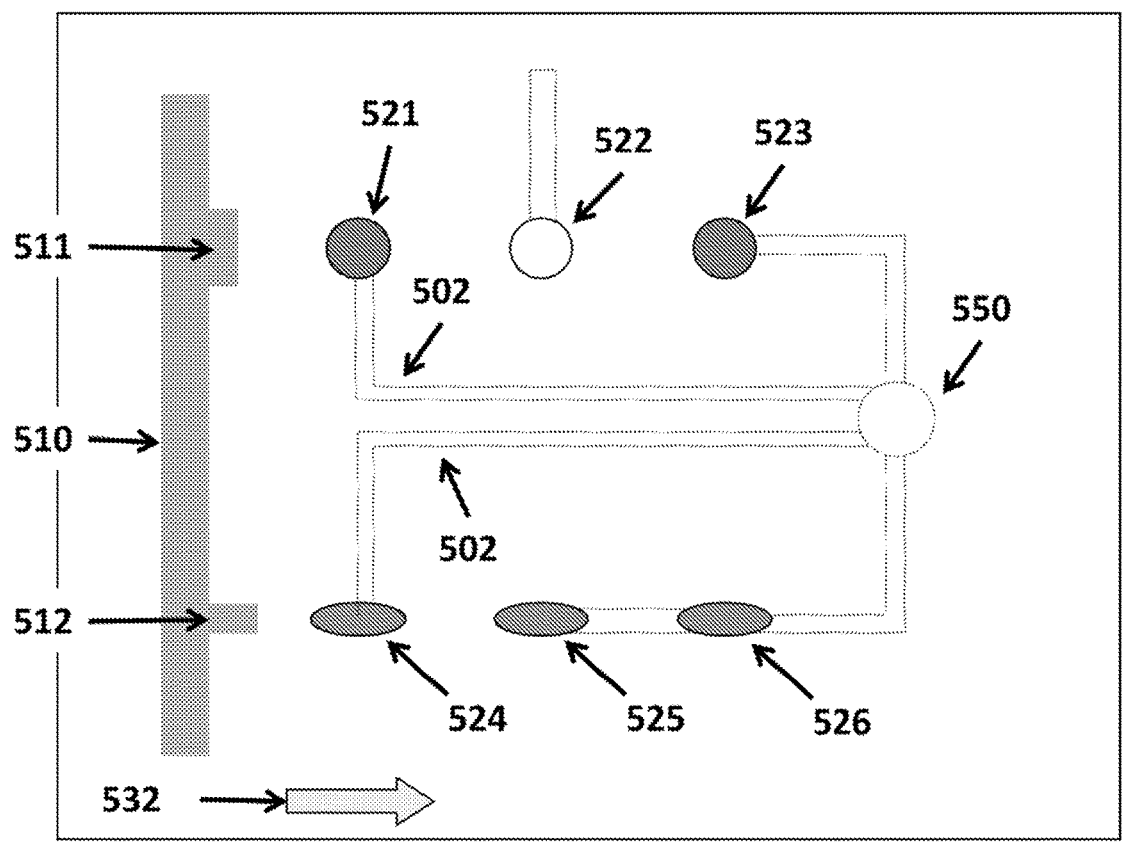
FIG. 5B shows an exemplary schematic of a pushing unit moving linearly toward multiple resistant units.

As can be seen in FIG. 5 (top view of the device and the fluid dispensing system), the pushing unit 510 can be configured to provide direct contact with various resistant units (i.e., 521, 522, 523, 524, 525, 526). For instance, the pushing unit can include protrusions 511 and 512, which are designed to contact the resistant units when the pushing unit is moved. Any useful physical feature or structure can be used to configure the pushing unit. For instance, the pushing unit can include a roller or a drum having a main central axle to allow for rotation of the roller, where the axle can be further attached to a rod to maintain the position of the roller. In this manner, more than one roller can be mounted on a rod, thereby providing a configuration that can be used to interact with one or more resistant units and/or barrier units or one or more arrays of such units. In another example, the pushing unit can include one or more protrusions, rollers, drums, plungers, barbs, springs, etc., in any useful combination. The pushing unit can be configured to provide any useful relative movement 530, 531. For instance, the relative movement can include rotation 530 (e.g., as in FIG. 5A) and/or translation 531 (e.g., as FIG. 5B) across the first surface of the device and/or surface of the one or more resistant unit (e.g., when the resistant units are present in a second substrate, then across the surface of this second substrate).

The relative movement of the pushing unit can cause one or more fluids and/or reagents to enter a first chamber 502 (e.g., a channel, a reservoir, etc.). In FIG. 5A-B, these chambers are shown as dotted lines 502. As can be seen in FIG. 5A, relative movement of the pushing unit causes the fluid/reagent in resistant unit 521 to enter a chamber and in resistant unit 524 to enter another chamber. Further progression of the pushing unit causes interaction of this pushing unit with resistant units 522 and 525. As can be seen, upon relative movement, the fluid/reagent in resistant units 522 and 525 enter a common chamber. Relative timing and/or addition of the fluid/reagent in the resistant units are controlled by the resistant units (e.g., the geometric arrangement of these units). For example, the distance between resistant units 521 and 522 control the timing of dispensing of the reagents within these resistant units. To increase the time between adding the reagent in unit 521 and in unit 522, the distance between units 521 and 522 can be increased. Of course, further time delay can be added by reducing the speed or rate of the pushing unit. Relative timing and/or addition of the fluid/reagent can also be controlled by the contents of the resistant units. For example, as shown in FIG. 5B, resistant units 521 and 523 include a fluid/reagent to be added to process chamber 550. In contrast, resistant unit 522 includes a sacrificial fluid (e.g., an immiscible fluid, such as a lubricant or an oil), which is fluidically connected to a chamber that does not connect to process chamber 550. As the fluid in resistant unit 522 is not included in the process chamber, there is a time delay in adding the fluid/reagent in resistant unit 521 and in resistant unit 523, which can be determined by, in part, the distance between resistant units 521 and 523. Such a time delay may be caused by the reduced speed of the pushing unit when encountering the resistance provided by resistant unit 522. Thus, time delay may include additional factors, such as the extent to which there is feedback in speed and/or rate between the pushing unit and/or resistant units, as well as the additional time that may be required to overcome one or more barrier units, if present.

Dispensing of fluid (e.g., into process chamber 550) can occur in any useful order, which can be determined (in part) by the resistant units and/or barrier units. As can be seen in FIG. 5B, two sets or arrays of resistant units are provided (i.e., 521, 522, 523 in one array, and 524, 525, 526 in another array). In this configuration, the fluid/reagent in resistant units 521 and 524 are added at the same time to process chamber 550. Additional time delay can be included by any useful change to one or more resistant units, such as the channels that connect 521 to 550 or connect 524 to 550. For instance, the channel connecting 521 to 550 can be further narrowed (e.g., by decreasing the cross-sectional dimension of this channel), thus increasing the resistance encountered by the pushing unit. In another instance, the content within 521 can be pre-mixed with a viscous agent (e.g., polyethylene glycol) to increase resistance. In another example, 522 can include a sacrificial fluid (e.g., as described herein) or be connected to a dead-end channel to introduce a time delay in adding the fluid/reagent in 521 and 523. In yet another example, the one resistant unit can be fluidically connected to another resistant unit, thereby allowing the fluid in the first resistant unit to reconstitute or hydrate the reagent in a second resistant unit. As provided in FIG. 5B as one non-limiting example, relative movement causes the fluid in resistant unit 525 to enter resistant unit 526 containing a dry reagent. After hydration and pushing by the pushing unit, the combined fluid is introduced into process chamber 550.

Although this section describes time control with resistant units, the same considerations can be applied when designing and applying resistant units. Furthermore, between any pushing unit and resistant unit, a barrier unit can be present to facilitate dispensing of fluid and/or time control (e.g., controlling relative timing in adding one or more fluids and/or sequential addition of one or more fluids).

Time control does not necessarily require fluid dispensing. For example, the pushing unit can interact with a resistant unit that is a spring or any other deformable material, such that the pushing unit requires certain time to overcome the resistant unit. This can be applied to introduce a certain time pulse, and it can be used for incubation (such as for sample preparation in lysis), rehydration, reaction (such as for amplification), and other operations.

Autonomous Controller

An autonomous controller may be present in the system. For instance, relative movement of a fluidic dispensing system, a pushing unit, a device, one or more substrates or layers of a device, or one or more device components can be effected by any useful autonomous controller. The autonomous controller can include any mechanism or assembly described herein. An autonomous controller can be useful for controlling the operations of a SlipChip, a thin-film SlipChip, or another device. Various functions can be part of the design of the controller to provide a hands-off interface for untrained user. These include, but are not limited to (1) pumping or dispensing fluid employing one or more pushing units, (2) slipping, and/or (3) timing control of the first two operations and any of the device's operations. For example, multi-step pumping, dispensing, and slipping can be programmed by using timing control. These operations can also be performed, for example, without the need of an energy source stored in the SlipChip devices (such as, for example, a battery). An autonomous controller can be integrated into a device, or can be located in a base station or base unit capable of coupling to a device to control it.

In some cases, the autonomous controller can allow for controlling one or more processes (e.g., dispensing, analyzing, or any described herein) without user input. For instance, such control can be achieved by turning on a switch, which activates the autonomous controller. In some cases, the controller can include one or more elements that allow for hand-held or portable use. For instance, any of the components herein (e.g., a power element; a regulating element; a timing element; a moving element; a transfer element; a switch; and/or a linkage) can be provided in a miniaturized format that uses minimal power or no external power source.

An autonomous controller can comprise a mechanical, pneumatic, fluidic, electromechanical, or electronic mechanism, or combinations thereof. A non-limiting exemplary controller includes a power element; a regulating element, which is optional and serves to maintains a relatively constant rate for the source of power; a timing element, which determines the rate of the relative movement of the device; a moving element, which promotes relative movement of the pushing unit, device, substrate(s) of the device, or layer(s) of the device; a transfer element, which transfers the force of the power source to the moving element and/or the timing element; and/or a switch, which is optional and serves to connect the power element either directly or indirectly to the moving element, where each of these elements can be interconnected either directly or indirectly (e.g., by a linkage, such as any described herein).

A power element may be any source of power, including mechanical, electrical, electromechanical, pneumatic, or fluidic sources, that drives relative movement (e.g., any relative movement described herein, such as relative movement of the pushing unit, device, substrate(s) of the device, or layer(s) of the device). Examples of power elements include but are not limited to a winder, a spring (e.g., a mainspring, a spiral torsional spring, a semi-reverse torsional spring, or a reverse torsional spring), a rubber band, a hand crank, a rotor mechanism (e.g., having a rotating pendulum and a pinion movable by kinetic energy generated by movement of the user, where the pinion is coupled to a generator and energy is stored in a capacitor or battery), a photovoltaic cell, a battery, a solar cell, a generator (e.g., an electric generator, such as a dynamo, a magnetohydrodynamic generator, an induction generator, a homopolar generator, or an excited generator), an alternator, and/or a capacitor. The power element can interconnect directly with a moving element or indirectly with a moving element (e.g., through one or more transfer elements or linkages).

The power element can be connected to one or more optional regulating elements that can maintain a relatively constant rate for the source of power. For example, in a mechanical power element, the regulating element can be selected from a pendulum, a balance wheel, a stackfreed (e.g., a spring-loaded cam mounted on an axle of the power element and including a spring-loaded roller), a cam, a ratchet, a fusee (e.g., a cone-shaped pulley system attached to the power element by a chain or another useful linkage), a stopwork, a remontoire (e.g., a secondary spring or weight that powers an escapement), a going barrel (e.g., a structure that contains the mechanical power element under tension and allows for use of the mechanical power element to provide constant torque), a motor barrel, or a pinion (e.g., a safety pinion that engages a barrel, such as a going barrel), as well as combinations thereof. For example, in an electrical power element, the regulating element can be selected from a connector, a coil, a fuse, a resistor, a transformer, a thermistor, a capacitor, and/or a diode.

In one non-limiting example, the assembly includes a spring as the power element and one or more regulating elements. In some cases, the assembly includes a spring, an arbor that serves as an axle for the spring, a ratchet movably connected to the arbor to prevent unwinding of the spring, a going barrel having gear teeth and containing the spring, and a pinion (e.g. a center wheel pinion) movably connected to the gear teeth of the going barrel, where the gear is optionally connected directly or indirectly to a transfer element (e.g., a gear train, or any described herein).

The assembly can include a timing element that determines the rate of relative movement. The timing element can include a balance wheel (e.g., a weighted wheel including a spiral spring or balance spring), a pendulum, a tuning fork, a synchronous motor, a synchronized motor, a directly synchronized oscillating system, a stepping motor, an electro-mechanical stepping mechanism, or a crystal oscillator (e.g., a quartz oscillator). The timing element can comprise an electronic timer or integrated circuit. The timing element can be designed to effect particular reaction times (e.g., including time periods for sample incubation, reaction, preservation, storage, processing, or analysis). The timing element (e.g., a balance wheel or a pendulum) can optionally include an escapement mechanism, which transfers the force of the power source to the timing element, monitors the number of oscillations in the timing element, and connects to the moving element (e.g., through one or more linkages or one or more transfer elements) in order to effect relative movement commensurate with the oscillations of the timing element. Exemplary, non-limiting escapement mechanisms include, a verge escapement, an anchor escapement (e.g., a deadbeat escapement), a detached escapement (e.g., a detent escapement or a co-axial escapement), a cross-beat escapement, a cylinder escapement, a duplex escapement, a lever escapement, a grasshopper escapement, a gravity escapement, or an electromagnetic escapement (e.g., a switch or a phototube including an electromagnet coupled to the timing element), as well as any described herein. The timing element (e.g., a motor system or a crystal oscillator) can optionally include an oscillation monitor, an oscillation divider (e.g., a frequency divider connected to an output of a crystal oscillator), a storage circuit (e.g., a bistable multivibrator, which is connected to the output of the frequency divider), a switching circuit (e.g., connected to the output of the storage circuit), and/or an electronic balance wheel system (e.g., connected to the output of the switching circuit). Exemplary timing elements are provided in U.S. Pat. Nos. 344,922; 1,489,762; 4,036,006; 7,3526,55; 8,308,346; and 8,263,883 each of which is incorporated herein in its entirety.

To achieve relative movement in the system and/or device, the assembly can include a moving element. The moving element can be connected directly or indirectly to the device or a portion thereof (e.g., one or more layers, such as through a central axle for rotational movement) using any useful linkage or transfer element (e.g., as described herein). Exemplary moving elements include one or more of a gear, a spring, a fly wheel, a pendulum, and/or a motor. In particular example, the moving element is connected to the timing element to ensure that relative movement occurs at a particular rate. In a further example, this connection between the moving element and the timing element is an escapement mechanism (e.g., any described herein).

To transfer power to the timing element and/or moving element, the assembly can include one or more transfer elements. Exemplary transfer elements include one or more of the following: a gear train (e.g., including one or more wheels and one or more pinions), a wheel, a pinion, a gear, a plate, a bar, a cam, a ratchet, a lever, an escapement, a cable, and/or a pulley.

The assembly can optionally include a switch, which controls the connection between the power element and the moving element. Exemplary switches include a toggle switch, a momentary switch, a rocker switch, a rotary switch, a biased switch (e.g., a push button switch), a float switch, a limit switch (or microswitch stimulated by rotary movement), a reed switch, a key switch, a control switch, a sail switch, a pressure switch, a tilt switch, a knife switch, an electronic switch (e.g., a relay, such as an analogue switch), a membrane switch, a piezo switch, or a touch switch (e.g., a capacitance touch switch, a resistance touch switch, or a piezo touch switch), as well as those described in U.S. Pat. Nos. 4,001,527; 4,021,626; 4,912,376; 5,160,853; 6,861,601; 7,251,142; 7,579,565; and 8,263,883, each of which is incorporated herein by reference in its entirety.

An exemplary mechanical mechanism can include a movable winder as a power element mechanically connected to a spring as a moving element; a gear train including an input gear, an output gear, and an intermediate gear; an escapement driven by the output gear; and a linkage coupled to the gear train for movement with this gear train. A non-limiting mechanism is provided in FIGS. 23-31 of U.S. Pat. No. 5,926,660, incorporated herein by reference in its entirety.

Another exemplary mechanical mechanism can include a knob (power element) fixed to a spring (movement element) through a rotatable shaft and a contact member moveable by the shaft (transfer element) to transfer the mechanical force of the spring to one or more layers of the device thereby effecting motion of these layers. A non-limiting mechanism is provided in U.S. Pat. No. 7,579,565, incorporated herein by reference in its entirety.

Another exemplary mechanism can include a winder (power element) fixed to a rotatable shaft bearing a spring (moving element). The shaft can be interconnected with a transfer element consisting of a gear mechanism and a shaped cam, which can be interconnected with one or more movable layers via one or more cams or optionally cogged wheels. A non-limiting exemplary mechanism is provided in FIGS. 3-6 of U.S. Pat. No. 2,895,547, incorporated herein by reference in its entirety.

Another exemplary mechanism may include a flywheel (moving element) interconnected through gears and/or shaped cams (transfer element) to movable layers. The flywheel is capable of being set in motion by an external power element and consisting essentially of an element rotatably mounted and having members that are centrifugally movable and yieldably held in place against centrifugal movement. A non-limiting mechanism is provided in U.S. Pat. No. 1,926,276, incorporated herein by reference in its entirety.

Another exemplary mechanism may include an input for a fluid (power element), one or more reservoirs for storing this fluid, a timer valve, one or more time selector valves, and an output such as a piston (moving element) interconnected either directly or through a gear train or a pulley with movable layers. The input is connected through the timer valve to both the output and one or more selector valves. Each of the selector valves is then connected individually to a separate reservoir for storing fluid. The timer valve is engaged to switch the flow of fluid away from supplying the reservoirs to supplying the output upon reaching a threshold pressure within all reservoirs, to which time selector valves are open. A non-limiting example is provided in U.S. Pat. No. 6,070,610, incorporated herein by reference in its entirety.

Another exemplary mechanism includes an electric power element such as batteries, a moving element such as electric timer coupled to a motor, and a transfer element including at least a shaft of the motor to effect movement of movable layers. The electric timer includes a motor; at least one memory for storing a programmable schedule and one or more controller settings; a controller coupled to the memory for controlling the switching of power to the motor according to the programmable schedule; a user interface including a display and at least one button. The controller is programmed such that a user can program the programmable schedule and the one or more controller settings by interacting with at least one button. The controller has an operating mode and a setup mode that can be toggled between by interacting with at least one button. A non-limiting example is provided in U.S. Pat. No. 8,314,517, incorporated herein by reference in its entirety.

The energy source for various manipulations, which may include slipping, pumping, and timing control, may be created, for example, by using a standard mechanical structure that can store potential energy in its deformed state. In one non-limiting example, the constant-force spring may be used to provide energy and a constant force for achieving autonomous operations. In some cases, a single and simple winding maneuver is the only required action that the end user needs to perform in order to initiate the operation of a SlipChip (similar to using a mechanical timer). In this example, once the potential energy is stored in the deformed spring and the user initiates the controller, the stored potential energy will be released to form a mechanical force in a constant speed that controls the position of the architecture for driving the SlipChip to dispense, pump, and slip (or relatively move the layers of a device) at a certain time point.

In some examples, the continuous released potential energy rotates an unwinding structure in a constant speed. In some cases, a rotating architecture may be attached to this unwinding structure and follow the timed rotation movement. In this instance, the mechanical force to complete each operation is provided by the unwinding force generated from the deformed springs. By using this concept, multiple operations, including dispensing, pumping, and slipping steps, can be achieved. Additional exemplary controller mechanisms include any useful mechanical systems, such as those for controlling multiple valves or switches at a certain time point, and any described in U.S. Pat. Nos. 6,325,172; 6,354,172; 5,590,687; and 8,263,883, each of which is incorporated herein by reference.

In another example, the design concept of autonomous controller is similar to the standard design of a mechanical timer. It may contain, for example, a main spring to provide the energy source, and a verge and an escape wheel (or similar design) to provide timing control (e.g., any described in Glasgow, David (1885). Watch and Clock Making. London: Cassel & Co.; Milham, Willis I. (1945). Time and Timekeepers. New York: MacMillan. ISBN 0-7808-0008-7; and Britten, Frederick J. (1881). The Watch and Clockmaker's Handbook, 4th Ed. London: W. Kent & Co., p. 56-58, each of which is incorporated herein by reference). To optimize total operation time of a device (e.g., from one minute to several minutes), the complicated gear train of a normal mechanical timing system can be minimized, if desired.

In some cases, the timing system is achieved by three components on the controller. Here, it can include (1) at least one main spring made by a constant force spring, (2) at least one timing spring, and (3) an escape ring. In this case, a main spring is fixed on to the base of the controller and connected to one part of the latch system. In this case, the latch system is designed in a way that the unwinding maneuver does not initiate or introduce uncontrolled operations to the device (e.g., a SlipChip device). In this case, once it is unwound (t=0) and then released, it provides a constant winding force on the blue latch system while rotating the second part of the latch system at the same time. The timing control may, for example, be created by using timing springs and timing teeth. In this particular case, while the latch system is rotating, the timing springs move against the designed topology of the timing teeth, and the escape ring is designed in a way that it introduces deformation to the timing spring. This mechanism creates a periodic resistant force against the winding force from the constant force spring. It can, for example, slow down the winding motion and create a timed rotation motion to the latch system. This timed rotation motion is one of various options for governing the timing of device operations. In this iteration, a control pin can be attached to the latch system and moved along with the latch system while initiating multiple pumping and slipping steps sequentially.

In other cases, an autonomous controller includes (1) a main spring, (2) an escape wheel, and (3) a verge. Similar to the runaway escapement design of a standard mechanical clocking system, the verge serves as a non-resonant oscillating mass and it interacts with the rotation of the escape wheel. As the main spring winds back to its original shape and rotates the escape wheel, the wedge may, for example, oscillate periodically to interfere with the rotations and slow down the rotation speed. A control pin can be attached to the escape wheel and move along with the latch system while initiating multiple dispensing, pumping, and slipping steps sequentially.

In one non-limiting example, the control of various functions—including, but not limited to pumping and slipping—can be achieved by using a rail system. In one example, the pumping method is based on creating a positive pressure in a sealed cavity above the device (e.g., a thin-film SlipChip). In one non-limiting example, the cap is connected to the autonomous controller when closing the cap. First, the user may, for example, turn the cap in order to store energy in the constant-force spring; then, the user may release the whole SlipChip assembly, and the constant-force spring recoils and operates the SlipChip device autonomously. In one non-limiting arrangement, the cap and the architecture holding the SlipChip are then automatically rotated against each other, thus initiating a series of sequential operations in the SlipChip device. In other arrangements, the system includes a base for holding the components of the autonomous controller, where at least two thin-film SlipChip layers are sandwiched between a top-clamp and a bottom-clamp. In this case, the small gap between thin-film SlipChips is maintained by two C-clamps that provide a clamping force on to the top-clamp and the bottom-clamp. A slipping controller is placed between the thin-film SlipChip and the top-clamp. In this non-limiting example, the slipping controller serves as the architecture for introducing slipping to the top layer, which can, for example, be slipped by a rotating pin attached to a mechanical timer. In one non-limiting example, autonomous operation is achieved by allowing the control pin to rotate along the rail system designed on the C-clamp. In a further non-limiting example, a rotating movement is introduced by connecting the cap to a timing system.

Integration with Other Devices for Sample Preparation

Fluid dispensing devices and systems can be integrated with other devices to allow multistep processes. For example, the sample preparation modules can be included in the device by exploiting the modularity of SlipChip devices, in order to prepare the sample before storage. Examples include but are not limited to devices for multistep protocols for nucleic acid extraction and filtration elements to separate plasma from whole blood using membranes and/or integrated filtration elements such as geometrical features in the device (for example, restrictions or a gap between the plates).

For instance, the system or device of the invention can be integrated with one or more of devices having a barrier layer, blocks configured to slide relative to each other, a sample metering channel, a cover plate, a separator for separating blood constituents in the sample liquid, a venting device, an entry port, an elongated separation chamber, one or more particles, one or more capillary passageways, one or more flow channels in combination with one or more separation means, a loading chamber, a separation chamber, a waste chamber, one or more material separation regions, one or more dispensers, one or more porous membranes including a semi-permeable barrier, one or more charge-switch nucleotide probes, one or more enrichment channels including enrichment medium, one or more storage compartments, one or more seals, one or more reaction layers having one or more reaction areas, one or more lysing chambers, one or more mixers, one or more reservoirs, one or more reaction chambers, one or more exhaust chambers, one or more enrichment columns, one or more reservoirs, one or more diaphragm valves, one or more fluid transporters, one or more flow activators, one or more actuators, one or more vacuum chambers, one or more valves, one or more gas-filled reservoirs, one or more rotatable housing members, one or more separation means, one or more temperature zones, one or more cartridges, one or more processing chambers, one or more sealing apparatuses, one or more sliders, one or more valves, and/or one or more microcapillary tubes, see e.g., the devices, including each and every one of the devices recited in the claims of the following patents and applications: U.S. Pat. Nos. 4,978,502; 5,310,523; 5,922,604; 5,935,858; 5,922,288; 6,143,496; 6,391,559; 6,453,928; 6,488,896; 6,613,525; 6,702,256; 6,812,038; 6,875,403; 6,989,128; 7,004,184; 7,077,175; 7,094,354; 7,118,907; 7,270,786; 7,279,134; 7,329,391; 7,445,754; 7,459,315; 7,732,136; 7,736,907; 7,811,452; 7,914, 994; 7,927,798; 7,972,778; 7,998,437; 8,008,080; 8,067, 159; 8,178,352; 8,182,765; 8,202,492; 8,247,176; 8,252, 160; 8,257,925; and 8,278,071; and U.S. Pub. Nos. 2007-0295372, 2008-0171325, 2010-0028204, 2010-0129827, 2011-0172510, 2011-0244466, 2011-0318728, 2012-0058519, 2012-0142070, 2012-0156750, 2012-0181460, 2012-0261013, 2012-0277629, 2012-0277696, 2012-0295269, and 2013-0034869, each of which is incorporated herein by reference in its entirety.

For example, FIG. 7 shows a schematic of a device comprising resistant units (e.g., blisters or blister packs) in a linear configuration, including a lysis resistant unit 701, a first air resistant unit 702, a washing resistant unit 703, a second air resistant unit 704, and an elution resistant unit 705; a barrier unit (e.g., a blister actuator) 711; a sample well 720 with cap 721; valves 731 732; matrix and housing 740; and an elution outlet 733. FIG. 7A shows a three-quarters view of such an exemplary device, FIG. 7B shows a top view of such an exemplary device, and FIG. 7C shows a bottom view of such an exemplary device, with channels 750 which can be used for movement of samples, reagents, and other fluids. FIG. 7D shows a side view, with a view of a cap lock 722 on the sample well. FIG. 7E shows an exploded view of such an exemplary device, with a blister clamp layer 760 capable of holding or securing resistant units; a top layer 770; a sealing layer 780; and a bottom layer 790 comprising fluidic channels 750. FIG. 7F shows an exploded view of the matrix and housing 740, including a cover plate 741, a silicone seal 742, a filter clamp plate 743, a filter top gasket 744, and a filter or matrix 745. FIG. 7G shows an exploded view of the top layer 770 and the bottom layer 790. FIG. 7H shows a sample well 720 and cap 721 open (left), closed (middle), and locked (right) with a cap lock 722.

FIG. 8 shows an exemplary sample preparation operation conducted using a device like that shown in FIG. 7, with views from three-quarters (upper), top (middle), and bottom (lower) perspectives. FIG. 8A shows the device 800, comprising a rail 801 which can guide the motion of a pushing unit (e.g., a cam) 811. The pushing unit can comprise features 802 capable of pushing valves 821 831. As the pushing unit advances along the rail, it can push barrier units and/or resistant units, thereby conducting a fluid dispensing protocol. FIG. 8B shows the pushing unit advanced to a second position 812, where the first resistant unit containing lysis buffer has been activated and lysis buffer 803 enters the sample well. FIG. 8C shows the pushing unit advanced to a third position 813, where it has moved the first valve to its second position 822. The pushing unit has also activated a first air resistant unit, pressurizing the sample well and driving lysed sample through a nucleic acid sample preparation matrix 805, with waste exiting through a waste vent 806. FIG. 8D shows the pushing unit advanced to a fourth position 814, where it has moved the first valve to its third position 823. The pushing unit has also activated a washing resistant unit, driving washing buffer through the nucleic acid sample preparation matrix 805, with waste exiting through a waste vent 806. FIG. 8E shows the pushing unit advanced to a fifth position 815, where it has activated a second air resistant unit, driving air flow to dry the matrix 805. FIG. 8F shows the pushing unit advanced to a sixth position 816, where it has moved the second valve to its second position 832. The pushing unit has also activated an elution resistant unit, pushing elution buffer through the matrix 805 and into an elution well 850.

FIG. 9A and FIG. 9B show an exemplary sample preparation device similar to that shown in FIG. 7 and FIG. 8. In this example, the resistant units 901 902 903 904 905 comprise syringes, each with its own pushing unit (e.g., plunger). The device further comprises a sample well 920, valves 931 932, and a filter or matrix 940. Resistant unit 901 comprises lysis buffer, resistant unit 902 comprises air, resistant unit 903 comprises a washing buffer, resistant unit 904 comprises air or a second washing buffer, and resistant unit 905 comprises an elution buffer.

Figure 11:
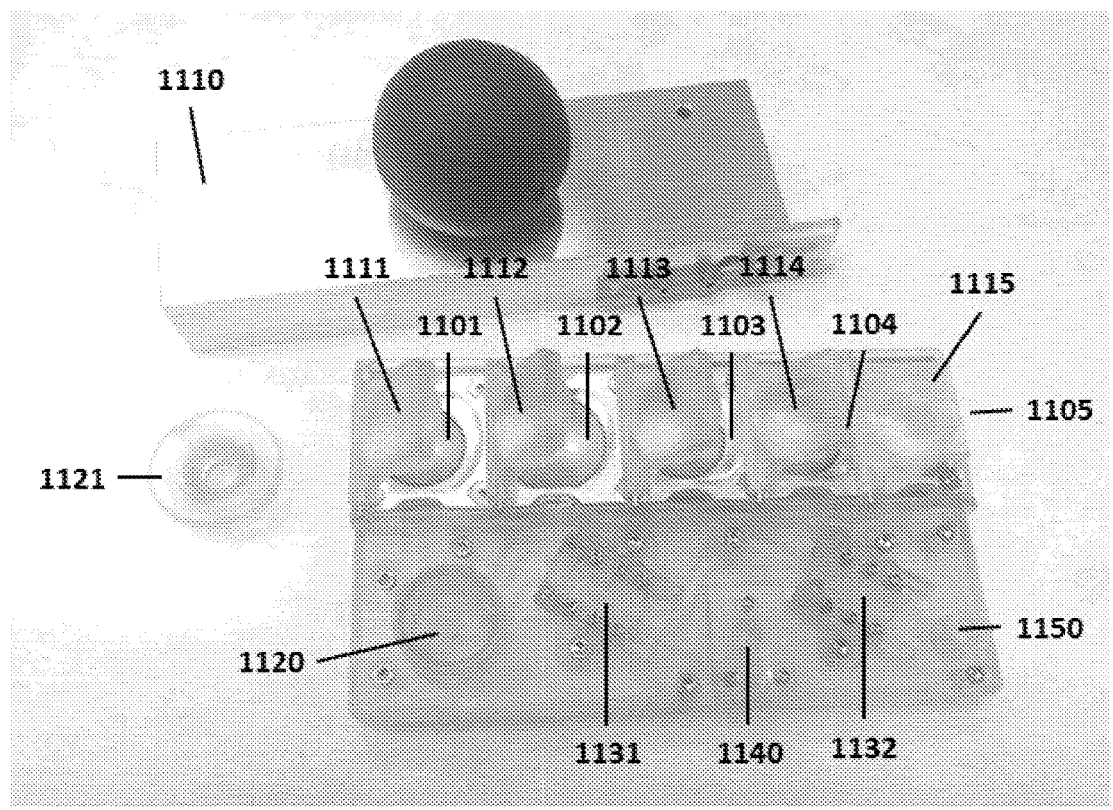
FIG. 11 shows an exemplary sample preparation device and pushing unit.

FIG. 11 shows a photograph of an exemplary sample preparation device similar to that shown in FIG. 7 and FIG. 8. The device comprises a pushing unit (e.g., a cam) 1110, resistant units (e.g., blisters or blister packs) 1101 1102 1103 1104 1105 and barrier units (e.g., blister actuators) 1111 1112 1113 1114 1115. The device further comprises a sample well 1120 and sample well cap 1121, valves 1131 1132, a matrix or filter 1140, and an elution or collection well or outlet 1150.

Figure 14:
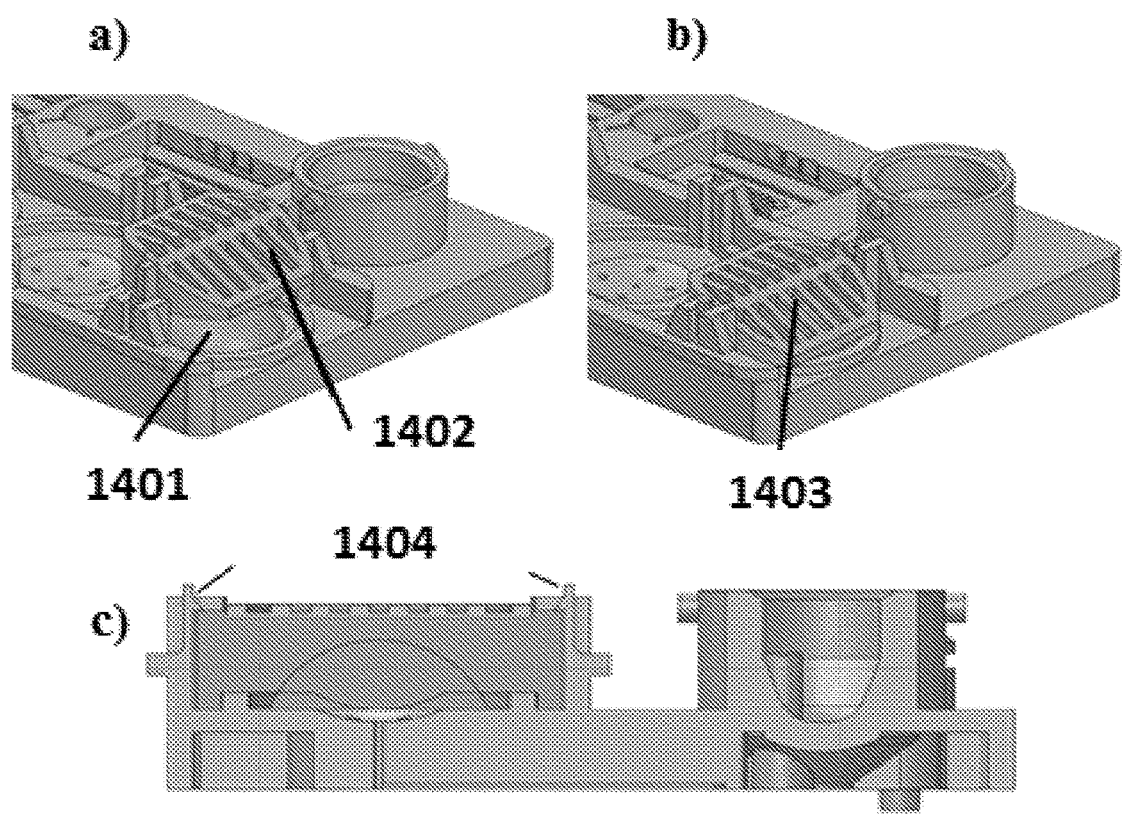
FIG. 14A shows an exemplary schematic of a barrier unit with a snap-fit feature positioned above a resistant unit.
FIG. 14B shows an exemplary schematic of a barrier unit with a snap-fit feature in contact with a resistant unit.
FIG. 14C shows an exemplary schematic of a snap-fit feature from a side view.

A snap-fit can be used to hold barrier units (e.g., blister actuators) in position after being activated (e.g., FIG. 14). A resistant unit (e.g., a blister or blister pack) 1401 can be aligned with a barrier unit (e.g. a blister actuator) 1402 (e.g., FIG. 14A). The barrier unit can be pushed by a pushing unit and can thereby activate the resistant unit 1403 (e.g., FIG. 14B). The barrier unit can be held in place by snap-fits, tabs, or other structures 1404 (e.g., FIG. 14C), thereby maintaining activation of the resistant unit (e.g., maintaining compression or deformation of a blister) and allowing a fluid inside the resistant unit to be dispensed.

Figure 15:
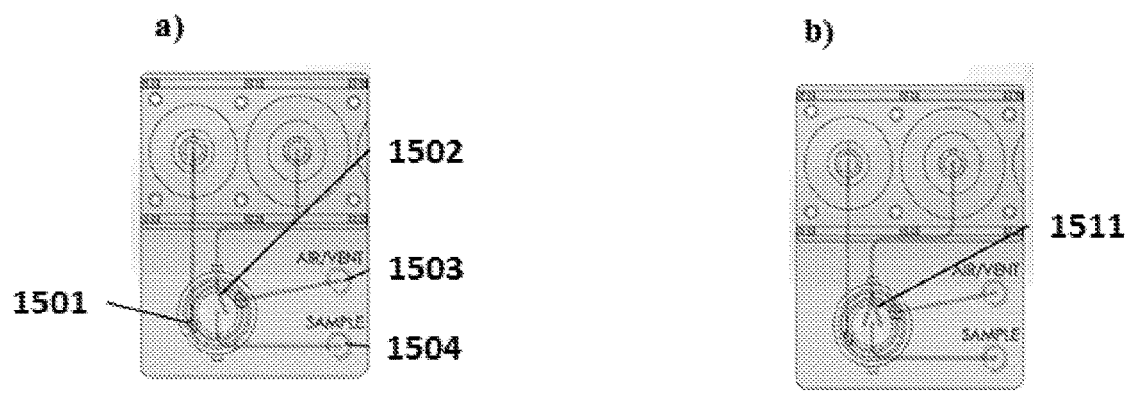
FIG. 15A shows an exemplary schematic of a bubble mixer.
FIG. 15B shows an exemplary schematic of a bubble mixer.

Air bubbles can be used for mixing of fluids. For example, FIG. 15A shows a sample well, with a lysis inlet 1501 located above the fluid line, a mixing air inlet 1502 located at the bottom of the well, an air vent 1503, and a sample outlet 1504. Sample and lysis buffer can be added into the sample well, and actuation of an air resistant unit can produce one or more air bubbles through a mixing air inlet, mixing the lysis buffer and sample. Multiple mixing air inlets 1511 can also be used, as shown in FIG. 15B. In some cases, the sample chamber can be vented to the atmosphere during mixing. In some cases, the sample chamber can be sealed from the atmosphere during mixing, allowing the chamber to be pressurized as well as mixed. Pressurization can allow for subsequent flow of the sample out of the sample chamber.

Figure 16:
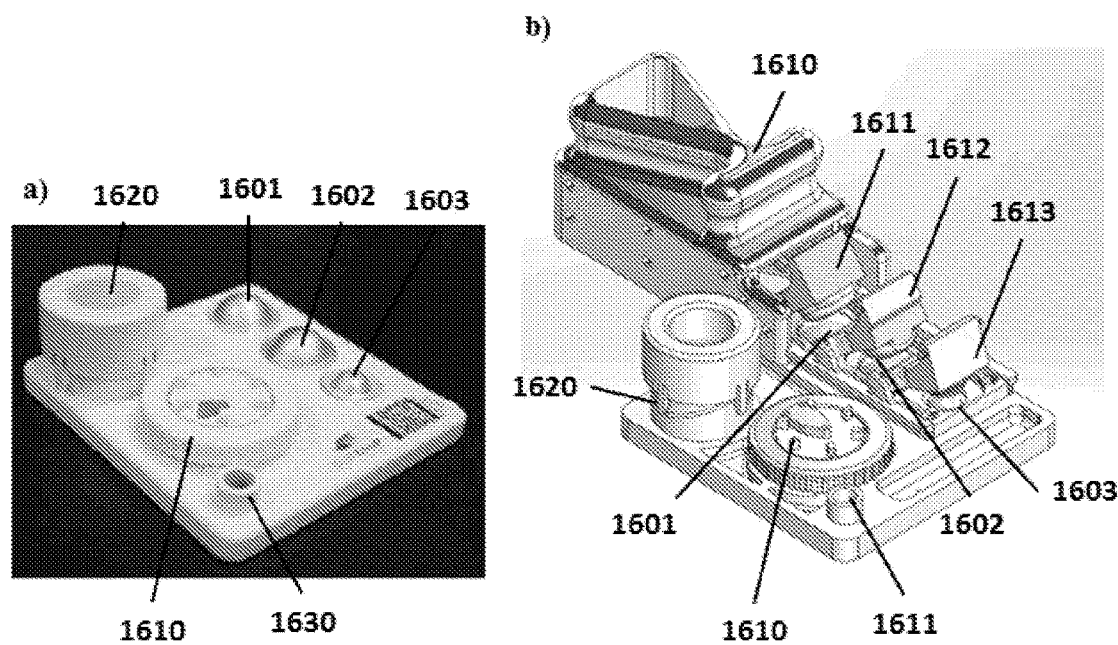
FIG. 16A shows an exemplary sample preparation device.
FIG. 16B shows an exemplary schematic of a sample preparation device.
Figure 17:
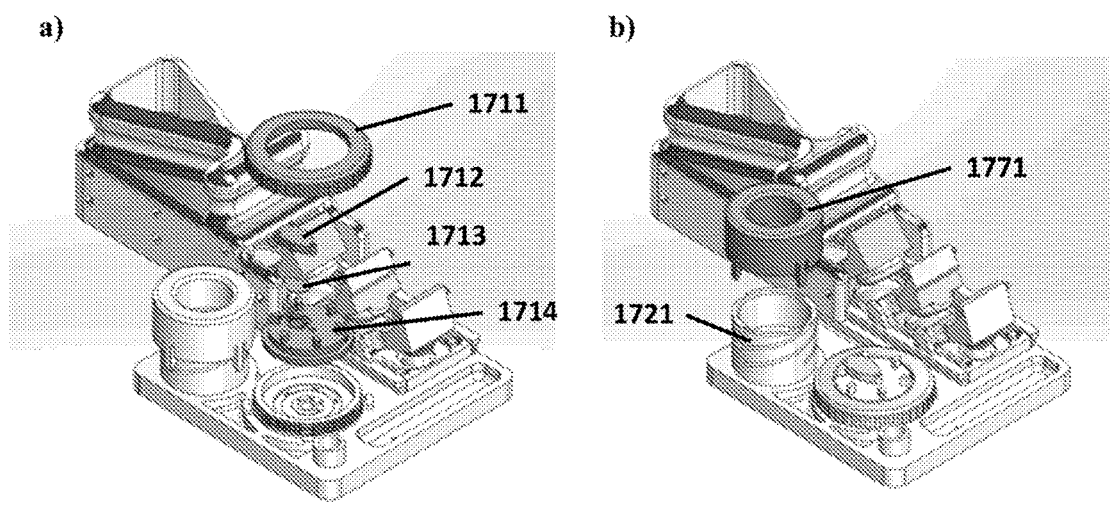
FIG. 17A shows an exemplary schematic of a sample preparation device with a rotational valve.
FIG. 17B shows an exemplary schematic of a sample preparation device with a sample chamber and cap.

A device with resistant units can be activated manually or with a guided pushing unit. For example, FIG. 16A shows a device with resistant units 1601 1602 1603, a valve 1610, a sample well 1620, and an elution well 1630, where the resistant units and valve are accessible for manual operation. In another example, FIG. 16B shows a device with barrier units 1611 1612 1613 associated with the resistant units, and with a pushing unit (e.g., a cam) 1610) positioned for actuation of the resistant units. A device can comprise a rotational valve, with components 1711 1712 1713 1714, for example as shown in FIG. 17A. A device can comprise a sample well 1721 with a cap 1771, for example as shown in FIG. 17B. In some examples, the valve can contain a matrix or filter 1714 for sample preparation. The sample preparation matrix or filter can be part of the fluidic path in the valve. Different solutions or gas can be driven through the matrix or filter while the valve connects or disconnects different fluidic paths. For example, the sample preparation matrix or filter 1714 can be embedded in a valve component as demonstrated in FIG. 17A. The rotary valve can rotate can connect the matrix or filter to different fluidic path, sample preparation solution can be delivered through the matrix or filter while pushing down the resistant units (e.g., blisters or blister packs) as driving force. The pushing unit (e.g., cam)

can be used to both actuate the resistant units (e.g., blisters or blister packs) and slip the rotary valve to the designed position.

Figure 18:
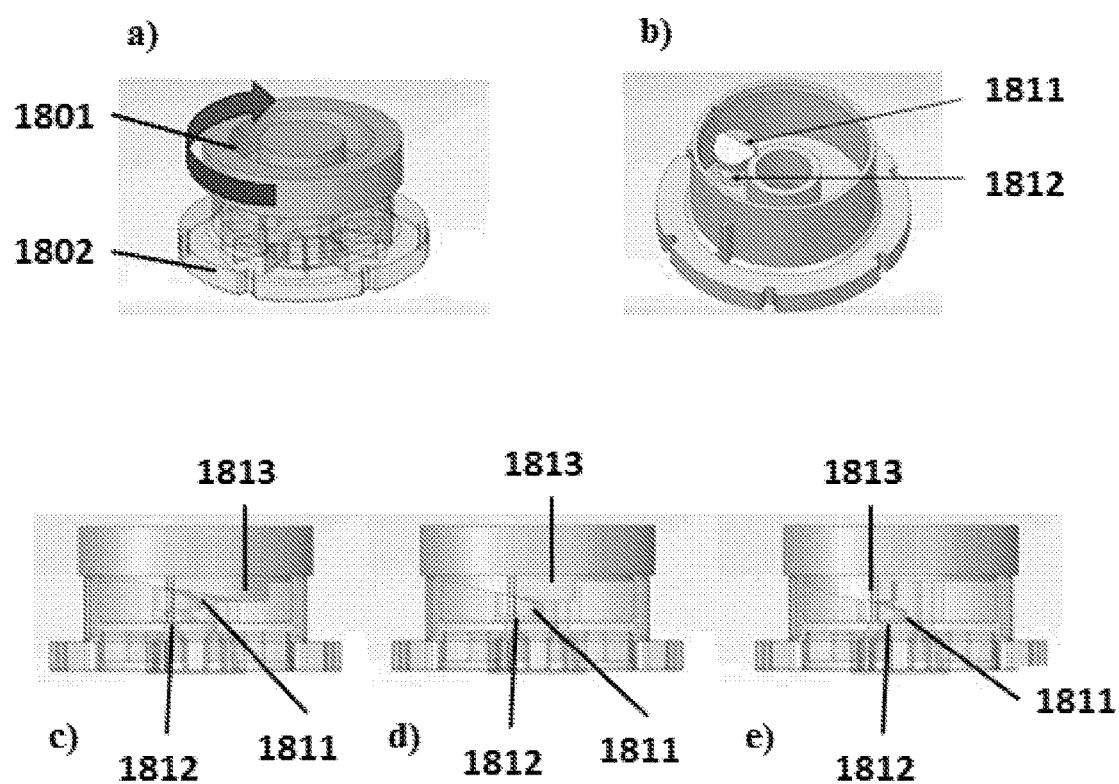
FIG. 18A shows an exemplary schematic of a rotational sample preparation device.
FIG. 18B shows an exemplary schematic of a rotational sample preparation device with a resistant unit and barrier unit.
FIG. 18C shows an exemplary schematic of a pushing unit beginning to contact a barrier unit and a resistant unit in a rotational sample preparation device.
FIG. 18D shows an exemplary schematic of a pushing unit continuing to contact a barrier unit and a resistant unit in a rotational sample preparation device.
FIG. 18E shows an exemplary schematic of a pushing unit overcoming a barrier unit and a resistant unit in a rotational sample preparation device.

A device with resistant units can also be configured for rotational operation, for example as shown in FIG. 18. FIG. 18A shows a rotating cap 1801 on top of a base 1802. FIG. 18B shows a barrier unit (e.g., a blister actuator) 1811 positioned over a resistant unit (e.g., a blister or blister pack) 1812. FIG. 18C shows a pushing unit 1813 beginning to push the barrier unit 1811 and the resistant unit 1812. FIG. 18D shows the cap rotated farther and the pushing unit further pushing the barrier unit and resistant unit. FIG. 18E shows the cap rotated farther and the pushing unit having fully depressed the barrier unit and resistant unit.

Figure 19:
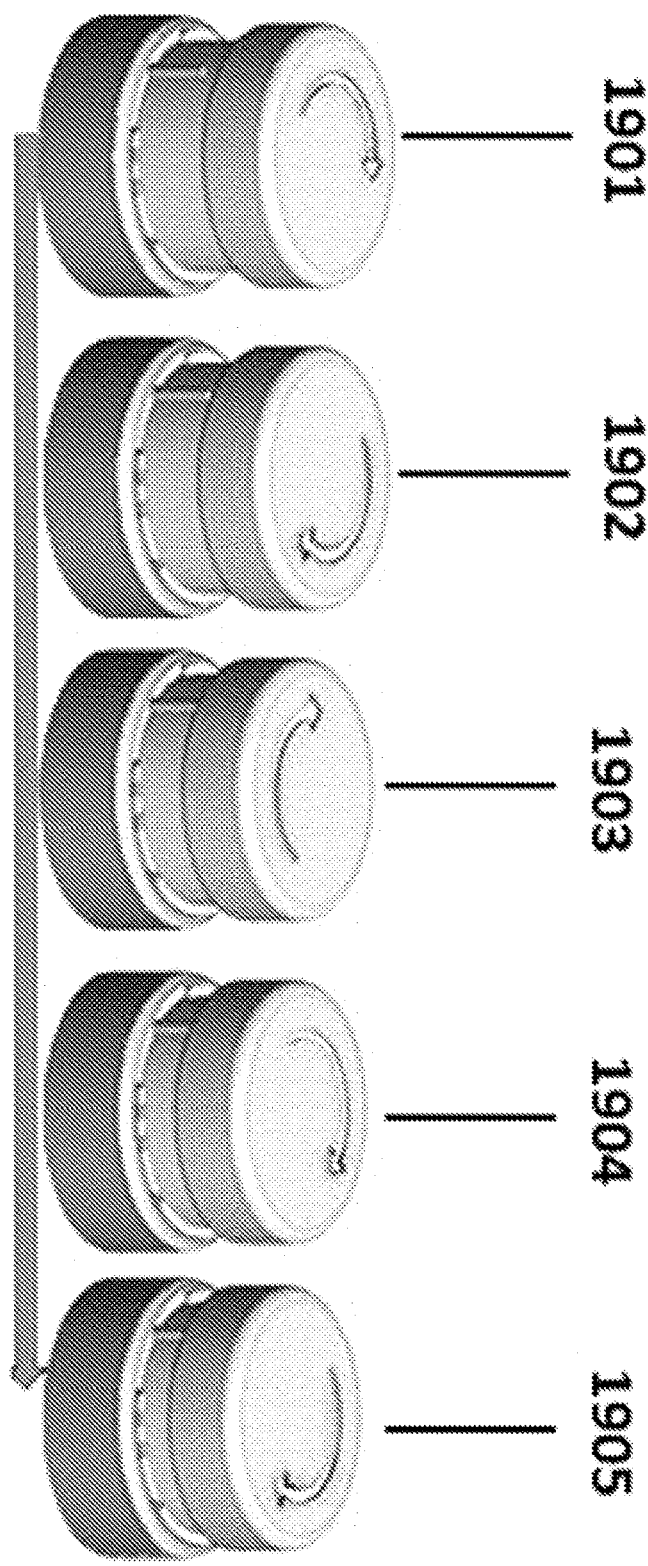
FIG. 19 shows an exemplary schematic of a rotational sample preparation device with a pressure-increasing cap.

A rotational device can also be configured to increase pressure within the device as the cap is rotated. For example, FIG. 19 shows a cap designed to add additional pressure by each rotation step 1901 1902 1903 1904 1905. This pressure can be generated by the decreasing internal volume of the device as the cap lowers toward the base. Such a device can comprise a center post 2001 (e.g., FIG. 20) with a thread, allowing the cap to thread onto the post and screw down with rotation. Pressure generated by the cap can be used to drive fluid flow within the device. For example, solution can be flowed through a matrix or filter, or air can be driven to dry a matrix or filter. The graduated application of pressure can also reduce the risk of leakage compared to a sudden application of pressure.

An exemplary application of a rotational device with stepwise increasing pressure is shown in FIG. 21. A device 2100 with cap 2101 can be loaded with sample 2110 by a user 2120 (e.g., FIG. 21A). Reagents such as lysis buffer, washing buffer, and elution buffer can be preloaded on the device during manufacturing or prior to use. The cap can be placed on the device (e.g., FIG. 21B). The cap can be rotated into position for activation of a lysis buffer resistant unit (e.g., FIG. 21C), and positive pressure generated by the cap can drive lysed sample through a matrix, followed by air flow through the matrix for drying. The cap can be rotated into position for activation of a washing buffer resistant unit (e.g., FIG. 21D), and positive pressure generated by the cap can drive washing buffer through the matrix, followed by air flow through the matrix for drying. The cap can be rotated into position for activation of an elution buffer resistant unit (e.g., FIG. 21E), and positive pressure can drive elution buffer through the matrix to elute sample (e.g., nucleic acid). Eluted sample (e.g., purified nucleic acid) can be collected from a collection well 2102 (e.g., FIG. 21F).

Figure 22A:
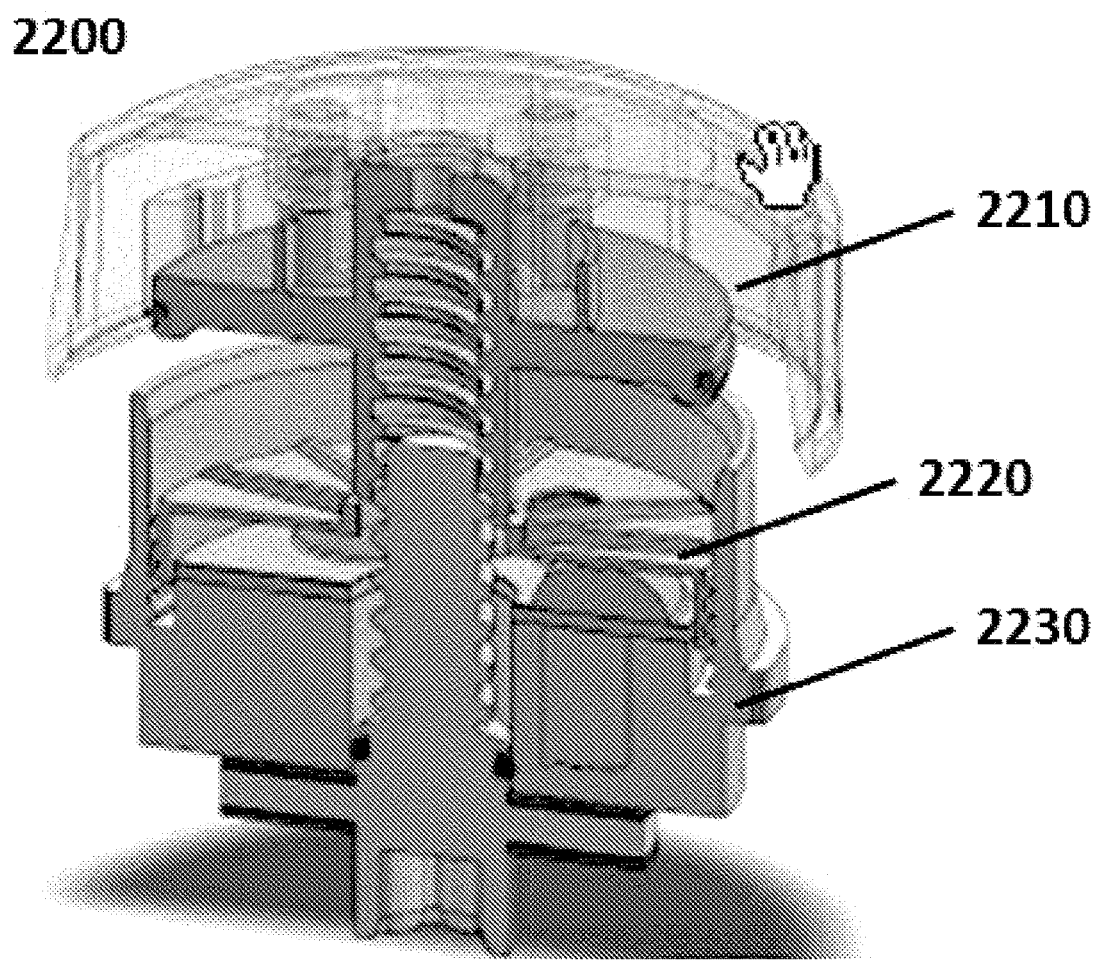
FIG. 22A shows an exemplary schematic of a rotational sample preparation device with a cap, a press disk, and a reagent layer.
Figure 22B:
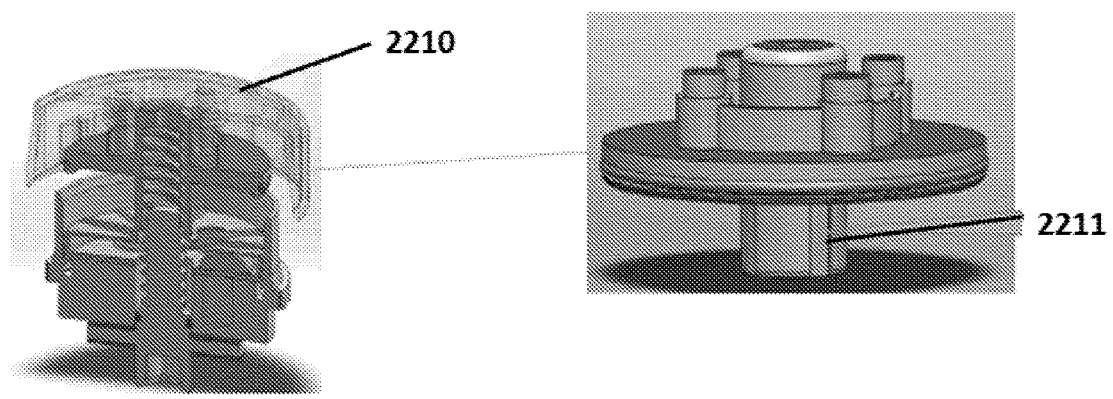
FIG. 22B shows an exemplary schematic of a rotational sample preparation device with a cap, a press disk, and a reagent layer, with keyways on the cap.
Figure 22C:
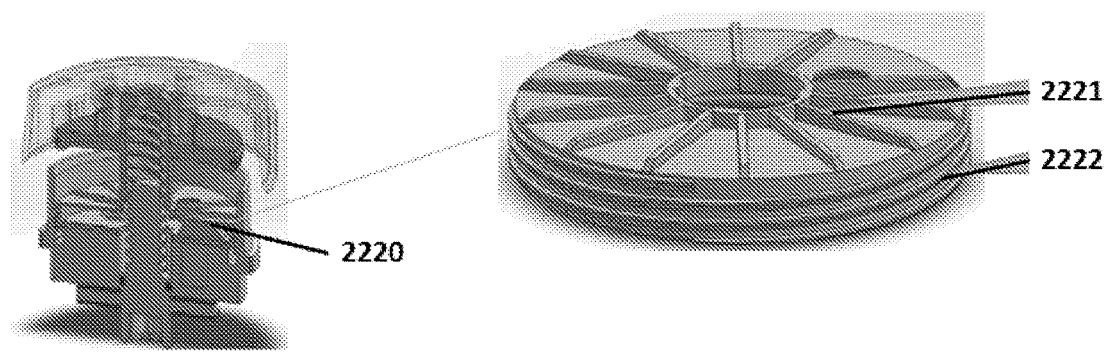
FIG. 22C shows an exemplary schematic of a rotational sample preparation device with a cap, a press disk, and a reagent layer, with keyways and threads on the press disk.
Figure 22D:
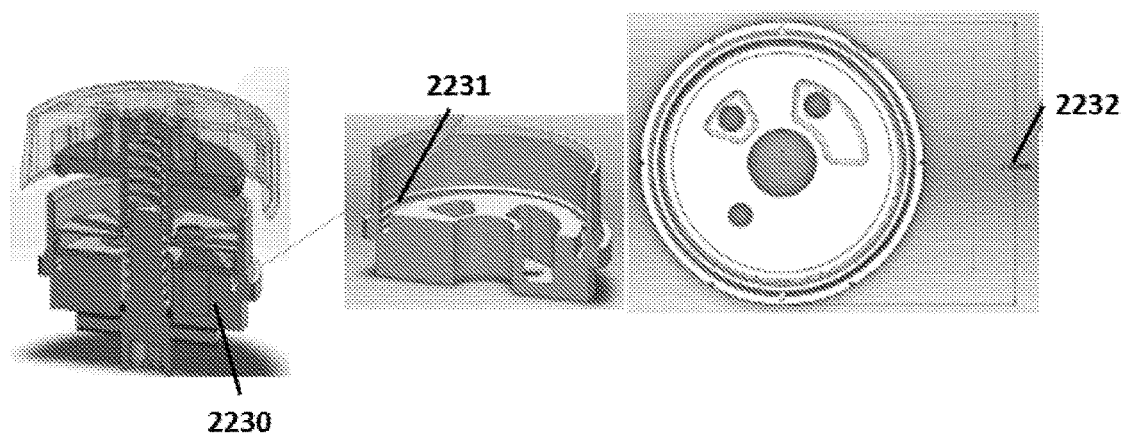
FIG. 22D shows an exemplary schematic of a rotational sample preparation device with a cap, a press disk, and a reagent layer, with threads on the reagent layer.
Figure 22E:
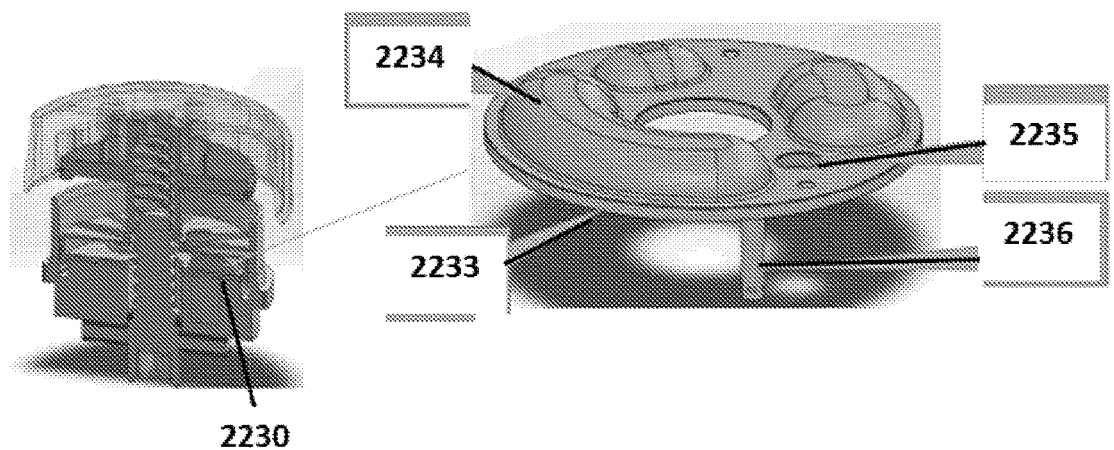
FIG. 22E shows an exemplary schematic of a rotational sample preparation device with a cap, a press disk, and a reagent layer, with resistant units on the reagent layer.
Figure 22F:
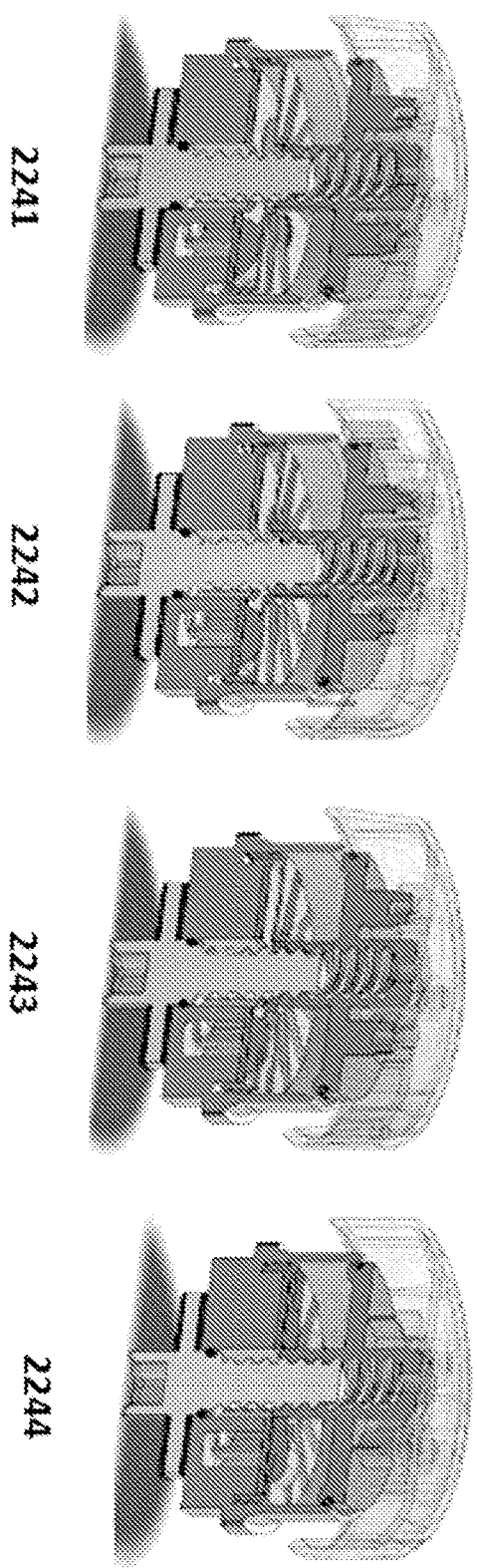
FIG. 22F shows an exemplary schematic of operation of a rotational sample preparation device with a cap, a press disk, and a reagent layer.

A sample preparation device 2200 can comprise a cap 2210, a press disk or press ring layer 2220, and a reagent layer comprising resistant units (e.g., blisters or blister packs) 2230, for example as shown in FIG. 22A. The cap 2210 can comprise keyways 2211 to engage the press disk, for example as shown in FIG. 22B. The press disk can also comprise keyways 2221 to engage the cap, as well as threads 2222 which can engage with the reagent layer to draw the disk down and allow resistant units (e.g., blisters or blister packs) to be pushed and activated, for example as shown in FIG. 22C. The reagent layer 2230 can comprise threads 2231 which can engage with the press disk, for example as shown in FIG. 22D. The reagent layer can have a particular diameter 2232. The reagent layer 2230 can comprise a molded substrate 2233 to which resistant units (e.g., blister packs) 2234 can be mounted, for example as shown in FIG. 22E. The substrate can also comprise a sample inlet 2235 and a dispensing nozzle or other outlet 2236. The molded substrate can provide a rigid surface against which resistant units can be pressed. An example operation of a sample preparation device is shown in FIG. 22F, wherein first a cap is placed on the device 2241, second the cap engages the press disk and begins rotation of the disk to drive the disk downward 2242, third the cap continues to be rotated and the blisters are crushed, with the dispensing nozzle promoting mixing 2243, and fourth after a full rotation the blisters are fully crushed and rotation of the cap is stopped 2244. The device can comprise a filter or matrix layer, through which sample material can be filtered. The filter or matrix layer can be disposed adjacent to or be in fluid communication with a reagent layer, allowing application of reagents, buffers, or other fluids to the filter. Filters and matrices are further discussed herein.

Figure 23:
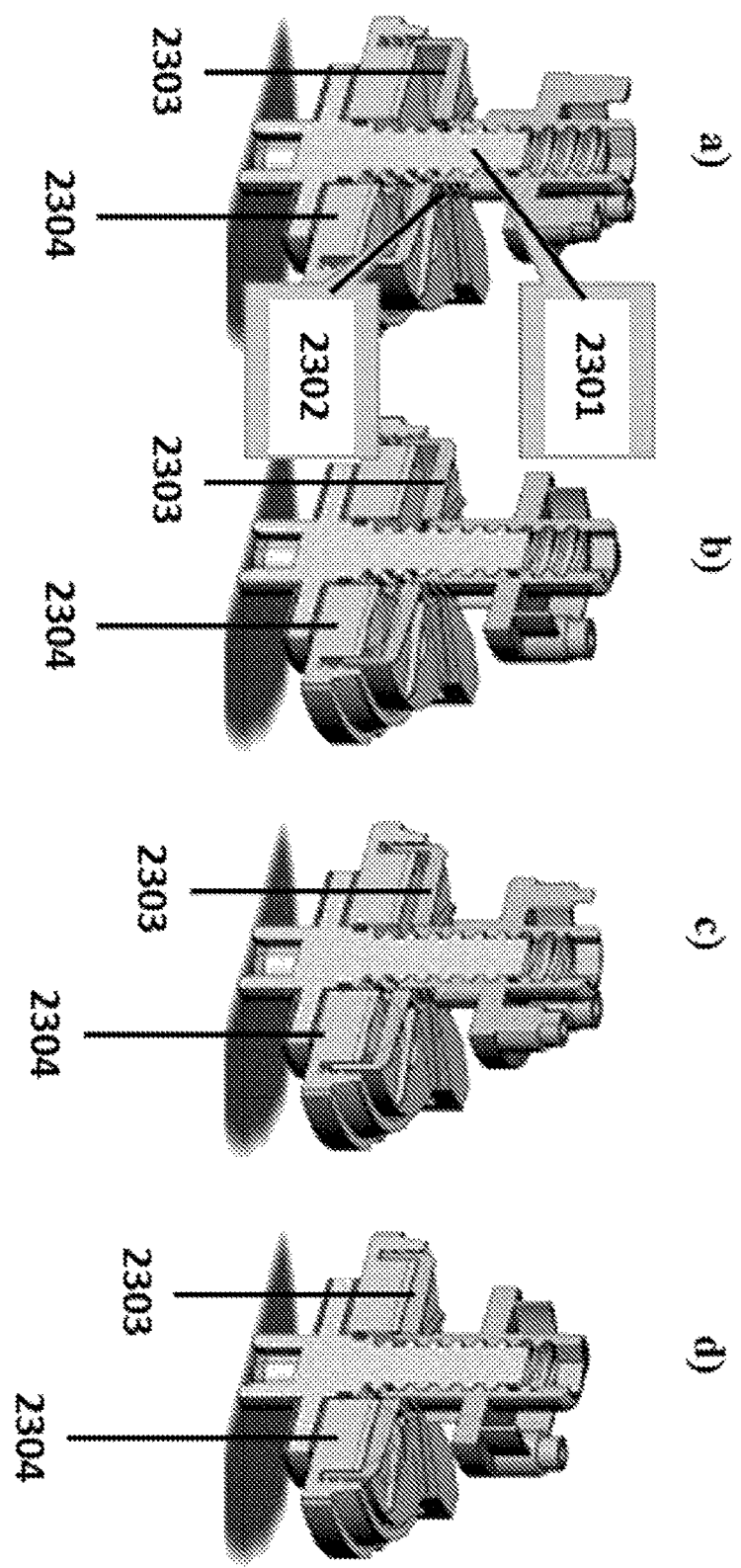
FIG. 23A shows an exemplary schematic of a rotational sample preparation device with a cap, a press disk, and a reagent layer in a first operational position.
FIG. 23B shows an exemplary schematic of a rotational sample preparation device with a cap, a press disk, and a reagent layer in a second operational position.
FIG. 23C shows an exemplary schematic of a rotational sample preparation device with a cap, a press disk, and a reagent layer in a third operational position.
FIG. 23D shows an exemplary schematic of a rotational sample preparation device with a cap, a press disk, and a reagent layer in a fourth operational position.
Figure 24:
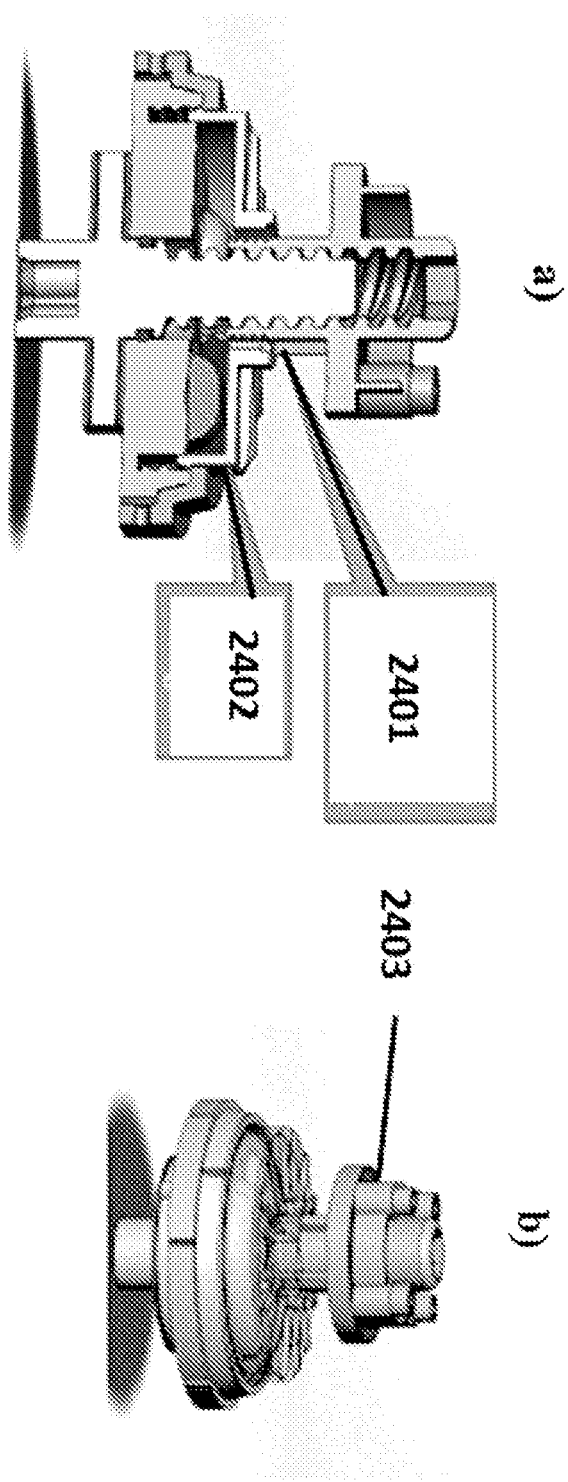
FIG. 24A shows an exemplary schematic of a rotational sample preparation device with a cap, a press disk, and a reagent layer with keyways allowing the cap to engage the press disk.
FIG. 24B shows an exemplary schematic of a rotational sample preparation device with a cap, a press disk, and a reagent layer with the cap pushing resistant units.
FIG. 24C shows an exemplary deformable layer.
Figure 24:
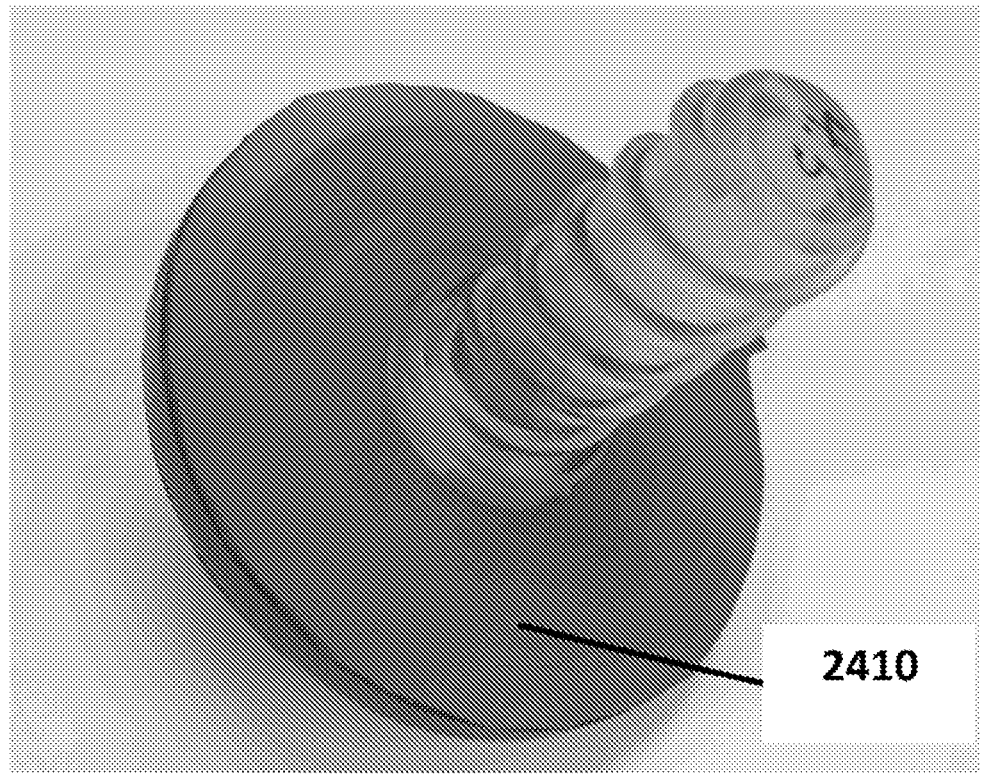
Figure 25:
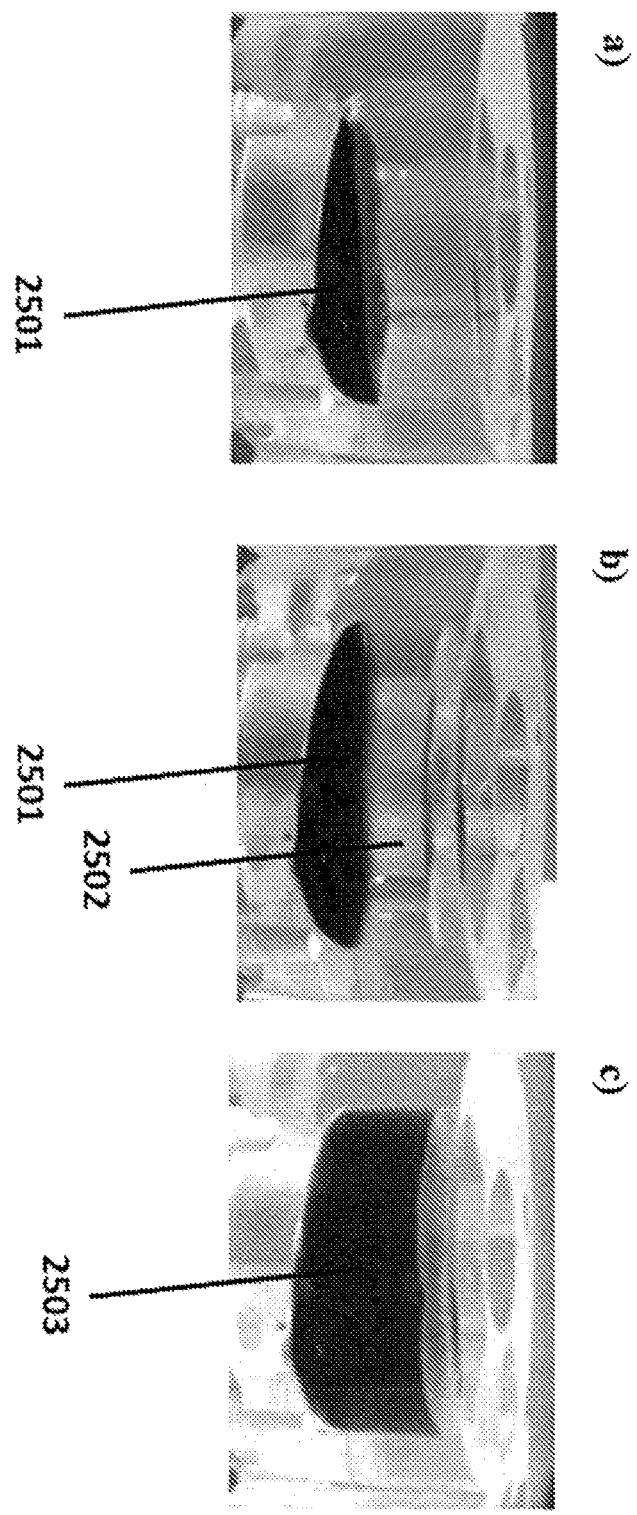
FIG. 25A shows an exemplary sample chamber with sample.
FIG. 25B shows an exemplary sample chamber with unmixed sample and reagent.
FIG. 25C shows an exemplary sample chamber with mixed sample and reagent.
Figure 26:
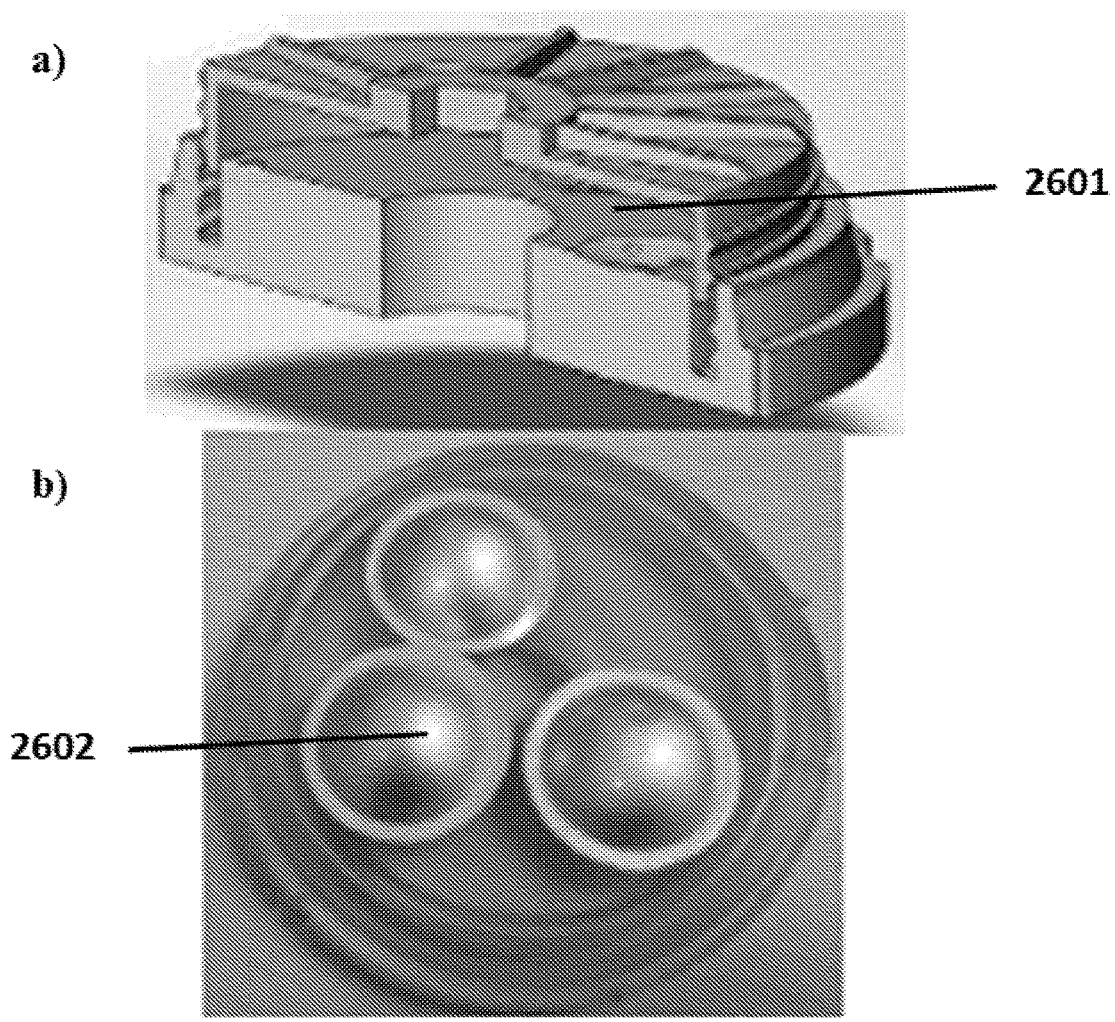
FIG. 26A shows an exemplary schematic of a reagent layer.
FIG. 26B shows an exemplary reagent layer with resistant units.
FIG. 26C shows an exemplary schematic of a multi-layer resistant unit with sequential fluid dispensing.
FIG. 26D shows an exemplary schematic of a multi-layer resistant unit with parallel fluid dispensing.
FIG. 26E shows an exemplary schematic of a multi-layer resistant unit with sequential and parallel fluid dispensing.
Figure 26:
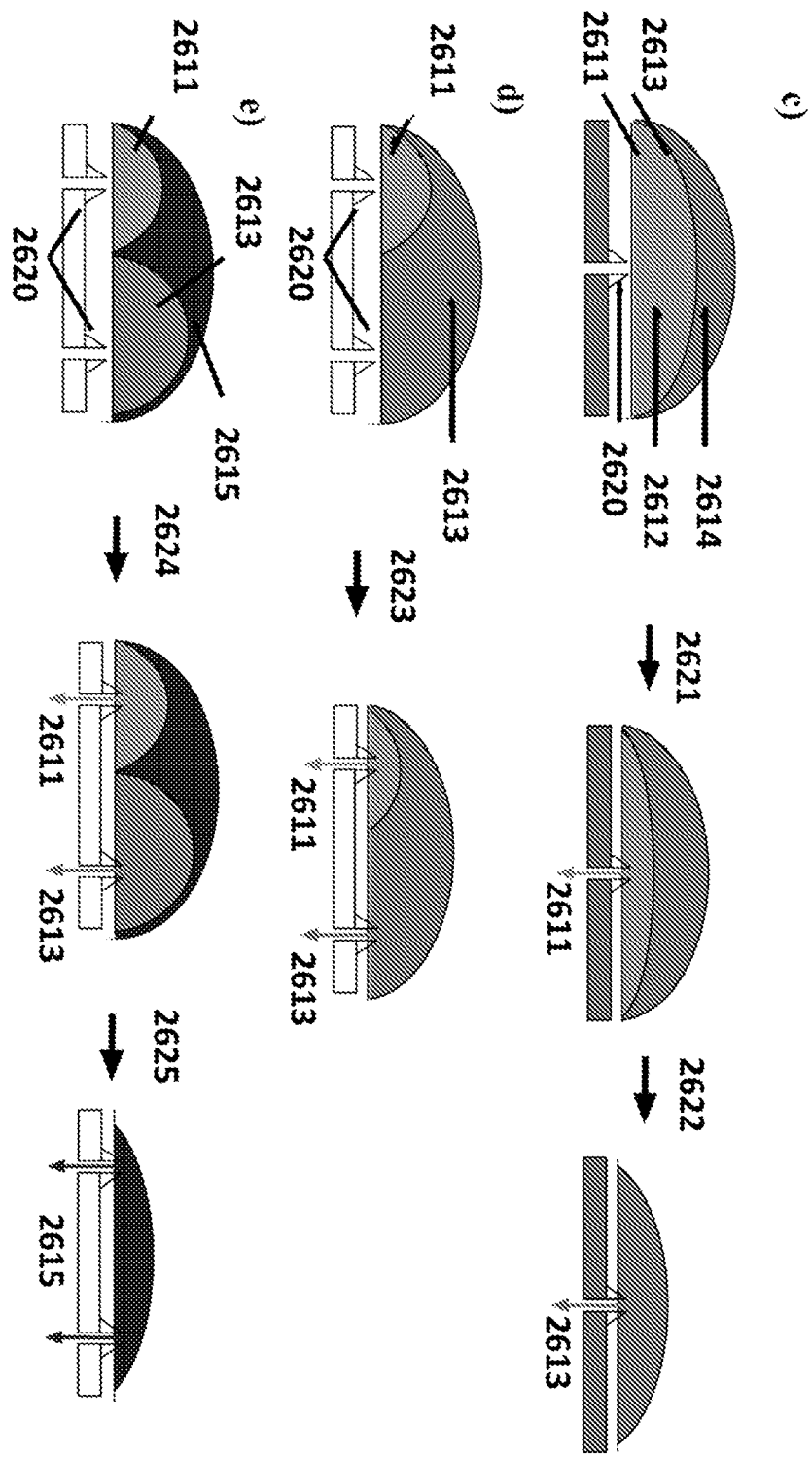

A center post or screw can be used in the operation of a device, for example as shown in FIG. 23. The center post or screw can comprise internal threads 2301. The cap can engage the internal threads of the center post, and the cap can comprise external threads 2302 which can engage the press disk 2303, for example as shown in FIG. 23A. The cap can rotate but the press disk can be fixed and unable to rotate, such that rotation of the cap threads the external threads into the press disk, for example as shown in FIG. 23B. The internal threads can have a different pitch than the external threads (e.g., internal threads 3 mm/revolution, external threads 8 mm/revolution). The difference in thread pitch can cause the press disk to move down toward the reagent layer 2304 during cap rotation, for example as shown in FIG. 23C. After further rotation (e.g., one full rotation) reagent units (e.g., blisters or blister packs) on the press disk can be fully pushed or crushed, for example as shown in FIG. 23D. Resistant units (e.g., blisters or blister packs) in a device can be pushed, activated, or crushed simultaneously or sequentially. For example, keyways 2401 can allow the cap to engage the press disk 2402, fixing the rotation of the cap and press disk to each other, as shown in FIG. 24A. Rotation of the cap 2403 can rotate the press disk and sequentially push or crush resistant units, for example as shown in FIG. 24B. A deformable layer 2410 can be applied on top of a filter layer to provide good sealing between the reagent layer and filter layer, for example as shown in FIG. 24C. A deformable layer can comprise, for example, plastic or rubber, such as a compliant rubber coating. A lubricant layer can be applied on the deformable layer to reduce the friction between filter layer and the contacting layers. A deformable layer can comprise suitable materials, including but not limited to elastomers such as silicone and polyurethane.

The device can comprise nozzles or other structures to promote mixing of dispensed fluids. For example, FIG. 25A shows an example of a chamber with sample 2501. FIG. 25B shows an example of a chamber with unmixed sample 2501 and reagent (e.g., lysis buffer) 2502. FIG. 25C shows an example of a chamber with mixed sample and reagent 2503. Resistant units in a device can comprise various structures. For example, a press disk engaged with a reagent layer 2601 (e.g., FIG. 26A) can comprise round resistant units (e.g., blisters) 2602 (e.g., FIG. 26B).

Resistant units can comprise multiple layers, for example as shown in FIG. 26C, FIG. 26D, and FIG. 26E. In some cases, a resistant unit (e.g., blister or blister pack) with multiple layers or compartments can be used to deliver fluid or reagent in a programmable workflow. For example, a first layer or compartment 2611 of a resistant unit can store a first fluid 2612 and a second layer or compartment 2613 can store a second fluid 2614; a piercing structure 2620 can pierce the first layer and dispense the first fluid 2621, then pierce the second layer and dispense the second fluid 2622, for example as shown in FIG. 26C. Multiple fluids or reagents can be delivered in a programmable workflow. In another example, the resistant unit can contain multiple compartments storing a first fluid 2612 and a second fluid 2614; multiple piercing structures 2620 can pierce and dispense both fluids in parallel 2623, for example as shown in FIG. 26D. In another example, fluids can be dispensed in parallel and in series; the resistant unit can comprise a first fluid 2611, a second fluid 2613, and a third fluid 2615, piercing structures 2620 can pierce and dispense the first and second fluids in parallel 2624, followed by piercing and dispensing the third fluid 2625.

Figure 27:
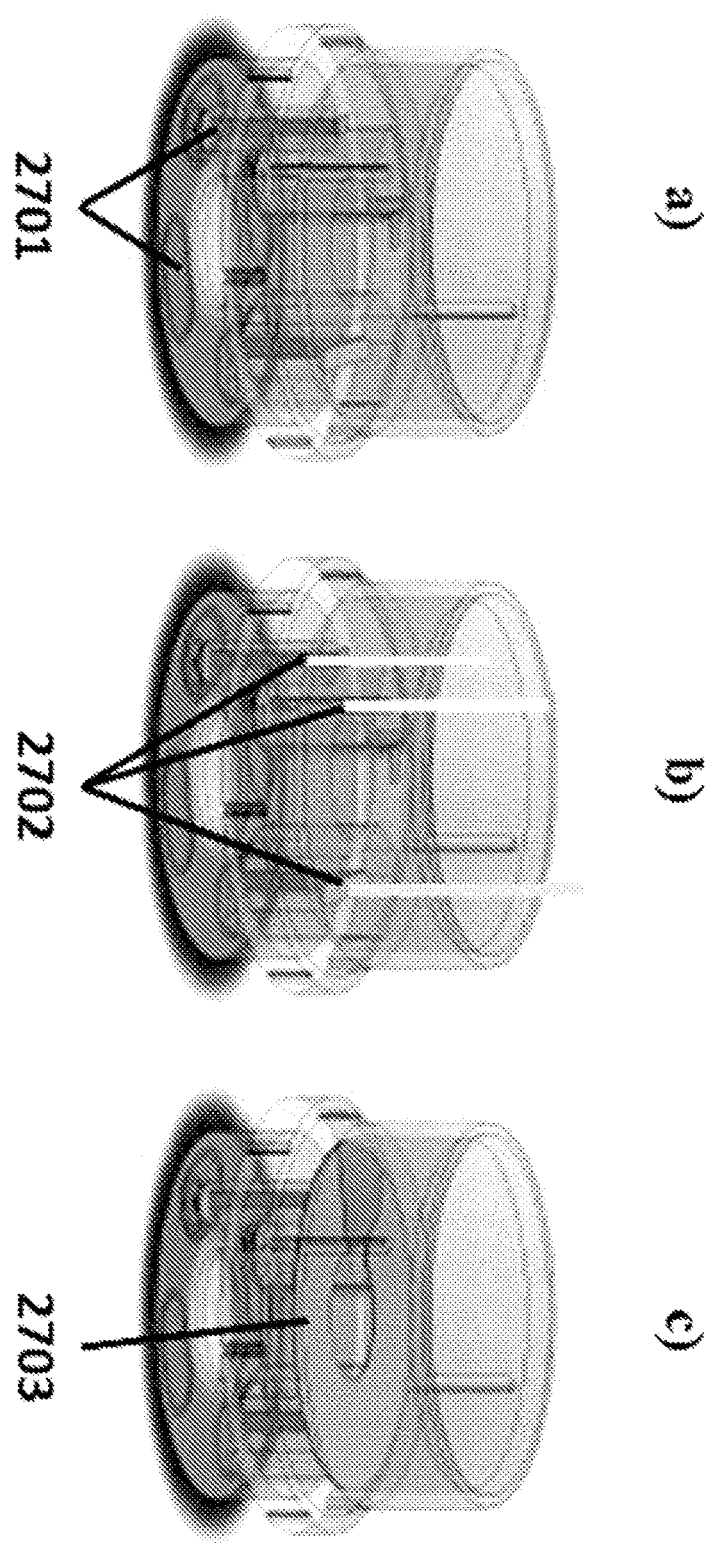
FIG. 27A shows an exemplary schematic of a rotational sample preparation device with bottom-sealed chambers.
FIG. 27B shows an exemplary schematic of a rotational sample preparation device with fluids loading into chambers.
FIG. 27C shows an exemplary schematic of a rotational sample preparation device with top-sealed chambers.
Figure 28:
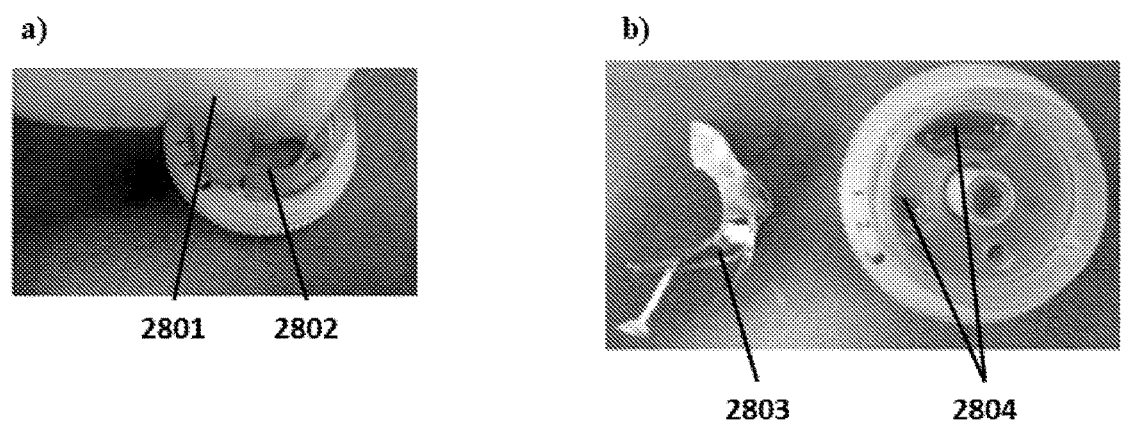
FIG. 28A shows a user removing a seal layer from an exemplary sample preparation device.
FIG. 28B shows a seal removed from an exemplary sample preparation device.

Resistant units can also comprise oval or oblong shapes. Resistant units can comprise wells or chambers, for example as shown in FIG. 27. Bottom holes of wells 2701 can be sealed, for example with foil, as shown in FIG. 27A. Reagents and other fluids 2702 can be added to the wells, as shown in FIG. 27B. Top holes of wells can be sealed 2703, for example with foil, as shown in FIG. 27C. In some cases, prior to use of the device, a user 2801 can remove top and bottom seals from the device 2802, for example as shown in FIG. 28A. Removal of seals 2803 can result in fluid volumes 2804 available for use in the device, for example as shown in FIG. 28B.

Figure 29A:
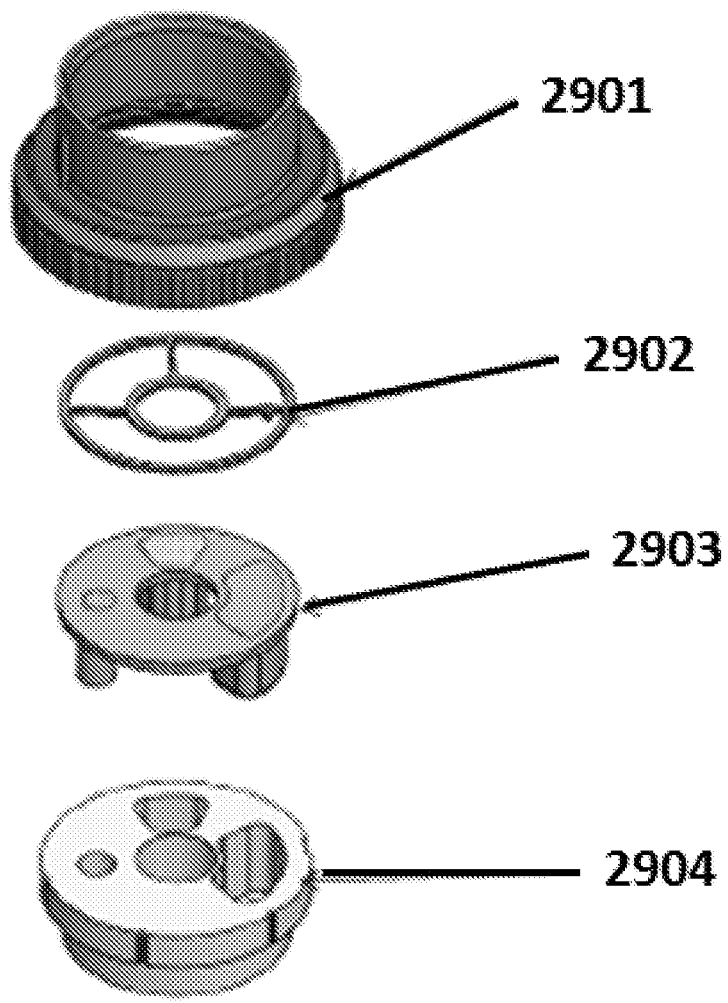
FIG. 29A shows an exemplary schematic of a lock ring and bore seal, a piercing ring, a resistant unit pack layer, and a second layer.
Figure 29B:
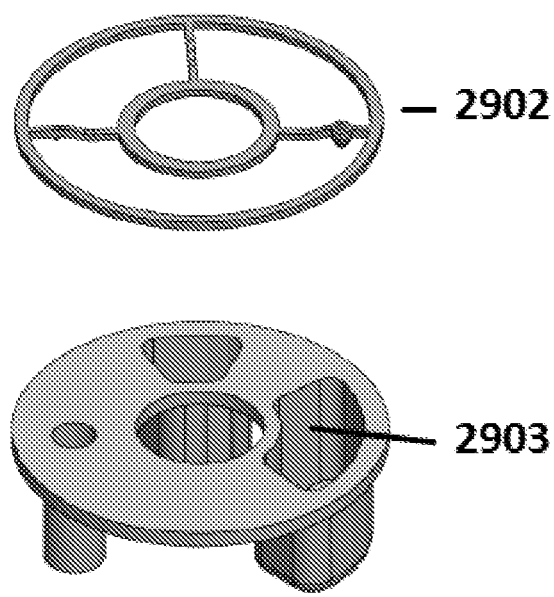
FIG. 29B shows an exemplary schematic of a piercing ring and a resistant unit pack layer.
Figure 30A:
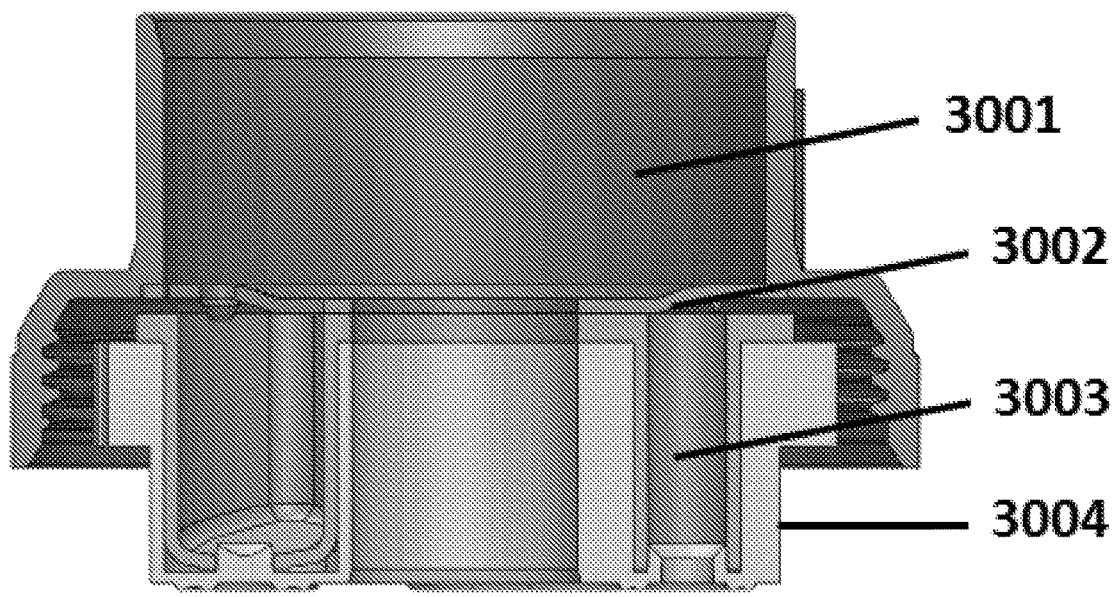
FIG. 30A shows an exemplary schematic of a bottom seal of a chamber being pierced.
Figure 30B:
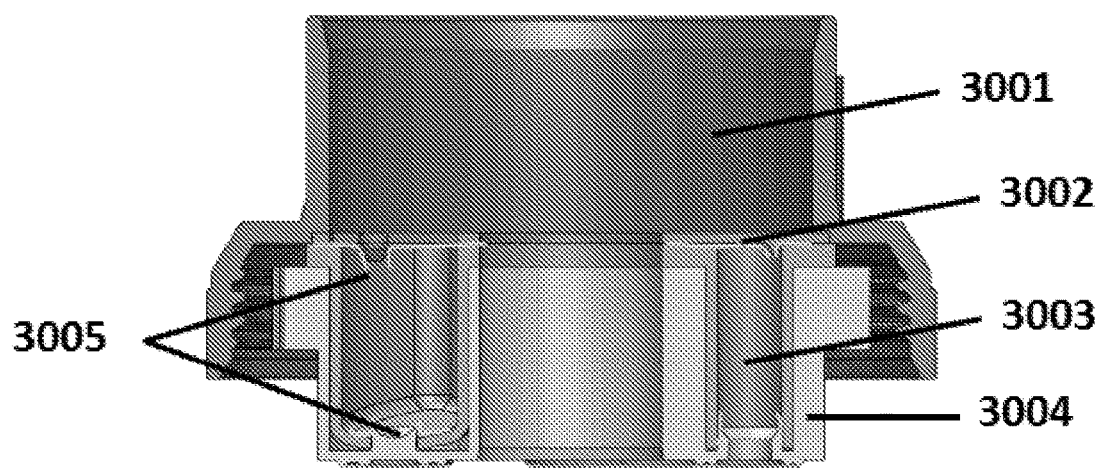
FIG. 30B shows an exemplary schematic of a top seal of a chamber being pierced.
Figure 31:
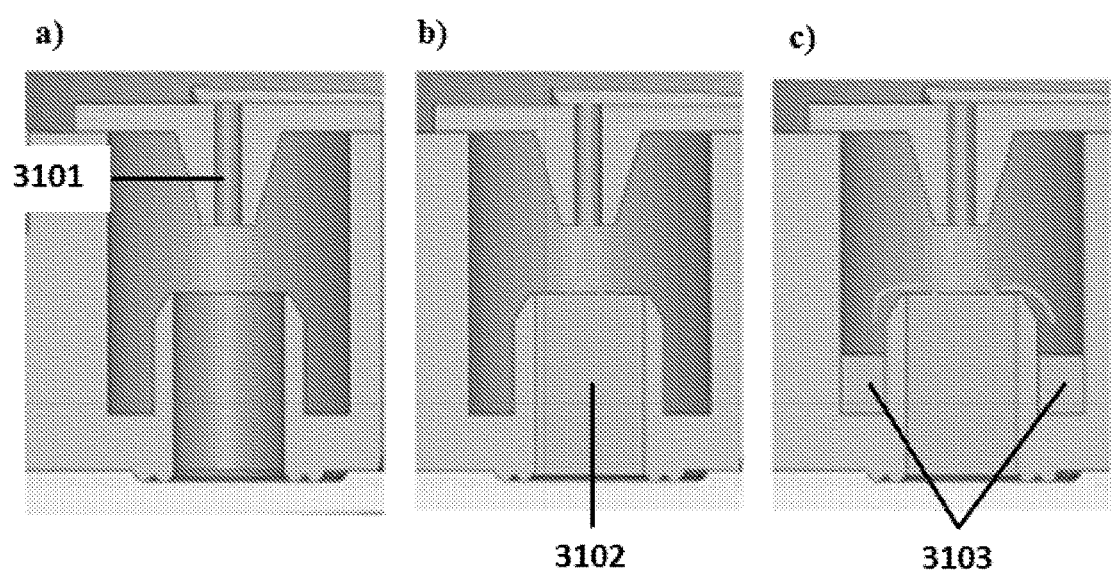
FIG. 31A shows an exemplary schematic of a fluid metering structure.
FIG. 31B shows an exemplary schematic of a fluid metering structure full of fluid.
FIG. 31C shows an exemplary schematic of a fluid metering structure full of fluid, with excess fluid overflowing into an outer chamber.

In some cases, a device can comprise a lock ring and bore seal 2901, a piercing ring 2902, a resistant unit pack or reagent pack 2903, and a second layer 2904, for example as shown in FIG. 29A and FIG. 29B. The second layer 3004 can pierce a bottom seal on the resistant unit pack or reagent pack 3003, for example as shown in FIG. 30A. The lock ring and bore seal 3001 can push the piercing ring 3002 to pierce a top seal and allow fluid dispensing 3005, for example as shown in FIG. 30B.

A component for precise volume quantification can be combined with the device, method, or system of the invention. The total collected volume can be quantified digitally by counting the number of wells that have been filled. Sequential filling, as described herein, can be used to ensure that the wells are filled one by one, so the quantification becomes trivial.

A plasma separation component can be easily integrated with the device, method, or system of the invention. A membrane for plasma separation can be integrated as a top layer for any device described herein. In some examples, the pressure needed to filter whole blood through a membrane (~10-50 mm Hg) is enough to load a device. Preliminary data show that plasma separation and device filling can be achieved at the same time with a single pressure source. This pressure source can be an external device (for example, a pipettor or a glued syringe) or integrated in the device itself.

Some of these systems and devices can allow multiplexed, multi-purpose stabilization. Each sample can be split or partitioned into multiple parts and preserved dry in order to store a different analyte (including but not limited to proteins, DNA, RNA). Drying times for digitized volumes are considerably shorter than those for bulk solution, so this technology can allow for stabilization of very fragile biomarkers (e.g., HCV viral RNA). Multiple preservation matrices (e.g., any described herein) for the same sample or analyte can also be used (e.g., different chemistries to preserve RNA and protein, or different chemistries just to preserve RNA in different ways).

Some of these systems and devices can enable the collection of several samples in the same device. Parallel collection of several independent samples at the same time can be achieved by using a commensurate array of inlets. Contamination-free collection of samples at different timepoints can be achieved by using incommensurate inlets.

For any of the devices or systems herein, a sample recovery component can be included. Recovery can be achieved by re-hydration, where a solution (e.g., water or a buffer) can be injected into the device and used to re-disperse the dried sample. At first, an immiscible fluid (e.g., such as an oil, a lubricant, or an immiscible aqueous solution) may or may not be injected in the chambers, followed by a known water volume (which may be the same as the starting volume of the preserved solution). Recovery can be possible by re-injecting a solution (e.g., water or a buffer) to rehydrate the sample. Applying external pressure, applying an external low vacuum, or exploiting capillary pressure can allow the extraction of the liquid from the device. Recovery can include full or partial recovery, as described herein.

For any of the devices or systems herein, sample analysis can be performed either on-site (for example, using the SlipChip detection modules) or off-site (for example in a central facility). For on-site analysis, a partial recovery may be sufficient (e.g., a total volume of few µL), and the sample can be directly transferred to a detection module for purposes such as digital nucleic acid or protein detection. For analysis in a central facility, a total recovery (e.g., 10-50 µL) may be necessary. In this case, all the chambers containing preserved sample can be rehydrated at the same time, and the total recovered volume can be collected for further analysis.

Devices for Integration

The present fluid dispensing system and methods can be integrated with any useful device. This device can include multiple substrates or layers. This system can be integrated with a SlipChip device (as described herein), or with any type of device having any useful structure. The present fluid dispensing system can be integrated with any device by providing fluidic connections between the components of this system (i.e., the one or more resistant units, pushing units, and, if present, barrier units) with a chamber within the device.

The device can include one or more substrates, layers, chambers, capture regions, or other structures having any useful dimension. Useful dimensions include any length, width, or depth that can be uniform or varied along any useful axis. Exemplary dimensions in any useful axis (e.g., perpendicular to the axis of fluid flow) include less than about 50 mm (e.g., less than about 40 mm, 20 mm, 15 mm, 10 mm, 5 mm, 2 mm, 1 mm, 500 µm, 200 µm, 60 µm, 50 µm, 40 µm, 30 µm, 15 µm, 10 µm, 3 µm, 1 µm, 300 nm, 100 nm, 50 nm, 30 nm, or 10 nm), or from about 10 nm to about 50 mm (e.g., 10 nm to 40 mm, 10 nm to 20 mm, 10 nm to 15 mm, 10 nm to 10 mm, 10 nm to 5 mm, 10 nm to 2 mm, 10 nm to 1 mm, 10 nm to 500 µm, 10 nm to 200 µm, 10 nm to 60 µm, 10 nm to 50 µm, 10 nm to 40 µm, 10 nm to 30 µm, 10 nm to 15 µm, 10 nm to 10 µm, 10 nm to 3 µm, 10 nm to 1 µm, 100 nm to 50 mm, 100 nm to 40 mm, 100 nm to 20 mm, 100 nm to 15 mm, 100 nm to 10 mm, 100 nm to 5 mm, 100 nm to 2 mm, 100 nm to 1 mm, 100 nm to 500 µm, 100 nm to 200 µm, 100 nm to 60 µm, 100 nm to 50 µm, 100 nm to 40 µm, 100 nm to 30 µm, 100 nm to 15 µm, 100 nm to 10 µm, 100 nm to 3 µm, 100 nm to 1 µm, 1 µm to 50 mm, 1 µm to 40 mm, 1 µm to 20 mm, 1 µm to 15 mm, 1 µm to 10 mm, 1 µm to 5 mm, 1 µm to 2 mm, 1 µm to 1 mm, 1 µm to 500 µm, 1 µm to 200 µm, 1 µm to 60 µm, 1 µm to 50 µm, 1 µm to 40 µm, 1 µm to 30 µm, 1 µm to 15 µm, 1 µm to 10 µm, 1 µm to 3 µm, 10 µm to 50 mm, 10 µm to 40 mm, 10 µm to 20 mm, 10 µm to 15 mm, 10 µm to 10 mm, 10 µm to 5 mm, 10 µm to 2 mm, 10 µm to 1 mm, 10 µm to 500 µm, 10 µm to 200 µm, 10 µm to 60 µm, 10 µm to 50 µm, 10 µm to 40 µm, 10 µm to 30 µm, 10 µm to 15 µm, 50 µm to 50 mm, 50 µm to 40 mm, 50 µm to 20 mm, 50 µm to 15 mm, 50 µm to 10 mm, 50 µm to 5 mm, 50 µm to 2 mm, 50 µm to 1 mm, 50 µm to 500 µm, 50 µm to 200 µm, 50 µm to 60 µm, 100 µm to 50 mm, 100 µm to 40 mm, 100 µm to 20 mm, 100 µm to 15 mm, 100 µm to 10 mm, 100 µm to 5 mm, 100 µm to 2 mm, 100 µm to 1 mm, 100 µm to 500 µm, or 100 µm to 200 µm).

The dimensions of any structure (e.g., one or more chambers) can be chosen to maintain a particular volumetric or linear flow rate of a fluid in the device. For example, such dimensions can be useful to control the filling of the device with particular fluids or the flow rate of such fluids through the areas and/or capture regions.

The substrate, layer, chamber, capture region, or other structure can include any useful cross-section. Cross-sections can be of any useful shape (e.g., rectangular, square, circular, oval, irregular, or triangular cross-sections) that can optionally vary along the axis of any structure. For instance, when the structure is a channel, the cross-section of the channel along the axis of fluid flow can change from one cross-sectional shape to another, such as from a circular to a rectangular cross-section. In another instance, the dimensions of the cross-section can be uniform or can vary along any axis, such as a channel that tapers or expands along the axis of fluid flow.

Planarity

The substrate, layer, chamber, capture region, or other structure can include any useful planarity. In some instances, the surfaces of the first and second layers are substantially planar to facilitate movement of these layers. Such substrates or layers can further be uniform or non-uniform in other characteristics, such as height, width, and/or depth.

Alternatively, the surfaces of the structures can be non-planar and substantially complementary to allow for movement. For instance, one or more layers can include a curvilinear surface, such as the surface of a cylinder, a concave surface, or a convex surface. In one example, the first layer can include a first cylindrical surface, and the second layer includes an annular cylinder having an opening, an inner cylindrical surface, and an outer cylindrical surface. When the first layer is inserted into the opening of second layer, the first cylindrical surface and the inner cylindrical surface of the second layer are complementary, thereby allowing the first layer to move within the second layer. Accordingly, the layers can include any useful complementary surfaces, such as concentric spheres, cones, cylinders, etc.

Further, the device can include additional layers having any useful planarity, and each layer can have similar, different, or complementary structure characteristics (e.g., planarity). Moreover, to ensure that uniform pressure is applied over the first and second areas or layers, the surface may vary to ensure when pressure is applied in discrete locations along the device, a uniform pressure can be applied. For example, when the two surfaces are conical, pressure may be applied to bring two surfaces into close contact. Exemplary devices and their characteristics are described in U.S. Pub. No. 2012-0028342, U.S. Pub. No. 2012-0264132, U.S. Pub. No. 2012-0329038, Int. Pub. No. WO 2010/111265, as well as U.S. Provisional Application Nos. 61/162,922, filed Mar. 24, 2009; 61/262,375, filed Nov. 18, 2009; 61/340,872, filed Mar. 22, 2010; 61/516,628, filed Apr. 5, 2011; and 61/518,601, filed on May 9, 2011, each of which is incorporated herein by reference in its entirety.

Surface Characteristics

The substrate, layer, chamber, capture region, or other structure can include any useful surface characteristics. Exemplary surface characteristics include differentially wetting (e.g., hydrophobic, lipophobic, fluorophilic, or hydrophilic), smoothness, or porosity. Each layer can have substantially the same or different surface characteristics. For instance, both the first and second layers can be substantially hydrophobic, or the first layer can be substantially hydrophobic, and the second layer can be substantially hydrophilic. Similarly, each of the first chambers of the first layer can have substantially the same or different surface characteristics. In one example, all of the first chambers are substantially hydrophilic, and the remaining portions of the first layer are hydrophobic, thereby allowing for preferentially wetting of aqueous reagents within the first chambers as compared to other portions of the first layer. In another example, the entire first layer, including the first chambers, is substantially fluorophilic, and the capture regions are substantially hydrophilic. In this way, aqueous reagents and/or samples will preferentially flow through capture regions, as compared to remaining in the first layer. Furthermore, if the lubricant is a fluorous liquid, then this fluid will preferentially wet the first chamber as compared to the capture regions. As can be seen, by controlling the surface characteristics, fluid flow and/or compartmentalization can be controlled. For example, where an open chamber (e.g., an open well) is used, a fluid may be held within an open chamber using surface tension (i.e., a concave or convex meniscus), particularly if the open chamber has a surface characteristic allowing for preferentially wetting of the fluid.

Surface characteristics can be obtained by using any useful material or surface modification process. For instance, one or more chambers can include porous materials, e.g., porous glass, aluminum oxide, or a cellulose matrix. Such chambers may be made by depositing a matrix into the area, by patterning a porous layer, and/or by filling or coating a porous layer around areas. Exemplary cellulose patterning processes are described in Martinez et al., Anal. Chem. 80:3699-3707 (2008), Martinez et al., Angew. Chemie Int. Ed. 46:1318-1320 (2007), Martinez et al., Lab Chip 8:2146-2150 (2008), and Macek et al., Chromatographic Rev. 15:1-28 (1971); and other materials may be patterned by methods described in Vozzi et al., Biomaterials 24:2533-2540 (2003) for PLGA scaffolds; Desai et al., Biosens. Bioelectron. 15: 453-462 (2000), Pichonat et al., J. Micromech. Microeng. 15:S179-S184 (2005), Cohen et al., Biomed. Microdevices 5:253-259 (2003), Ohji et al., Proc. SPIE Int'l Soc. Optical Eng. 3223:189-197 (1997), and Chu et al., J. Microelectromech. Sys. 15: 671-677 (2006) for porous silicon membranes; De Jong et al., Lab Chip 5: 1240-1247 (2005) for thin devices; Petronis et al., J. Biomed. Mater. Res. 66:707-721 (2003) for silicon substrates; and Wang et al., Sens. Actuat. B 123:101-106 (2007) for palladium-silver thin film for hydrogen sensing, each of which is incorporated herein by reference in its entirety.

The substrate, layer, chamber, capture region, or other structure can be formed from any useful material. The materials used to form the devices of the invention are selected with regard to physical and chemical characteristics that are desirable for proper functioning of the device. Suitable, non-limiting materials include polymeric materials, such as silicone polymers (e.g., polydimethylsiloxane and epoxy polymers), polyimides (e.g., commercially available Kapton® (poly(4,4'-oxydiphenylene-pyromellitimide, from DuPont, Wilmington, Del.) and Upilex™ (poly(biphenyl tetracarboxylic dianhydride), from Ube Industries, Ltd., Japan)), polycarbonates, polyesters, polyamides, polyethers, polyurethanes, polyfluorocarbons, fluorinated polymers (e.g., polyvinylfluoride, polyvinylidene fluoride, polytetrafluoroethylene, polychlorotrifluoroethylene, perfluoroalkoxy polymer, fluorinated ethylene-propylene, polyethylenetetrafluoroethylene, polyethylenechlorotrifluoroethylene, perfluoropolyether, perfluorosulfonic acid, perfluoropolyoxetane, FFPM/FFKM (perfluorinated elastomer [perfluoroelastomer]), FPM/FKM (fluorocarbon [chlorotrifluoroethylenevinylidene fluoride]), as well as copolymers thereof), polyetheretherketones (PEEK), polystyrenes, poly(acrylonitrile-butadiene-styrene) (ABS), acrylate and acrylic acid polymers such as polymethyl methacrylate, and other substituted and unsubstituted polyolefins (e.g, cycloolefin polymer, polypropylene, polybutylene, polyethylene (PE, e.g., cross-linked PE, high-density PE, medium-density PE, linear low-density PE, low-density PE, or ultra-high-molecular-weight PE), polymethylpentene, polybutene-1, polyisobutylene, ethylene propylene rubber, ethylene propylene diene monomer (M-class) rubber), and copolymers thereof (e.g., cycloolefin copolymer); ceramics, such as aluminum oxide, silicon oxide, zirconium oxide, and the like); semiconductors, such as silicon, gallium arsenide, and the like; glass; metals; as well as coated combinations, composites (e.g., a block composite, e.g., an A-B-A block composite, an A-B-C block composite, or the like, of any materials described herein), and laminates (e.g., a composite material formed from several different bonded layers of identical or different materials, such as polymer laminate or polymer-metal laminates, e.g., polymer coated with copper, a ceramic-in-metal or a polymer-in-metal composite) thereof.

The device can be formed by any useful process, including but not limited to molding (e.g., injection molding, vacuum molding, or overmolding), machining (e.g., drilling, milling, or sanding), and etching (e.g., deep reactive ion etching, KOH etching, or HF etching). In microfluidic applications, the layers can be fabricated from a material that enables formation of high resolution features (e.g., microchannels, chambers, mixing features, and the like, that are of millimeter, micron, or submicron dimensions), such as by using microfabrication techniques (e.g., dry etching, wet etching, laser etching, laser ablation, molding, embossing, or the like, to have desired miniaturized surface features). Further, the material can be optionally treated to provide a chemically inert surface (e.g., by silanization with tridecafluoro-1,1,2,2-tetrahydrooctyl-1-trichlorosilane), a biocompatible surface (e.g., by treatment with bovine serum albumin), and/or a physically stable material (e.g., by extensive cross-linking).

The substrates or layers can include any useful material. For instance, a portion of a layer can include a membrane, or the entire layer can include a continuous membrane or a patterned membrane. Furthermore, such membranes can be integrated with one or more layers (e.g., by overmolding or lamination) having one or more chambers and/or inlets. Alternatively, such membranes can be present in a separate layer. Exemplary membranes include a PTFE (e.g., Teflon®) membrane, a polycarbonate membrane, a cellulose membrane, a nitrocellulose membrane, a nylon membrane, a paper membrane, or other membranes that are known in the art.

The device can also include one or more deformable layers. Such deformable layers can be designed to deform as pressure is applied, such as to redistribute local pressure into uniform pressure over a surface of the device and/or to control connection or disconnection between layers or chambers.

Furthermore, one or more substrates, one or more layers, and/or chambers can be optionally coated. In particular cases, a coating can be used to minimize cross-contamination between layers, where relative movement between layers can result in thin films of reagents forming between layers. The coating can be used to control surface chemistry (e.g., by increasing the contact angle to about 154° with water). In particular cases, one or more layers and/or chambers are coated with a fluoropolymer. Exemplary fluoropolymers include fluorinated ethylene propylene resin (e.g., Teflon® FEP TE-9568, a dispersion composed of approximately 54% (by total weight) of a negatively charged, hydrophobic colloidal fluoropolymer resin (0.1 to 0.30 μm FEP particles suspended in water) and approximately 6% (by weight of FEP resin) of a nonionic wetting agent and stabilizer based on the weight of the FEP solids), perfluoroalkoxy copolymer resin (e.g., Teflon® PFA TE-7224, a dispersion composed of approximately 60% (by total weight) of PFA resin (0.05 to 0.5 μm particles) dispersed in water and approximately 5% by weight of a nonionic wetting agent and stabilizer based on the weight of the PFA solids; or Teflon® PFAD 335D, a dispersion composed of approximately 60% (by total weight) of PFA resin (0.20 μm average diameter particles) dispersed in water and approximately 6% by weight of a nonionic surfactant based on the weight of the PFA solids), polytetrafluoroethylene (e.g., Teflon® PTFE DISP 30, a dispersion composed of approximately 60% (by total weight) of PTFE resin (0.220 μm average diameter particles) dispersed in water and approximately 6% by weight of a nonionic surfactant based on the weight of the PTFE solids), or a copolymer of tetrafluoroethylene and ethylene (e.g., Tefzel® Type LZ, CLZ, or CLZ-20, available in nominal gauges of 50, 100, 200, 500, 750, 1000, or 2000, having a thickness of 0.0005, 0.0010, 0.0020, 0.0050, 0.0075, 0.0100, or 0.0200 inches).

The device can include multiple substrates of layers to accommodate multiplexed sample processing, preparation, and/or analysis. In particular examples, the layers are provided in a stacked configuration having a top layer, a bottom layer, and a plurality of intermediate layers. The intermediate layers can have one or more openings and/or capture regions such that various chambers and/or capture regions are able to be connected by relative movement. Each of the layers can be connected and disconnected separately from the other layers within the stack. In this manner, connections and disconnections between layers can be controlled to perform the desired reactions or multiplexed analysis.

The substrates or layers can include a plurality of chambers, where each chamber may be the same or different. Furthermore, a plurality of arrays of such chambers can be present in one or more layers (e.g., arrays that can be connected sequentially or serially). Such chambers can include any volumetric structure. Each chamber in a layer or an array may have the same surface dimension, cross-section, planarity, or surface characteristic. Alternatively, each chamber in a layer or an array may have different surface dimensions, cross-sections, planarity, or surface characteristics. Exemplary chambers include an open groove or trench, a closed channel, an open or closed well, etc. Such chambers are useful for holding or transporting one or more reagents, samples, or fluids (e.g., a lubricant).

One exemplary chamber is a bridge, which can allow for connecting two other chambers in the same layer or two other chambers, each in a separate layer. The surface dimensions, cross-sections, planarity, or surface characteristics of the bridge can be optimized to promote rapid vapor diffusion or fluidic communication, such as in devices for sample storage or preservation. For example, a bridge structure can be used to dry a sample. In some cases, the bridge is not preferentially wetted by liquid water under the conditions of device use (e.g., the surface of the bridge is substantially hydrophobic and/or the bridge is filled with a gas). In some cases, the bridge and the distance between two chambers is less than about 500 μm (e.g., less than about 300 μm, 100 μm, 50 μm, or 20 μm).

Capture Regions

The systems and devices of the invention can include one or more capture regions. The capture region can include any useful material to capture one or more targets or analytes (e.g., a nucleic acid or any described herein).

The capture region can include any useful material for capturing one or more analytes. Exemplary materials includes a filter, a matrix, a polymer, a charge switch material, a gel, and a membrane (e.g., a silica membrane, a glass-fiber membrane, a cellulose membrane, a nitrocellulose membrane, a polysulfone membrane, a nylon membrane, a polyvinylidene difluoride membrane, a vinyl copolymer membrane, or an ion exchange membrane, including any described herein), a fiber (e.g., a glass fiber), or a particle (e.g., a silica particle, a bead, an affinity resin, or an ion exchange resin).

The capture region can include any useful dimension. In some particular examples, the capture region has one or more dimensions that are less than about 1,000 μm. In some cases, the capture region has a largest lateral dimension of at most about 900 μm, 800 μm, 700 μm, 600 μm, 500 μm, 400 μm, 300 μm, 200 μm, 100 μm, 90 μm, 80 μm, 70 μm, 60 μm, 50 μm, 40 μm, 30 μm, 20 μm, 10 μm, 9 μm, 8 μm, 7 μm, 6 μm, 5 μm, 4 μm, 3 μm, 2 μm, 1 μm, 900 nm, 800 nm, 700 nm, 600 nm, or 500 nm.

In some examples, the capture region includes a charge switch material having an ionizable group that changes charge based on ambient conditions. Such charge switch materials can be useful for ion exchange procedures to capture a target (e.g., a negatively charged target, such as a nucleic acid) with a charge switch material having positive charge at low pH (e.g., a pH<6.0 or 6.5 or a pH lower than or equal to the pKa of the ionizable group). Then, the target can be eluted by releasing it from the charge switch material, such as by elution at a raised pH (e.g., a pH>8.5 or a pH higher than the pKa of the ionizable group). Exemplary charge switch materials include those with an ionizable group selected from a biological buffer (e.g., -2-acetamido-2-aminoethanesulfonic acid (ACES); N-2-acetamido-2-iminodiacetic acid (ADA); amino methyl propanediol (AMP); 3-1,1-dimethyl-2-hydroxyethylamino-2-hydroxy propanesulfonic acid (AMPSO); N,N-bis2-hydroxyethyl-2-aminoethanesulfonic acid (BES); N,N-bis-2-hydroxyethylglycine (BICINE); bis-2-hydroxyethyliminotrishydroxymethylmethane (Bis-Tris); 1,3-bistrishydroxymethylmethylaminopropane (Bis-Tris Propane); 4-cyclohexylamino-1-butane sulfonic acid (CABS); 3-cyclohexylamino-1-propane sulfonic acid (CAPS); 3-cyclohexylamino-2-hydroxy-1-propane sulfonic acid (CAPSO); 2-N-cyclohexylaminoethanesulfonic acid (CHES); 3-N,N-bis-2-hydroxyethylamino-2-hydroxypropanesulfonic acid (DIPSO); -2-hydroxyethylpiperazine-N-3-propanesulfonic acid (EPPS); -2-hydroxyethylpiperazine-N-4-butanesulfonic acid (HEPBS); -2-hydroxyethylpiperazine-N-2-ethanesulfonic acid (HEPES); -2-hydroxyethylpiperazine-N-2-propanesulfonic acid (HEPPSO); 2-N-morpholinoethanesulfonic acid (MES); 4-N-morpholinobutanesulfonic acid (MOBS); 3-N-morpholinopropanesulfonic acid (MOPS); 3-N-morpholino-2-hydroxypropanesulfonic acid (MOPSO); piperazine-N—N-bis-2-ethanesulfonic acid (PIPES); piperazine-N—N-bis-2-hydroxypropanesulfonic acid (POPSO); N-trishydroxymethyl-methyl-4-aminobutanesulfonic acid (TABS); N-trishydroxymethyl-methyl-3-aminopropanesulfonic acid (TAPS); 3-N-trishydroxymethyl-methylamino-2-hydroxypropanesulfonic acid (TAPSO); N-trishydroxymethyl-methyl-2-aminoethanesulfonic acid (TES); N-trishydroxymethylmethylglycine (TRICINE); trishydroxymethylaminomethane (Tris); polyhydroxylated imidazoles; triethanolamine dimers and polymers; and di/tri/oligo amino acids, for example Gly-Gly, Ser-Ser, Gly-Gly-Gly, and Ser-Gly), a polyhydroxylated amine (e.g., TRIS or Bis-Tris), imidazole, histidine, and polyhistidine. In some cases, the charge switch material can include Bis-Tris, a Bis-Tris polymer (e.g., formed by attachment of Bis-Tris monomers to a polyacrylic acid (PAA) backbone), PAA, or a combination of Bis-Tris and PAA (e.g., where both Bis-Tris and PAA are in polymeric form and can formed as a co-polymer or as layers including alternating Bis-Tris and PAA layers). In other cases, the charge switch material is a weakly basic polymer that has a cationic charge at acidic pH but has a neutral charge at basic pH. Such materials include poly[N-(3-imidazolylpropyl)methacrylamide hydrochloride-co-acrylamide], poly[N-(3-imidazolylpropyl)methacrylamide hydrochloride-co-2-hydroxyethyl methacrylate], poly(1-vinylimidazole), poly(2-aminoethyl methacrylate hydrochloride-co-2-hydroxyethyl methacrylate), poly(l-vinylimidazole-co-2-hydroxyethyl methacrylate), poly[N-(1,1-dimethyl-3-imidazolylpropyl)acrylamide], or poly(N-2-methyl-1-vinylimidazole). Additional charge switch materials include those that are pH-insensitive but targets charge changes. Further charge switch materials are described in U.S. Pat. Nos. 5,582,988, 6,914,137 and 7,319,004, each of which is incorporated herein by reference.

Such materials and procedures are commercially available, such as in ChargeSwitch® Technology (available in numerous formats from Invitrogen Corp. or Life Technologies™ Corp., Carlsbad, Calif., such as in a ChargeSwitch® coated membrane, magnetic bead, or well plate). Further charge switch materials and/or ion exchange processes are described in U.S. Pat. Nos. 5,234,809, 6,718,742, 6,914,137, and 7,319,004; U.S. Pub. Nos. 2003/0008320, 2005/0053941, 2003/0054395, 2003/0173284, 2003/0130499, 2005/0053941, 2006/0154247, 2006/0263780, 2007/0122809, 2006/0024712, 2012/0196944, and 2012/0197009; and Int. Pub. Nos. WO 02/48164, WO 99/29703, WO 01/88185, WO 01/03149, WO 03/101494, WO 03/046177, WO 2005/012521, and WO 2006/004611, each of which is incorporated by reference in its entirety.

The charge switch material can be combined with any useful format. In some instances, the charge switch material is combined with a magnetic particle (e.g., having a diameter between 20 μm and 1 mm) formed from any useful material (e.g., formed from magnetite, iron oxides, transition metal oxides, ferromagnetic materials, or paramagnetic materials). Exemplary charge switch materials include polymethacrylate carboxy ion-exchangers, silica particles coated with a negative charge, cellulose or agarose with phosphate or sulfate groups, or any negatively charged species. Exemplary magnetic particles are described in U.S. Pat. No. 6,718,742, which is incorporated herein by reference.

Furthermore, the capture region can include any useful substance for capturing one or more analytes. Exemplary substances include one or more of inhibitors, osmolytes, trehalose, oligosaccharides (sucrose, maltose, etc.), N-oxides, liposaccharides, alcohols (e.g., ethanol or isopropanol for precipitation), a chaotropic substance (e.g., guanidinium salt such as guanidinium (iso)thiocyanate, guanidinium thiocyanate, or guanidinium HCl, sodium iodide (NaI), sodium perchlorate ($NaClO_4$), potassium iodide, potassium bromide, sodium thiocyanate, or urea), an organic reagent, an antibody including fragments thereof, a protein (e.g., bovine serum albumin, ovalbumin, β-lactoglobulin, α-lactalbumin, myoglobin, lactoferrin, ribonuclease A, or cytochrome C), a hydrophobic or hydrophilic surface, a ligand (e.g., biotin, or any other useful ligand), etc. The capture regions can include any useful combinations of substances (e.g., any described herein), such as the combination of a chaotropic substance with one or more particles (e.g., any described herein, such as silica particles, glass particles, or diatoms).

Integration with Devices

The present system and methods can be used with any useful device, such as a microfluidic device or a macrofluidic device (i.e., a device lacking any microfluidic features). The devices of the invention can include one or more structural features, such as a substrate, a layer, a chamber (e.g., a well, a channel, a hole, a bridge, or a cavity, or any described herein), or a capture region. In particular, the chamber can be completed or partially enclosed (e.g., such as in an enclosed channel) or be open (e.g., such as in a well). The various structures described herein can have any useful dimension, cross-section, planarity, or surface characteristic. Any of the devices described herein can be used individually or in combination with the devices or with one or more features of the devices described in, e.g., U.S. Pub. Nos. 2006-0003439; 2007-0172954; 2010-0078077; 2010-0233026; 2011-0112503; 2011-0142734; 2011-0165037; 2011-0176966; 2011-0177586; and 2012-0329171; U.S. Pat. Nos. 7,129,091; 7,655,470; 7,901,939; 8,304,193; 8,273,573; and 8,329,407; U.S. patent application Ser. No. 13/648,922, filed Oct. 10, 2012; Int. Pub. Nos. WO 2004/038363; WO 2009/149257; WO 2008/079274; and WO 2006/101851; and U.S. Provisional Pat. Appl. Nos. 60/379,927; 60/394,544; 60/585,801; 60/623,261; 60/763,574; 60/875,856; 60/881,012; 60/899,449; 60/930,316; 60/936,606; 60/962,426; 61/130,930; and 61/335,570. Further, any of these devices can be used in any method described herein, as well as those methods described in the above-mentioned U.S. Pat. Nos., U.S. Pub. Nos., U.S. Pat. Appl. No., Int. Pub. Nos., and U.S. Provisional Pat. Appl. Nos., which are incorporated herein by reference.

Furthermore, any one of the devices herein can be integrated with another device. For example, the system can include a first device for nucleic acid sample preparation and a second device for amplification, where the first device is fluidically connected to the second device, and the fluid dispensing system is fluidically connected to the first device and/or the second device. In yet another example, the functionalities that can be performed in two or more devices can be built into a single, multi-structured device (e.g., a device having multiple substrates, where each functionality occurs in a separate substrate, or a device having multiple sections, where each functionality occurs in a separate section).

Integration with SlipChip Devices

In some cases, these approaches are used to control the movement of components of a SlipChip-type device. For example, the movement of the pushing unit may be used to drive the movement of a plate of a SlipChip, either directly or indirectly via an appropriate mechanical coupling mechanism. In some cases, the movement of one pushing unit may be used to initiate or stop the movement of another pushing unit.

When the system includes a SlipChip, the first relative movement of the pushing unit can be integrated with one or more components to induce slipping between the substrates in a SlipChip.

A SlipChip device can comprise one or more layers that allow for connection and disconnection of one or more chambers by relative movement. For example, in a first position, a first chamber is not connected to a second chamber (i.e., the first chamber does not fluidically communicate with the second chamber). Upon moving the first chamber relative to the second chamber, a connection is formed. This movement can be accomplished by moving the first layer having the first chamber relative to the second layer. Alternatively, this movement can include moving the second layer having the second chamber relative to the second layer. The connection between chambers can also occur via a capture region, a bridge, a membrane, or any other structure described to provide fluidic communication between a first and second chamber.

The SlipChip can include further components. For example, in a translational SlipChip design, a membrane matrix can be included in one or more layers. The layers can further include one or more fluidic connections that allow for one or more lysing steps, one or more washing steps, and one or more eluting steps. The membrane matrix, filter, or any other matrix can be integrated within a single substrate of the device, within multiple substrates of the device, or be inserted within a cavity of the device. In addition, the SlipChip device can be integrated with a capping system which can be tightened to provide positive pressure, rotate one or more layers within the device, align one or more resistant units with one or more chambers, and/or align one or more filters with one or more chambers.

This SlipChip platform can be fabricated from a variety of materials, such as glass and plastic. We have previously demonstrated a plastic rotational SlipChip with user friendly features by using 3D-printing. A user simply loads the sample into the sample chamber, close the lid to apply pressure, hold bottom disc and rotate the top portion to perform sample preparation.

The SlipChip platform can be compatible with a large variety of nucleic acid sample preparation methods, such as, for example, a combination of a chaotropic substance and a particle (e.g., any described herein, such as guanidinium thiocyanate with size-fractionated $SiO_2$ particles or with diatomaceous silicas (e.g., Celite®), as described in Boom et al., J. Clin. Microbiol. 28:495-503 (1990)), ChargeSwitch® and FTA (Whatman, GE) Chemistry. For example, SlipChip platform with ChargeSwitch® membrane has been validated with extraction of HIV viral RNA from spiked human plasma sample with efficiency comparable to commercial nucleic acid preparation method (see Examples herein).

SlipChip devices can integrate temperature control methods suitable for sample lysis for nucleic acid extraction, such as, temperature control methods based on simple phase transitions, where temperature is maintained constant during solid-liquid and liquid-solid phase transition, as described in the original application. As another example, SlipChip can be integrated with on-chip initiation mechanisms for temperature control such as initiation by slipping and mixing.

The movement of the system (e.g., for one or more pushing units) and/or device (e.g., for one or more substrates or layers) can be any useful relative movement. For instance, such movement can include axial rotation of two or more layers in the device on the same axis or rotation of two or more layers on different axes. For example, the device can include three layers, each having a cylindrical, generally planar surface. The relative movement can include axial translation of one or more layers relative to other layer(s) and/or longitudinal translation between two or more layers. In yet another instance, the movement can be a combination of axial rotation and longitudinal translation.

Accordingly, the relative movement may be linear, rotational, or a combination of both. In some instances, two-dimensional motion (e.g., X-Y motion) may be accomplished through a combination of linear and/or rotational movements. For example, sliding and rotating means may be employed to effect linear and rotational sliding motion. In addition, such means for producing relative sliding motion may be constructed from, for example, motors, levers, pulleys, gears, hydraulics, pneumatics, a combination thereof, or other electromechanical or mechanical means known to one of ordinary skill in the art. Other examples of methods of controlling the motion of one part relative to another include, but are not limited to, sliding guides, rack and pinion systems (U.S. Pat. No. 7,136,688), rotational plates (U.S. Pat. No. 7,003,104), slider assemblies (U.S. Pub. Nos. 2007-0155451 and 2008-0058039), guide grooves (U.S. Pat. Nos. 5,805,947 and 5,026,113), piezoelectric actuators (U.S. Pub. No. 2005-0009582), ball bearings and notches (U.S. Pat. No. 2,541,413), and drive cables (U.S. Pat. No. 5,114,208), each of which is incorporated herein by reference in its entirety. Moreover, motion of layers relative to one another may be constrained by notches, retainers, and/or a system of holes and mating pins, for example, as are typically used alone or in combination in electrical connectors. Also, the motion of the layers relative to one another may be constrained by a case, posts, grooves and ridges, gears, or, for example in the case of rotational motion, a central axis. In certain cases, the device is configured to be manipulated by a robot.

For any of the layers described herein, the distance between layers may vary depending on the type of substrate. In certain examples, the distance may vary in different device positions, for example due to design or surface roughness. Generally speaking, the gap may range anywhere from 0.2 nanometers to 20 micrometers. In particular examples, the gap between layers is filled with any useful lubricant, such as those described herein.

The structures within the device and/or layers can be designed to accommodate the relative movement to be exerted. For instance, when rotation movement is used to connect or disconnect the layers, then the structural elements (e.g., chambers or channels) within the layer can be arrayed in a radial or spiral pattern.

Relative movement (e.g., for the device or the components of the fluid dispensing system, such as the pushing unit) can be effected by any useful assembly. Exemplary assemblies for rotation include a rotary joint mechanism, a rotational actuation mechanism (e.g., employing a pull string for rotational actuation), and a rotational shaft assembly. The rotational motion may be achieved by standard mechanisms, including motors, springs, e.g., clock springs, pull strings, bearings, cams, rotatable hubs, cable elements, gears, and/or actuators. These mechanisms can be designed to control the number, force, and/or speed of rotations. The device may be designed to be activated only once, or it may be used indefinitely. The device may include one or more switches to prevent actuation prior to use. Switches may be disposed on the surface of the device, cap, or lid to ensure proper contact between these structures. Translation between layers may be guided by a guide/track configuration, or a ball bearing configured to slidingly engage the layers in order to limit the direction and amount of relative movement. In addition, the relative movement between the layers may be automated (e.g., using any useful mechanism, such as those described herein).

In one exemplary rotary joint mechanism, a rotatable layer is connected with a fixed layer. To achieve rotation, the rotatable layer can include an outer bearing (e.g., an outer ring bearing), and the fixed layer can include an inner bearing (e.g., an inner ring bearing), where these bearings allow for the outer bearing to rotate with respect to the inner bearing. Such bearing can include or be coupled to at least one motor (e.g., through a cable element, gear mechanism, etc.). Another exemplary assembly includes a stationary shaft interconnected to a base that is included in a fixed layer, and a rotatable layer that includes a hub rotatably interconnected to the stationary shaft. The hub can be supported in axial and radial directions by a bearing (e.g., oil- or air-filled bearing). The rotatable layer can include or be coupled to at least one motor (e.g., through a cable element, gear mechanism, etc.). The motor can be an actuator of any type, e.g., electrical motor, electroactive polymer, galvanometer actuator, hydraulic piston, microelectromechanical system (MEMS) actuator, piezoelectric actuator, relay, or stepper motor.

Additional Components of the System or Device

Fluid dispensing systems, integrated devices, and other aspects of this disclosure can employ other useful components, including but not limited to air vents, electrical circuits, pressurization apparatuses, loading apparatuses, injection ports, heating elements, cooling elements, lysis components, detectors, electrodes, markers, and other elements.

Fluid metering structures can be present in a system or device. For example, fluid from a resistant unit (e.g., a blister or blister pack) can be dispensed through an inlet 3101, as shown in FIG. 31A. An inner well or chamber with a metered volume 3102 can be filled with fluid, as shown in FIG. 31B. Excess fluid can overflow into an outer overflow well or chamber 3103, allowing only the metered fluid volume to be used in subsequent operations, for example as shown in FIG. 31C.

Air vents can be present in a system or device. For instance, when particular assays require heating, having an open system may be useful in order to prevent pressure buildup. Accordingly, one or more air vents can be fluidically connected to a chamber in the device (e.g., one or more process chambers) that allows for access to the environment. In some cases, the air vent further includes a valve, whereby the valve can be opened to fluidically connect the air vent to the chamber. Valves can be controlled manually or automatically. A valve may be useful when reagents are provided within the device in a stored, dried, or inactivated state.

One or more valving systems can be present in the system or device. For instance, one or more valves can be included in the device to control the fluidic communication between chambers or between chambers and resistant units. One or more valves can be used to control a fluid connection between one or more resistant units or between resistant units and chambers. Valves can be controlled manually or automatically.

Electrical circuits can be present in a system or device. For instance, a circuit may underlie the fluid dispensing system, the device, or both. In some cases, a circuit can include one or more conductive structures having junctions that can be reversibly contacted with one or more conductive materials, where such conductive materials can be dispensed in a time-dependent manner from one or more resistant units (e.g., as described herein). The electrical circuit can used to connect one or more components, including but not limited to coolers, heaters, valves, switches, pushing units, resistant units, barrier units, power sources (e.g., batteries), sensors, detectors, communications equipment, and other components.

Any of the devices or systems herein can include electrically conductive material (e.g., one or more electrodes, including arrays thereof). Such electrodes and arrays may be useful for conducting electrochemical reactions for detection, separation (e.g., electrophoretic separation), transport, and/or synthesis. In some cases, one or more electrodes are arranged to allow for connection or disconnection upon relative movement of the layers.

Detectors can be present in a system or device. For example, imaging or sensor components can be used to record or measure reactions within a device by techniques including but not limited to optical detection, x-ray detection, absorption spectrometry, matrix-assisted laser desorption/ionization (MALDI), mass spectrometry, Raman spectrometry, fluorescence correlation spectroscopy (FCS), fluorescence polarization/fluorescence correlation spectroscopy (FP/FCS), fluorometric detection, colorimetric detection, chemiluminescence, bioluminescence, scattering, surface plasmon resonance, electrochemical detection, electrophoresis, lasers, or fluorescent imaging plate reader (FLIPR®, Molecular Devices) assays. Examples of such detectors and imaging devices can be found in U.S. Pub. No. 2009-0010804 and Int. Pub. No. WO 2008/002267, both of which are incorporated herein by reference. The detector can comprise any detector suitable to detect a signal from a device, and can be selected from the group consisting of: a web camera, a digital camera, a digital camera in a mobile phone and a video camera, as described in Int. Pub. No. WO 2008/002267, incorporated by reference herein in its entirety. The detector can comprise a camera or imaging device which has adequate lighting and resolution for spatially resolving individual signals produced by the device, as described in U.S. Pub. No. 2009-0010804, incorporated by reference in its entirety. The detector can comprise any solid state image sensor including a charged coupled device (CCD), charge injection device (CID), photo diode array (PDA), or complementary metal oxide semiconductor (CMOS). The detector can comprise a photomultiplier tube (PMT).

Markers, such as lines, dots or visible substances in ducts and/or chambers can be present in a system or device. Markers can be used to enable registration or analysis. Registration marks may be included on the device to allow for automatic correction of optical aberrations, or adjustment of the image for the angle and orientation at which the picture was taken. For detecting fluorescent output, chirped excitation/readout can be used. For example, a device can be exposed to blue excitation light for, for example, nanoseconds, then turned off, and fluorescence may be detected, for example, a nanosecond later. Then, ten nanoseconds later, for example, another image is collected (without an initial excitation flash) to produce a background intensity image for subtraction. In this manner, fluorescence can be analyzed even in daylight. For safety, the detector could be designed to recognize the device automatically, for example if the device includes a recognizable pattern, such that the detector would only produce the excitation light when pointed at the device (see Sia et al., Angewandte Chemie Int. Ed. 43:498-502 (2004), incorporated by reference herein, which describes additional means for detecting signals in multifluidic devices, including using pulse modulation to reduce noise). Detection can also be improved by using the polarization of excited/emitted light, as is known to those skilled in the art.

Any of the devices or systems herein can be integrated with a pressurization apparatus (e.g., any described herein), a loading apparatus (e.g., any described herein), an injection port for serial and/or sequential filling of the chamber(s), a heating element, an on-chip lysis component, or molecular recognition module. For instance, the device can be integrated temperature control methods suitable for sample lysis for nucleic acid extraction, such as, temperature control methods based on simple phase transitions, where temperature is maintained constant during solid-liquid and liquid-solid phase transition, as described in the original application. As another example, the device can be integrated with on-chip initiation mechanisms for temperature control, such as initiation by relative movement (e.g., slipping) and mixing.

Lids or caps to generate pressure can be present in a system or device. A housing for a system or device can include a lid having a through-hole. In an open or partially open system, the relevant volume is $V=V_0=V_1+\Delta V$, where $\Delta V$ encompasses any volume difference between a completely closed system (complete closure of the lid) and an open system (without a lid) or a partially open system (partial closure of the lid). In a completely closed system, the relevant volume is $V=V_1$, where $V_1$ is the volume of the cavity when completely enclosed. The generated pressure P is commensurate with these changes in volume V and the force applied during closing. In an open or partially open system, generated pressure $P=P_0$, which is not sufficient to drive a sample into the device. In a closed system, generated pressure $P=P_0+\Delta P$, where $\Delta P=P_0*\Delta V/V_1$. Thus, the volume difference induced by closing the lid generates additional pressure which can be used to fill the device. A positive pressure can be created by pushing a rigid cap or lid on to the on-chip reservoir or housing system. The cap or lid can be designed so that it cannot be 'half on' but and only be 'fully off' or 'fully on'. Attaching a cap can apply a positive pressure of around 50 mBar to a well, which pressure can be generated by compressing a gas (e.g., air) in the well. Making the well quite large, and optionally conical in shape, can reduce the effect on the generated pressure due to variations in the volume to be loaded.

The devices, methods, and systems of the invention can include any number of characteristics, elements, modifications, or benefits, including but not limited to being sterile before use (e.g., the device can be assembled in a sterile environment and then packed in a sealed container until sample collection); being resistant to interference and contaminants until final analysis (e.g., a lubricant can be provided between the layers and can act as a barrier between the sample and the external world to prevents contamination and avoids leaks of potentially dangerous analytes present in the stored samples); being capable of electrical power-free usage, wherein a device or system can require no power for fluid handling (autonomous biospecimen collection) or drying (no need for heating or ventilation); being adaptable for easy digitized storage and rehydration (e.g., the device allows for precise manipulation of many volumes in parallel, where the sample can be split or partitioned into small volumes or aliquots and preserved in a digitized format, and such samples can be selectively, fully, or partially recovery for on-chip or off-chip analysis); being easy to manufacture (e.g., amenable to mass production using inexpensive materials and fabrication techniques); being modular and reconfigurable (e.g., some of these devices allow for the development of separate modules, which can be combined to produce a complete device, and each module can thus be developed separately and then integrated in the platform); being easy to use (e.g., samples can be collected by users with minimal training and without any external equipment, where necessary steps from biospecimen collection to sample preservation can be either autonomous or require minimal action from the user (e.g. slipping the plates or pushing a button)); being adaptable for various sample sizes (e.g., some of these devices allow for easy manipulation of volumes in a wide range (1 nL-1 mL), which includes the typical volume of biospecimen collection in limited-resource settings (e.g. the amount of blood obtained from a finger prick)); being compatible with commercial dry preservation matrices or desiccants (e.g., multi-target or multi-analyte stabilization can be achieved (including for DNA, RNA, and/or proteins), for instance by using different matrices in different parts of the storage device); being upgradable with different matrices or desiccants (e.g., new matrices, desiccants, or drying agents can be easily incorporated in the platform, accommodating integration of new developments in matrix formulation); being capable of rapid drying (e.g., drying in less than 10 minutes, which arises from working at small dimensions and can be a critical issue in preserving samples sensitive to degradation); and being adaptable for sample re-collection and downstream analysis (e.g., rehydration can be easily achieved on chip in order to recover the preserved sample).

Assays and Operations

Assays

This disclosure provides systems, devices, and methods for performing assays, reactions, and other operations. The assays, reactions, and other operations include but are not limited to sample preparation, sample purification, sample enrichment, detection, high throughput screening, multiplex assays, nucleic acid amplification (e.g., PCR, ramification amplification (RAM)), TaqMan assays, immunoassays, sandwich immunoassays, ELISA, chemotaxis, and synthesis reactions (e.g., catalysis, multistep reactions, immobilized multistep synthesis (e.g., small molecule, peptide and nucleic acid syntheses), solid state synthesis, or radioisotope synthesis). The assays, reactions, and other operations can also comprise digital PCR or digital isothermal recombinase-polymerase amplification (RPA) amplification technologies using commercially available stock reagents. Many other isothermal techniques can be performed, including but not limited to loop-mediated isothermal amplification (LAMP) and nucleic acid sequence-based amplification (NASBA), for quantification of analytes (even in the presence of interference).

Systems, devices, and methods can also be used to detect and quantify analytes including pathogens involved in pneumonia and/or quantification of viral load. In some cases, the resistant units can contain preloaded reagents for isothermal amplification chemistry for various pathogens, bacteria, or viruses (e.g., CMV, HRV, HIV, hepatitis C virus, *Chlamydia* spp., gonorrhea, *S. pneumonia*, HIV, *Mycobacterium tuberculosis*, or *H. influenzae* type b) with an optional additional reverse transcription step for detection of RNA viruses. Diagnosis of tuberculosis can be performed by stochastic confinement on a device, which can be used to amplify physiological responses of *Mycobacterium tuberculosis* and enable rapid detection and phenotypic testing of drug resistance. Quantification of CD4 count (e.g., using PCR), for example in HIV/AIDS patients, can be performed efficiently using multivolume stochastic confinement.

Samples and Reagents

The systems, devices, and methods described herein can be used with any useful sample and/or reagent. In particular, a system (e.g., in one or more resistant units) and/or device can be pre-loaded with any useful reagent (e.g., a desiccant, a matrix, or any described herein), or the device can be provided as part of a kit including the device and one or more useful reagents.

Samples can be obtained from a subject (e.g., human subject, an animal subject, a plant subject), a food sample (e.g., including an organism), or an environmental sample (e.g., including one or more organisms). Exemplary, non-limiting samples include blood, plasma, serum, sputum, urine, fecal matter (e.g., stool sample), swab, sweat, spinal fluid, amniotic fluid, interstitial fluid, tear fluid, bone marrow, tissue sample (e.g., a skin sample or a biopsy sample), a buccal mouthwash sample, an aerosol (e.g., produced by coughing), nucleic acid, cell (e.g., tumor cells, fetal cells in blood, stem cells, bacterial and fungal cells, T-cells, or B-cells), protein, enzyme, soil, water, compost pile, manure pile, sediment (e.g., marine or freshwater sediment), a water sample, an air sample, rock, a plant sample, a food sample, or a gut sample. The sample can include any useful target or analyte to be detected, filtered, concentrated, and/or processed.

Any analyte of interest can be present in the sample. Such analytes can be processed, captured, preserved, and/or removed for further analysis, treatment, reaction, and/or detection. Exemplary analytes include those described herein, such as those present in a test sample (e.g., any described herein), as well as one or more of the following: a protein (e.g., one or more antibodies such as Epstein-Barr virus (EBV) antibodies, hepatitis antigen/antibodies (e.g., hepatitis A, B, or C), or HIV antibodies, C-reactive protein (CRP), apolipoprotein (e.g., A-I or B), IGFBP-2, IGFB-3, transferrin receptor, lipoprotein (e.g., (a), B/A-1, or β), thyroglobulin, or hemoglobin (e.g., including glycosylated hemoglobin or HbA1c)), a nucleic acid (e.g., RNA or DNA), a cell (e.g., CD4+ lymphocyte), a virus (e.g., a whole virus, including HIV, CMV, hepatitis C virus, hepatitis B virus, hepatitis A virus, or herpes simplex virus), a parasite (e.g., *Toxoplasma gondii, Plasmodium falciparum, Trypanosoma cruzi, Giardia lamblia, Leishmania* spp, *Echinococcus granulosus, Schistosoma haematobium*, or *Brugia malayi*), bacteria (e.g., *Chlamydia* spp., *Neisseria gonorrhoeae, Mycobacterium leprae, Helicobacter pylori, Brucella* sp, or *Treponema pallidum*), a cytokine (e.g., IL-1, IL-1b, IL-2, IL-6, IL-7, IL-10, IL-13, IL-17, IFN, IFNg, TNF, or TNF-beta), an antibody (e.g., any herein), a hormone (e.g., estradiol, progesterone, prolactin, cortisol, dehydroepiandrosterone (DHEA, including its sulfate ester, DHEA-S), follicle-stimulating hormone (FSH), thyrotropin (TSH), thyroxine (T4), triiodothyronine (T3), luteinizing hormone (LH), insulin, leptin, sex hormone binding globulin (SHBG), somatomedin-C(IGF-1), testosterone, or androstenedione), an amino acid (e.g., arginine, histidine/urocanic acid, homocysteine, phenylalanine/tyrosine, and/or tryptophan), a drug (including candidate drugs or investigational new drugs for clinical trials), a small molecule (e.g., a peptide or peptoid, folate, or glucose), a contaminant (e.g., Hg, $H_2S$, sulfur oxides, etc.), a gas or vapor (e.g., oxygen, CO, $CO_2$, or any described herein), a volatile component (e.g., a volatile organic compound), an enzyme (e.g., a proteinase, an amylase, a protease, a glucanase, a lipase, a lactase, an amyloglucosidase, a glucoamylase, a protease, an isomerase, a cellulase, a ligninase, a xylanase, a catalase, a polymerase, trypsin, prostate-specific antigen (PSA), iduronidase, acid α-glucocerebrosidase (ABG), acid α-galactosidase A (GLA), lysosomal acid α-glucosidase (GAA), galactocerebroside α-galactosidase (GALC), or acid sphingomyelinase (ASM)), a sterol (e.g., cholesterol (e.g., including total cholesterol or high-density lipoprotein cholesterol (HDL)), or triglycerides).

Such analytes can be preserved (e.g., using any device herein, such as those having one or more membranes and/or bridges), analyzed (e.g., using any device herein, such as those having one or more capture regions), or preserved and analyzed (e.g., using any device herein, such as those having one or more membranes, bridges, and/or capture regions).

The system (e.g., in one or more resistant units) and/or device can be pre-loaded prior to use or subsequently loaded during use with any useful reagents. These reagents could also be included in any feature of the device, such as one or more chambers, layers (including portions thereof, such as, e.g., the portion of the layer lacking one or more chambers), capture regions, bridges, and/or membranes. Furthermore, such reagents can be used in gas, liquid, or solid form, as well as in a coating on the one or more features or in a coating on one or more solid supports (e.g., beads, particles, etc.) within one or more features, where such features include, e.g., one or more chambers, layers (including portions thereof, such as, e.g., the portion of the layer lacking one or more chambers), capture regions, bridges, and/or membranes.

Exemplary reagents include a desiccant (e.g., any described herein), a matrix (e.g., a stabilization matrix, such as any described herein), an organic or inorganic chemical, a compound, a mixture, a solution, an emulsion, a dispersion, a suspension, a molecule, an ion, a dimer, a macromolecule such as a polymer or protein, a nucleic acid, a biomolecule, an oligosaccharide (e.g., trehalose, sucrose, or maltose), an anticoagulant (e.g., heparin, EDTA, citrate, or oxalate), an inhibitor (e.g., to inhibit growth of one or more bacteria and/or other organisms, such as a chelator (e.g., any described herein), an antibiotic, a fluorinated polymer, PEG, albumin, a biocompatible coating (e.g., PDMS), an antifouling agent (e.g., tributyltin), or a biocide), a precipitate, a crystal, a chemical moiety or group, a particle, a nanoparticle, a reaction product, a solvent, a buffer (e.g., a washing buffer (e.g., Tris/EDTA; 70% ethanol; STET (Saline/Tris/EDTA/Triton* X-100 Solution); saline-sodium citrate (SSC) buffer; SSPE (0.2 M phosphate buffer, pH approx. 7.4, containing 2.98 M NaCl, and 0.02 M EDTA); FTA purification reagent, and the like) or an elution buffer (e.g., TRIS/EDTA; TRIS/acetate/EDTA, for example 4 mM Tris-acetate (pH 7.8), 0.1 mM EDTA, and 50 mM NaCl; TRIS/borate; TRIS/borate/EDTA; potassium phosphate/DMSO/glycerol; NaCl/TRIS/EDTA; NaCl/TRIS/EDTA/TWEEN; TRIS/NaCl/TWEEN; phosphate buffers; TRIS buffers; HEPES buffers; nucleic acid amplification buffers; or nucleic acid hybridization buffers)), a lysis agent (e.g., an enzyme (e.g., a lysosyme, a trypsin, proteinase K, or other proteases), a detergent (e.g., Triton X-100 (polyethylene glycol p-(1,1,3,3-tetramethylbutyl)-phenyl ether) or sodium dodecyl sulfate), or a chaotropic substance, such as any described herein), a chelating agent (e.g., diethylenetriaminepentaacetic acid (DTPA), ethylenediaminetetraacetic acid (EDTA), ethylene glycol tetraacetic acid (EGTA), trans-1,2-diaminocyclohexane-N,N,N',N'-tetraacetic acid (CDTA), 1,2-bis(2-aminophenoxy)ethane-N,N,N',N'-tetraacetic acid (BAPTA), 1,4,7,10-tetraazacyclododecane-1,4,7,10-tetraacetic acid (DOTA), N-(2-hydroxyethyl)ethylenediamine-N,N',N'-triacetic acid, or nitrilotriacetic acid (NTA)), a reducing agent (e.g., 2-mercaptoethanol, thiosulfate, TCEP (tris-(2-carboxyethyl)phosphine), dithiothreitol, or dithioerythritol), a dye, a stabilizer, a marker, a salt (e.g., a urate salt), a surfactant (e.g., an anionic surfactant, such as sodium dodecyl sulfate, or a cationic surfactant), a base (e.g., a weak base, such as trishydroxymethyl methane), a fluorophore, or a fluid, any one of which may exist in the solid, liquid, or gaseous state. Further, any of these reagents can be combined with any other useful structure or solid support described herein, such as a filter, a membrane, or a particle, or any described for a capture region. In addition, one or more reagents can be combined in any useful manner.

In particular, one or more desiccants can be useful when storing, preserving, treating, and/or preparing a sample. Exemplary desiccants include anhydrous calcium sulfate (gypsum, such as Drierite® (particle size (mesh) from 4, 6, 8, 10-20, or 20-40)), aluminas (such as activated aluminas, e.g., aluminum oxide or $Al_2O_3$), glass, silicas (e.g., $SiO_2$ (e.g., size-fractionated $SiO_2$ particles, such as those having a diameter of about 2 μm to about 10 μm), silica gel, Ascarite II® absorbents (e.g., carbon dioxide adsorbents including sodium hydroxide-coated silica), or diatomaceous silicas (e.g., Celite®, Celatom®, CAFA (Celite® Analytical Filter Aid))), a hygroscopic polymer and/or salt (e.g., including but not limited to $CaCl_2$, CaO, $ZnCl_2$, KOH, NaOH, $CaH_2$, $CaSO_4$, and $Na_2SO_4$), molecular sieves (or crystalline metal aluminosilicates, e.g., 3A, 4A, 5A, or 13X types in powder or bead forms), activated carbon (e.g., lignite carbon in granular or powder forms), montmorillonites (e.g., ($Al_2O_3.4SiO_2.xH_2O$)), or drying agents (e.g., barium oxide, boron oxide, calcium salts (e.g., calcium chloride or calcium hydride), copper(II) sulfate, lithium aluminum hydride, magnesium oxide, magnesium perchlorate, magnesium sulfate, phosphorus pentoxide, potassium hydroxide, sodium, sodium hydroxide, or sodium-potassium alloy (e.g., 22% sodium or 44% sodium)).

Lubricants

The systems, devices, and methods can include any useful lubricant. In some examples, the lubricant is used as a sacrificial fluid (e.g., as described herein), facilitates movement of the first, second, and/or intermediate substrates or layers, and/or minimizes contamination between the first, second, and/or intermediate layers or chambers within these layers or substrates.

In addition, the lubricant can be selected to be substantially inert with respect to the substances (e.g., reagents and/or samples) that will be in contact with and/or transported through the device. For instance, the lubricant can optionally be a fluid that is substantially immiscible with the reagent(s) and/or sample(s). The lubricant can optionally be selected to have physical characteristics that promote compartmentalization of the reagent(s) and/or sample(s). For instance, the layers and/or chambers can be fluorophilic, and the lubricant can be a fluorous liquid. In this example, compartmentalization occurs by competing surface characteristics, where surface tension results in separating reagent and/or sample fluids into separate plugs or droplets encapsulated by the lubricant.

Exemplary lubricants include a hydrocarbon, a fluorous substance, an ionic liquid, a non-Newtonian fluid, or a lubricating powder or bead. Exemplary hydrocarbons include alkanes, paraffin oils, hexane, hexadecane, silicon oil, greases (e.g., Dow Corning high vacuum grease, Fomblin vacuum grease, Krytox greases), mineral oil, and other organic materials or polymers, as well as mixtures thereof. Exemplary fluorous substances include fluorocarbons (including perfluorinated and semifluorinated alkanes, e.g., octadecafluoro-decahydronaphthalene and perfluorooctylethane), alkyl and aryl fluorocarbons, halofluorocarbons (e.g., perfluorooctyl bromide), fluorinated alcohols (e.g., 1-(1,2,2,3,3,4,4,5,5,6,6-undeca-fluorocyclohexyl)ethanol or $C_6F_{11}C_2H_4OH$), fluorinated oils, liquid fluoropolymers (e.g., perfluoropolyethers), Fluorinert (3M), Krytox oils, Fomblin oils, and Demnum oils.

Ionic liquids include a cation and an anion, which form a salt and are in a liquid state. Exemplary cations include choline; imidazolium-based cations, such as optionally substituted imidazolium-based cations (e.g., 1-$C_{1-10}$ alkyl-3-$C_{1-10}$ alkyl-imidazolium, (3-$C_{1-10}$ alkyl-imidazolium-1-yl)-$C_{1-10}$ alkanol, or 1-$C_{1-10}$ alkyl-2,3-di-$C_{1-10}$ alkyl-imidazolium, such as 1-$C_{1-10}$ alkyl-3-methyl-imidazolium, (3-methylimidazolium-1-yl)-$C_{1-10}$ alkanol, or 1-$C_{1-10}$ alkyl-2,3-dimethylimidazolium) or bicyclic imidazolium-based cations (e.g., optionally substituted 2,3-$(CH_2)_{2-6}$-imidazolium, such as 1-alkyl-2,3-trimethyleneimidazolium or 1-alkyl-2,3-tetramethyleneimidazolium); pyridinium-based cations, such as 1-$C_{1-10}$ alkyl-pyridinium; pyrrolidinium-based cations, such as 1-$R_1$-1-$R_2$-pyrrolidinium, where each of $R_1$ and $R_2$ is independently $C_{1-10}$ alkyl; ammonium-based cations, such as $NR_1R_2R_3R_4$, where each of $R_1$, $R_2$, $R_3$, and $R_4$ is independently $C_{1-10}$ alkyl; and phosphonium-based cations, such as $PR_1R_2R_3R_4$, where each of $R_1$, $R_2$, $R_3$, and $R_4$ is independently $C_{1-10}$ alkyl. Exemplary anions (e.g., such as X for any ionic liquid described herein) include a halogen (e.g., fluoride, bromide, chloride, or iodide); a phosphate anion (e.g., hexafluorophosphate [$PF_6$], dihydrogen phosphate [dhp], or tris(pentafluoroethyl) trifluorophosphate [FAP]); a borate anion (e.g., tetracyanoborate [TCB], tetrafluoroborate [$BF_4$], or bis(oxalato)borate [BOB]); a sulfonylimide anion $N(SO_2C_nF_{2n+1})(SO_2C_mY_{2m+1})$, where each of n and m is, independently, an integer between 1 to 10, and optionally n=m, such as bis(trifluoromethanesulfonyl)imide ($N(SO_2CF_3)_2$ or [TFSI]) or bis(perfluoroethanesulfonyl) imide ($N(SO_2C_2F_5)_2$; [BETI] or [PFSI]); a sulfonate anion (e.g., triflate [$SO_3CF_3$], mesylate [$SO_3CH_3$], or tosylate [$SO_3C_6R_1CH_3$]); an alkylsulfate anion (e.g., $C_{1-10}$ alkyl-$OSO_3$); a cyanimide anion (e.g., [$(CN)_2N$]); or a carboxylate anion (e.g., formate, acetate, lactate, oxalate, citrate, malate, glycolate, or saccharinate).

Exemplary ionic liquids include choline ionic liquids (e.g., choline dihydrogen phosphate (choline dhp) or choline saccharinate); 1-alkyl-3-methylimidazolium [R-mim] ionic liquids (e.g., such as 1-alkyl-3-methylimidazolium anion [R-mim][X] ionic liquids, including 1,3-dimethylimidazolium iodide, 1-ethyl-3-methylimidazolium bromide, 1-propyl-3-methylimidazolium bromide, 1-propyl-3-methylimidazolium chloride, 1-propyl-3-methylimidazolium bis(trifluoromethanesulfonyl)imide, 1-propyl-3-methylimidazolium bis(perfluoroethanesulfonyl)imide, 1-butyl-3-methylimidazolium bromide, 1-butyl-3-methylimidazolium chloride, 1-butyl-3-methylimidazolium bis(trifluoromethanesulfonyl)imide, 1-butyl-3-methylimidazolium bis(perfluoroethanesulfonyl)imide, 1-pentyl-3-methylimidazolium bromide, 1-hexyl-3-methylimidazolium bromide, 1-heptyl-3-methylimidazolium bromide, 1-octyl-3-methylimidazolium bromide, or 1-nonyl-3-methylimidazolium bromide); (3-methylimidazolium-1-yl)alkanol [ROH-mim] ionic liquids (e.g., such as (3-methylimidazolium-1-yl)alkanol anion [ROH-mim][X] ionic liquids, including 3-(3-methylimidazol-3-ium-1-yl)propan-1-ol bromide, 3-(3-methylimidazol-3-ium-1-yl)propan-1-ol chloride, 4-(3-methylimidazol-3-ium-1-yl)butan-1-ol bromide, 5-(3-methylimidazol-3-ium-1-yl)pentan-1-ol bromide, or 6-(3-methylimidazol-3-ium-1-yl)hexan-1-ol bromide); 1-alkyl-2,3-dimethylimidazolium [R-dmim] ionic liquids (e.g., such as 1-alkyl-2,3-dimethylimidazolium anion [R-dmim][X] ionic liquids, including 1,2,3-trimethylimidazolium iodide, 1-ethyl-2,3-dimethylimidazolium bromide, 1-propyl-2,3-dimethylimidazolium bromide, 1-butyl-2,3-dimethylimidazolium bromide, 1-pentyl-2,3-dimethylimidazolium bromide, 1-hexyl-2,3-dimethylimidazolium bromide, 1-heptyl-2,3-dimethylimidazolium bromide, 1-octyl-2,3-dimethylimidazolium bromide, or 1-nonyl-2,3-dimethylimidazolium bromide); 1-alkyl-2,3-trimethyleneimidazolium [R-3C-im] ionic liquids (e.g., such as 1-alkyl-2,3-trimethyleneimidazolium anion [R-3C-im] [X] ionic liquids, including 1-methyl-2,3-trimethyleneimidazolium iodide, 1-ethyl-2,3-dimethyleneimidazolium bromide, 1-propyl-2,3-dimethyleneimidazolium bromide, 1-butyl-2,3-dimethyleneimidazolium bromide, 1-pentyl-2,3-dimethyleneimidazolium bromide, or 1-hexyl-2,3-dimethyleneimidazolium bromide); 1-alkyl-2,3-tetramethyleneimidazolium [R-4C-im] ionic liquids (e.g., such as 1-alkyl-2,3-tetramethyleneimidazolium anion [R-4C-im][X] ionic liquids, including 1-methyl-2,3-tetramethyleneimidazolium iodide, 1-ethyl-2,3-tetramethyleneimidazolium bromide, 1-propyl-2,3-tetramethyleneimidazolium bromide, 1-butyl-2,3-tetramethyleneimidazolium bromide, 1-pentyl-2,3-tetramethyleneimidazolium bromide, or 1-hexyl-2,3-tetramethyleneimidazolium bromide); and 1-butyl-3-methylimidazolium [Bmim] ionic liquids (e.g., such as 1-butyl-3-methylimidazolium anion [Bmim][X] ionic liquids, including 1-butyl-3-methylimidazolium hexafluorophosphate (Bmim $PF_6$) or 1-butyl 3-methylimidazolium lactate (Bmim lactate)).

In particular examples, the following ionic liquids can be used in combination with a nucleic acid (e.g., DNA and/or RNA): 1-alkyl-3-methylimidazolium [R-mim] ionic liquids (e.g., such as [R-mim] [X] ionic liquids or any described herein); (3-methylimidazolium-1-yl)alkanol [ROH-mim] ionic liquids (e.g., such as [ROH-mim][X] ionic liquids or any described herein); 1-alkyl-2,3-dimethylimidazolium [R-dmim] ionic liquids (e.g., such as [R-dmim][X] ionic liquids or any described herein); [R-3C-im] ionic liquids (e.g., such as [R-3C-im] [X] ionic liquids or any described herein); [R-4C-im] ionic liquids (e.g., such as [R-4C-im][X] ionic liquids or any described herein); or [Bmim] ionic liquids (e.g., [Bmim][X] ionic liquids or any described herein). Further ionic liquid are described in Shi et al., Chem. Commun. 48:5325-5327 (2012), Wang et al., Anal. Chem. 79:620-625 (2007), and Fukaya et al., AE1—Fourteenth International Symposium on Molten Salts Joint International Meeting, Oct. 3-Oct. 8, 2004, "Evaluation of a series of imidazolium based ionic liquids as solvents for nucleic acids," Abstract 2437, each of which is incorporated herein by reference in its entirety.

Exemplary non-Newtonian fluids include shear-thickening fluids, gels, including hydrogels, and carbohydrate-rich or lipid-rich phases, including lipidic cubic phase and other lipid mesophases. In some cases, permeability to gases may be desirable, for example in some applications that use live cells and tissues inside the device. Exemplary lubricating powders or beads include various Teflon® beads or powders (e.g., composed of PTFE (poly(1,1,2,2-tetrafluoroethylene), PFA (perfluoroalkoxy copolymer resin), or FEP (fluorinated ethylene propylene resin)), graphite, molybdenum disulfide, or tungsten disulfide. Any of these lubricants can optionally include one or more surfactants, for example to cause or prevent surface aggregation and/or to influence the stability of substances.

Immiscible Fluid

The systems, devices, and methods can include any useful immiscible fluid. In some examples, the immiscible fluid is used as a sacrificial fluid (e.g., as described herein) and/or facilitates compartmentalization of one or more substances (e.g., a sample, a reagent, or any other useful substance, as described herein) in one or more first, second, and/or intermediate layers or chambers within these layers. In other examples, the immiscible fluid facilitates flow through one or more capture regions (e.g., as described herein).

An immiscible fluid is a fluid (e.g., a gas or a liquid) that is immiscible with one or more of the second fluids at certain ranges of temperature, pressure, and composition useful for storing, preserving, processing, or analyzing the sample. In some cases, the second fluid is an aqueous solution, a sample for storage, preservation, processing, or analysis, and/or a reagent for storing, preserving, processing, or analyzing the sample. In other cases, the fluid is immiscible with water or an aqueous solution.

Miscibility can be tested with any useful method under useful conditions for temperature, pressure, and composition. Generally, these useful conditions will be similar to those useful for sample storage, preservation, processing, or analysis. Useful temperature and pressure conditions include those for maintaining stability of the desired sample to be tested and/or the reagent(s) for use with this sample (e.g., a temperature of from about −80° C. to about 150° C., as well as any ranges therein, and a pressure generally of about 1 atm), as well as those for conducting the storage, preservation, processing, or analysis methods described herein. For instance, when the sample is a human blood sample, this sample should be maintained at or below the physiological temperature of about 37° C. Thus, useful immiscible fluids can be tested at a range of from about −80° C. to about 40° C. Further, if the human blood sample includes one or more nucleic acids that require additional analysis (e.g., by PCR requiring thermocycling at increased temperature of >90° C.), then useful immiscible fluids can be tested at a range from about −80° C. to about 100° C. Useful compositions include various ratios of the fluid to be tested for immiscibility in a mixture with a test sample, reagent, or substance, such as ratios to be used within the device for sample storage, preservation, processing, or analysis.

Methods for testing miscibility include, but are not limited to, light scattering, X-ray scattering, and/or neutron scattering to determine whether a single phase is present in a mixture (indicating miscibility) or multiple phases are present in a mixture (indicating immiscibility).

Exemplary immiscible fluids include ionic fluids, aqueous—aqueous immiscible fluids., oils, fluorocarbons, etc., as well as any lubricant described herein.

The immiscible fluid can be used as a component of any fluid, solution, or buffer described herein. For instance, the immiscible fluid can be included in one or more of a lubricant, a washing buffer, and/or an elution buffer. In some cases, the elution buffer (e.g., as described herein, such as for sample preparation) includes one or more immiscible fluids. For example, the immiscible fluid can be used to elute small volumes (e.g., about 750 µL, 500 µL, 250 µL, 100 µL, 50 µL, 10 µL, 5 µL, 1 µL, 750 nL, 500 nL, 250 nL, 100 nL, 50 nL, 10 nL, 5 nL, 1 nL, 750 pL, 500 pL, 250 pL, 100 pL, 50 pL, 10 pL, 5 pL, 1 pL, 750 fL, 500 fL, 250 fL, 100 fL, 50 fL, 10 fL, 5 fL, 1 fL, 750 aL, 500 aL, 250 aL, 100 aL, 50 aL, 10 aL, 5 aL, or 1 aL, including any ranges for these values, as described herein) from a chamber or a capture region. In one non-limiting example, the elution buffer, which can include one or more immiscible fluids (e.g., one or more ionic fluids, such as any described herein), removes water from the substance passing through the capture region. For example, the method includes filling or adding an elution buffer (e.g. including one or more immiscible fluids, such as an ionic liquid) to one or more capture regions, thereby removing and/or capturing an eluent (e.g., water, a target, an analyte, a nucleic acid, a sample, an impurity, etc.) with the elution buffer (e.g., immiscible fluid). In yet other non-limiting examples, the elution buffer including one or more immiscible fluids (e.g., one or more ionic fluids, such as any described herein) extracts an analyte (e.g., a nucleic acid, a target, a protein, an impurity, or any useful component of a sample).

Temperature Control

The systems, devices, and methods described in this disclosure can comprise a temperature controller. A temperature controller can generate heat or provide cooling in a controlled manner.

A temperature controller can comprise a heater/cooler unit. A heater/cooler unit can generate heat or consume heat by one mechanism or by a combination of mechanisms, including but not limited to chemical reactions (e.g., endothermic or exothermic chemical reactions), electrical heating/cooling (e.g., resistive heating, Peltier devices), optical heating/cooling, physical mechanisms (e.g., such as for example phase transitions, dilution, mixing, dissolution, nucleation, crystallization) and mechanical mechanisms (e.g., example friction). For example, a chemical reaction can comprise one or a combination of endothermic/exothermic chemical reactions, such as for sample, an acid-base reaction, a reaction of Mg/Fe alloy with a reaction buffer, or a reaction of CaO with water buffer. Reagents, buffers, and other components for temperature control can be stored in resistant units, and can be physically separated by methods such as blisters, blister packs, foil packs, capsules, membranes, gels, fluids, gases and any other compartment or chamber described herein.

A temperature controller can control the temperature in a temperature control area. The temperature control area can comprise one area or multiple areas that require temperature control, such as for example, reaction areas, mixing areas, imaging areas, or incubation areas. Thermal gradients can be generated by using a combination of multiple elements above. These thermal gradients can be used for continuous flow PCR, for example. Additionally, relative movement or slipping can be applied to change temperature over time. A temperature controller can provide rapid heat conduction. A temperature controller can reach a set point temperature in less than or equal to about 10 minutes, 5 minutes, 2 minutes, 1 minutes, or 10 seconds. A temperature controller can change temperature in a temperature control area at a rate greater than or equal to about 100° C./second, 90° C./second, 80° C./second, 70° C./second, 60° C./second, 50° C./second, 40° C./second, 30° C./second, 20° C./second, 10° C./second, 9° C./second, 8° C./second, 7° C./second, 6° C./second, 5° C./second, 4° C./second, 3° C./second, 2° C./second, or 1° C./second. The temperature controller can provide a well-controlled temperature, with temperature variation around the set point of less than 6° C., 5° C., 4° C., 3° C., 2° C., 1° C., 0.9° C., 0.8° C., 0.7° C., 0.6° C., 0.5° C., 0.4° C., 0.3° C., 0.2° C., or 0.1° C., for example.

A temperature controller can comprise a temperature sensor. A temperature controller can comprise an electronic temperature regulator. An electronic temperature regulator can receive temperature information from a temperature sensor. An electronic temperature regulator can adjust the heating or cooling provided by the temperature controller in response to temperature information from the temperature sensor, in order to achieve or maintain a desired temperature or temperature range. An electronic temperature regulator can comprise, for example, a proportional (P) controller, an integral controller (I), a derivative controller (D), a PI controller, a PD controller, a PID controller, or a closed-loop transfer function controller.

A temperature controller can comprise a phase change material (PCM) (e.g., a fluid that boils at a desired temperature, a solid that melts at a desired temperature). A phase change material can be disposed between a temperature control area and a heater/cooler unit. A phase change material can be disposed within a temperature control area. In some cases, the amount of phase change material is configured to provide a controlled, substantially constant temperature to the process chamber for an assay (e.g., including one or more biochemical, chemical, or biological reactions by being at least partially converted from its solid form to its liquid form when heated by an exothermic chemical reaction generated by the exothermic chemical reagent mixture). Phase change materials can include, without limitation, paraffin, wax, polymer, salt hydrate, non-paraffin organics, metals, inorganic compounds, or inorganic eutectics.

Heating can be generated, for example, by dispensing a heating medium (e.g., a fluid or any exothermic chemical reagent or mixture described herein) to induce an exothermic chemical reaction. Examples of chemical heaters are provided in U.S. Pat. No. 8,431,387, "Chemical Temperature Control," date of patent Apr. 30, 2013, US 2012-0031390, WO2009006521A2, and WO1989005948A1, each of which is incorporated herein by reference in its entirety. Exemplary chemical heaters include an exothermic chemical reagent mixture; and a phase change material disposed between a process chamber and the exothermic chemical reagent mixture or disposed within a process chamber. Exothermic chemical reagents can include, without limitation, iron powder, iron powder and an oxidizing agent (e.g., resulting in the formation of rust, $4Fe+3O_2+H_2O \rightarrow 2Fe_2O_3.H_2O$, where the oxidizing agent can be sodium chlorate, potassium chlorate, lithium chlorate, and sodium, potassium and lithium perchlorates, or other inorganic chlorates, perchlorates, or super-oxides), iron powder and carbon powder (e.g., activated carbon, non-activated carbon, and mixtures thereof), a reduction of copper with magnesium (e.g., with dry magnesium powder and dry cupric sulfate in an equal molar ratio in the presence of water, which results in the following exothermic reaction $Mg_{(s)}+CuSO_{(s)} \rightarrow MgSO(s)+Cu_{(s)}$), calcium oxide hydration (e.g., with calcium oxide, optionally with 5-10% trehalose, packed into a tablet in the presence of 1M HCl, which results in the following exothermic reaction $CaO+2HCl+H_2O \rightarrow CaCl_2.2H_2O$), a supercooled solution (e.g., a supercooled solution of sodium acetate, which when seeded with a small crystal of sodium acetate, mechanical friction, or shock results in the following exothermic reaction, $CH_3COONa_{(l)} \rightarrow CH_3COONa_{(s)}$), an acid and a base (e.g., $H_3O^+ + OH^- \rightarrow H_2O$), a magnesium oxidation reaction (e.g., with dry magnesium powder and HCl, $Mg+2HCl \rightarrow MgCl_2+H_2$), or an oxidation-reduction reaction (e.g., between aluminum metal (e.g., Al, $Al_2O_3$, or $AlCl_3$) and a water-soluble copper halide, such as either anhydrous or hydrated, such as copper chloride, preferably copper chloride hydrate, $CuCl_2.H_2O$, copper acetate $Cu(C_2H_3O_2)_2$, copper formate $Cu(CHO_2)_2$ and copper lactate $Cu(C_3H_5O_3)_2$).

A temperature controller can comprise a heat transmitter. A heat transmitter can conduct heat from a heater or to a cooler, to or from an area of interest (e.g. a sample, a reaction chamber) through one material or a combination of materials with high thermal conductivity. Highly thermal conductive materials can include but are not limited to metals (e.g., aluminum, copper), liquids, solid materials, crystals, ceramics, graphene, graphitic materials, silicone, polymers, and nano-materials. A heat transmitter can be in thermal contact with a temperature control material comprising material to control temperature, such as for example, a phase change material (PCM).

Figure 32:
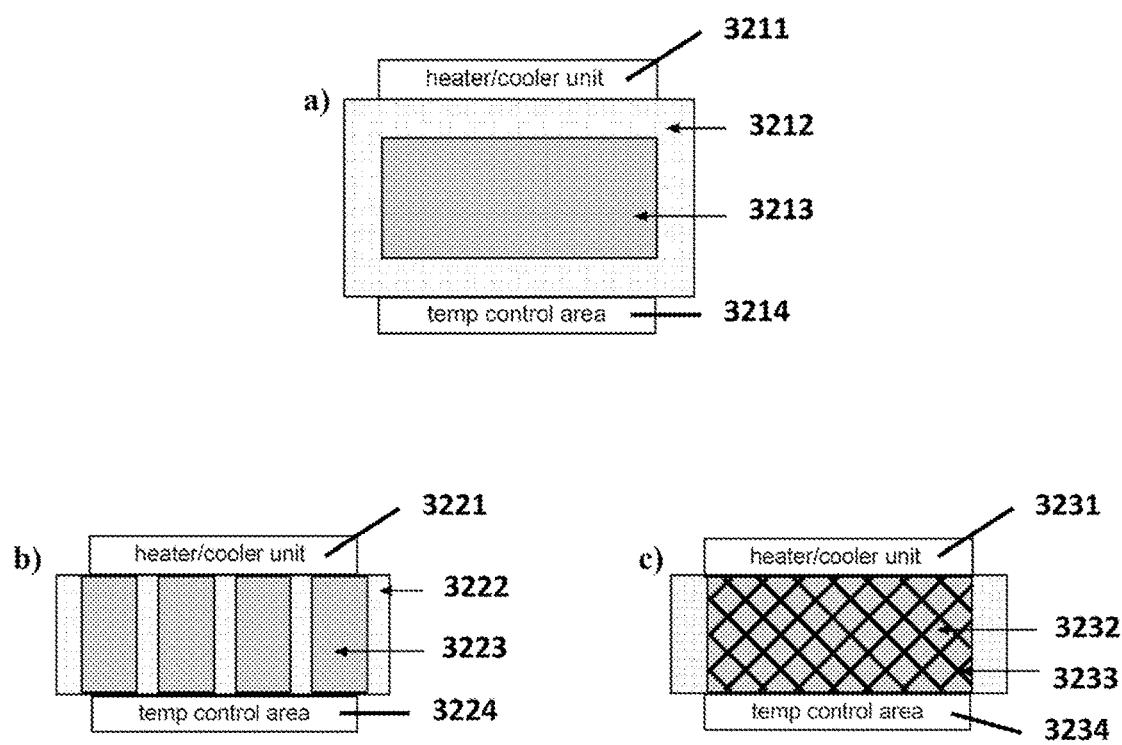
FIG. 32A shows an exemplary schematic of a temperature controller.
FIG. 32B shows an exemplary schematic of a temperature controller with a post-shaped heat transmitter.
FIG. 32C shows an exemplary schematic of a temperature controller with a mesh-shaped heat transmitter.
FIG. 32D shows an exemplary schematic of a heat transmitter inserted into a temperature control area.
FIG. 32E shows an exemplary schematic of a temperature controller with a temperature control region insulated from a heat source.
Figure 32:
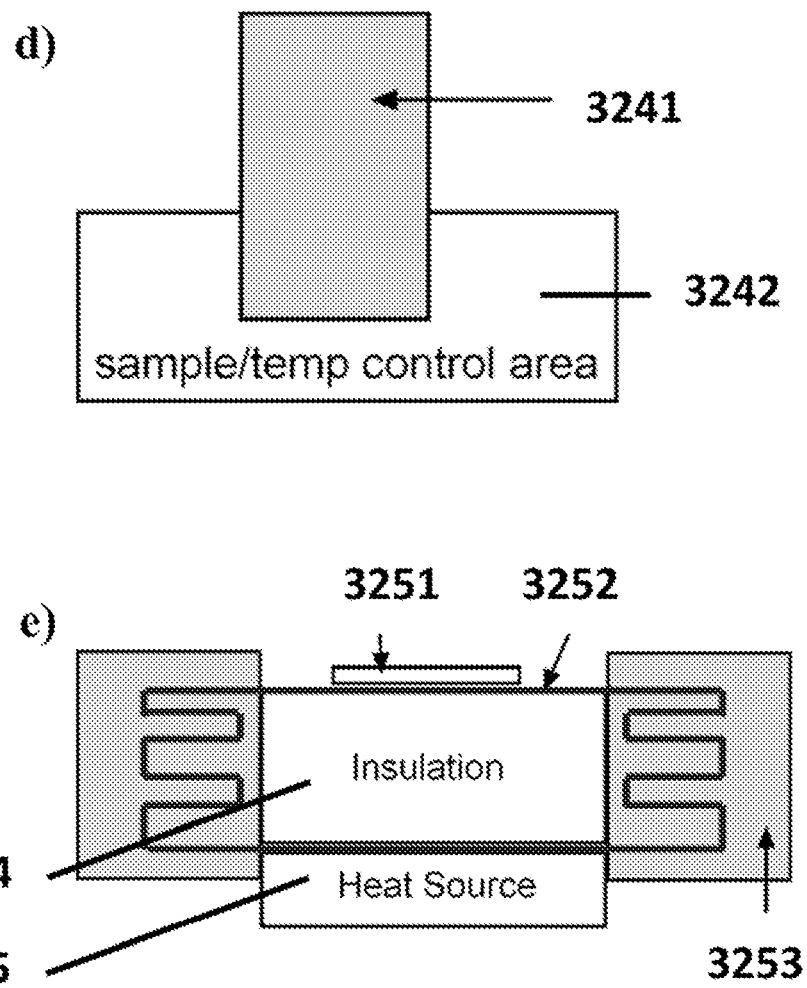

A temperature controller can comprise different geometries or positions of temperature controllers, heat transmitters, temperature control areas, and heater/cooler units. For example, a temperature controller can modulate the temperature of a temperature control area and conduct heat directly through a heat transmitter, while the temperature controller is in contact with the heat transmitter but not require direct heat transfer through the temperature controller. A temperature controller does not need to be in direct thermal contact with a temperature control area. Heat transmitters can comprise different geometries including but not limited to boxes, fingers, posts, wires, mesh, rings, donut shapes, or cups. For example, posts, wires, fingers, or mesh can be used to increase the contacting area of a heat transmitter and a temperature controller. FIG. 32A shows, for example, a configuration of a heater/cooler unit 3211, a heat transmitter 3212, a temperature controller 3213, and a temperature control area 3214. FIG. 32B shows, in another example, a configuration with a heater/cooler unit 3221, a post-shaped heat transmitter 3222, a temperature controller 3223, and a temperature control area 3224. FIG. 32C shows in another example, a configuration with a heater/cooler unit 3231, a mesh-shaped heat transmitter 3232, a temperature controller 3233, and a temperature control area 3234. Part or all of a heat transmitter 3241 can be inserted into a temperature control area 3242, for example as shown in FIG. 32D.

Mixing or other flow can be introduced by a heating element, such as for example, part or entire of heat transmitter or temperature controller. For example, convective flow can be generated and controlled by choice of heat transmitter geometry. The heating element can contact the sample directly, such as for example, by inserting a thermal transfer element or indirectly. The thermal transfer element can contact the center or off-center of the sample or temperature control area to generate convection by thermal gradient. To promote mixing, the temperature control area can be symmetric or asymmetric; the heat transmitter can be symmetric or asymmetric. All or part of the heat transmitter can comprise various geometries or relative positions, such as screw shape, spiral shape, twisting shape, coiled shape, curved shape, tapered shape, or swirl shape.

In some examples, the heat source is separated from the area to be heated by an insulating material, and the heat transfer is performed through a material with sufficient heat conductivity. In some examples a portion of the heat conductive material may be embedded into a phase change material to regulate heat. This phase change material may be of many different compositions, such as for example, paraffin wax, metal alloys, or other materials or combinations of materials as discussed elsewhere in this disclosure. In some examples, the heating material may comprise a compound that undergoes an exothermic reaction when in contact with water, such as for example the dissolution of $CaCl_2$ salts or the reaction of CaO. The insulating material separating the heat source from the area to be heated may be of a variety of formulations, such as for example, foams of different varieties, still air, vacuum pumped void space, or various ceramics. In some examples the area to be heated is insulated from the surrounding environment. In some examples the heat source is separated from the area to be heated using a variety of heat conductive sheets and insulating materials. These sheets may continuous or discontinuous. One or many different points of the sheets may also be in contact with a phase change material. For example, FIG. 32E shows a temperature control area 3251 in contact with a heat transmitter 3252, which is in contact with a temperature controller 3253 and a heat source 3254, while the heat source is separated from the temperature control area by insulation 3255.

Phase change material can be used to control temperature within a desired range. Heat can be generated by a heater/cooler unit, for example by an exothermic reaction (e.g., Mg/Fe alloy with reaction buffer, CaO with water buffer). Reagents and buffers can be stored within resistant units, such as for example blisters, blister packs, wells, or sponges. Upon activation of the resistant unit, reagents can mix and react exothermically. Phase change material can then be used to control temperature within a desired range, as phase change materials can maintain a relatively stable temperature during the phase transition period of the material. Phase change materials can be selected based on a desired temperature range. In some examples, the phase change materials, heat transmitters, or heater/cooler units can be wrapped by insulation layers, allowing more efficient heating of the temperature control area.

Figure 33:
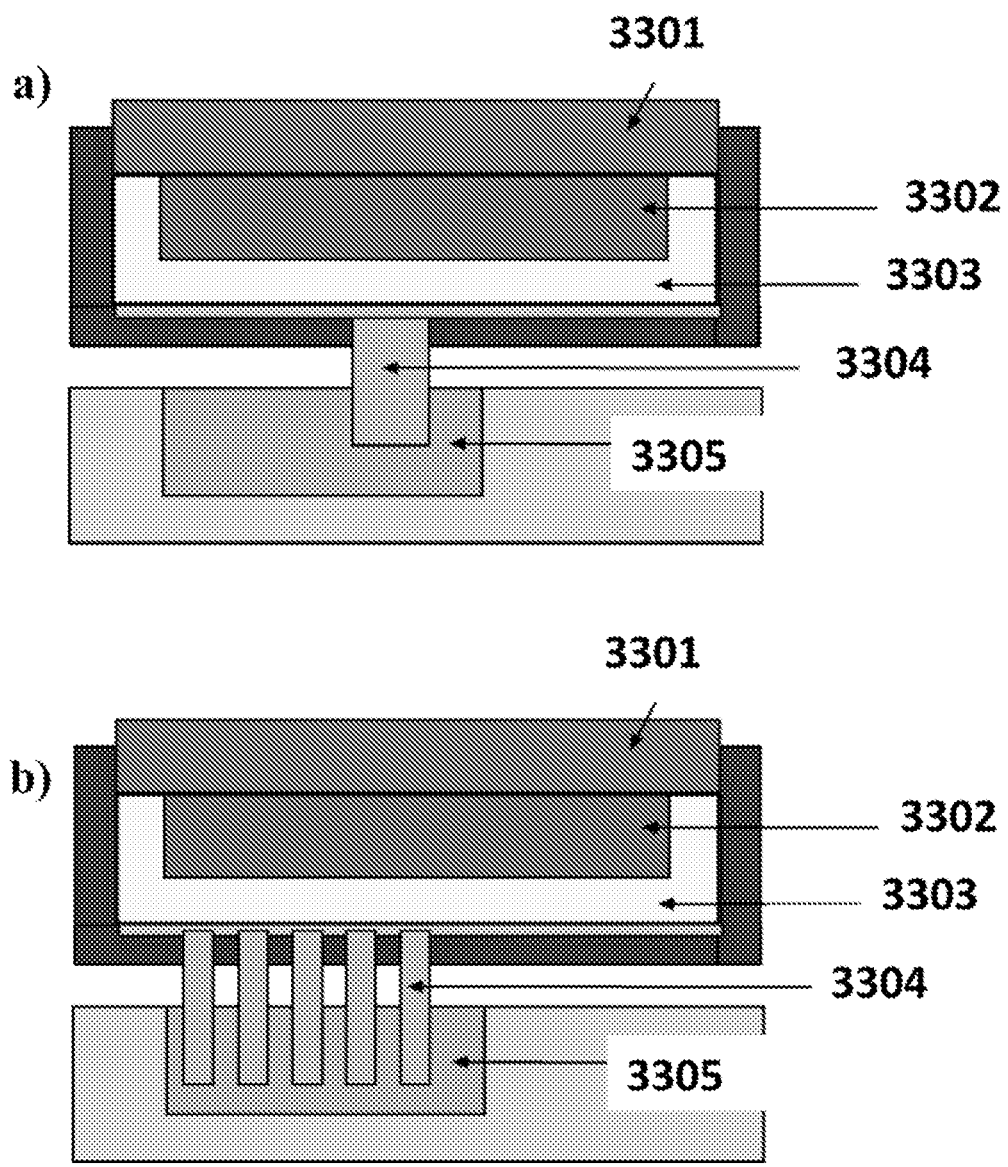
FIG. 33A shows an exemplary schematic of a temperature controller with a heat transmitter comprising a single finger.
FIG. 33B shows an exemplary schematic of a temperature controller with a heat transmitter comprising multiple fingers.
FIG. 33C shows an exemplary schematic of a temperature controller with a heat transmitter located partially through a temperature control area.
FIG. 33D shows an exemplary schematic of a temperature controller with a heat transmitter located completely through a temperature control area.
FIG. 33E shows an exemplary schematic of a heat transmitter located through a temperature control area with a ring structure.
FIG. 33F shows an exemplary schematic of a temperature controller with posts embedded in a phase change material.
FIG. 33G shows an exemplary schematic of a temperature controller with posts embedded in a phase change material and in a heater/cooler unit.
FIG. 33H shows an exemplary schematic of a temperature controller with wires embedded in a phase change material.
FIG. 33I shows an exemplary schematic of a temperature controller with wires embedded in a phase change material and in a heater/cooler unit.
FIG. 33J shows an exemplary schematic of a temperature controller with posts embedded in a phase change material.
FIG. 33K shows an exemplary schematic of a temperature controller with posts embedded in a phase change material and in a heater/cooler unit.
FIG. 33L shows an exemplary schematic of a temperature controller with wires embedded in a phase change material.
FIG. 33M shows an exemplary schematic of a temperature controller with wires embedded in a phase change material and in a heater/cooler unit.
FIG. 33N shows an exemplary schematic of a temperature controller with a large thermal mass of phase change material.
FIG. 33O shows an exemplary schematic of a temperature controller with a heater/cooler unit and a phase change material located within a heat transmitter.
Figure 33:
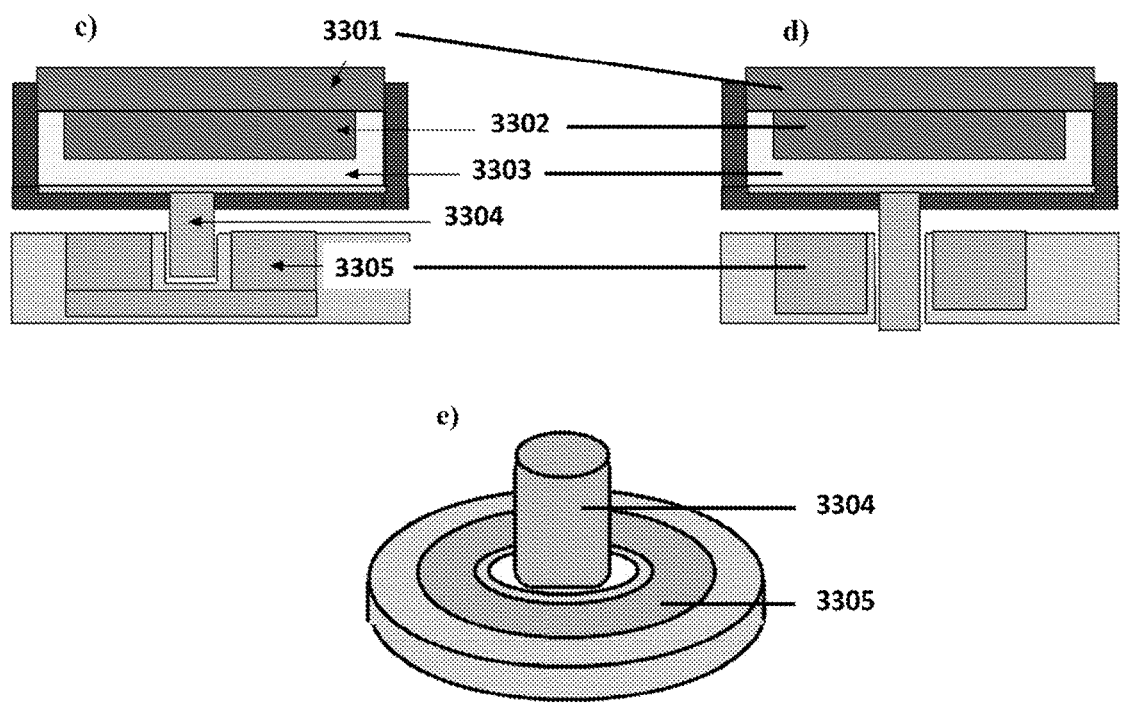
Figure 33:
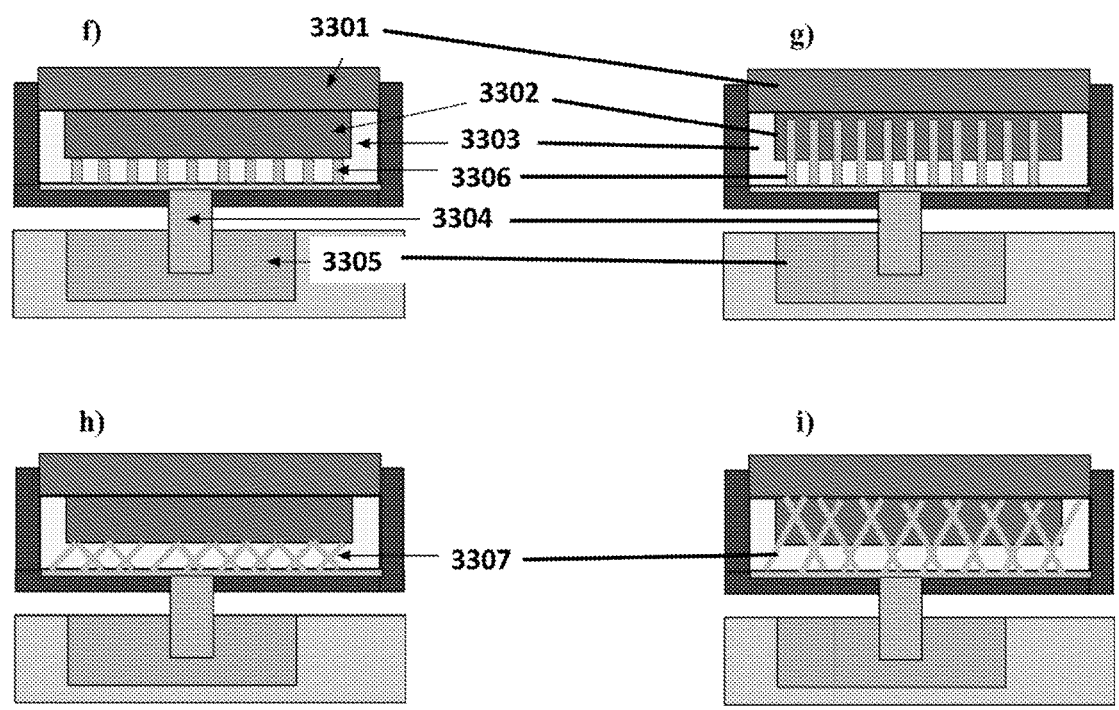
Figure 33:
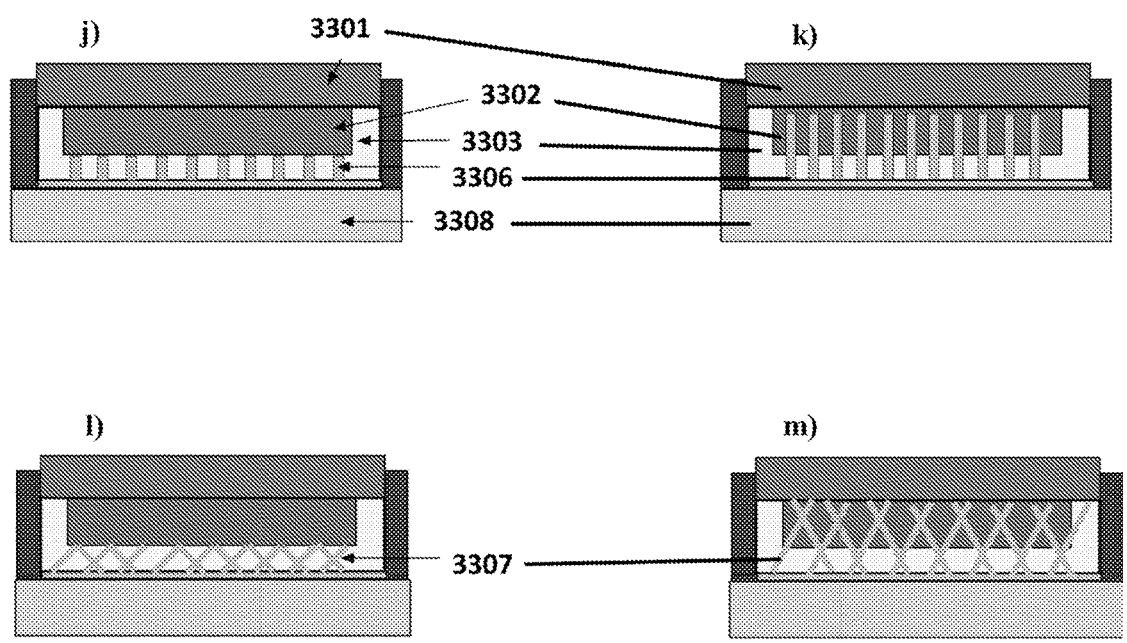
Figure 33:
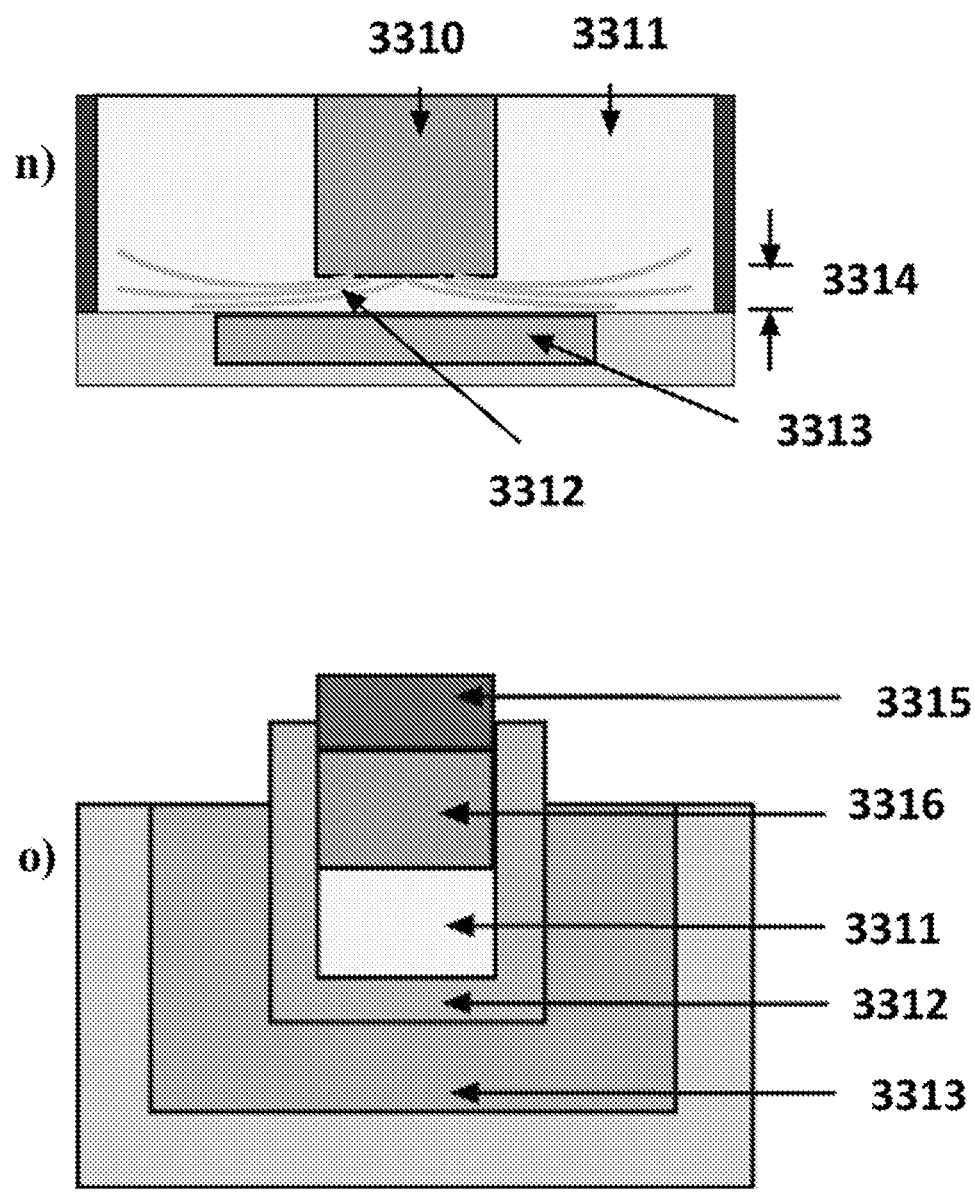

In order to have fast heat transfer, one or multiple heat transmitters can be used in direct or indirect contact with a temperature control area. For example, FIG. 33A shows temperature controller with a module containing a reaction buffer 3301 positioned next to exothermic reagents 3202 in thermal contact with a phase change material 3303; the phase change material is in contact with a heat transmitter 3304 comprising a single finger in contact with a temperature control area 3305. In another example, FIG. 33B shows a temperature controller with a heat transmitter comprising multiple fingers. For some applications, a coating can be applied on top of the heat transmitter to reduce non-specific adsorption. In some applications, indirect heating can be preferred. For example, FIG. 33C shows a heat transmitter with a finger located partially through a temperature control area. In another example, FIG. 33D shows a heat transmitter with a finger located completely through a temperature control area. A temperature control area can be placed in a ring structure, and a heat transmitter can heat from the center. For example, FIG. 33E shows a heat transmitter with located through a temperature control area with a ring structure.

Heat transmitters can comprise posts or wires, and can be embedded in a phase change material, a heater/cooler unit, or both. This positioning can increase the rate of heat transfer. The posts or wires can be kept in contact with rest of the heat transmitter either directly or through other high thermal-conductive materials. After heating is initiated (e.g. by exothermal reaction), the wires or posts can quickly transfer heat to the rest of the heat transmitter and heat up the temperature control area. As more heat is generated and the temperature keeps increasing, the wires or posts can melt the surrounding phase change material while the rest of the heat transmitter can still maintain at desired temperature. For example, FIG. 33F shows a temperature controller with posts 3306 embedded in a phase change material. In another example, FIG. 33G shows a temperature controller with posts embedded in a phase change material and a heater/cooler unit. In another example, FIG. 33H shows a temperature controller with wires 3307 embedded in a phase change material. In another example, FIG. 33I shows a temperature controller with wires embedded in a phase change material and a heater/cooler unit.

In some cases, the heat transmitter does not comprise a heat finger, but rather posts, wires or a mesh with high thermal conductivity can be used for fast thermal transfer directly. For example, FIG. 33J shows a temperature controller with posts embedded in a phase change material, with the posts in direct thermal contact with a temperature control area. In another example, FIG. 33K shows a temperature controller with posts embedded in a phase change material and a heater/cooler unit, with the posts in direct thermal contact with a temperature control area. In another example, FIG. 33L shows a temperature controller with wires embedded in a phase change material, with the wires in direct thermal contact with a temperature control area. In another example, FIG. 33M shows a temperature controller with wires embedded in a phase change material and a heater/cooler unit, with the wires in direct thermal contact with a temperature control area. This can be used to heat up the entire temperature control area with fast heating (e.g., fast heat transfer from posts or wires) while maintaining the desired temperature, which is set by the property of surrounding phase change material.

The amount of phase change material used can be large, to provide a large thermal mass and prevent over-heating. For example, FIG. 33N shows a heater/cooler unit 3310 surrounded by phase change material 3311 and in contact with a heat transmitter 3312 which is in thermal contact with a temperature control area 3313; the gap 3313 between the heater/cooler unit and the temperature control area is thin. Heat transfer can generate convective mixing.

The heater/cooler unit, the phase change material, or both can be located within the heat transmitter. For example, FIG. 33O shows a heater/cooler unit (e.g., reaction buffer 3315 and exothermic reagents 3316) and a phase change material 3311 located within a heat transmitter 3312, and the heat transmitter is in thermal contact with a temperature control area 3313.

In some examples, a heater with windows for imaging can be used, such as in a reaction chamber (e.g., an isothermal amplification module). For example, a foil heater can be placed in contact with the side wall of a chamber, and the bottom of the chamber can be used for imaging, such as for example fluorescence detection, colorimetric detection, turbidity detection. In another example, the heater can be placed in contact with the bottom of a reaction chamber (e.g., an amplification module), and the detection and imaging can be achieved through the side of the chamber. In some examples, a transparent heater can be applied for both heating and imaging, such as imaging of an integrated SlipChip device. A heater can comprise a transparent plastic with electrically conductive coatings. In another example, transparent heater can be made from indium tin oxide (ITO). In some examples, an electric heater can be directly printed in or on a chamber, such as amplification well. Additional coatings can be applied on top of the printed heater to prevent disruption of reactions.

We describe a number of devices and methods in this disclosure that may be used individually or in various combinations for applications including but not limited to those listed herein. Furthermore, they can be used in various combinations with previously disclosed devices and methods for previously-described applications. The present application incorporates the following applications by reference in their entireties for any and all purposes: U.S. Application 61/516,628, "Digital Isothermal Quantification of Nucleic Acids Via Simultaneous Chemical Initiation of Recombinase Polymerase Amplification (RPA) Reactions on Slip Chip," filed on Apr. 5, 2011, and also to U.S. Application 61/518,601, "Quantification of Nucleic Acids With Large Dynamic Range Using Multivolume Digital Reverse Transcription PCR (RT-PCR) On A Rotational Slip Chip Tested With Viral Load," filed on May 9, 2011; U.S. application Ser. No. 13/257,811, "Slip Chip Device and Methods," filed on Sep. 20, 2011. That United States application is a national stage entry of international application PCT/US2010/028361, "Slip Chip Device and Methods," filed on Mar. 23, 2010, which international application claimed priority to U.S. Application 61/262,375, "Slip Chip Device and Methods," filed on Nov. 18, 2009, to U.S. Application 61/162,922, "Sip Chip Device and Methods," filed on Mar. 24, 2009, to U.S. Application 61/340,872, "Slip Chip Device and Methods," filed on Mar. 22, 2010, to U.S. application Ser. No. 13/440,371, "Analysis Devices, Kits, And Related Methods For Digital Quantification Of Nucleic Acids And Other Analytes," filed on Apr. 5, 2012, and to U.S. application Ser. No. 13/467,482, "Multivolume Devices, Kits, and Related Methods for Quantification and Detection of Nucleic Acids and Other Analytes," filed on May 9, 2012. Furthermore, the present application incorporates the following applications by reference in their entireties for any and all purposes U.S. Pat. No. 8,431,387 "Chemical Temperature Control" date of patent Apr. 30, 2013.

Electrical Conduction

A resistant unit can include one or more conductive materials, such as any phase change material, a metal, a metallic powder, an electrolyte, a polymer, or a combination thereof, described herein. In particular, a conductive material may be used to provide an electrical contact between the conductive material and a conductive structure (e.g., an electrical circuit, such as one connecting a power source to another device component, such as a heating element). This electrical contact can affect the current and/or voltage in the electrical circuit. Furthermore, dispensing of a conductive material may be used to close an open circuit, thereby functioning as a switch; to activate or deactivate a device component in a time-dependent manner, where such components include a heater, a mixer, a cooler, etc.; to act as a resistant unit, where a dispensed conductive material can block one or more chambers, which only melt upon reaching a certain temperature, thereby acting as a temperature switch; and/or to electrically contact a portion of the device or system with the pushing unit, where the pushing unit can be connected to a power source and/or heating element.

In some examples, electric contact can be connected or disconnected by relative movement of the device (e.g., rotation or linear motion), such as slipping of device plates or discs. Electric contact can provide source for on-chip temperature control. For example, an electric contact can generate a short circuit or other electrical connection, and it can be used as a heating source on the device. In addition, this heat generated by slipping can be a method for autonomous control for device operation, such as changing the viscosity or phase of a material in a resistant or barrier unit.

Sample Loading

Loading of a substance may be performed by a number of methods, as described herein. Loading can be performed to fill ducts or other areas of the device, for example by designing the outlets to increase flow resistance when the substance reaches the outlets. This approach is valuable for volume-limited samples or to flow the excess volume through the outlets, while optionally capturing analyte from the substance. Analytes can be essentially any discrete material which can be flowed through a microscale or macroscale system. Analyte capture may be accomplished for example by preloading the areas of the device with capture elements that are trapped in the areas (such as particles, beads or gels, retained within areas via magnetic forces or by geometry or with relative sizes of beads and ducts or with a membrane), thus whatever absorbs, adsorbs, or reacts with these beads or gels is also trapped. These areas will then retain an amount or component or analyte of the substances they are exposed to. Retaining of the sample can also be achieved by functionalization of the surface of an area, deposition of a material on an area, attaching a monomer in a polymerization reaction (such as peptide or DNA synthesis) to an area, etc.

In some cases, a loading apparatus loads a reagent, a sample, or a fluid into a device by using an external component or combining one or multiple on-chip components to create either positive or negative pressure. Such pressure can result in a pressure gradient to pump one or multiple reagents, samples, or fluids into a single-layered or multi-layered device. The loading apparatus can include any useful on-chip, off-chip, or a combination of on-chip and off-chip apparatuses that can create a pressure gradient for loading a reagent, a sample, or a fluid into a device. The disclosed apparatus can include a rigid structure, a flexible structure, or a porous structure, as well as other components that can create a pressure gradient in a device. The loading apparatus can comprise a pipette, syringe, or other fluid handling device.

A loading apparatus can create positive pressure and/or negative pressure to drive fluid flow. Accordingly, apparatuses can be combined to create positive and negative pressure at separate positions in a device for creating any useful pressure gradient. Such apparatuses can control the magnitude of positive or negative pressures or the magnitude of the pressure gradient.

In one non-limiting example, the device includes a receiving chamber for controlling the volume of a reaction fluid and/or a lubricant, if present, in the first and/or second chambers. In further examples, the loading apparatus includes a rigid structure to create positive pressure. By designing the rigid structure appropriately, the magnitude of this positive pressure can be controlled. In this method, a modified pipette tip and a stopper is used to load the device. When the tip was immersed into a solution to be loaded, pulling the stopper created an instant vacuum that pushed the solution into the tip. Due to capillary pressure, a certain amount of solution was contained in the tip, which was then inserted into an inlet). Pushing back in the stopper first sealed the pipette tip and then a positive pressure was created to drive the solution into the connected fluidic path to load the chip by dead-end filling. Increasing the created pressure (e.g., by simply increasing the depth the stopper can be pushed in) increases the loading speed. The stopper is designed such that a controlled volume is compressed, and loading can be finished in one minute without leaking. A color-change reaction can be conducted in 5 minutes by an untrained person. Optionally, to avoid trapping of air bubble, a female luer lock at the inlet may be incorporated to contain lubricant oil that covers the inlet orifice. Optionally, the device can be clamped together with magnets. Magnetic force is proportional to the size of magnets as well as their grades. Two sets of N42 magnets, ⅛ inch (D) by ¼ inch (W) by ½ inch in size, provided enough force to hold the chip (1.5 inches (W) by 2 inches (L)) in close contact, not causing leak during solution loading. The magnets can be placed along the width of the chip at the edge so that they did not block the view of reaction wells. In other cases, a modified syringe can be used to load solution into a device. A controlled positive pressure can be created by decreasing the volume in the closed cavity in the syringe. By pushing down the plunger to a pre-determined stroke, a pre-determined positive pressure can be created and initiate loading.

In some cases, dead-end filling can be employed for sample loading. In dead-end filling, a gap between two layers connects the main filling channels or chambers to the outlets. In this way, the filling liquid (e.g., a sample, a reagent, or any substance described herein) is confined in the channels or chambers, while the immiscible phase (e.g., a lubricant or an oil, as described herein) can be evacuated from the channels to the outlets through the gap. In particular, the devices and methods presented here to control pressure and filing can be used in other applications other than just filling channels. These devices and methods can be used to control pressure to open and close valves (e.g., capillary or hydrophobic valves, or any described herein). Exemplary valves include a hydrophobic valve having a structure (e.g., a decrease in a hydrophobic channel cross-section) that prevents or hinders aqueous fluid flow; a capillary valve having a structure (e.g., an increase in a channel cross-section) that exerts a capillary pressure barrier to prevent or hinder fluid flow. The devices and methods described herein can also be used to control flow rate, such as by considering both applied pressure and flow resistance in the device.

Loading such devices can be achieved using any useful method. Precise quantification can be achieved by sequential filling of the chambers. Specific designs of chip geometry can be used to allow sequential filling. Chambers can be filled one by one, and each one will be completely filled before the next one starts filling. In this way, the collected volume can be easily quantified by counting how many wells/channels have been filled. Partial recovery (only from the chambers that were filled in the collection) allows precise quantification of the target molecules of interest. Sequential filling can be obtained using passive strategies, including but not limited to: changing the channel geometry by reducing the cross-section (e.g., by changing one or both the dimensions, producing a narrower or shallower channel to create a "neck"), progressively changing the chamber geometry to increase capillary resistance (e.g., creating a channel with diverging/converging geometry), and changing the local wetting properties of the chambers (e.g., microchannel).

Loading can occur in series or in parallel. For loading in series for one non-limiting example, one inlet is used to load the device, and the device includes a fluidic pathway for sequential filling, where disconnection produces separate aliquots. For loading in parallel for one non-limiting example, one inlet is used to load a sample, and the device includes branched pathways that are filled at the same time. For one non-limiting example, different loading rates can be used for an array of chambers. For one non-limiting example, different samples can be loaded in the device at the same time. For each of these loading strategies, conditions can be controlled so that each chamber is completely filled before filling the next or filled at a particular rate. Exemplary strategies to achieve this controlled loading include tuning the chamber geometry (e.g. to create a neck that delays filling), controlling the evacuation speed for the fluid originally present in the chambers (e.g., such as by using air, oil etc.), tuning the geometry so that the fluid is evacuated with a higher or lower fluidic resistance (e.g. evacuation channels at different distance from the sample chambers), using dead-end filling (e.g., as described herein), or using a porous material to achieve sequential filling.

Loading (e.g., by a lid or cap, as described herein) can incorporate features to irreversibly clip the lid to the main device (e.g., to keep the lid in place during transport and to prevent the user from unintentionally opening the lid after loading). Such features can be added externally (e.g., to a housing, as described herein) or to the device itself. Optionally, the lid may include one or more desiccants and/or matrices to dry any excess sample, if present.

In a non-limiting example, the loading apparatus includes a flexible structure to create a magnitude controlled positive pressure. A positive pressure can be created by using a flexible structure; such as using a thin plastic film to serve as a buckle pump. By using a curved thin plastic film, the curved 3D structure becomes mechanically unstable toward the center of the curvature. A buckle motion can be easily created by applying an external force, such as a finger tip or a lever. A sealed cavity can be created by placing a buckle pump on top of a device (e.g., a SlipChip device). A positive pressure can be created inside the cavity by applying a force on the buckle pump. This concept was verified by using a thin-film buckle pump in combination with a thin-film device. For example, a positive pressure can be created by using a finger tip to deform the thin-film buckle pump, thus creating a sealed cavity between the thin-film buckle pump and the SlipChip. The geometry of the flexible structure is not limited to a curved structure, and all deformable structures, including a flat thin plastic film, can create similar pumping mechanism by introducing a deformation, should be included.

In another non-limiting example, the loading apparatus includes a rigid structure and a flexible structure to create a magnitude controlled positive pressure. Controlled magnitude of positive pressure can be created by combing a flexible structure against a rigid structure. The flexible structure can be deformed by moving a rigid structure to first create a sealed cavity between the rigid structure and the device. Further deformation by moving the rigid structure can continue to decrease the volume in the sealed cavity, thus creating a positive pressure for pumping the sample into the device. The flexible structure can be attached to the rigid structure or on the device (e.g., a SlipChip device). Another exemplary structure is a pumping cup, where a sealed cavity is created by the deformed pumping cup against the device, and the positive pressure is created by further deformation of the pumping cup.

In one non-limiting example, the loading apparatus includes a rigid structure to create a magnitude controlled negative pressure. A gas impermeable sealant is applied between the layers of the device to create a closed cavity for the lubricant. A negative pressure can be created by increasing the volume of a sealed cavity. In this manner, a negative pressure is applied to the oil lubrication layer, thus creating a pressure gradient in the device between the loading apparatus and chambers. A circular channel was designed around the chambers for applying silicone grease to serve as a gasket. Thus, a closed oil cavity is created between the layers, and the only connections to outside world are the solution reservoir and the negative pressure source. Once a negative pressure is provided from the modified syringe (by pulling the plunger with a predefined stroke) solution will be drawn into the chambers in the device. This apparatus works by first reducing the gap between the layers of the device before loading followed by drawing the solution into chambers with created vacuum.

In another non-limiting example, the loading apparatus includes a flexible structure to create a magnitude controlled negative pressure. The flexible structures described herein are not limited to creating positive pressure. For example, a buckle pump can be connected to a device and be deformed by applying an external force. Once releasing the external force, a negative pressure can be created when the flexible buckle pump restores to its original shape. In this manner, a pressure gradient can be created to draw a sample, reagent, or fluid into the device from a solution reservoir.

In one non-limiting example, the loading apparatus includes a rigid structure and a flexible structure to create a magnitude controlled negative pressure. For example, a pumping cup can serve as a sucking cup to create a negative pressure. By increase the cavity in the sealed cavity between the rigid cap and the device (e.g., by simply rotating the cap up from the device), a negative pressure can be applied to the device.

In one non-limiting example, the loading apparatus includes a porous structure to create a magnitude controlled negative pressure. Negative pressure can be created by applying or connecting a porous material to the lubricant between the layers of the device. A porous material can serve as an absorbent for the lubricant and create a pressure gradient in the device from the solution reservoir. This filling apparatus is distinguished from the previously described apparatuses in that the negative pressure (suction) is created by withdrawing lubricant away from the sealed cavity between layers. The magnitude of negative pressure is controlled to be equal or higher than the pressure necessary to draw solution into the device but to be less than the sealing pressure for preventing leakage of solutions. Negative pressure can be created directly by an oleophilic porous material (for example, a sponge), where suction is created by the lubricant wicking inside the sponge forcing aqueous solution flow into the SlipChip; or by an elastic porous material, where suction is introduced by an increase in volume of the pores in the porous material.

Sample Preservation

The systems, methods, and devices of the invention can be useful for performing sample (e.g., biospecimen) preservation, such as by sample storage and stabilization in the liquid state or dry state, including molecular (e.g. proteins, nucleic acids) and cellular and multiple biospecimens (e.g., biological fluids and human biological fluids such as blood and plasma). Systems and devices may include optional collection and/or optional sample preparation capabilities. In general, the devices allow for loading a sample, optionally combining the sample with a matrix, storing the resultant sample in the liquid or dry state for a desired time, and then recovering the sample. The matrix (e.g., stabilization matrix) can be liquid or solid, which can optionally be pre-loaded in the device, mixed with the sample prior to loading, or loaded in the device at the same time as the sample or at a different time.

Currently, there are two major ways to handle biological samples that need to be transported for analysis or stored and archived for long term use: freezing and drying (lyophilization is the combination of the two). The disadvantages of freezing and lyophilization are energy consumption, inaccessibility for resource-limited areas, and subject to failure if there is a power outage.

Drying and storing biological samples on the system of the invention (e.g., using a SlipChip device), e.g., blood samples, can provide several advantages. Such advantages may include drying within minutes without any outside power supply; being ready to transport after samples are collected after a single relative movement (e.g., by slipping); integration of sample collection, drying, storage, and analysis on a single device; and/or application of microfluidic features (e.g., as in a microfluidic device) to provide miniaturized, fast, digital, and high throughput analysis.

Drying can be performed in the device in any number of ways. In one instance, a highly active and high-capacity desiccant can be preloaded into the device. The device is sealed (e.g., by any useful method, such as those described herein by closing a valve) to prevent the desiccant from absorbing ambient moisture before the sample is loaded. The sample chamber can be optionally pre-coated with a preservative matrix to avoid degradation of the sample during drying and storage. For example, a 10 μL sample can be digitized or partitioned into hundreds of aliquots to make rapid drying and digital analysis both possible.

The matrices described herein (e.g., stabilization matrices) can allow for liquid sample preservation or dry sample preservation at room temperature. Exemplary matrices can be liquid or dry and are available from suppliers including but not limited to Biomatrica, IntegenX/Genvault, Qiagen, and General Electric. Exemplary commercially available stabilization matrices include Biomatrica, DNAstable®/DNAstable® LD, DNAstable® Blood, DNAgard® Blood, DNAgard® Saliva, DNAgard® Tissue, RNAstable®, RNAgard®, Clonestable®, IntegenX/Genvault, GenTegra DNA, GenTegra RNA, GenPlate, Luna Innovations, Qiagen, Allprotect Tissue Reagent, RNAlater® RNA Stabilization Reagent, GE Healthcare/Whatman plc, and FTA paper. Additional matrices include those having a desiccant (e.g., any described herein), a weak base, a chelating agent, an anionic surfactant or detergent, a uric acid, a salt (e.g., a urate salt, either alone or added to a cellulose based matrix (filter paper) to inactivate nuclease; or a sulfate salt, such as ammonium sulfate, ammonium bisulfate, cesium sulfate, cadmium sulfate, cesium iron (II) sulfate, chromium (III) sulfate, cobalt (II) sulfate, copper (II) sulfate, lithium sulfate, magnesium sulfate, manganese sulfate, potassium sulfate, sodium sulfate, or zinc sulfate), and/or an oligosaccharide (e.g., trehalose, sucrose, maltose, etc. to stabilize DNA, RNA, or protein for anhydrobiosis, lyophilization, vitrification, and/or room temperature air drying). In particular examples, the matrix includes a sulfate salt (e.g., an ammonium sulfate, including a final salt concentration in solution is between 10 g/100 ml and a saturating concentration (e.g., 100 g/100 mL)), an optional chelator (e.g., EDTA), a buffer (e.g., having a pH between 4 and 8), or a precipitant (e.g., ethanol, methanol, acetone, trichloroacetic acid, 1-propanol, 2-propanol, polyethylene glycol, or acetic acid). In other examples, the matrix includes (i) 1-methyl-3-carboxyethylimidazolium bromide, 1-hexyl-3-methylimidazolium bromide, 1-decyl-3-methylimidazolium bromide, 1-(2-hydroxyethyl)-3-methylimidazolium bromide, or 1-benzyl-3-hexylimidazolium bromide; and (ii) one or more of a precipitating agent (e.g., 5-(4-dimethyl)amino benzylidene rhodanine, sulfosalicylic acid, lithium chloride, or lithium hydroxide), a lower alcohol (e.g., methanol, ethanol, n-propanol, isopropanol, n-butanol, or isobutanol (2-methylpropan-1-ol)), or a chaotropic substance (e.g., any described herein). Such matrices can also include an optional chelating agent (e.g., any described herein), an optional reducing agent (e.g., any described herein), an optional pH buffer (e.g., any described herein), and optionally water. In some examples, the matrix includes (i) a borate composition (e.g., boric acid, boric anhydride, dihydrogen borate, hydrogen borate, diborate, triborate, tetraborate, metaborate, hydroxoborate (borax), borate salt, boric acid-glycerol, or boric-acid-1,3 propanediol) and (b) at least one stabilizer (e.g., hydroxyectoine, ectoine, homoectoine, betaine, L-carnitine, sarcosine, N,N-dimethylglycine, triethylammonium acetate, glycerol phosphate, N-(2-hydroxy-1,1-bis(hydroxymethyl)ethyl)glycine (tricine), 3-(N-morpholino)-2-hydroxypropanesulfonic acid (MOPSO), pentaerythritol, N-ethyl-N,N-bis-(2-hydroxyethyl)ammonium-N-4-butyl sulfonate, glycolic acid, lactic acid, malic acid, tartaric acid, 2-hydroxybutyric acid, 3-hydroxybutyric acid, 4-amino-3-hydroxybutyric acid, pyridine 2,5-dicarboxylic acid, 3-(1-azoniabicyclo[2.2.2]oct-1-yl)propane-1-sulfonate, 1-(2-carboxylatoethyl)-1-azabicyclo[2.2.2]octan-1-ium, or 4-[benzyl(2-hydroxyethyl)methylazaniumyl]butane-1-sulfonate). In yet other examples, the matrix includes (i) a liquid or dry material (e.g., polyvinyl alcohol) and (ii) a stabilizer (e.g., any described herein, including a trehalase stabilizer, a glycosidase inhibitor, a trehalase inhibitor (e.g., suidatrestin, validamycin A, validoxylamine A, MDL 26537, trehazolin, salbostatin, or casuarine-6-O-alpha-D-glucopyranoside), a chitinase inhibitor, an alpha-glucosidase inhibitor, a glycogen phosphorylase inhibitor, a neuraminidase inhibitor, a ceramide glucosyltransferase inhibitor, a beta-fructofuranosidase inhibitor (e.g. alpha-methyl glucoside, cellobiose, D-fructose, D-glucose, fructose, galactose, glucose, lactose, maltose, melezitose, melibiose, sucrose, trehalose, or turanose), or a lysosomal glycosidase inhibitor. In other examples, the matrix includes (i) a liquid or dry material (e.g., polyvinyl alcohol) and (ii) a stabilizer (e.g., any described herein, including a combination of trehalose and a trehalase inhibitor, such as any described herein). Further matrices are provided in U.S. Pat. Nos. 6,528,641 or 5,256,571, as well as U.S. Pub. Nos. 2005-0276728, 2006-0099567, 2008-0176209, 2008-0268514, 2011-0081363, and 2012-0052572, each of which is incorporated by reference in its entirety.

A sample, either before or after processing or analysis, as well as any substance described herein (e.g., a reagent, a buffer, etc.) can be preserved or stored either in the dry state or in the liquid state. In some instances, the sample is a liquid sample, and preservation in the liquid state may be preferable. In other instances, the sample is a liquid sample intended for long term storage (e.g., more than six months) and/or for storage at high temperatures (e.g., more than about 4° C.), and preservation in the dry state may be preferable. In yet other instances, the sample is a dried liquid sample (e.g., a dried blood spot, such as for DNA analysis, clinical testing, or any analysis described herein).

Liquid sample storage and preservation can be performed using the system and/or device. A liquid sample (such as blood, saliva, urine, blood plasma, serum, purified protein or nucleic acid solution, cell culture medium, environmental sample etc., or any other described herein) can be loaded in the device. Dry preservation and storage can be performed by adding an extra drying step. Drying the sample can be done with several strategies, such as by using a device including desiccant and a bridge, a device including desiccant and a porous membrane, a device including a first module having a porous material and a second module having a desiccant, or a device including a module including a porous material that allows for drying under ambient conditions. Such devices are described herein and allow for a drying strategy that is not dependent on external ambient conditions (such as humidity). The desiccant can be any useful desiccant, e.g., described herein. Furthermore, the drying process can result from water transport occurring through a gas (e.g., air), a liquid (e.g., an immiscible fluid, such as a lubricant or oil), or a solid (e.g., a porous membrane, which can include but are not limited to Gore-Tex, and porous membranes made of PE, PP, PTFE, PES, PC (commercially available from Millipore and Whatman/General Electrics), as well as any described herein).

In particular examples, the timescales for preserving (e.g., in the dry state or in the liquid state) the sample (e.g., aliquots of such samples) and for loading the sample can be controlled. In some cases, these two processes can run simultaneously. For instance, the device can be loaded in parallel or in series. The matrices can be preloaded in the device or pre-mixed with the sample. Loading and drying can be achieved simultaneously, in which volume can be controlled by controlling the rate of filling and/or the rate of evaporation. Such an approach can allow for storing sample volumes that are larger than the actual volume of the chambers, if the timescales of loading and drying are comparable.

Various strategies can be implemented for samples preserving (e.g., in a dry state or in a liquid state). In one example, vapor contact can be achieved through shallow empty bridges connecting the sample and the desiccant chambers. In this strategy, the sample to be preserved is digitized in a large number of chambers (e.g., volumes on the order of 10-100 nL). During drying, each sample chamber is connected to another chamber containing a desiccant (e.g., a solid desiccant salt) through a duct ("bridge"). In particular instances, the bridge is shallow enough to allow vapor diffusion, while preventing any physical contact between the liquid(s) and/or content(s) of the two chambers.

In one example, the device includes a desiccant and a bridge. To implement this drying strategy, a "dry-chip configuration" can be applied, in which the lubricant is a very viscous material (e.g., a viscosity $>>10,000$ cst) present in the gap between the layers. Examples of these materials include but are not limited to silicone greases, fluorinated greases (such as DuPont Krytox), high molecular weight polymers (PDMS, etc), and partially cured elastomers. The sample can be loaded in the sample chambers by any useful method, such as any described herein. Vapor contact is reversible and can be initiated by relative movement (e.g., by slipping). Direct contact between the sample and the desiccant is prevented by using a shallow bridge, and the liquid is confined in the sample chamber by surface tension. The desiccant can be pre-loaded before assembling the device. In case the desiccant is a liquid, it can also be loaded after assembling the device. Alternatively, the devices can be produced using different bridge-like strategies, such as pneumatic valves. Preliminary tests showed that this configuration is suitable for drying solutions stored in 10 nL chambers in less than 10 minutes. Another relative movement (e.g., by slipping) brings the dehydrated sample in contact with a chamber that has been injected with water in order to re-hydrate it at the desired time. Further details concerning rehydration are provided herein.

In another example, the device includes a porous membrane and a desiccant. In this approach, the device includes at least one chamber for sample drying ("sample chamber") and at least one of the chambers includes a hydrophobic porous material, such as a polymeric membrane. The device also includes at least one chamber containing desiccant ("desiccant chamber"). A sample can be injected in the device using any useful loading strategy, e.g., any described herein. Vapor contact is reversible and can be initiated by relative movement (e.g., by slipping). The desiccant can be pre-loaded before assembling the device.

In yet another example, the device includes a first module including a porous material and a second module containing a desiccant. In this approach, a module ("storage module") includes at least one chamber for sample drying ("sample chamber") and at least one of the chambers includes a hydrophobic porous material, such as a polymeric membrane. After loading the sample, the storage module can be combined with a second module ("drying module") that includes at least one chamber containing a desiccant. Combining the two can result in fluidic communication (e.g., vapor contact) between the desiccant and the sample chamber, thereby initiating drying.

In another example, the device includes a module including a porous material, which allows for drying under ambient conditions. In this approach, a module ("storage module") includes at least one chamber for sample drying ("sample well") and at least one of the chambers include a hydrophobic porous material, such as a polymeric membrane. After loading, drying is achieved automatically by exposing the module to an external atmosphere, such as ambient atmosphere or a controlled environment (such as drying cabinet, laminar flow hood, or a closed container containing desiccant).

In one example, the device includes a membrane as a layer within the device. Vapor diffusion is allowed between the chambers because the pores of the membrane are too small for aqueous solutions to penetrate. Further, such porous materials may be used to support the drying matrix and/or the sample. Use of a membrane can decrease drying time. For instance, such membranes can maximize the effective interaction area between the sample and the desiccant, as compared to structures including a bridge. As an example, a total volume of 50 µL can be easily dried in less than 10 minutes, while allowing subsequent recovery of RNA even at low concentrations (1000-100 copies/µL). Gel experiments showed recovery of concentrated RNA with no detectable depletion, while qPCR results confirmed the possibility to detect samples as dilute as 100 copies per µL. In addition, a "dry-chip configuration" can be compatible with this strategy, i.e., using a viscous fluid to fill the gap and isolate the chambers, without the need to use a lubricant between the layers of the device.

Sample storage can include mixing with a stabilization matrix. Several matrices are commercially available (e.g., as described herein) and allow stabilization of analytes (such as proteins, RNA, DNA, cells, viruses) in a variety of liquid samples (such as blood, saliva, urine, blood plasma, serum, cell culture medium, environmental sample etc.). The matrix can be introduced to the sample in any useful manner, such as by mixing with the sample prior to loading, pre-loading in the device prior to introducing a sample, or loading the matrix in the device after introducing a sample. In particular examples, the matrix can be pre-loaded in the SlipChip device in the liquid or solid state and then mixed with the sample. Prior to mixing, the loaded sample can be split into aliquots, and relative movement can be used to mix each aliquot with the appropriate quantity of matrix. Further, different regions or chambers of the device can be loaded with different stabilization matrices to allow multiplex stabilization.

Multilayer devices can be also used to increase the amount of stored sample. In some cases the architecture may be reproduced several times by stacking several layers, so that total time of drying is preserved (as drying depends on the effective surface for vapor diffusion) or even increased (e.g., each sample can be dried by multiple layers of desiccant). The desiccant can optionally be embedded in a matrix for ease of fabrication. Exemplary matrices for multilayer devices include but are not limited to paper, hydrogels, or any porous hydrophilic medium, such as those described herein. The device can be produced by lamination of several layers, so that each layer can be used as an independent device (e.g., by using strategies such as the valving systems described for a single layer device), and/or by including more than one sample modules and drying modules, as described herein.

Devices can also include automated compartmentalization with simultaneous loading and drying. Drying rate can be controlled so that the sample is distributed in all the channel length. Recovery can then be achieved only in portions of the channel, using for example an external valving system. Selective rehydration can be achieved by strategies including but not limited to using different inlet holes that can be opened independently (e.g., using commensurate/incommensurate inlets in a layer, as described herein, and/or controlling the external valves). Grooves or other geometrical features can be included in the channel to create "capillary valves" that prevent the injected liquid from diffusing in the lines that should not be rehydrated. Such techniques can also be included in a multilayer device. Multilayer fabrication techniques allow integration of membranes in the device. Reversible vapor contact between the membrane and the desiccant can be achieved with the proposed geometry, where the membrane is embedded in the central layer, and partial recovery can be achieved. An external valving system may be achieved without using a SlipChip device (e.g., by using lids or caps to close the inlets).

For any of the devices described herein, the membrane can be integrated into the device using any useful method. Exemplary methods include but are not limited to bonding using glues or adhesives, bonding using adhesive tapes, bonding using techniques commonly used for thermoplastic materials (such as solvent bonding, thermal bonding), embedding the membrane in a curable material before curing (examples include but are not limited to: epoxy resins, thiolene based optical adhesives, thermal curable materials and photocurable materials), and deposition of a viscous material that can be embedded in the pores by thermal transfer.

In any of the devices herein, samples, analytes, or solutions can be retrieved from a device by connecting a chamber or series of chambers to inlet/outlet holes and then injecting an immiscible fluid (e.g., such as air, gas, mineral oil, a lubricant, etc.) in the chambers so that the samples, analytes, or solutions are pushed out of the device. Alternatively, the samples, analytes, or solutions can be recovered by aspiration through via holes (e.g., using for example a pipettor, or a low vacuum source).

In any of the devices herein, the sample can be rehydrated by injecting a solvent (e.g., water) in the device, and recovery can be performed on all stored samples or only on the sample stored in a particular chamber or subset of chambers. Further, one or more fluids (e.g., a sample, a reagent, a lubricant, or a matrix) can be injected in the device using any useful loading strategy, e.g., any described herein. Alternatively, some fluids can be pre-loaded in the device before assembly, by depositing such fluids (e.g., as droplets or microdroplets) in a set of chambers. The devices of the invention can be also used for other fluidic operations, such as splitting one volume into further aliquots, creating several sets of aliquots from different solutions, combining two sets of aliquots by mixing each aliquot of solution A with an aliquot of solution B, and/or sequentially mixing each aliquot with a sequence of solution contained in different wells, etc. Sample recovery can include full recovery and recollection or partial recovery and recollection, with storage of the remaining sample. For full recovery, all of the stored sample is rehydrated and recollected from the device at the same time. For example, by re-aligning the chambers so that they form a single path connected to one inlet and one outlet, the single path is filled with a solvent (e.g., water or buffer) to recover the analyte from the device. The final path can be the same used for loading. For particulate recovery, a subset of chambers can be aligned in order to form several paths. Each path can be connected to one inlet and one outlet and can be individually addressed. Recovery can thus be performed on the desired subset of chambers, while the remaining chambers are preserved for later recovery. In some examples, each chamber can be connected to one inlet and one outlet, and recovery can be performed in a single chamber.

In any of the devices herein, compartmentalization or partition of the sample can include any useful method. For instance, compartmentalization can be achieved by inducing the breaking of the liquid layer by passive or active strategies. Passive strategies include but are not limited to changing the channel geometry, changing the channel wetting properties, and/or creating specific channel networks to induce liquid breaking during the drying process (including but not limited to channels that are not going to be filled with water during the device loading, for example dead-end channels or by-pass channels). Active strategies include but are not limited to use of relative movement (e.g., by slipping one or more layers to connect or disconnect chambers) and/or use of standard valving systems (e.g., pneumatic or electrovalves) to separate the different portions of the device. Compartmentalization and recovery can be obtained combining a microfluidic device with a valving system. In some cases, the device includes multiple layers, and some of the layers may be bonded together (i.e., not slippable).

Sample Concentration

The systems, methods, and devices of the invention can be useful for concentrating one or more samples. The sample and/or one or more analytes within the sample can be concentrated by any useful methods, e.g., evaporation. In one non-limiting example, a sample is injected in the device and then exposed to a desiccant or an external atmosphere via a porous material (e.g. membrane). Here, the solvent of the sample will be removed, thus increasing the concentration of the analytes. In further examples, evaporation is used to initiate flow within a device, such as using the principles provided in, e.g., Randall et al., Proc. Natl. Acad. Sci. 102:10813-10818 (2005) and Merline et al., Soft Matter 8:3526-3537 (2012), each of which is incorporated by reference in its entirety.

Evaporation can be controlled by any useful device or method. In one non-limiting example, evaporation results in complete drying of a sample. For instance, the solvent for the sample is removed completely, and the resultant analytes are eluted with a known volume of a solution (e.g., water, a buffer, or any fluid described herein). The factor of concentration can be controlled, for example, by controlling the geometry of one or more chambers and/or capture regions. In another non-limiting examples, evaporation results in partial drying of a sample. For instance, evaporation occurs in a controlled region of the device for a given time. Then, the resultant concentrated solution can be used for further processing. The factor of concentration can be controlled, for example, by controlling the geometry of one or more chambers and/or capture regions, the total evaporation area (e.g., total area of the membrane exposed to the sample), and/or the evaporation time.

For any of the total drying and partial drying approaches, multivolume experiments can be conducted, where a series of aliquots can be processed in different ways and parameters can be tuned to achieve different concentrating factors. Such methods can increase the dynamic range of analyses. Furthermore, these methods can allow for simultaneous loading and drying to maximize the factor of concentration. For example, if the device loading speed is matched with the speed at which the solvent is removed by evaporation, then a steady state flow can be created to maximize the extent of concentrating the analyte.

Optionally, evaporation can be automatically controlled in a device by using any useful structure. In one non-limiting example, the device includes a reservoir filled with water, and a portion of the reservoir includes a porous material (such as, for example, a porous membrane). Here, evaporation occurs so long as the sample is still in contact with the porous walls, and the rate of evaporation will decrease as soon as the sample reaches the enclosed extremity of the reservoir. Evaporation rate can be reduced or suppressed by tuning the geometry, e.g., by using a constriction to minimize the exposed liquid interface after the liquid reaches the enclosed extremity of the reservoir. At this point, the evaporation rate will decrease, and a defined volume of the concentrated sample will be kept in place by gravity (in which case the device may or may not need to be kept in a vertical position), by capillary action (in which case the device may or may not include a constriction), or by any other method.

All the above strategies can, for example, be implemented using a device including a membrane (e.g., as described herein), as well as using any of the methods described herein for fluid handling and/or controlled activation/deactivation of preservation of samples.

In some examples, rehydration of the preserved sample includes using a volume of fluid (e.g., water, a buffer, or any liquid described herein) that is smaller than the volume of the chamber to be filled with the fluid. In this manner, the final analyte concentration will be greater than the concentration of the analyte in the original sample. Strategies to achieve rehydration with a smaller volume include the use of plug-based microfluidics, such as by partitioning the sample either before or after preservation. In some cases, one or more chambers can be loaded with an immiscible fluid (e.g., an oil, a lubricant, or any immiscible fluid, including those any described herein). Then, a droplet (e.g., microdroplet or plug) of a fluid (e.g., aqueous fluid, such as water, a buffer, or any liquid described herein) can be used to recover the preserved sample (e.g., completely or partially dried sample in a solid or liquid state) in the chamber. Exemplary methods and devices are described in U.S. Pat. Nos. 8,304,193; 8,329,407; 8,273,573; 7,901,939; 7,129,091; and 7,655,470, each of which is incorporated herein by reference in its entirety.

Sample preservation can be combined with any sample treatment, sample analysis, or sample concentration methods described herein. For example, sample preservation can be combined with one or more of newborn screening, drug testing, drug discovery, clinical trials, remote clinical trials, sample transportation, transporting, bio-banking, biomarker discovery, archiving (e.g., for tracking an individual patient's history of pathology), long term storage, remote analysis, collateral analysis to point-of-care (POC) or limited-resource settings (LRS) tests, follow up analysis after POC or LRS tests, nucleic acid tests, protein tests, serology, sample processing, analyte stabilization in raw samples, analyte stabilization in purified samples, as well as any additional sample treatment, sample analysis, or sample concentration methods described herein.

Sample Treatment

The systems, methods, and devices of the invention can be useful for performing sample treatment (e.g., for detoxifying a sample, preserving a sample, analyzing a sample, or determining the reaction progress of a sample). In particular examples, the device for sample treatment is any described herein for preserving or storing a sample (e.g., including one or more membranes and/or bridges). In particular examples, the device for sample treatment is any described herein for processing or analyzing a sample (e.g., including one or more capture regions).

In some examples, the device (e.g., including one or more membranes and/or bridges, as described herein) is useful for removing and/or collecting a vapor or a gas from the sample. In particular instances, the device includes a matrix (e.g., a collection matrix with appropriate selectivity for the vapor or gas of interest, or any described herein), where exposure of the sample to the matrix results in removing and/or collecting the vapor or gas of interest. Exemplary vapors and gases include $H_2S$, oxygen (e.g., $O_2$, as well as radical oxygen species), CO, $CO_2$, methane, sulfur oxides, mercury vapors, vapors of volatile organic compounds, carboxylic acids, amines, aldehydes, odorants, etc. In other examples, the device includes a matrix (e.g., a collection matrix with appropriate selectivity for one or more physical or chemical properties, such as polarity, size, charge, density, acidity, basicity, hydrophobicity, lipophilicity, or any described herein), where exposure of the sample to the matrix results in removing and/or collecting the analyte of interest having the desired physical or chemical property.

Exemplary collection matrices include hollow fiber membranes (e.g., poly 2,6-dimethyl-1,4-phenylene oxide) (PPO) and cardo-type polyimide (PI) hollow fiber membranes), nylon membranes (e.g., nylon 6 or nylon 6.6 (polyimide)), polyvinyl alcohol (PVA) membranes, polyacrylonitrile (PAN) membranes, polyurethane (PU) membranes, polyurethane-urea (PUU) membranes, cellulose acetate (CA) membranes, ionic liquids, gels (e.g., a silica gel, such as for adsorption of heavy (polar) hydrocarbons from natural gas), activated carbon/charcoal (e.g., such as for gas storage, trapping mercury vapors, or other odorants), as well as any described herein.

In some examples, the matrices may be designed to release a particular substance (e.g., in response to the presence of the target vapor, gas, or analyte, so an exchange process occurs). This could be desirable when the target vapor, gas, or analyte would benefit from being supplemented with the particular substance (e.g., an inert vapor, a preservation vapor, a reaction vapor, a solubilizing agent, a reagent, a buffer, or any useful substance described herein). For example, via such an exchange, a sample (e.g., a biological sample) may be protected, preserved, and/or stabilized.

Various types of sample can be used for sample treatment. Exemplary samples include liquid samples (e.g., for the removal of volatile compounds) or gas samples (e.g., for the removal of some compounds from the gas mixture), as well as any described herein. Exemplary sample treatment steps include removing one or more contaminants, such as, for example, one or more toxic components, interfering components, or volatile components (e.g., prior to sample analysis in the device or prior to sample stabilization or preservation in the device), removing substances (e.g., oxygen) for enhancing preservation of such sample, and/or capturing one or more analytes of interest. In any of these cases, the matrix can be further analyzed, such as by removing the matrix from the device or by exposing the matrix to one or more elution buffer and analyzing the resultant eluent. In particular non-limiting cases, the device is made from materials not permeable or minimally permeable to the vapors being collected. A substantial expertise exists in the industry, for example, in plastic films that reduce oxygen and water vapor permeability. For example, permeability of cyclic olefin copolymer (COC) and cyclic olefin polymer (COP) is generally lower than that of polycarbonate (PC). Exemplary COC and COP include copolymers including norbornene (e.g., with ethene or ethylene), copolymers including tetra-cyclododecene (e.g., with ethene or ethylene), including TOPAS® COC containing an ethylene-norbornene copolymer (e.g., TOPAS-8007 (Tg=78° C.), TOPAS-5013 (Tg=130° C.), TOPAS-6015 (Tg=160° C.), and TOPAS 6017 (Tg=130° C.)), as well as any described herein.

Sample Preparation

The systems, methods, and devices of the invention are useful for methods of processing, preparing, and/or analyzing a sample (e.g., any described herein). Such methods benefit from the devices of the invention, which include one or more layers, one or more chambers, and/or one or more capture regions capable of being connected or disconnected by relative movement. In particular, each step of these methods can be accomplished by controlling such relative movement, where even complicated or reiterated steps can be accommodated by controlling relative movement and by designing appropriate layers. For instance, a particular relative step between reagent(s) and the sample in different layers can be initiated by relatively moving the layers of the device to connect chambers containing the desired reagent(s) and sample.

The methods can further include partitioning a test sample (e.g., having a volume of more than about 1 mL) into separate aliquots (e.g., a plurality of droplets or a plurality of microdroplets each having a volume of less than about 1 mL), drying one or more of the aliquots (e.g., using one or more desiccants, as described herein), and/or recovering one or more of the aliquots (e.g., using one or more solvents, such as water, a buffer, or an organic solvent, as described herein). The volume of each aliquot can be controlled by appropriately sized chambers. Furthermore, such aliquots can be further compartmentalized by use of a lubricant to encapsulate the aliquot within a droplet or microdroplet. In particular cases, the volume is less than about 1 mL, 750 µL, 500 µL, 250 µL, 100 µL, 50 µL, 10 µL, 5 µL, 1 µL, 750 nL, 500 nL, 250 nL, 100 nL, 50 nL, 10 nL, 5 nL, 1 nL, 750 pL, 500 pL, 250 pL, 100 pL, 50 pL, 10 pL, 5 pL, 1 pL, 750 fL, 500 fL, 250 fL, 100 fL, 50 fL, 10 fL, 5 fL, 1 fL, 750 aL, 500 aL, 250 aL, 100 aL, 50 aL, 10 aL, 5 aL, or 1 aL. In other cases, the volume is from about 1 aL to about 1 mL (e.g., 1 aL to 750 µL, 1 aL to 500 µL, 1 aL to 250 µL, 1 aL to 100 µL, 1 aL to 50 µL, 1 aL to 10 µL, 1 aL to 5 µL, 1 aL to 1 µL, 1 aL to 750 nL, 1 aL to 500 nL, 1 aL to 250 nL, 1 aL to 100 nL, 1 aL to 50 nL, 1 aL to 10 nL, 1 aL to 5 nL, 1 aL to 1 nL, 1 aL to 750 pL, 1 aL to 500 pL, 1 aL to 250 pL, 1 aL to 100 pL, 1 aL to 50 pL, 1 aL to 10 pL, 1 aL to 5 pL, 1 aL to 1 pL, 1 aL to 750 fL, 5 aL to 1 mL, 5 aL to 750 µL, 5 aL to 500 µL, 5 aL to 250 µL, 5 aL to 100 µL, 5 aL to 50 µL, 5 aL to 10 µL, 5 aL to 5 µL, 5 aL to 1 µL, 5 aL to 750 nL, 5 aL to 500 nL, 5 aL to 250 nL, 5 aL to 100 nL, 5 aL to 50 nL, 5 aL to 10 nL, 5 aL to 5 nL, 5 aL to 1 nL, 5 aL to 750 pL, 5 aL to 500 pL, 5 aL to 250 pL, 5 aL to 100 pL, 5 aL to 50 pL, 5 aL to 10 pL, 5 aL to 5 pL, 5 aL to 1 pL, 5 aL to 750 fL, 1 fL to 1 mL, 1 fL to 750 µL, 1 fL to 500 µL, 1 fL to 250 µL, 1 fL to 100 µL, 1 fL to 50 µL, 1 fL to 10 µL, 1 fL to 5

μL, 1 fL to 1 μL, 1 fL to 750 nL, 1 fL to 500 nL, 1 fL to 250 nL, 1 fL to 100 nL, 1 fL to 50 nL, 1 fL to 10 nL, 1 fL to 5 nL, 1 fL to 1 nL, 1 fL to 750 pL, 1 fL to 500 pL, 1 fL to 250 pL, 1 fL to 100 pL, 1 fL to 50 pL, 1 fL to 10 pL, 1 fL to 5 pL, 1 fL to 1 pL, 1 fL to 750 fL, 1 pL to 1 mL, 1 pL to 750 μL, 1 pL to 500 μL, 1 pL to 250 μL, 1 pL to 100 μL, 1 pL to 50 μL, 1 pL to 10 μL, 1 pL to 5 μL, 1 pL to 1 μL, 1 pL to 750 nL, 1 pL to 500 nL, 1 pL to 250 nL, 1 pL to 100 nL, 1 pL to 50 nL, 1 pL to 10 nL, 1 pL to 5 nL, 1 pL to 1 nL, 1 pL to 750 pL, 1 pL to 500 pL, 1 pL to 250 pL, 1 pL to 100 pL, 1 pL to 50 pL, 1 pL to 10 pL, 1 pL to 5 pL, 1 nL to 1 mL, 1 nL to 750 μL, 1 nL to 500 μL, 1 nL to 250 μL, 1 nL to 100 μL, 1 nL to 50 μL, 1 nL to 10 μL, 1 nL to 5 μL, 1 nL to 1 μL, 1 nL to 750 nL, 1 nL to 500 nL, 1 nL to 250 nL, 1 nL to 100 nL, 1 nL to 50 nL, 1 nL to 10 nL, or 1 nL to 5 nL).

Various types of sample preparation and analysis can be conducted in the devices of the invention. Exemplary sample preparation and analysis include nucleic acid extraction, nucleic acid purification, nucleic acid enrichment, nucleic acid concentration, protein extraction, protein purification, protein enrichment, protein concentration, cell separation, sample enrichment, nucleic acid amplification, nucleic acid detection, protein detection, filtration, lysis, dehydration, rehydration, a binding reaction, a washing step, elution, an assay reaction, and/or detection of one or more samples or one or more analytes within a sample.

In particular, the methods described herein can be beneficial when analyzing samples with low concentrations of analytes, for example, dilute samples; rare nucleic acids, proteins, markers, and biomarkers of genetic or infectious disease; environmental pollutants; rare cells, such as circulating cancer cells, stem cells, or fetal cells in maternal blood for prenatal diagnostics; microbial cells in blood, sputum, bone marrow aspirates and other bodily fluids such as urine and cerebral spinal fluid for rapid early diagnostics of infections; viral loads (e.g., for HIV and/or HCV) in samples (e.g., in samples from subjects having or suspected of having chlamydia, gonorrhea, and/or HIV); enzymatic assays; cellular assays, such as to determine cell viability, cell adhesion, cell binding etc.; biological or chemical screens for catalytic activity, selectivity, or storage ability or sequestration (such as absorption of gas or trapping of toxic compounds, etc.); or analytical testing various properties such as electrical, magnetic, optical, etc. See e.g., U.S. Pub. Nos. 2005/0003399 and Int. Pub. No. WO 2009/048673, incorporated herein by reference. In particular, detecting low concentrations of an analyte (e.g., a single molecule or a single bacterium) remains a challenge in food, medical, and security industries. The device of the invention could be useful for concentrating such samples and performing analysis. In one example, the devices of the invention can be useful for creating a high local concentration of an analyte (e.g., by compartmentalization within a chamber and/or a droplet or by concentration by using a capture region) that would only be present in dilute concentrations for a bulk solution. In another example, devices of the invention can create high local concentrations of an analyte that can further be amplified, such as by PCR with a DNA sample or by quorum sensing with a bacterial sample. Accordingly, the devices of the invention can be used in combination with any useful PCR technique. Exemplary PCR techniques are disclosed in the following publications: US 2008/0166793, WO 08/069884, US 2005/0019792, WO 07/081386, WO 07/081387, WO 07/133710, WO 07/081385, WO 08/063227, US 2007/0195127, WO 07/089541, WO 07/030501, US 2007/0052781, WO 06/096571, US 2006/0078893, US 2006/0078888, US 2007/0184489, US 2007/0092914, US 2005/0221339, US 2007/0003442, US 2006/0163385, US 2005/0172476, US 2008/0003142, and US 2008/0014589, each of which is incorporated by reference herein in its entirety. The following articles, describing methods for concentrating cells and/or chemicals by making small volume areas with low numbers of items to no items being incorporated into the areas, with specific applications involving PCR, are incorporated by reference herein: Koh et al., Anal. Chem. 75:4591-4598 (2003); Gulliksen et al., Lab Chip. 5:416-420 (2005); Abrams et al., Ann N Y Acad. Sci. 1098:375-388 (2007); Cady et al., Proc. IEEE Sensors, 24-27 Oct. 2004 3:1191-1194 (2004); Ottesen et al., Science 314:1464-1467 (2006); Govind et al., Electrophoresis 27:3753-3763 (2006); Lapizco-Encinas et al., J. Microbiol. Methods 62:317-326 (2005); Wong et al., Anal. Chem. 76:6908-6914 (2004); Yang et al., Lab Chip 2:179-187 (2002); Du et al., Anal. Chem. 77:1330-1337 (2005); Huang et al., Science 315:81-84 (2004); Hong et al., Nat. Biotechnol. 22:435-439 (2004); Liu et al., Electrophoresis 23:1531-1536 (2003); Matsubara et al., Biosens. Bioelectron. 20:1482-1490 (2005); and Leamon et al., Nat. Methods 3:541-543 (2006).

The systems, methods, and devices of the present invention can be used to study and perform coagulation or clotting assays, protein aggregation, protein crystallization (including the use of lipidic cubic phase), crystallization and analysis of small molecules, macromolecules, and particles, crystallization and analysis of polymorphs, crystallization of pharmaceuticals, drugs and drug candidates, biomineralization, nanoparticle formation, the environment (via aqueous and air sampling), culturing conditions (e.g., stochastic confinement, lysis of cells, etc.), drug susceptibility, drug interactions, high throughput screening (e.g., one first substance with many, different second substances, or many, different first substances with many, different second substances), multiplex assays (e.g. PCR, Taqman, immunoassays (e.g., ELISA, FISH, etc.)), amplification (e.g., PCR, ligase chain reaction (LCR), transcription mediated amplification (TMA), reverse transcriptase initiated PCR, DNA or RNA hybridization techniques, sequencing, and the like), sandwich immunoassays, chemotaxis assays, ramification amplification (RAM), etc. Exemplary techniques for blood assays, crystallization assays, protein aggregation assays, culturing assays are described in U.S. Pat. Nos. 7,129,091, 6,949,575, 5,688,651, 7,329,485, 6,949,575, 5,688,651, 7,329,485, and 7,375,190; U.S. Pub. Nos. 2007/0172954, 2006/0003439, 2003/0022243, and 2005/0087122; and Int. Pub. Nos. WO 2007/089777 and WO 2009/015390, each of which is incorporated herein by reference in its entireties. The device of the present invention can be used for various syntheses, including catalysis, multistep reactions, immobilized multistep synthesis (e.g., small molecule, peptide and nucleic acid syntheses), solid state synthesis, radioisotope synthesis, etc. Finally, the device of the present invention can be used for purification and enrichment of samples.

In some examples, the device can contain chambers that are used as a positive control (e.g., an analyte pre-loaded in a chamber) and/or a negative control (e.g., a buffer pre-loaded in a chamber).

The systems, devices, and methods of the invention can be used to conduct any useful reaction. Exemplary, non-limiting reactions include photochemical and electrochemical reactions, chemical reactions such as amplification reactions (e.g., amplification of nucleic acids), synthetic reactions (e.g., synthesis of radioisotopes), neutralization reactions, decomposition reactions, displacement reactions, reduction-oxidation reactions, precipitation, crystallization (e.g., protein crystallization by free interface diffusion and/or vapor diffusion), combustion reactions, and polymerization reactions, as well as covalent and noncovalent binding, phase change, color change, phase formation, dissolution, light emission, changes of light absorption or emissive properties, temperature change or heat absorption or emission, conformational change, and folding or unfolding of a macromolecule such as a protein. Multistep reactions may be performed by controlling conditions at each subsequent relative movement of the device.

The systems, methods, and devices of the present invention can be designed to load multiple areas with different substances easily and economically. For example, the device can be manufactured to include multiple chambers for preserving and analyzing samples 1, 2, and 3. Furthermore, each layer can be designed to perform a particular function. For example, a first layer allows for sample preparation (e.g., by including one or more desiccants, such as any described herein), a second layer allows for sample purification (e.g., by use of one or more capture regions, such as any described herein), and a third layer allows for sample collection (e.g., any useful sample described herein).

In other examples, the device can contain a plurality of chambers configured in the same locations as a standard multi-well plate or configured radially. Each layer can contain, for example, 6, 24, 96, 384, 1536, 3456, or 9600 chambers. In other examples, the device could contain at least about 1, 2, 3, 4, 5, 6, 7, 8, 9, 10, 20, 24, 30, 40, 48, 50, 60, 70, 80, 90, 96, 100, 200, 300, 384, 400, 500, 512, 1000, 1500, 1536, 2000, 2500, 3000, 3456, 3500, 4000, 4500, 5000, 6000, 7000, 8000, 9000, 9600, 10000, 1500, 2000, 2500, 3000, 4000, 5000, 6000, 7000, 8000, 9000, 10000, 20000, 30000, 40000, 50000, 60000, 70000, 80000, 90000, 100000, 200000, 200000, 400000, 500000, 600000, 700000, 800000, 900000, 1000000, or more chambers.

The system and device of the invention can be able to perform sample preparation by filtration, and the same approach can also be used for target enrichment. A matrix, such as a filtration membrane, gel, and through holes/pores, can be brought in contact with collected sample by slipping the first layer with respect to the second and/or third layer, e.g., in a SlipChip device. With a driving force, such as positive pressure, negative pressure, or gradient, only the particles and molecules in the sample layer with size smaller than the matrix pore size (i.e., particles) can pass through the matrix in the second layer and enter the receiving well in the third layer. Larger particles will remain in the sample well or be captured in the matrix. In some cases, the material passing through the size selection matrix can be used for downstream analysis, such as immunoassay, or further sample manipulation, such as nucleic acid extraction. In some cases, particles larger than the pore size (i.e., particles) can be enriched on the matrix, and further analysis can be directly applied on the matrix, such as, cell counting, cell lysis, and nucleic acid extraction.

Alternatively, the matrix may contain capture molecules, such as aptamers and ChargeSwitch® materials to concentrate/enrich target molecule. In other cases, the matrix may contain capture molecules to remove target molecules or analytes, such as inhibitors, from the sample solution.

For example, this general method can be applied for plasma separation from whole blood. We designed and optimized a plasma separation module with Pall® vivid plasma separation membrane as the matrix. Approximately 1/50 of atmosphere positive pressure is applied to increase the speed of plasma filtration. This plasma preparation device was able to prepare approximately 10 to 20 µL of cell-free plasma from 100 µL of whole human blood within 60 seconds. Free flow plasma can be collected from the bottom of the device. No blood cells from prepared plasma were observed by using stereoscope.

Alternatively, the device (e.g., a SlipChip device) can be applied for white blood cell enrichment. A membrane of white blood cell isolation (leukosorb) medium can be integrated in the device as matrix. Whole blood can be driven through the matrix by pressure or gravity, and the white blood cells can be trapped in the matrix for downstream analysis.

The device can control the total volume passing through separation matrix by a dead-end filling method instead of using valves, plungers or other fluidic control methods. The total passing volume during sample preparation is defined by the volumes of receiving chambers. Therefore, as long as the process pressure is less than the leaking pressure, the aqueous fluid will be contained without leaking by capillary force. This dead-end filling feature enables the device to process multiple samples in parallel, manipulate single or multiple samples with multistep procedure and process samples in multiple volumes. This method also enables robust and accurate volume control which is defined by the volume of receiving wells.

Sample preparation can enable downstream reactions and analysis, such as nucleic acid amplification and immunoassays. Current sample preparation methods generally require multiple instruments, plug-in power supply, and trained personnel, which are less favorable in point-of-care and resource limited settings. The device of the invention can perform sample preparation without complex fluidic manipulation systems, such as pumps, valve, syringe barrels, etc. Such devices can perform sample preparation by relative movement of layers to bring sample solution and different reagents, such as washing and elution buffers, in or out of contact with sample preparation matrix. Relative movement of different plates/layers can be translational, rotational or a combination of both.

A multilayer approach (e.g., using a SlipChip device or any device described herein) can be used to extend the capability of the device further, such as integration of modules with various functions. Each layer can be designed to move freely (e.g., slip) relative to other layers. For example, in sample preparation, the separation matrix or nucleic acid extraction matrix can be embedded in the intermediate layer, reagent chambers are provided in the top layer, and receiving chambers are provided in the bottom layer. By slipping the intermediate layer, the capture region or matrix is aligned with each set of reagent chamber and receiving chamber, respectively. Receiving chambers with dead-end filling design can be used to control precisely the solution volume passing through the matrix. The speed of oil or lubricant displacement can be controlled by the gap and surface chemistry.

In some other example, the system, method, or device includes a membrane, matrix, or filter that can be impregnated with at least one substance for lysing the cells, spores, or microorganisms in the sample, while drying the sample on the membrane, matrix, or filter by heating and/or absorbing moisture with the desiccant (e.g., such as described in U.S. Pat. Nos. 8,247,176 and 6,645,717, which is incorporated hereby by reference in its entirety). The released nucleic acid or other biomarkers can bind to the membrane matrix or filter, and further washing and elution can be applied.

Volume Quantification

The devices, methods, and systems of the invention can be used to quantify volumes of a sample, a reagent, or any useful substance (e.g., any described herein). In particular, quantification of volumes can be used in combination with any of the other devices and methods described herein, such as for sample preservation, sample treatment, sample preparation, and/or sample analysis. In particular, such volume quantification techniques can be useful for screening of special populations (such as newborns, infants, or small animals, e.g., for screening inherited metabolic disorders or lysosomal storage disorders, such as Fabry, Gaucher, Krabbe, Niemann—Pick A/B, and Pompe disease; for screening viral infections, such as HIV or CMV; or for screening other disorders using useful diagnostic markers, such as screening for succinylacetone, acylcarnitines, and amino acids to detect tyrosinemia type I (TYR 1) in newborns or infants), for use with a dried blood spot (DBS) sample (e.g., in combination with one or more sample preservation and/or storage devices and methods, as described herein), for screening metabolites (e.g., for pharmacokinetic, pharmacodynamic, toxicokinetic, or other drug monitoring assessments), for use in clinical trials (e.g., for pharmacokinetic or pharmacodynamic assessment of investigational drugs in clinical trials), and for determining adherence with particular drugs (e.g., for pharmacokinetic, pharmacodynamic, toxicokinetic, or other drug monitoring assessments). In particular casess, the test sample is a dried blood spot sample. In one non-limiting example, the device including one or more of a membrane, a bridge, a matrix, a capture region, and/or a desiccant (e.g., a device for sample preservation including one or more of a membrane, a bridge, and/or a desiccant) is used, either with or without a collector, and a blood sample is introduced into the device. Next, the blood sample is dried (either partially or completely, e.g., as described herein). In some cases, the blood sample is dried onto a cellulose membrane that is optionally in fluidic communication with a desiccant. Then, the dried blood sample is processed and/or analyzed using one or more useful substances or reagents. Exemplary substances or reagents include a buffer (e.g., a wash buffer or an elution buffer, e.g., PBS containing 0.05% Tween 80 and 0.005% sodium azide, or any described herein), such as those used for screening in DBS technology, including amplification (e.g., PCR); detection of a virus, bacteria, protozoa, and/or helminth (e.g., HIV, hepatitis C virus, hepatitis B virus, hepatitis A virus, herpes simplex virus, rubella, measles, MMR (measles, mumps, and rubella), diphtheria, dengue, tetanus antitoxin, cytomegalovirus, human T-cell leukemia/lymphoma virus I or II, *Mycobacterium leprae*, *Helicobacter pylori*, *Brucella* sp, *Treponema pallidum*, *Toxoplasma gondii*, *Plasmodium falciparum*, *Trypanosoma cruzi*, *Giardia lamblia*, *Leishmania* spp, *Echinococcus granulosus*, *Schistosoma haematobium*, or *Brugia malayi*); detection of one or more metabolites (e.g., drug metabolites); detection of one or more analytes (e.g., any described herein, and including androstenedione, amino acids (e.g., arginine (Krebs cycle), histidine/urocanic acid, homocysteine, phenylalanine/tyrosine, and/or tryptophan), apolipoprotein (e.g., A-I or B), cortisol, CD4+ lymphocytes, cholesterol (e.g., including total cholesterol or high-density lipoprotein cholesterol (HDL)), C-reactive protein (CRP), dehydroepiandrosterone (DHEA, including its sulfate ester, DHEA-S), Epstein-Ban virus (EBV) antibodies, estradiol, folate, follicle-stimulating hormone (FSH), glucose, hemoglobin (e.g., including glycosylated Hemoglobin or HbA1c), hepatitis antigen/antibodies (e.g., hepatitis A, B, or C), HIV antibodies, homocysteine, IFNg, IGF-I, IGFBP-2, IGFB-3, IL-1b, IL-6, insulin, leptin, luteinizing hormone (LH), lipoprotein (e.g., (a), B/A-1, or β), prostate-specific antigen (PSA), progesterone, prolactin, retinol, sex hormone binding globulin (SHBG), somatomedin-C, testosterone, transferrin receptor, thyrotropin (TSH), thyroxine (T4), thyroglobulin, triglycerides, triiodothyronine (T3), or TNF (e.g., TNFa)); detection of one or more diagnostic markers for special populations, such as a newborn, a neonate, or an infant (e.g., detection of IgG antibodies for diagnosing infections; detection of succinylacetone, acylcarnitines, and amino acids for diagnosing tyrosinemia type I (TYR 1); detection of medium chain acyl CoA dehydrogenase for diagnosing MCAD deficiency; detection of human chorionic gonadotropin (hCG) for diagnosing Down syndrome; detection of glycated hemoglobin for diagnosing insulin-dependent diabetes; detection of trypsin for diagnosing cystic fibrosis; detection of HIV-specific antibodies and/or of HIV virus in combination with PCR; detection of thyroxine (T4) and thyrotropin (TSH) for diagnosing congenital hypothyroidism; detection of one or more enzymes (e.g., acid α-glucocerebrosidase (ABG), acid α-galactosidase A (GLA), lysosomal acid α-glucosidase (GAA), galactocerebroside α-galactosidase (GALC), or acid sphingomyelinase (ASM)) involved in lysosomal metabolism for diagnosing lysosomal storage disorders (e.g., Pompe, mucopolysaccharidosis (e.g., type I), Fabry, Gaucher, or Niemann-Pick type A/B diseases); for DNA analysis in combination with PCR analysis (e.g., for detecting or diagnosing acetylator polymorphism, alcohol dehydrogenase, alpha 1-antitrypsin, cystic fibrosis, Duchenne/Becker muscular dystrophy, glucose-6-phosphate dehydrogenase, hemoglobinopathy A, hemoglobinopathy S, hemoglobinopathy C, hemoglobinopathy E, D-Punjab, beta-thalassemia, hepatitis B virus, HCMV, HIV-1, HTLV-1, Leber hereditary optic neuropathy, MCAD, PKU, *Plasmodium vivax*, sexual differentiation, or 21-deoxycortisol); for detecting certain antigens (e.g., hepatitis B virus or HIV-1); for detecting certain antibodies (e.g., adenovirus, anti-nuclear antibody, anti-zeta antibody, arbovirus, Aujeszky's disease virus, dengue virus, *Dracunculus medinensis*, *Echinococcus granulosus*, *Entamoeba histolytica*, enterovirus, *Giardia duodenalisa*, *Helicobacter pylori*, hepatitis B virus, herpes virus, HIV-1, IgE (atopic disease), influenza virus, *Leishmania donovani*, leptospira, measles/mumps/rubella *Mycobacterium leprae*, *Mycoplasma pneumoniae*, *Onchocerca volvulus*, parainfluenza virus, *Plasmodium falciparum*, poliovirus, *Pseudomonas aeruginosa*, respiratory syncytial virus, *rickettsia* (scrub typhus), *Schistosoma mansoni*, *Toxoplasma gondii*, *Trepenoma pallidium*, *Trypanosoma cruzi/rangeli* vesicular *stomatis* virus, *Wuchereria bancrofti*, or yellow fever virus); or screening of one or more drug metabolites or drug analytes (e.g., for pharmacokinetic, pharmacodynamic, toxicokinetic, or other drug monitoring assessments in clinical trials, in clinical monitoring, or in determining adherence with particular drugs, where exemplary drugs include anti-cancer drugs such as everolimus or tacrolimus; acetaminophen; investigational new drugs; or others). Further analytes, DBS assays, and methods are described in McDade et al., Demography 44:899-925 (2007); Cassol et al., J. Clin. Microbiol. 29:667-671 (1991); Bellisaro et al., Clin. Chem. 46:1422-1424 (2000); Williams et al., J. Gerontol. B Psychol. Sci. Soc. Sci. 64B(suppl_1): i131-i136 (2009); Parker et al., J. Clin. Pathol. 52:633-639 (1999); Li et al., Biomed. Chromatograph. 24:49-65 (2010); and De Jesus et al., Clin. Chem. 55:158-164 (2009), each of which is incorporated herein in its entirety.

Combined Sample Preservation, Sample Treatment, Sample Preparation, and/or Volume Quantification Any of the systems, devices, and/or methods herein can be combined to achieve multiplexed sample storage, sample preservation, and/or analysis. For instance, the devices herein for sample preservation and/or volume quantification (e.g., including one or more membranes, bridges, and/or desiccants) can be combined with one or more features provided for devices herein for sample treatment and/or sample analysis (e.g., including one or more capture regions). Accordingly, the devices of the invention encompass those having multiple layers, where at least one layer includes a plurality of first chambers, at least one layer includes one or more capture regions, and at least one or more layer includes a membrane or one or more bridges, where at least one of the plurality of first chamber, at least one of the one or more capture regions, and the membrane or at least one of the one or more bridges are able to be connected by relative movement. In further examples, the device includes a layer having at least one second chamber (e.g., a plurality of second chambers), where at least one of the plurality of first chamber, at least one of the one or more capture regions, or the membrane or at least one of the one or more bridges are able to be connected by relative movement to at least one second chamber. In a similar manner, such devices can have additional layers (e.g., any described herein, including one or more intermediate layers, deformable layers, and/or membranes), as well as any component (e.g., autonomous controller, housing, cap, system, or lid, of any described herein) or any modification (e.g., one or more coatings) described herein. Furthermore, the devices can include any useful reagent, substance, or sample (e.g., one or more desiccants, matrices, membranes, or any as described herein), and use of the device of any useful method (e.g., as described herein).

Operational Parameters

Assays and other operations performed by the systems, devices, or methods, as described herein (e.g., assays, sample loading, sample preservation, sample concentration, sample treatment, sample preparation, volume quantification, or combinations thereof) can be completed in a certain amount of time. In some cases, the amount of time to complete an assay or other operation can be about 60 minutes, 55 minutes, 50 minutes, 45 minutes, 40 minutes, 35 minutes, 30 minutes, 25 minutes, 20 minutes, 15 minutes, 10 minutes, 9 minutes, 8 minutes, 7 minutes, 6 minutes, 5 minutes, 4.5 minutes, 4 minutes, 3.5 minutes, 3 minutes, 2.5 minutes, 2 minutes, 1.5 minutes, 1 minute, 45 seconds, 30 seconds, or 15 seconds. In some cases, the amount of time to complete an assay or other operation can be less than or equal to about 60 minutes, 55 minutes, 50 minutes, 45 minutes, 40 minutes, 35 minutes, 30 minutes, 25 minutes, 20 minutes, 15 minutes, 10 minutes, 9 minutes, 8 minutes, 7 minutes, 6 minutes, 5 minutes, 4.5 minutes, 4 minutes, 3.5 minutes, 3 minutes, 2.5 minutes, 2 minutes, 1.5 minutes, 1 minute, 45 seconds, 30 seconds, or 15 seconds. For example, the time elapsed from sample loading to the completion of sample preparation (e.g., nucleic acid extraction and purification) can be less than or equal to about 10 minutes, 9 minutes, 8 minutes, 7 minutes, 6 minutes, 5 minutes, 4.5 minutes, 4 minutes, 3.5 minutes, 3 minutes, 2.5 minutes, 2 minutes, 1.5 minutes, 1 minute, 45 seconds, 30 seconds, or 15 seconds. In another example, the time elapsed from sample loading to presentation of an assay result can be less than or equal to about 60 minutes, 55 minutes, 50 minutes, 45 minutes, 40 minutes, 35 minutes, 30 minutes, 25 minutes, 20 minutes, 15 minutes, 10 minutes, 9 minutes, 8 minutes, 7 minutes, 6 minutes, 5 minutes, 4.5 minutes, 4 minutes, 3.5 minutes, 3 minutes, 2.5 minutes, 2 minutes, 1.5 minutes, 1 minute, 45 seconds, 30 seconds, or 15 seconds.

Sample preparation or purification operations performed by the systems, devices, or methods, as described herein, can provide a prepared, extracted, or purified sample (e.g., analyte, molecule, biological molecule, cell, nucleic acid, protein) of a certain purity. The prepared, extracted, or purified sample can be about 45% pure, 50% pure, 55% pure, 60% pure, 65% pure, 70% pure, 75% pure, 80% pure, 85% pure, 90% pure, 95% pure, 96% pure, 97% pure, 98% pure, 99% pure, or 100% pure. The prepared, extracted, or purified sample can be at least about 45% pure, 50% pure, 55% pure, 60% pure, 65% pure, 70% pure, 75% pure, 80% pure, 85% pure, 90% pure, 95% pure, 96% pure, 97% pure, 98% pure, 99% pure, or 100% pure.

Sample preparation or purification operations performed by the systems, devices, or methods, as described herein, can provide a prepared, extracted, or purified sample (e.g., analyte, molecule, biological molecule, cell, nucleic acid, protein) at a certain recovery rate or efficiency. The recovery of an analyte or other sample material can be about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100%. The recovery of an analyte or other sample material can be at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, or 100%. In one example, a sample (e.g. plasma or urine) is loaded onto a sample preparation device, and higher than 50% of the analytes (e.g., viral RNA, bacterial RNA, or bacterial DNA) in the sample are recovered in the prepared sample output.

Sample preparation or purification operations performed by the systems, devices, or methods, as described herein, can provide a prepared, extracted, or purified sample (e.g., analyte, molecule, biological molecule, cell, nucleic acid, protein) at a certain concentration factor. The concentration factor can be about 1.1 fold, 1.2 fold, 1.3 fold, 1.4 fold, 1.5 fold, 1.6 fold, 1.7 fold, 1.8 fold, 1.9 fold, 2 fold, 2.5 fold, 3 fold, 3.5 fold, 4 fold, 4.5 fold, 5 fold, 5.5 fold, 6 fold, 6.5 fold, 7 fold, 7.5 fold, 8 fold, 8.5 fold, 9 fold, 9.5 fold, 10 fold, 11 fold, 12 fold, 13 fold, 14 fold, 15 fold, 16 fold, 17 fold, 18 fold, 19 fold, 20 fold, 21 fold, 22 fold, 23 fold, 24 fold, 25 fold, 26 fold, 27 fold, 28 fold, 29 fold, 30 fold, 31 fold, 32 fold, 33 fold, 34 fold, 35 fold, 36 fold, 37 fold, 38 fold, 39 fold, 40 fold, 41 fold, 42 fold, 43 fold, 44 fold, 45 fold, 46 fold, 47 fold, 48 fold, 49 fold, 50 fold, 51 fold, 52 fold, 53 fold, 54 fold, 55 fold, 56 fold, 57 fold, 58 fold, 59 fold, 60 fold, 61 fold, 62 fold, 63 fold, 64 fold, 65 fold, 66 fold, 67 fold, 68 fold, 69 fold, 70 fold, 71 fold, 72 fold, 73 fold, 74 fold, 75 fold, 76 fold, 77 fold, 78 fold, 79 fold, 80 fold, 81 fold, 82 fold, 83 fold, 84 fold, 85 fold, 86 fold, 87 fold, 88 fold, 89 fold, 90 fold, 91 fold, 92 fold, 93 fold, 94 fold, 95 fold, 96 fold, 97 fold, 98 fold, 99 fold, 100 fold, 200 fold, 300 fold, 400 fold, 500 fold, 600 fold, 700 fold, 800 fold, 900 fold, or 1000 fold. The concentration factor can be at least about 1.1 fold, 1.2 fold, 1.3 fold, 1.4 fold, 1.5 fold, 1.6 fold, 1.7 fold, 1.8 fold, 1.9 fold, 2 fold, 2.5 fold, 3 fold, 3.5 fold, 4 fold, 4.5 fold, 5 fold, 5.5 fold, 6 fold, 6.5 fold, 7 fold, 7.5 fold, 8 fold, 8.5 fold, 9 fold, 9.5 fold, 10 fold, 11 fold, 12 fold, 13 fold, 14 fold, 15 fold, 16 fold, 17 fold, 18 fold, 19 fold, 20 fold, 21 fold, 22 fold, 23 fold, 24 fold, 25 fold, 26 fold, 27 fold, 28 fold, 29 fold, 30 fold, 31 fold, 32 fold, 33 fold, 34 fold, 35 fold, 36 fold, 37 fold, 38 fold, 39 fold, 40 fold, 41 fold, 42 fold, 43 fold, 44 fold, 45 fold, 46 fold, 47 fold, 48 fold, 49 fold, 50 fold, 51 fold, 52 fold, 53 fold, 54 fold, 55 fold, 56 fold, 57 fold, 58 fold, 59 fold, 60 fold, 61 fold, 62 fold, 63 fold, 64 fold, 65 fold, 66 fold, 67 fold, 68 fold, 69 fold, 70 fold, 71 fold, 72 fold, 73 fold, 74 fold, 75 fold, 76 fold, 77 fold, 78 fold, 79 fold, 80 fold, 81 fold, 82 fold, 83 fold, 84 fold, 85 fold, 86 fold, 87 fold, 88 fold, 89 fold, 90 fold, 91 fold, 92 fold, 93 fold, 94 fold, 95 fold, 96 fold, 97 fold, 98 fold, 99 fold, 100 fold, 200 fold, 300 fold, 400 fold, 500 fold, 600 fold, 700 fold, 800 fold, 900 fold, or 1000 fold.

Sample preparation or purification operations performed by the systems, devices, or methods, as described herein, can provide a prepared, extracted, or purified sample (e.g., analyte, molecule, biological molecule, cell, nucleic acid, protein) at a certain volume reduction factor. That is, the volume of prepared sample produced by or recovered from the device can be smaller than the volume of sample loaded into the device. In some cases, this can result in a concentration of the sample or analyte. The volume reduction factor can be about 1.1 fold, 1.2 fold, 1.3 fold, 1.4 fold, 1.5 fold, 1.6 fold, 1.7 fold, 1.8 fold, 1.9 fold, 2 fold, 2.5 fold, 3 fold, 3.5 fold, 4 fold, 4.5 fold, 5 fold, 5.5 fold, 6 fold, 6.5 fold, 7 fold, 7.5 fold, 8 fold, 8.5 fold, 9 fold, 9.5 fold, 10 fold, 11 fold, 12 fold, 13 fold, 14 fold, 15 fold, 16 fold, 17 fold, 18 fold, 19 fold, 20 fold, 21 fold, 22 fold, 23 fold, 24 fold, 25 fold, 26 fold, 27 fold, 28 fold, 29 fold, 30 fold, 31 fold, 32 fold, 33 fold, 34 fold, 35 fold, 36 fold, 37 fold, 38 fold, 39 fold, 40 fold, 41 fold, 42 fold, 43 fold, 44 fold, 45 fold, 46 fold, 47 fold, 48 fold, 49 fold, 50 fold, 51 fold, 52 fold, 53 fold, 54 fold, 55 fold, 56 fold, 57 fold, 58 fold, 59 fold, 60 fold, 61 fold, 62 fold, 63 fold, 64 fold, 65 fold, 66 fold, 67 fold, 68 fold, 69 fold, 70 fold, 71 fold, 72 fold, 73 fold, 74 fold, 75 fold, 76 fold, 77 fold, 78 fold, 79 fold, 80 fold, 81 fold, 82 fold, 83 fold, 84 fold, 85 fold, 86 fold, 87 fold, 88 fold, 89 fold, 90 fold, 91 fold, 92 fold, 93 fold, 94 fold, 95 fold, 96 fold, 97 fold, 98 fold, 99 fold, 100 fold, 200 fold, 300 fold, 400 fold, 500 fold, 600 fold, 700 fold, 800 fold, 900 fold, or 1000 fold. The volume reduction factor can be at least about 1.1 fold, 1.2 fold, 1.3 fold, 1.4 fold, 1.5 fold, 1.6 fold, 1.7 fold, 1.8 fold, 1.9 fold, 2 fold, 2.5 fold, 3 fold, 3.5 fold, 4 fold, 4.5 fold, 5 fold, 5.5 fold, 6 fold, 6.5 fold, 7 fold, 7.5 fold, 8 fold, 8.5 fold, 9 fold, 9.5 fold, 10 fold, 11 fold, 12 fold, 13 fold, 14 fold, 15 fold, 16 fold, 17 fold, 18 fold, 19 fold, 20 fold, 21 fold, 22 fold, 23 fold, 24 fold, 25 fold, 26 fold, 27 fold, 28 fold, 29 fold, 30 fold, 31 fold, 32 fold, 33 fold, 34 fold, 35 fold, 36 fold, 37 fold, 38 fold, 39 fold, 40 fold, 41 fold, 42 fold, 43 fold, 44 fold, 45 fold, 46 fold, 47 fold, 48 fold, 49 fold, 50 fold, 51 fold, 52 fold, 53 fold, 54 fold, 55 fold, 56 fold, 57 fold, 58 fold, 59 fold, 60 fold, 61 fold, 62 fold, 63 fold, 64 fold, 65 fold, 66 fold, 67 fold, 68 fold, 69 fold, 70 fold, 71 fold, 72 fold, 73 fold, 74 fold, 75 fold, 76 fold, 77 fold, 78 fold, 79 fold, 80 fold, 81 fold, 82 fold, 83 fold, 84 fold, 85 fold, 86 fold, 87 fold, 88 fold, 89 fold, 90 fold, 91 fold, 92 fold, 93 fold, 94 fold, 95 fold, 96 fold, 97 fold, 98 fold, 99 fold, 100 fold, 200 fold, 300 fold, 400 fold, 500 fold, 600 fold, 700 fold, 800 fold, 900 fold, or 1000 fold. In one example, 0.5 mL of sample (e.g., urine or plasma) is loaded onto a device, and the elution volume for prepared sample is 50 µL, resulting in a 10 fold reduction in volume and corresponding concentration in analytes. In another example, 1.0 mL of sample (e.g., urine or plasma) is loaded onto a device, and the elution volume for prepared sample is 20 µL, resulting in a 50 fold reduction in volume and corresponding concentration in analytes.

Sample preparation or purification operations performed by the systems, devices, or methods, as described herein, can provide a prepared, extracted, or purified sample (e.g., analyte, molecule, biological molecule, cell, nucleic acid, protein) with a reduced concentration or number of inhibitors. Inhibitors can be inhibitors of a reaction, such as any described herein, including but not limited to an amplification reaction (e.g., PCR, ramification amplification (RAM), digital PCR, digital isothermal recombinase-polymerase amplification (RPA), loop-mediated isothermal amplification (LAMP), nucleic acid sequence-based amplification (NASBA)), TaqMan assays, immunoassays, sandwich immunoassays, ELISA, chemotaxis, and synthesis reactions (e.g., catalysis, multistep reactions, immobilized multistep synthesis (e.g., small molecule, peptide and nucleic acid syntheses), solid state synthesis, or radioisotope synthesis). The concentration or number of inhibitors can be reduced by about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.9%, 99.99%, or 100%. The concentration or number of inhibitors can be reduced by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, 99%, 99.9%, 99.99%, or 100%. In one example, a sample (e.g. plasma or urine) is loaded onto a sample preparation device, and more than 75% of amplification inhibitors in the sample are removed and not present in the prepared sample output.

Assays and other analysis operations performed by the systems, devices, or methods, as described herein, can detect analytes or other sample material at certain sensitivities. In some cases, the sensitivity of an assay or other analysis operation can be about 1 molar (M), 100 millimolar (mM), 10 mM, 1 mM, 100 nanomolar (nM), 10 nm, 1 nm, 100 picomolar (pM), 10 pM, 1 pM, 100 femtomolar (fM), 10 fM, 1 fM, 100 attomolar (aM), 10 aM, 1 aM, 100 zeptomolar (zM), 10 zM, or 1 zM. In some cases, the sensitivity of an assay or other analysis operation can be at least about 1 molar (M), 100 millimolar (mM), 10 mM, 1 mM, 100 nanomolar (nM), 10 nm, 1 nm, 100 picomolar (pM), 10 pM, 1 pM, 100 femtomolar (fM), 10 fM, 1 fM, 100 attomolar (aM), 10 aM, 1 aM, 100 zeptomolar (zM), 10 zM, or 1 zM. In some cases, the sensitivity of an assay or other analysis operation can detect a single analyte (e.g., molecule, cell, virus, nucleic acid, protein). In some cases, the sensitivity of an assay or other analysis operation can detect at least about 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, 90, 95, or 100 analytes. In some cases, the sensitivity of an assay or other analysis operation can detect a concentration of less than about 1 part per thousand, 100 parts per million (ppm), 10 ppm, 1 ppm, 100 parts per billion (ppb), 10 ppb, 1 ppb, 100 parts per trillion (ppt), 10 ppt, 1 ppt, 100 parts per quadrillion, 10 parts per quadrillion, 1 part per quadrillion, 100 parts per quintillion, 10 parts per quintillion, 1 part per quintillion, 100 parts per sextillion, 10 parts per sextillion, or 1 part per sextillion.

Assays and other analysis operations performed by the systems, devices, or methods, as described herein, can detect analytes or other sample material at certain accuracies. In some cases, the false positive rate of an assay or other analysis operation can be about 20%, 15%, 10%, 9%, 8%, 7%, 6%, 5%, 4%, 3%, 2%, 1%, 0.5% 0.1%, 0.05%, or 0.01%. In some cases, the false positive rate of an assay or other analysis operation can be less than or equal to about 20%, 15%, 10%, 9%, 8%, 7%, 6%, 5%, 4%, 3%, 2%, 1%, 0.5% 0.1%, 0.05%, or 0.01%. In some cases, the false negative rate of an assay or other analysis operation can be about 20%, 15%, 10%, 9%, 8%, 7%, 6%, 5%, 4%, 3%, 2%, 1%, 0.5% 0.1%, 0.05%, or 0.01%. In some cases, the false negative rate of an assay or other analysis operation can be less than or equal to about 20%, 15%, 10%, 9%, 8%, 7%, 6%, 5%, 4%, 3%, 2%, 1%, 0.5% 0.1%, 0.05%, or 0.01%.

Fluid dispensing systems, sample preparation devices, integrated devices, and other devices and systems can have a particular weight. The weight of a device or system can be less than about 30 pounds, 20 pounds, 10 pounds, 9 pounds, 8 pounds, 7 pounds, 6 pounds, 5 pounds, 4 pounds, 3 pounds, 2 pounds, 1 pound, 15 ounces, 14 ounces, 13 ounces, 12 ounces, 11 ounces, 10 ounces, 9 ounces, 8 ounces, 7 ounces, 6 ounces, 5 ounces, 4 ounces, 3 ounces, 2 ounces, or 1 ounce. The weight of a device or system can be about 30 pounds, 20 pounds, 10 pounds, 9 pounds, 8 pounds, 7 pounds, 6 pounds, 5 pounds, 4 pounds, 3 pounds, 2 pounds, 1 pound, 15 ounces, 14 ounces, 13 ounces, 12 ounces, 11 ounces, 10 ounces, 9 ounces, 8 ounces, 7 ounces, 6 ounces, 5 ounces, 4 ounces, 3 ounces, 2 ounces, or 1 ounce.

Kits for Sample Preservation, Sample Treatment, Sample Preparation, and/or Volume Quantification Any of the system, devices, and/or methods herein can be provided with additional components to facilitate sample storage, sample preservation, and/or analysis. Further exemplary components include a collector (e.g., for collection fluid samples (e.g., blood, saliva, urine, sputum, feces, or tissue, or any described herein), such as a lancet (e.g., a Safety-Lancet, available from SARSTEDT, Nümbrecht, Germany), a capillary (e.g., a Microvette® capillary or a Multivette® capillary, available from SARSTEDT), a needle (e.g., a safety needle in combination with a syringe, such as an S-Monovette® system available from SARSTEDT), a syringe, a swab, a sample tube (e.g., a Monovette® tube, available from SARSTEDT), or a microtube), one or more reagents (e.g., any described herein, including those useful for collecting and/or preserving blood samples, such as heparin, citrate, a gel (e.g., a polyacrylic ester gel), a clotting activator (e.g., a particle, such as silicate particles), or EDTA and those useful for binding, reacting, or preserving one or more analytes of interest, such as any described herein), and/or one or more controls (e.g., one or more standard controls for an analyte of interest and/or one or more negative controls, such as buffer). The kit can optionally include instructions for use, such as providing step-by-step instructions for any method described herein.

Automated Analysis with System and/or Device

The invention can further include a housing system surrounding the device, where the housing system includes an access port for inserting a sample, and a cap or lid for enclosing the housing system. As described herein, closing the cap can result in introducing the sample into the device. To achieve automation, the cap or housing system can include one or more assemblies (e.g., an autonomous controller, such as any described herein) to effect relative movement of the first, second, and/or intermediate layers upon closing the cap. Such exemplary assembles are described herein and can include linear or rotational actuation mechanisms. Automation can be realized by using a cap to wind up the device, which results in relative movement of the layers for sample preparation. Further autonomous controllers are described herein.

Base Station

Figure 34A:
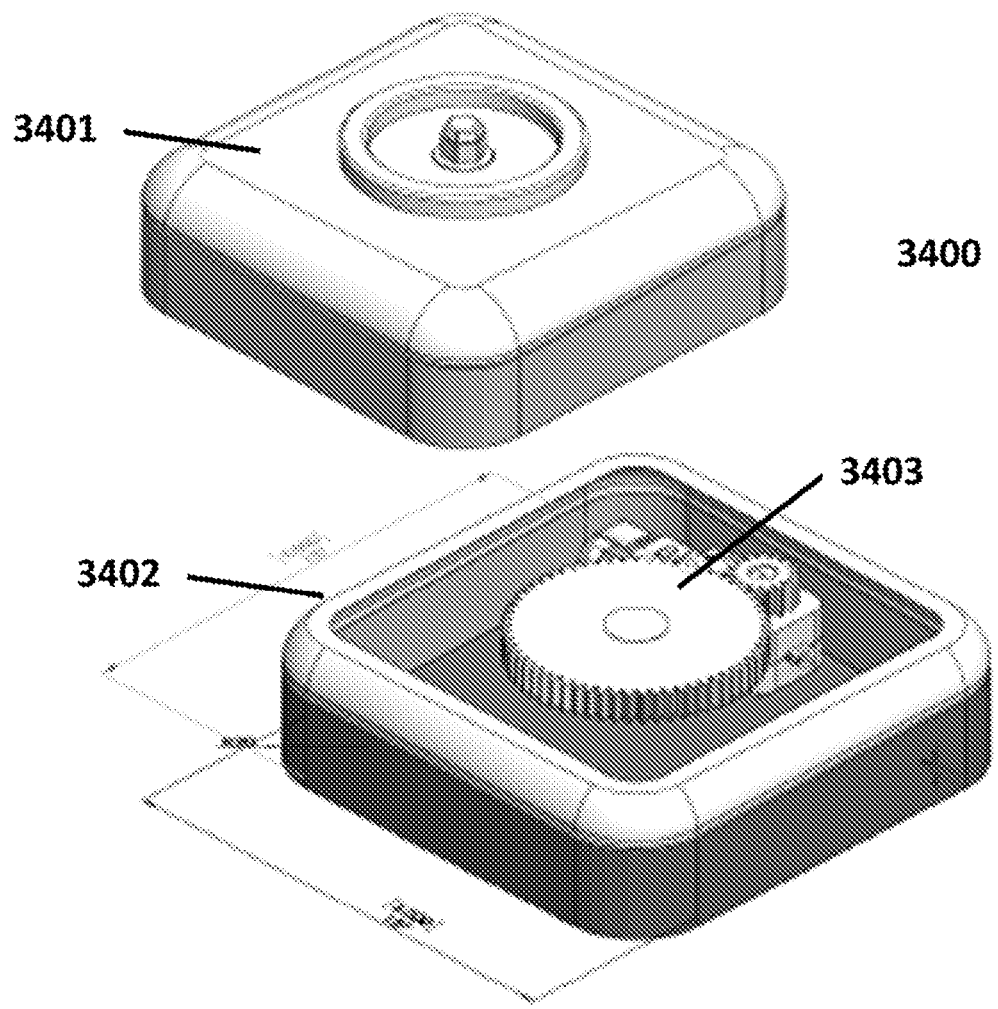

The devices and systems described herein can comprise or be used in conjunction with a base station. A base station can comprise equipment or components for a variety of functions, including but not limited to automation or operation of the device or system, temperature control, detection, power sources, and communications equipment. For example, FIG. 34A shows a base station 3400 comprising an upper housing 3401 and a lower housing 3402, with a motor and associated gear 3403. A base station can comprise an autonomous controller or any of the elements of an autonomous controller, as discussed herein, including power elements, regulating elements, timing elements, moving elements, transfer elements, switches, and linkages.

Figure 34B:
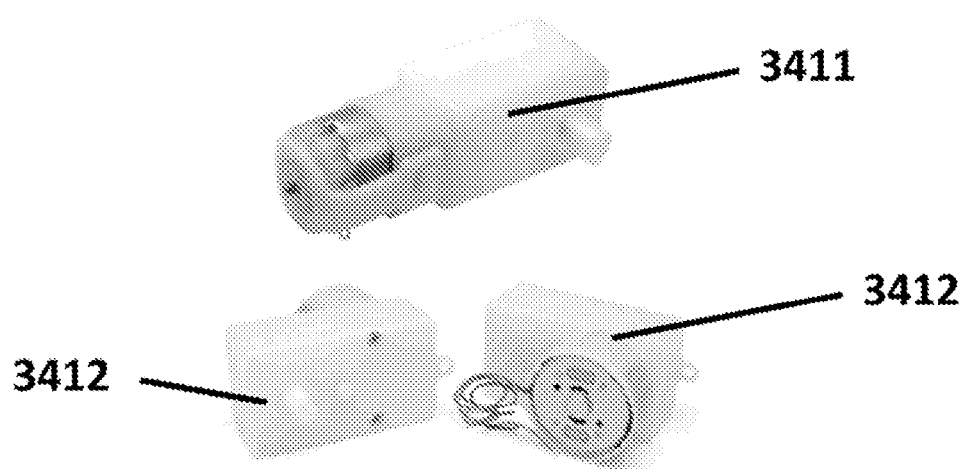

A base station can comprise a motor. A motor can comprise a reduction motor, such as a 90 degree reduction motor 3411 or a standard reduction motor 3412, for example as shown in FIG. 34B.

Figure 34C:
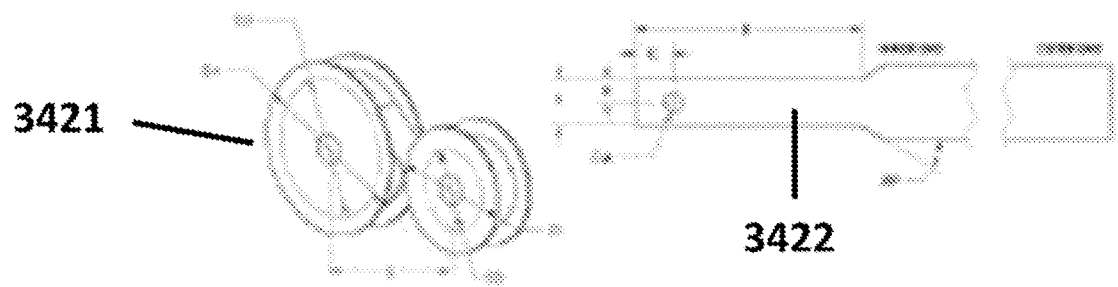
Figure 34C:
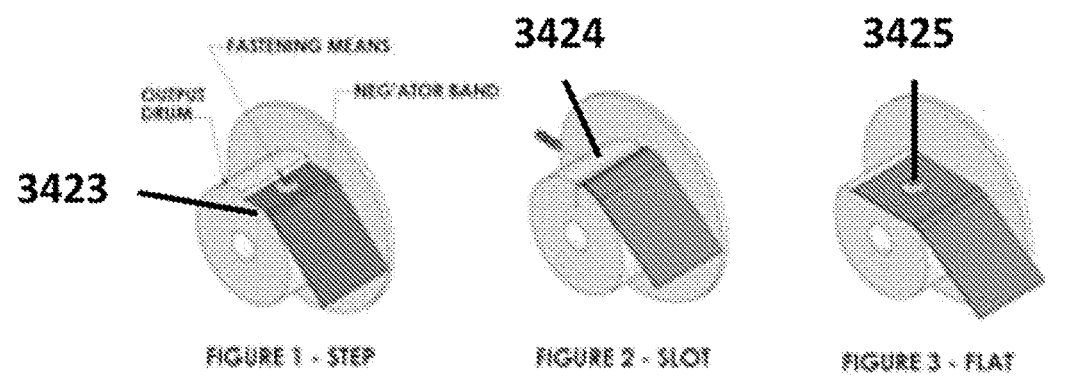
Figure 34C:
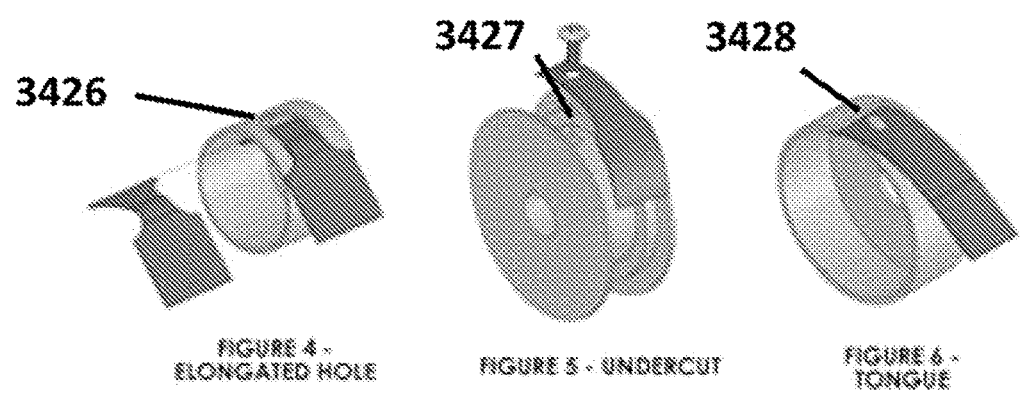

A base station can comprise a spring. A spring can comprise a windup spring 3421 with a band 3422, for example as shown in FIG. 34C. A band can be connected to the windup spring drum with a variety of methods or configurations, including but not limited to a step 3423, a slot 3424, flat 3425, an elongated hole 3426, an undercut 3427, or a tongue 3428.

Figure 34D:
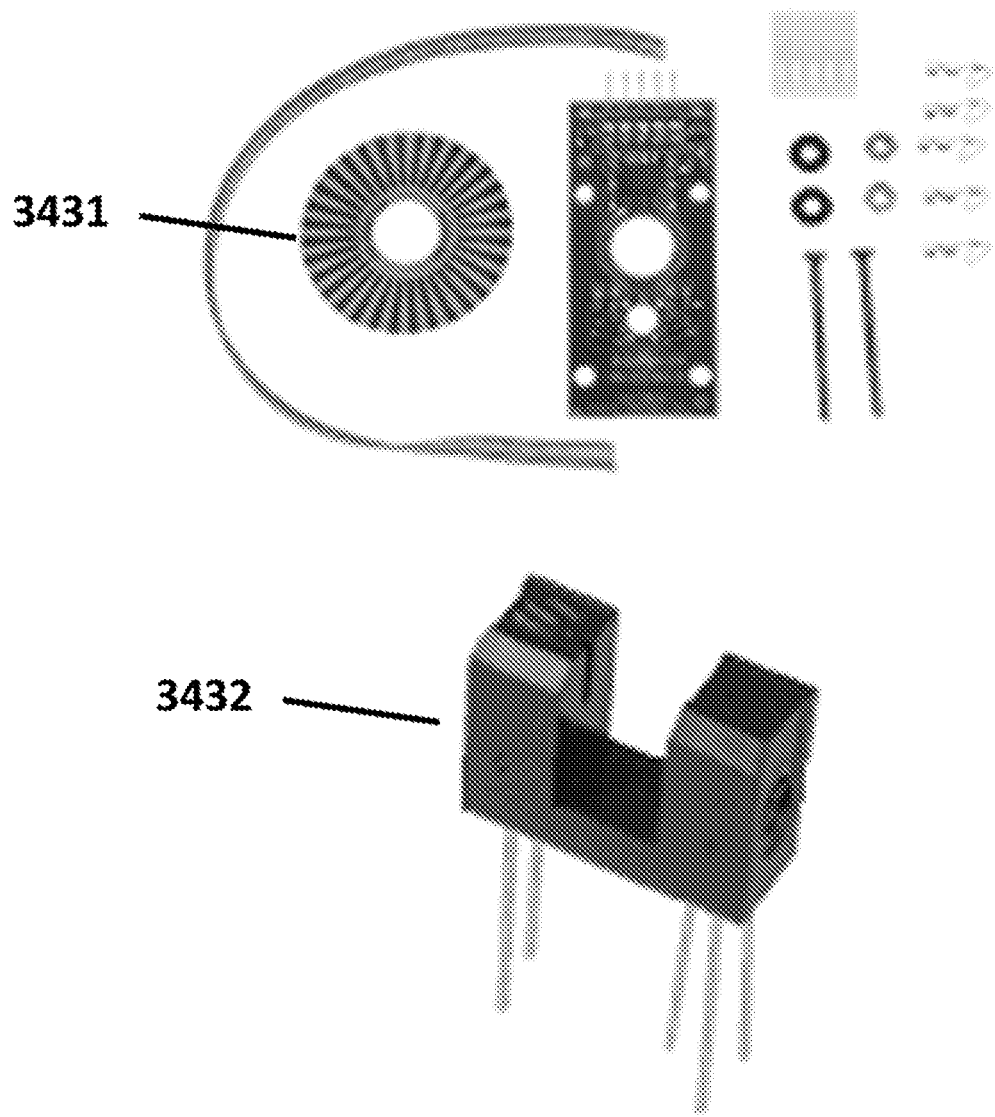

A base station can comprise a position sensor. A position sensor can comprise an encoder, such as a wheel encoder 3431, for example as shown in FIG. 34D. A wheel encoder can be compatible with a GM3 motor. A position sensor can comprise an optical sensor (e.g., an optical interruption switch) 3432, for example as shown in FIG. 34D.

A base station can comprise a temperature controller or any of the elements of a temperature controller as described herein. A temperature controller can provide heating or cooling to control the temperature in a specific region or regions. A temperature controller can comprise thermally conductive materials for coupling to a device.

A base station can comprise a detector. The detector can comprise one or more image sensors. The image sensor can be capable of optical detection. The image sensor can comprise a charge-coupled device (CCD) sensor, including a cooled CCD. The image sensor can comprise an active-pixel sensor (APS), such as a CMOS or NMOS sensor. The detector can comprise a photodiode, such as an avalanche photodiode. The detector can comprise a photomultiplier tube (PMT). The detector can comprise a laser sensor. The sensors can comprise a single sensor or multiple sensors, of the same type or of different types. The detector can comprise a light source. The light source can comprise a lamp, such as an incandescent, halogen, fluorescent, gas-discharge, arc, or LED lamp. The light source can comprise a laser. The light source can produce a specific wavelength or range or wavelengths (e.g., UV light). The light source can comprise filters for controlling the output wavelength or wavelengths. The light source can comprise multiple light sources, of the same or of different types, which can be used separately or in combination. The detector can comprise a filter or filters, including but not limited to wavelength filters (e.g., color filters, UV filters, IR filters), dichroic filters, and polarizing filters. The filters can comprise multiple filters, of the same or of different types, which can be used separately or in combination. The detector can comprise a lens or lenses. The lens can be a macro or "close-up" lens. The lens can be a zoom lens. The lens can be an infrared lens. The lens can be an ultraviolet lens. The lens can be a wide angle lens, including but not limited to wide angle lenses, ultra wide angle lenses, and fisheye lenses. The lenses can comprise multiple lenses, of the same or different types, which can be used separately or in combination.

A base station can comprise a power source. The power source can comprise a battery or battery pack. The power source can comprise any power or energy source described in this disclosure, including but not limited to winder, a spring (e.g., a mainspring, a spiral torsional spring, a semi-reverse torsional spring, or a reverse torsional spring), a hand crank, a rotor mechanism (e.g., having a rotating pendulum and a pinion movable by kinetic energy generated by movement of the user, where the pinion is coupled to a generator and energy is stored in a capacitor or battery), a photovoltaic cell, a battery, a solar cell, a generator (e.g., an electric generator, such as a dynamo, a magnetohydrodynamic generator, an induction generator, a homopolar generator, or an excited generator), an alternator, or a capacitor. The power source can be external to the base station housing or integrated within the base station housing. The power source can comprise adaptors for connection to external power sources. External power sources can include, but are not limited to residential, commercial, or industrial building power, solar panels, and batteries or other energy storage devices. The power source can comprise a combination of different power sources, such as for example a battery and a connection to an external power source.

A base station can comprise communications equipment. The communications equipment can comprise equipment for radio. The communications equipment can comprise equipment for free-space optical (FSO) communication, such as visible or infrared (IR) communication. The communications equipment can comprise equipment for wired communication, including but not limited to universal serial bus (USB), fiber-optics, peripheral component interconnect (PCI), PCI Express (PCIe), or Thunderbolt. The communications equipment can comprise equipment for Wi-Fi, such as IEEE 802.11 a, b, g, or n Wi-Fi. The communications equipment can comprise equipment for cellular data service, such as GSM, CDMA, GPRS, 3G, (e.g., W-CDMA, EDGE, CDMA2000), or 4G (e.g., Long Term Evolution (LTE), Mobile WiMAX). The communications equipment can comprise equipment for mobile satellite communications. The communications equipment can comprise equipment for Bluetooth communication. The communications equipment can comprise multiple types of communications equipment, such as USB and Wi-Fi, or Bluetooth and Wi-Fi. The communications equipment can transmit information from the detector, such as images recorded by the detector. The communications equipment can communicate with remote computer systems, such as desktop computers, laptop computers, tablet computers, smartphone devices, or servers. The communications equipment can communicate with display devices, such as handheld display devices. The communications equipment can transmit information, such as images, to a user or recipient at a separate location or facility.

A base station can be made of various materials, including but not limited to plastic and metal. A base station can be reusable. A base station can be disposable.

Cell Phone Detection

The systems of the invention can further include a detection system for detecting and/or relaying the results of the analysis. A cell phone (or equivalent hand held camera) can be used to image a pattern of dots on a device (e.g., a SlipChip device), to automatically process the photograph for analysis, and to autonomously send and receive results. To allow for a high level of medical care, results can be transmitted to reference laboratories or remote physicians without user effort. In some cases, the device and the cell phone can be provided together for maximum utility in the field.

EXAMPLES

Example 1

The system of the invention can be useful for dispensing fluid/reagent and/or controlling the reaction time with a sample. In particular, the system integrates a fluid dispensing system with a device, which allows for a simplified architecture. The device (e.g., a multilayered device) can include one or more chambers useful for introducing and/or storing a sample, conducting a reaction, and/or transporting a fluid.

In one non-limiting example, the pushing unit is a spring-loaded pusher that moves around or along a surface of a device. When the fluid dispensing system is activated, the pusher rolls over a blister pack and squeezes out fluid of the cavities of the blister pack. Each cavity of the blister pack can include a fluid (e.g., a reagent, a buffer, a sacrificial fluid, an immiscible fluid, etc.). In some cases, the pusher must fully dispense the fluid and cannot move past the first cavity to the next cavity. This ensures that fluids are dispensed in order. In addition, pauses (e.g., for incubation, such as 5 or more minutes) can be introduced by having the pusher run over a dummy blister pack or cavity filled a lubricant (e.g., an oil), where the lubricant is dispensed into a dummy narrow channel (e.g., so it takes the required delay time to push out the lubricant). In this manner, initiation of any useful process can be controlled. For instance and without limitation, heating can be initiated at the right time by dispensing fluid from the blister pack into the device to start a heating reaction within a chamber of the device.

Optionally, this system can be integrated with a SlipChip device. When such a device is used, the motion of the pusher can be used to slip SlipChip layers. By coordinating such movements of the fluid dispensing system with the device, the desired assay can be conducted in a fully autonomous device, where only a single touch is required for a complete pre-programmed operation. For instance, the user loads the sample and activates the device, whereby the remaining assays steps are conducted without further input from the user.

Example 2

The present systems and methods can be implemented with a device to conduct any useful assay or process. In one non-limiting example, the assay or process is selected from an ELISA assay, a sample preparation device (e.g., including one or more capture agents or capture regions, as described herein), a nucleic acid assay, an agricultural GMO assay, or a diagnostic assay. In another non-limiting example, the system includes one or more resistant units including one or more fluids or reagents to conduct the desired array or process. For instance, for an ELISA assay, the one or more resistant units can include one or more of the following: one or more beads, one or more capture antibodies, one or more detection antibodies, one or more enzyme-labeled antibodies, one or more dyes, one or more detection agents, one or more detergents, one or more blocking agents (e.g., bovine serum albumin), one or more washing agents, and one or more buffers.

For a sample preparation device, the one or more resistant units can include one or more of the following: one or more capture agents, one or more elution buffers, one or more washing buffers, one or more chaotropic agents, one or more lysis agents, one or more desiccants, one or more stabilizers, one or more filters, one or more membranes, and one or more markers.

For a nucleic acid assay, the one or more resistant units can include one or more of the following: one or more control nucleic acids, one or more lysis agents, one or more filters, one or more membranes, one or more capture agents, one or more stabilizers, one or more eluting buffers, one or more washing buffers, one or more primers (e.g., where each primer includes one or more sequences for hybridizing with the target, e.g., under stringent conditions), one or more blocking agents (e.g., bovine serum albumin), one or more deoxynucleoside triphosphates, one or more polymerases (e.g., T7 DNA polymerase, Taq polymerase, HotStarTaq Plus DNA Polymerase, etc.), one or more dyes, one or more salts (e.g., divalent salts, such as $MgCl_2$ and/or $MnCl_2$, and/or monovalent salts, such as KCl), one or more reverse transcriptases, and/or one or more templates (e.g., DNA and/or RNA templates).

For an agricultural GMO assay, the one or more resistant units can include one or more of described above for a nucleic acid assay, as well as one or more of the following: one or more primers including sequences for hybridizing with a target selected from DNA of Roundup Ready soy, Roundup Ready canola, MON 810 corn, Bt176 corn, Bt11 corn, StarLink corn, GA21 corn, T25 corn, NK603 corn, CGH351 corn, MON89788 soy, H7-1 sugar beet, GT73 rape, a cauliflower moasic virus (CaMV) regulatory element (e.g., CaMV P35S), a Figwort Mosaic Virus (FMV) regulatory element (e.g., FMV P34S), an *Agrobacterium tumefaciens* regulatory element (e.g., TNOS *A. tumefaciens*), *Salmonella, Listeria, Campylobacter, Shigella, Alicyclobacillus*, and/or *E. coli*.

For a diagnostic assay, the one or more resistant units can include one or more of the following: one or more primers including sequences for hybridizing with a target, one or more probes that hybridize with the target, one or more capture antibodies, one or more detection antibodies, one or more enzyme-labeled antibodies, one or more dyes, and one or more detection agents, where the target can optionally be selected from the following: HIV, hepatitis C virus, hepatitis B virus, chlamydia, gonorrhea, human papillomavirus, *mycobacterium tuberculosis*, gardnerella, trichonomonas, vaginalis and *candida* spp., *legionella* pneumophilia, MRSA, *Staphylococcus aureus*, Group B Streptococci, *mycoplasma* pneumonia, and/or pneumonia.

In any of these examples, the one or more resistant units can be provided in a continuous substrate, where each resistant unit is provided in a particular location of the continuous substrate to allow for integration with or fluidically connect with the device (e.g., a multilayered device) or chamber(s) therein.

Example 3

The present systems and methods can be implemented with a device to dispense one or more fluids/reagents in a controlled manner. A non-limiting example is provided in FIG. 6A-D.

As can be seen in FIG. 6A, the fluid dispensing system includes a pushing unit 610 and resistant units 621, 622, 623 in a channel 602, where the first resistant unit 621 includes lysis agent(s) and the sample, the second resistant unit 622 includes a washing buffer, and the third resistant unit 623 includes an elution buffer.

As also can be seen in FIG. 6A, the device includes a single substrate 601 having multiple chambers, including a sample chamber 603 and an elution chamber 604. The device also includes multiple channels to fluidically connect the resistant units to the sample and elution chambers. These multiple channels connect to a capture agent ("matrix") 660, which then connect to a main channel. To control fluidic connections, the device also includes a valve 670 to reversibly connect the main channel to either the sample chamber 603 or the elution chamber 604.

In use, a relative movement is used to advance the pushing unit and contact the pushing unit with the first resistant unit (FIG. 6A), which results in causing the contents of this resistant unit to enter the chamber (FIG. 6B). As the valve is positioned to provide fluidic communication from the first resistant unit to the sample chamber, the lysis agent(s) and sample are delivered to this chamber. Next, another relative movement (or the continued relative movement) results in the pushing unit contacting the second resistant unit (FIG. 6C). The elapsed time between contacting the first and second resistant units provides a time delay in adding the fluid of the first and second resistant units. If desired, one or more resistant units can be included between the first and second resistant units to further include a time delay between the sample loading/lysing step and the washing step. Then, another relative movement (or the continued relative movement) results in the pushing unit contacting the third resistant unit (FIG. 6D), thereby releasing the contents of this resistant unit into the main channel. As can be seen, the valve can be positioned to provide fluidic communication between the third resistant unit and the elution chamber.

The device and fluid dispensing system can be configured to execute the necessary steps to perform the desired assay or process. In the configuration provided in FIG. 6B, the sample is lysed, and the target from the sample (if any) would be captured on the matrix. To accomplish this step, the system is configured to have the first resistant unit contain the required agents to perform the lysis step and to deliver the lysed sample to the matrix. In FIG. 6C, the matrix is washed to remove non-binding materials. For this step, the system is configured to provide the wash buffer in the second resistant unit and to ensure that the speed of the pushing unit and the resistance of the resistant unit (e.g., including resistance from any other chamber) allow for sufficient washing time. In FIG. 6D, the captured target is eluted from the matrix and transported to the elution chamber. For this elution step, the system is configured to provide an elution buffer in the third resistant unit, to ensure that the pushing unit and resistant unit(s) allow for sufficient elution time, as well as flow rate of the elution buffer, and to provide a valve to deliver the eluted sample to a separate compartment. These configurations, as well as adaptations thereof, can be included in any system, device, or method herein.

Example 4

Sample Preparation on the Device with Blister and Cam

Figure 8A:
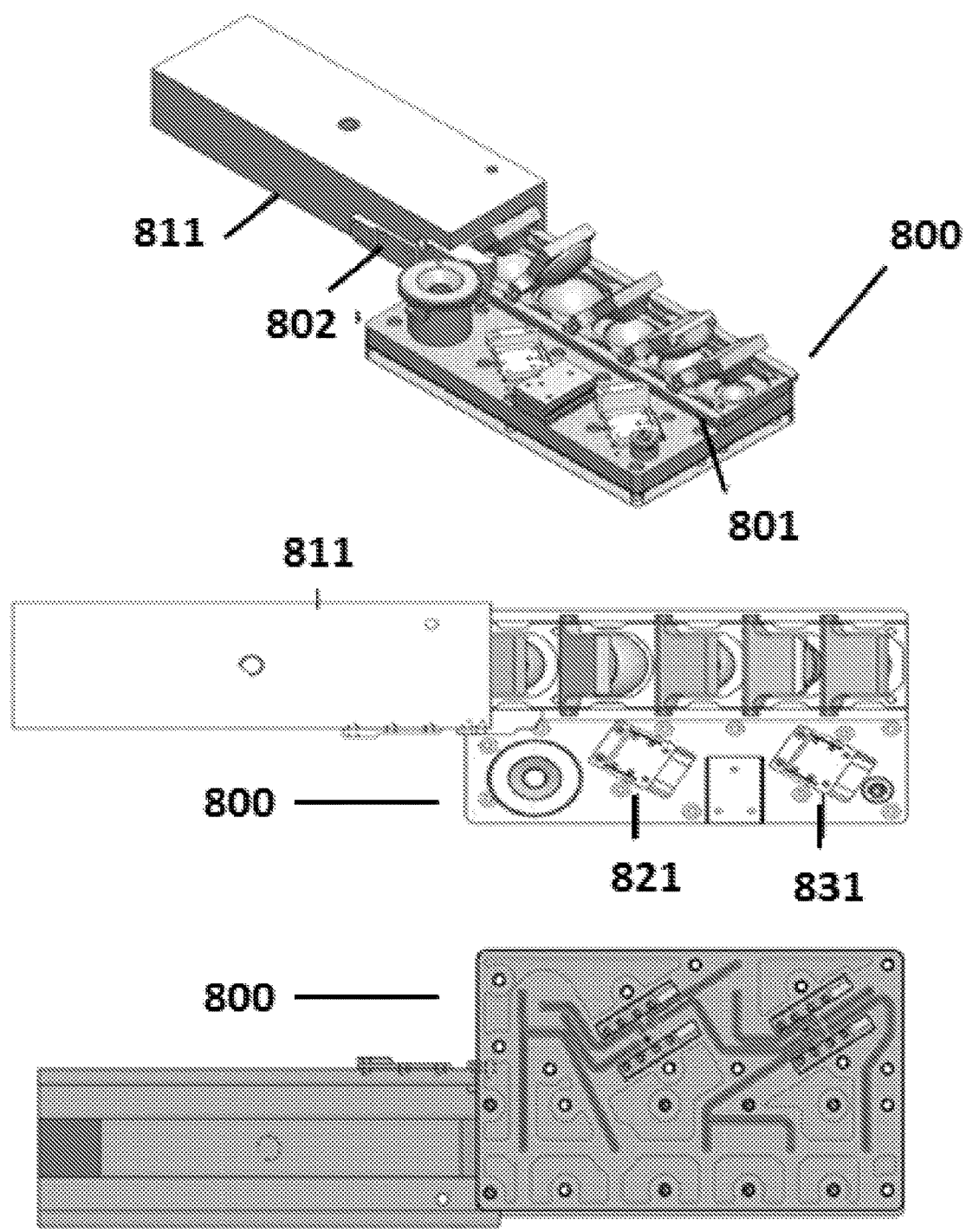
FIG. 8A shows an exemplary schematic of a sample preparation device in a first position.
Figure 8B:
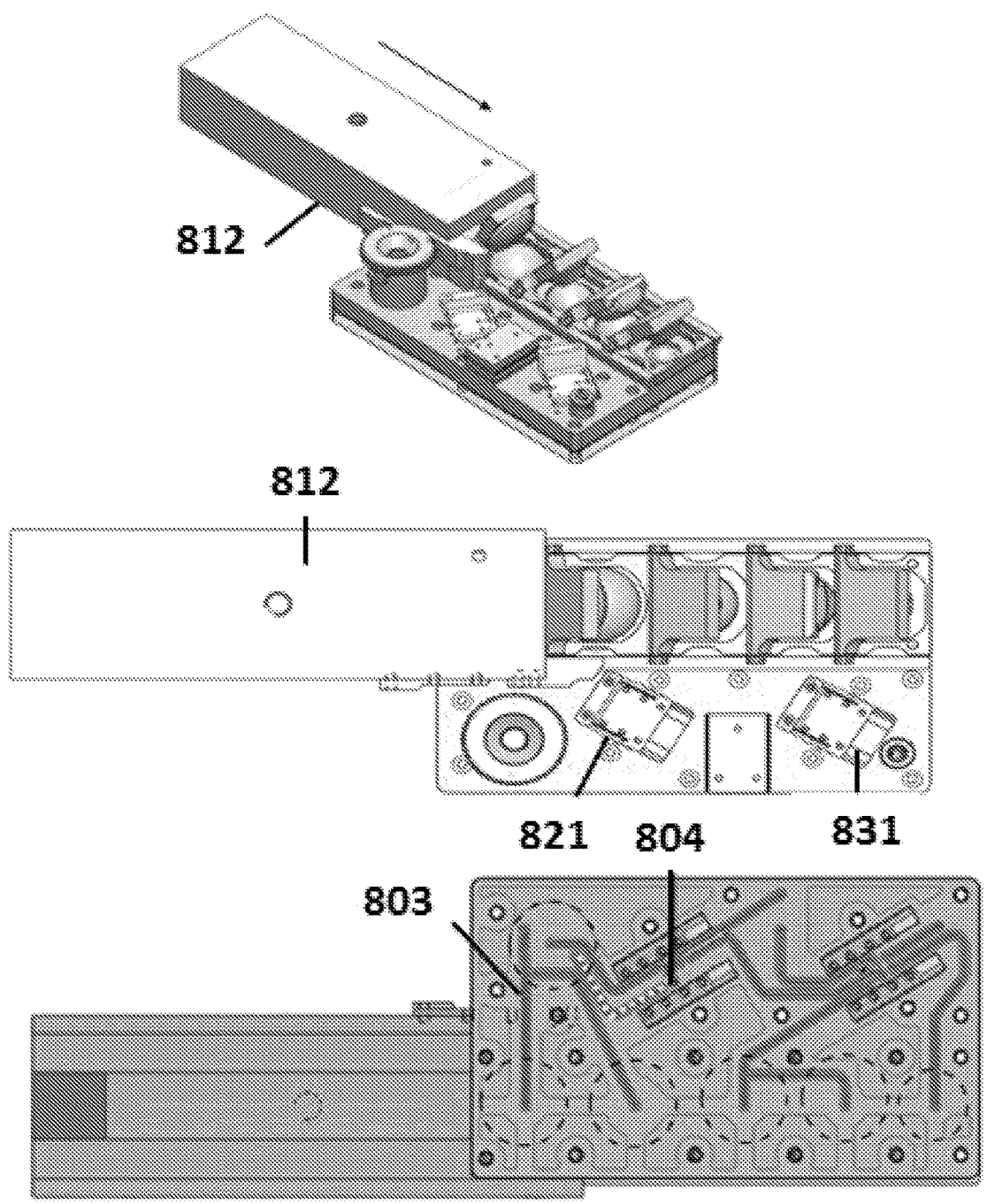
FIG. 8B shows an exemplary schematic of a sample preparation device in a second position.
Figure 8C:
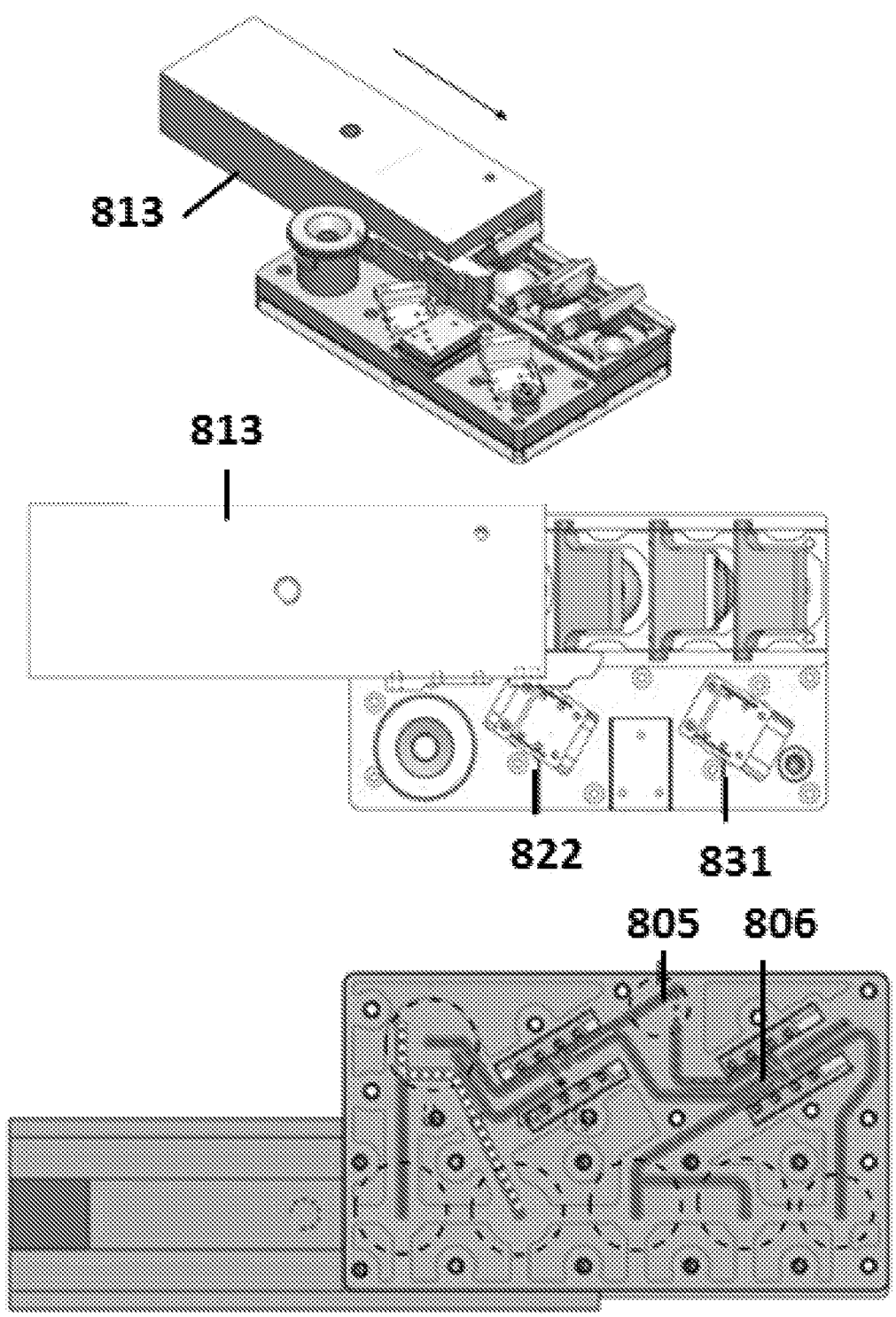
FIG. 8C shows an exemplary schematic of a sample preparation device in a third position.
Figure 8D:
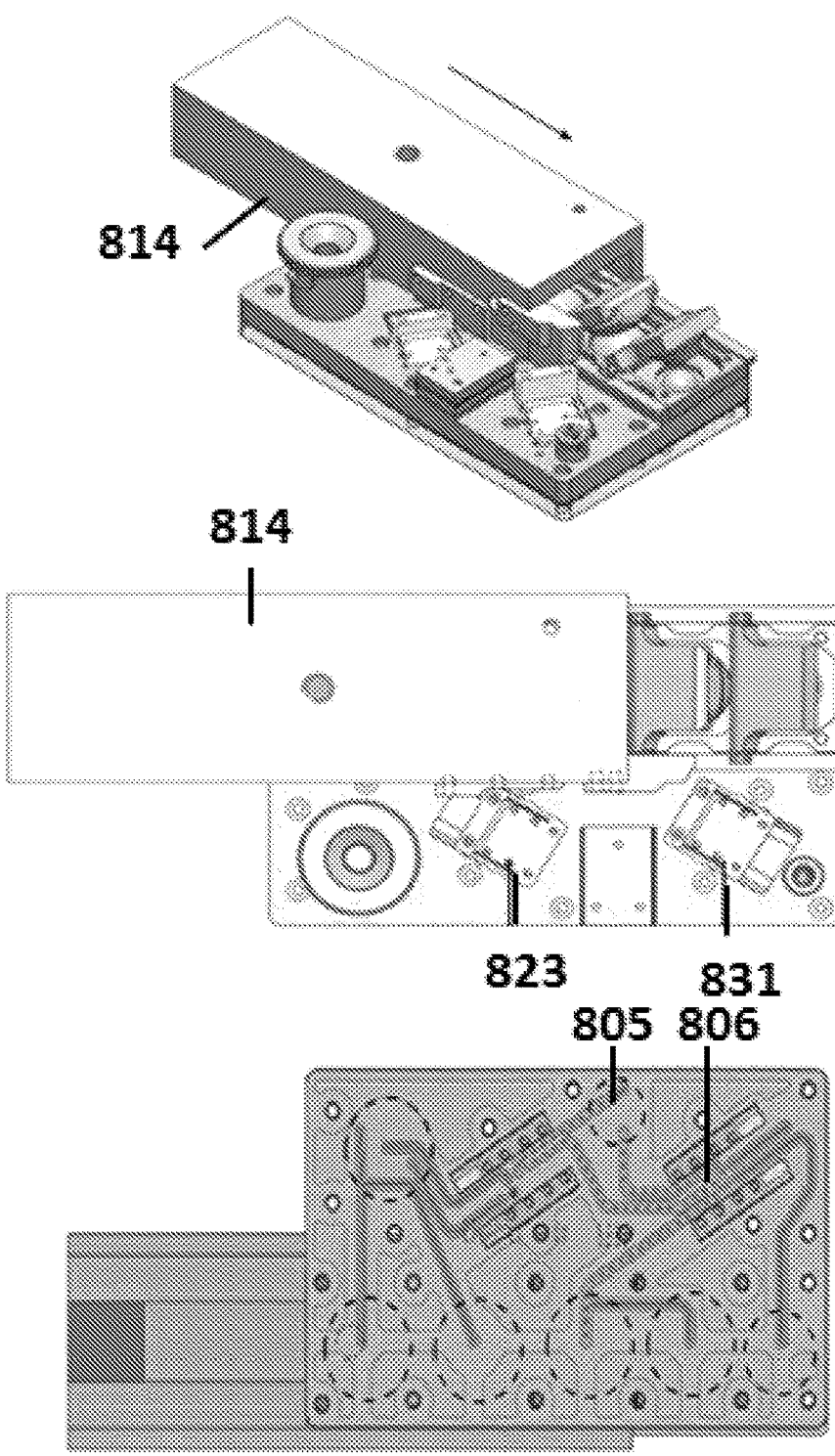
FIG. 8D shows an exemplary schematic of a sample preparation device in a fourth position.
Figure 8E:
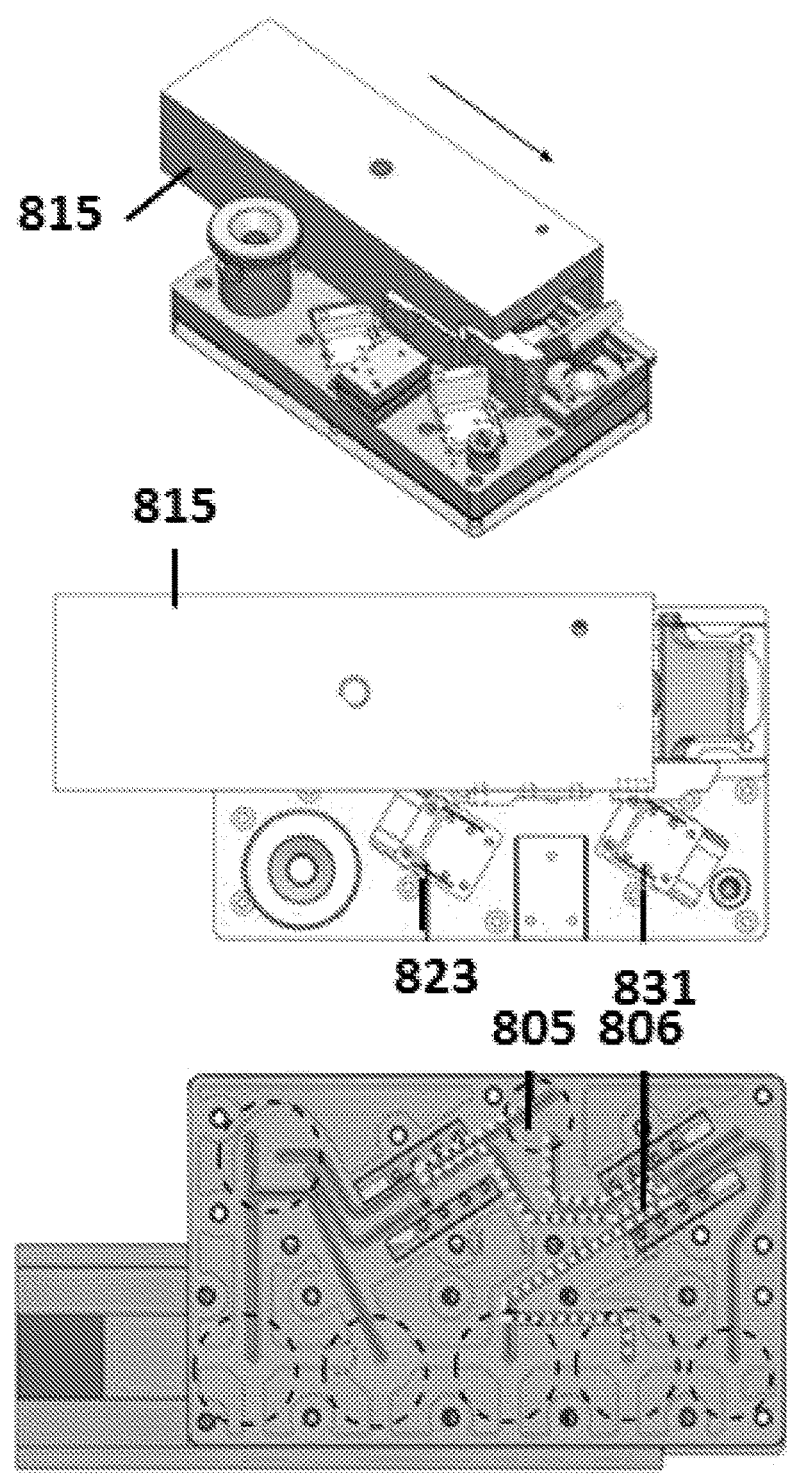
FIG. 8E shows an exemplary schematic of a sample preparation device in a fifth position.
Figure 8F:
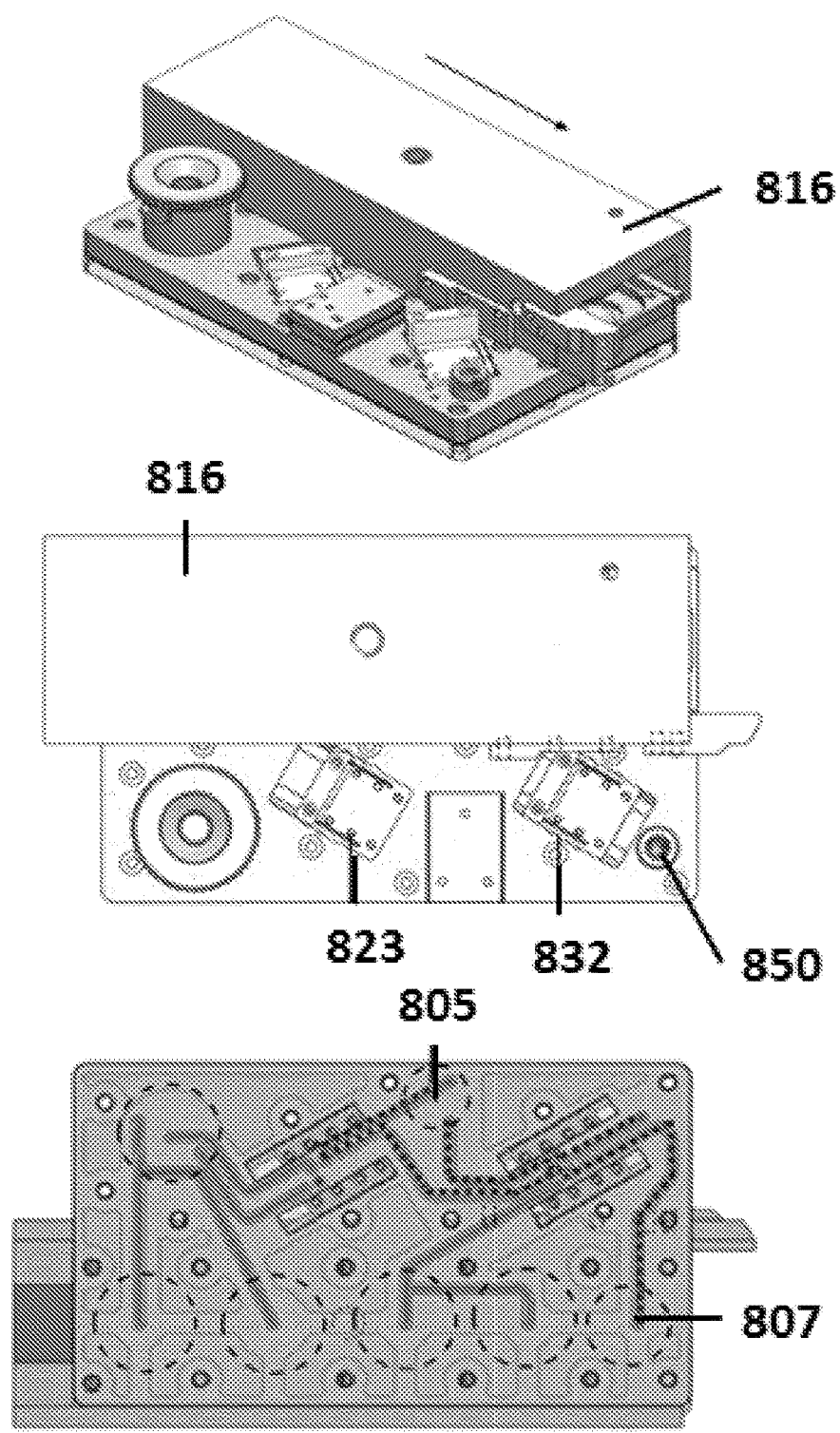
FIG. 8F shows an exemplary schematic of a sample preparation device in a sixth position.

FIG. 8A-8F and FIG. 11 show an exemplary method for preparing a sample comprising nucleic acid using a device provided in the present disclosure. First, 200 μL of plasma sample comprising HIV viral particles at a concentration of $5 \times 10^5$ copies/mL is loaded into the sample well 1120. The sample well cap 1121 is then closed and rotated to a lock position (FIG. 11). After the sample loading, a pushing unit (e.g., a cam) 811 is brought in contact with the rails 801, with valve-1 at position 1 821 connecting the sample well to the air vent 804 and valve-2 at position 1 831 connecting the filter to the waste vent 806 (FIG. 8A). The pushing unit is then moved forward to push down the lysis actuator 1111 and depress the lysis blister 1101. The lysis buffer enters the sample well 803 and mix with the sample therein FIG. 8B. Viral particles are broken apart with the effect of lysis and release the viral nucleic acid. Following the release of nucleic acid, the cam is moved forward for the second time, setting valve-1 to position 2 822 which connects the sample well to the filter 805; valve-2 remains at position 1 831 and it connects the filter to the waste vent 806. The pushing unit is then moved forward for the third time to push down the air actuator 1112 which can depress the air blister 1102 and displace the air to pressurize the sample well with positive air pressure. The lysed sample is pushed through the filter and exits from the waste vent, while nucleic acid is captured on the matrix 805; additional air can be used to dry the matrix (FIG. 8C). The cam is moved forward for the fourth time to the next position, moving valve-1 to position 3 823 and keeping valve-2 at position 1 831, which connect the washing channels to the filter and the filter to the waste vent, respectively. Subsequently, the cam is moved forward for the fifth time to push down the wash-1 actuator 1113 which can depress the first washing blister 1103 and displace the washing buffer. The washing buffer is passed through the matrix and removes inhibitors for downstream amplification (FIG. 8D). Next, the cam is moved forward for the sixth time, keeping valve-1 is at position 3 823 where it connects the washing channels to the filter, and keeping valve-2 at position 1 831 where it connects the filter to the waste vent. The cam is then moved forward for the seventh time to push down the wash-2 actuator 1114 which can depress the second washing blister 1104 and drive air through the matrix to dry the matrix (FIG. 8E). Afterwards, the cam is moved forward for the eighth time, with valve-1 remaining at position 3 823 connecting the washing channels to the filter and valve-2 being moved to position 2 832 connecting the filter to the elution well 1133. Finally, the cam is moved forward for the ninth time to depress the elution blister 1105 and drive elution buffer (e.g., water) through the matrix and elute nucleic acid from the matrix into an elution outlet 1150 (FIG. 8F).

Figure 12A:
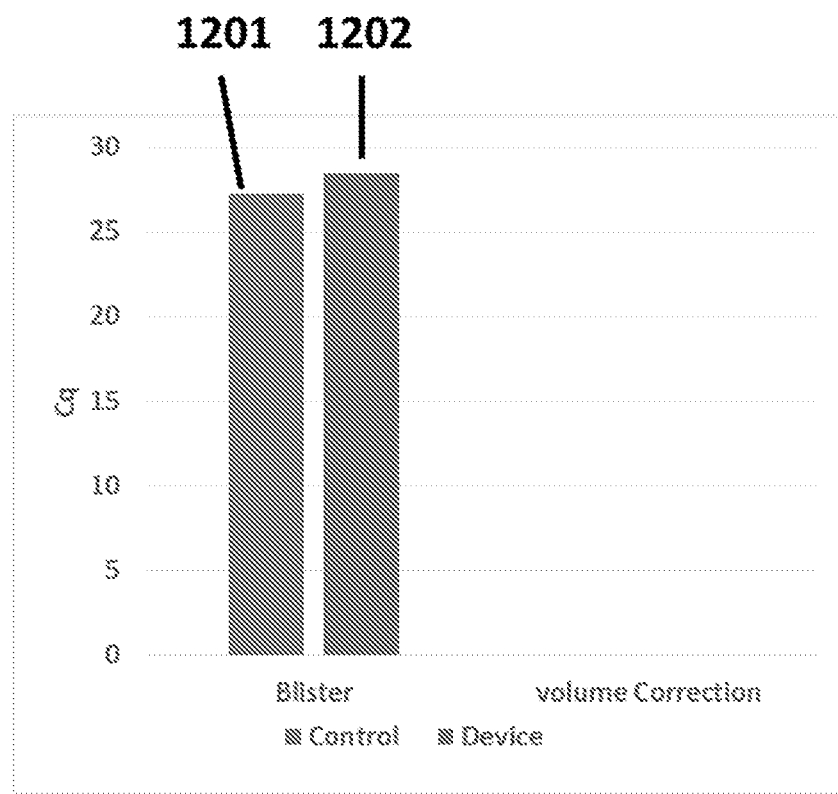
FIG. 12A shows a graph comparing exemplary sample preparation results between a sample preparation device and a control protocol.
Figure 12B:
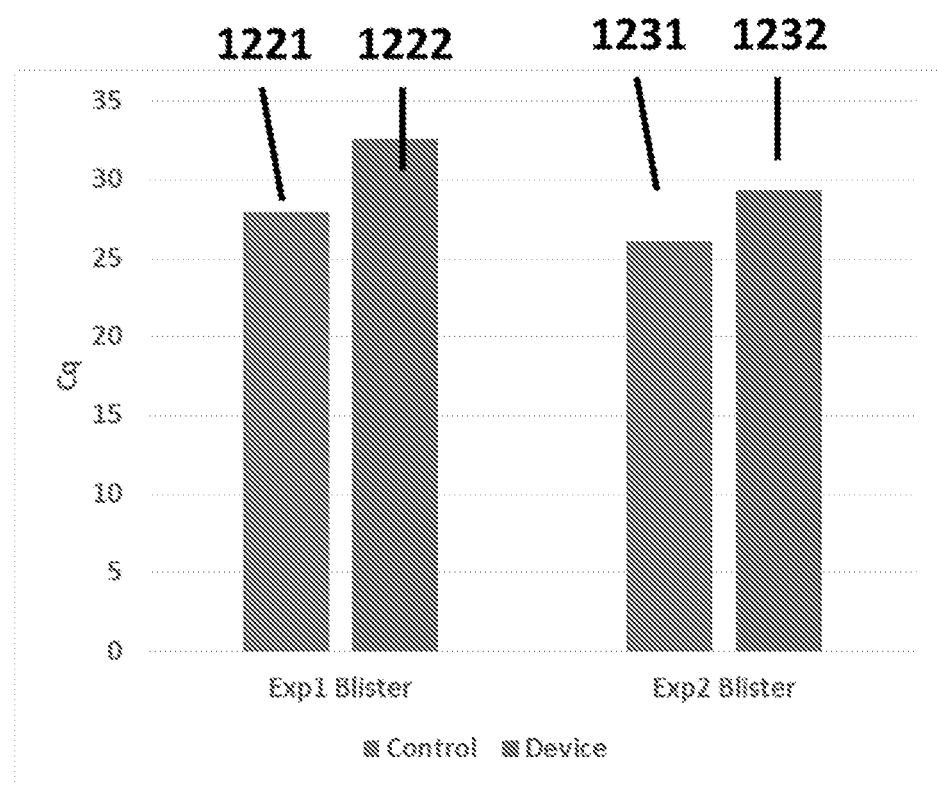
FIG. 12B shows a graph comparing exemplary sample preparation results between a sample preparation device and a control protocol.

FIG. 12A shows a comparison in real-time PCR quantification cycle (Cq) between HIV viral RNA purified by a standard centrifugation protocol 1201 and by a sample preparation device 1202 as described above in this example. FIG. 12B shows a comparison in real-time PCR quantification cycle (Cq) between HIV viral RNA purified by a standard centrifugation protocol 1221 1231 and by a sample preparation device 1222 1232 in first and second experiments, respectively, as described above in this example.

Example 5

Sample Purification on the Device with Syringes

Figure 9:
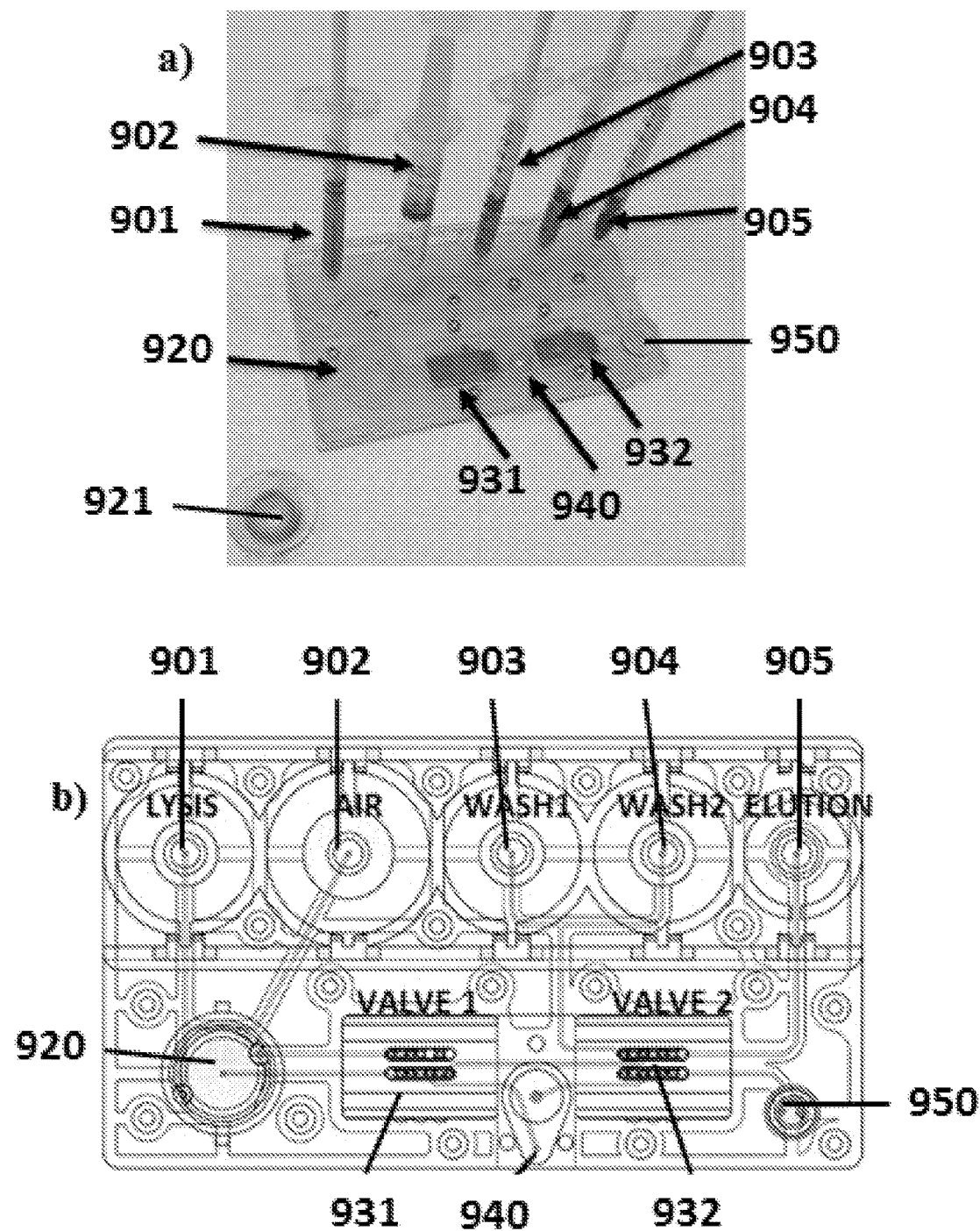
FIG. 9A shows an exemplary sample preparation device employing syringes.
FIG. 9B shows an exemplary schematic of a sample preparation device employing syringes.

An exemplary device that can be used to purify nucleic acid samples is depicted in FIG. 9; FIG. 9A shows a photograph and FIG. 9B shows a schematic. One or more syringes 901 902 903 904 905 comprising reagents can be used as the resistant units in the device. Reagents are stored in the syringes and can be displaced by pushing the pushing units (e.g., plungers). In FIG. 9, 901 902 903 904 905 are syringes loaded with different types of reagents for the sample purification. In detail, syringe-1 901 comprises 600 μL of lysis buffer. Syringe-2 902 comprises approximately 1.8 mL of air, which is used to pressurize the sample well and drive the solution through the matrix, as well as to dry the matrix after the sample passing through the matrix. Syringe-3 903 comprises 500 μL washing buffer. Syringe-4 904 comprises 500 μL of air, which is used to dry the matrix 940. Syringe-5 905 comprises 50 μL of water as elution buffer.

After the placement of the syringes onto the device, 200 μL of plasma sample which comprises HIV viral particles at a concentration of $5 \times 10^5$ copies/mL is loaded into the sample well 920. Valve-1 931 is set at position 1 and it connects the sample well to the air vent; valve-2 932 is set at position 1 and it connects the filter to the waste vent. The sample cap 921 is placed and locked on the sample well. Once the sample is loaded, the plunger of syringe-1 901 is pushed down to displace the lysis buffer through channel into the sample well where the lysis buffer and sample is mixed. Viral particles are broken apart with the presence of lysis buffer, and viral nucleic acid is released. Valve-1 is set at position 2 and it connects the sample well to the filter; valve-2 is set at position 1 and it connects the filter to the waste outlet. Next, the plunger of syringe-2 902 is pushed down to displace the air and pressurize the sample well with positive air pressure. The lysed sample is pushed through the filter and exits from the waste vent. Nucleic acid is captured on the matrix 940. Additional air can be used to dry the matrix. Valve-1 is set at position 3 and it connects the washing channels to the filter; valve-2 is set at position 1 and it connects the filter to the waste outlet. The plunger of syringe-3 903 is then pushed down to displace the washing buffer. The washing buffer passes through the matrix and removes inhibitors for downstream amplification. Valve-1 is set at position 3 and it connects the washing channels to the filter; valve-2 is set at position 1 and it connects the filter to the waste vent. Subsequently, the plunger of syringe-4 904 is pushed down to drive air through the matrix and dry the matrix. Valve-1 is set at position 3 and it connects the washing channels to the filter; valve-2 is set at position 2 and it connects the filter to the elution well. Lastly, the plunger of syringe-5 905 is pushed down to drive water (elution buffer) through the matrix and elute nucleic acid from the matrix into the elution or collection outlet 950.

Figure 10:
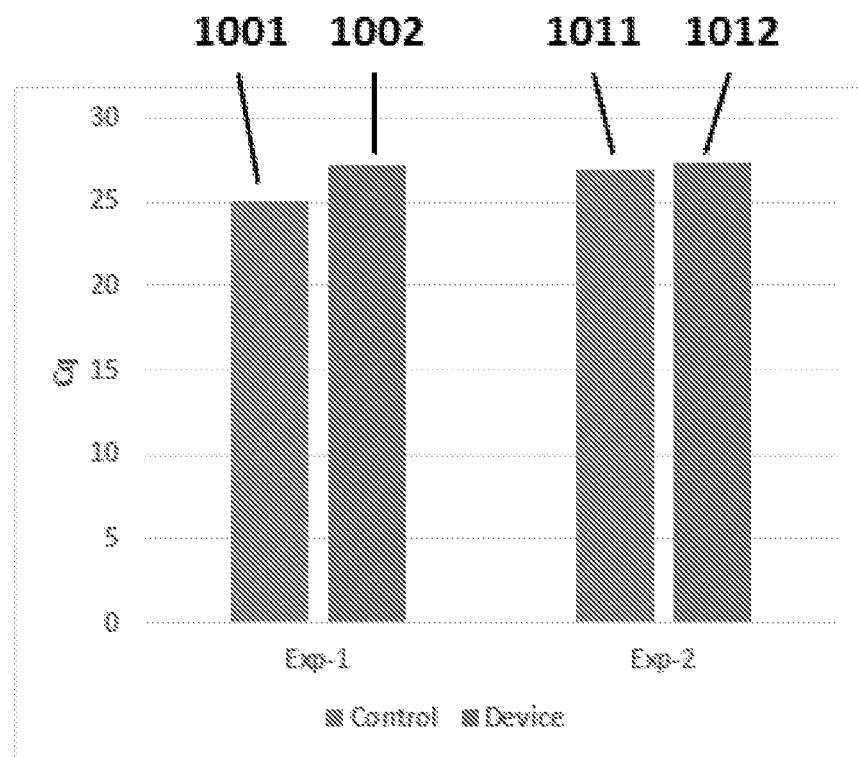
FIG. 10 shows a graph comparing exemplary sample preparation results between a sample preparation device and a control protocol.

FIG. 10 shows a comparison in real-time PCR quantification cycle (Cq) between HIV viral RNA purified by a standard centrifugation protocol 1001 1011 and by a sample preparation device 1002 1012 in first and second experiments, respectively, as described above in this example.

Example 6

Linear Device with Constant Force Spring

Figure 13:
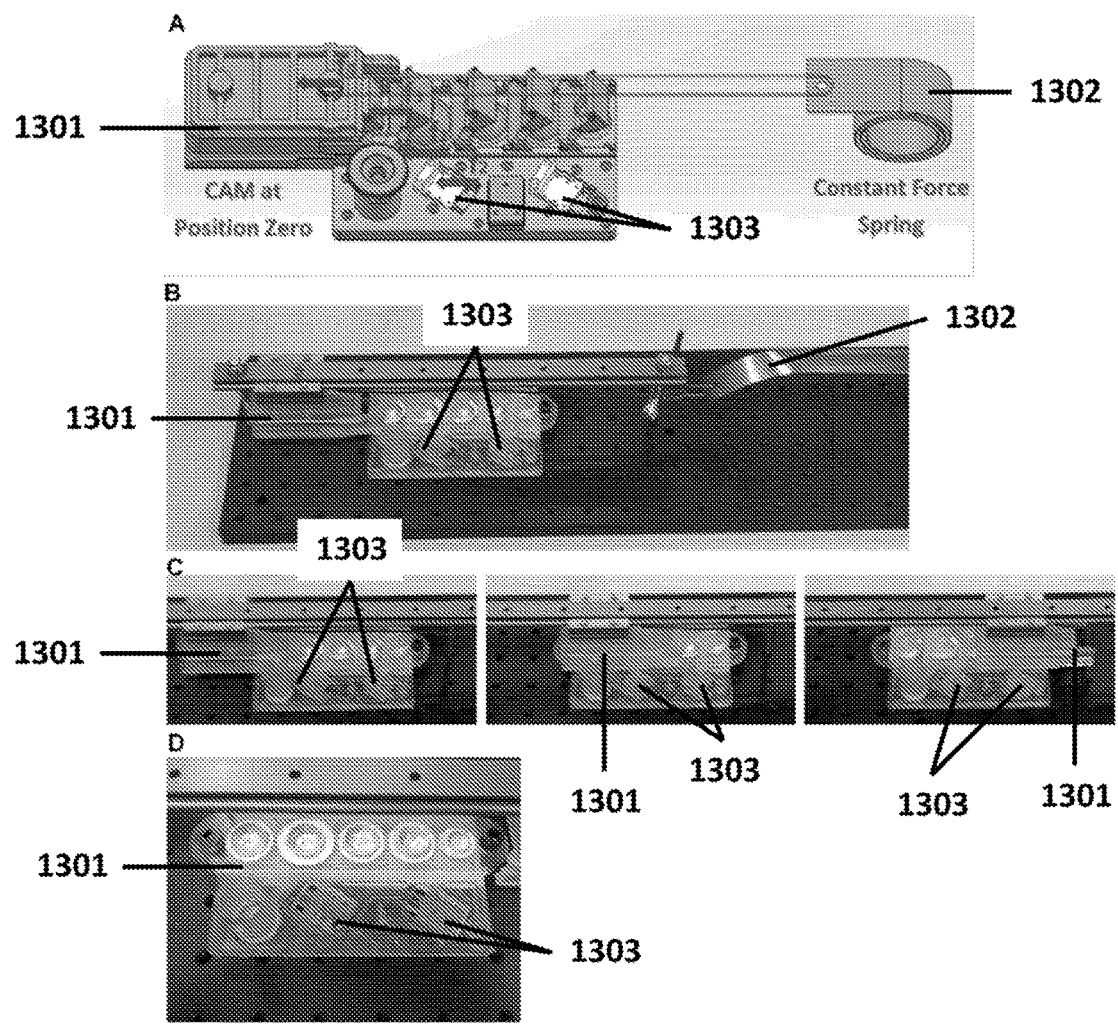
FIG. 13A shows an exemplary schematic of a linear sample preparation device with a constant force spring.
FIG. 13B shows an exemplary linear sample preparation device with a constant force spring prior to operation.
FIG. 13C shows an exemplary linear sample preparation device with a constant force spring in first, second, and third positions during operation.
FIG. 13D shows an exemplary linear sample preparation device with a constant force spring after operation.

An exemplary sample preparation device with a pushing unit (e.g., a cam) and a linear arrangement of resistant units and barrier units is shown in FIG. 13. FIG. 13A shows a schematic of a linear sample preparation device, such as those described previously (e.g., Example 4), with a pushing unit (e.g., cam) 1301, a constant force spring 1302 to drive the pushing unit, resistant units and barrier units, and valves 1303. FIG. 13B shows a photograph of such a device. FIG. 13C shows photographs of the pushing unit being driven by the spring and encountering resistant units and barrier units: on the left, the first resistant unit has been pushed; in the middle, the second, third, and fourth resistant units have been pushed and valves have been moved; on the right, the last resistant unit has been pushed and sample preparation is complete. FIG. 13D shows a photograph of the device after operation and the completion of sample preparation, with the pushing unit driven fully to the end by the spring.

Example 7

Sample Preparation on Rotational Device

An exemplary method for preparing a nucleic acid containing sample on a device utilizing a stepwise pressurization mechanism is illustrated in FIG. 20 and FIG. 21A-21F.

Figure 20:
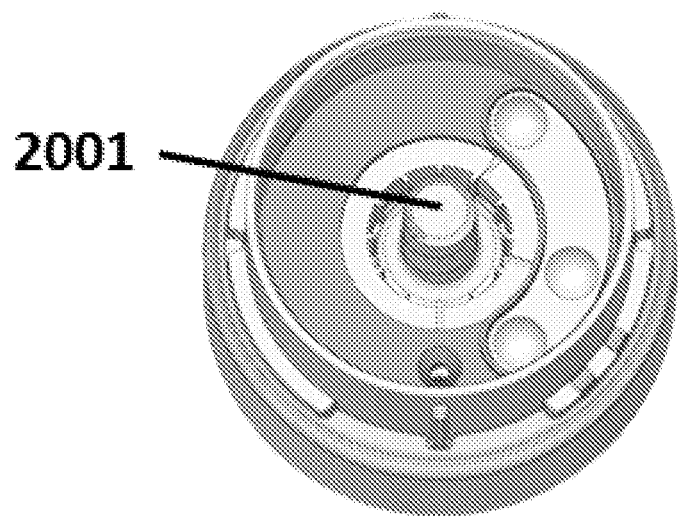
FIG. 20 shows an exemplary schematic of a rotational sample preparation device with a center post.
Figure 21A:
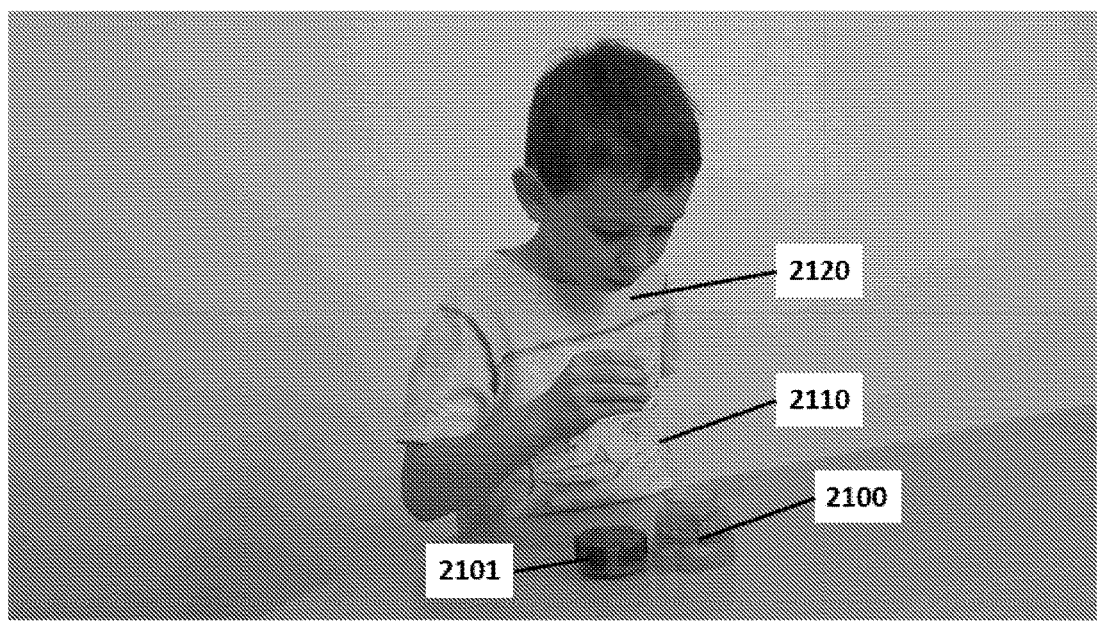
FIG. 21A shows a user loading a sample into an exemplary sample preparation device.
Figure 21B:
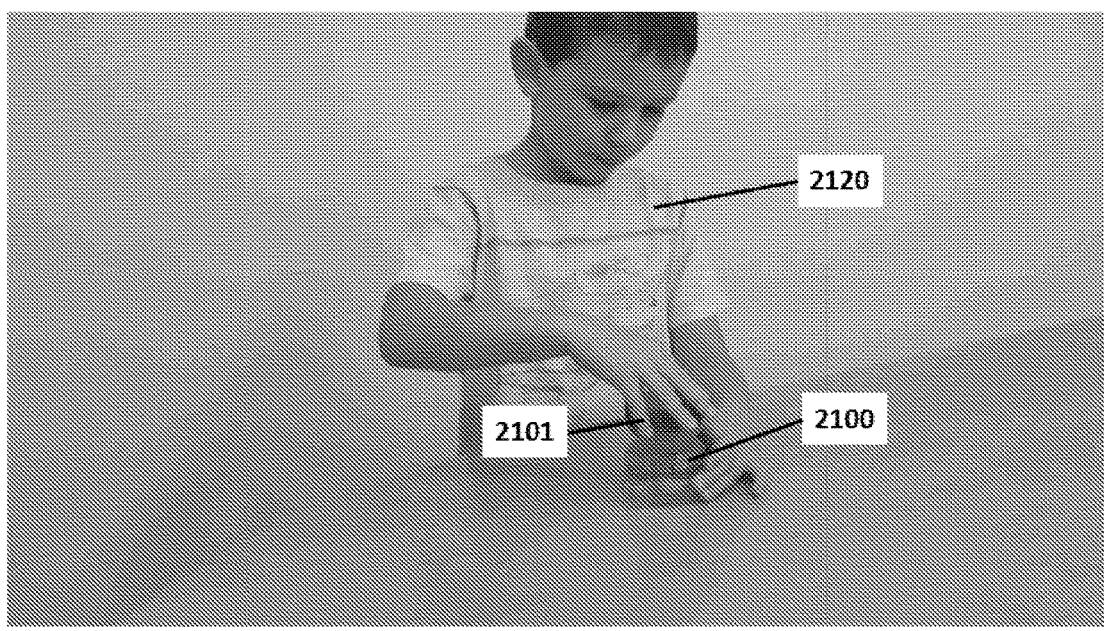
FIG. 21B shows a user placing a cap on an exemplary sample preparation device.
Figure 21C:
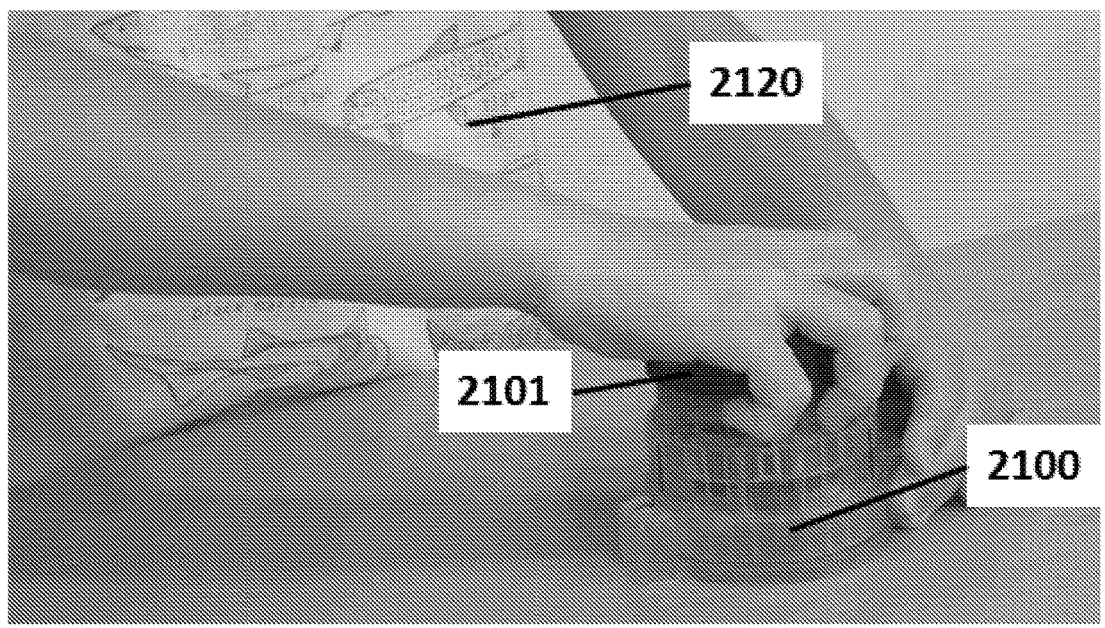
FIG. 21C shows a user rotating a cap into a lysis position on an exemplary sample preparation device.
Figure 21D:
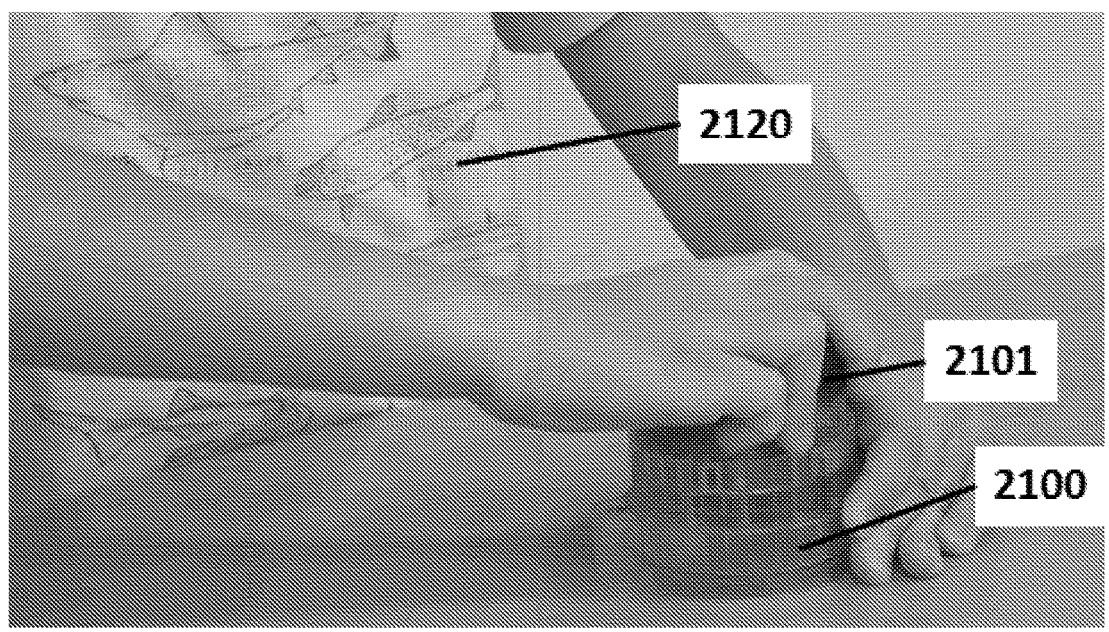
FIG. 21D shows a user rotating a cap into a washing position on an exemplary sample preparation device.
Figure 21E:
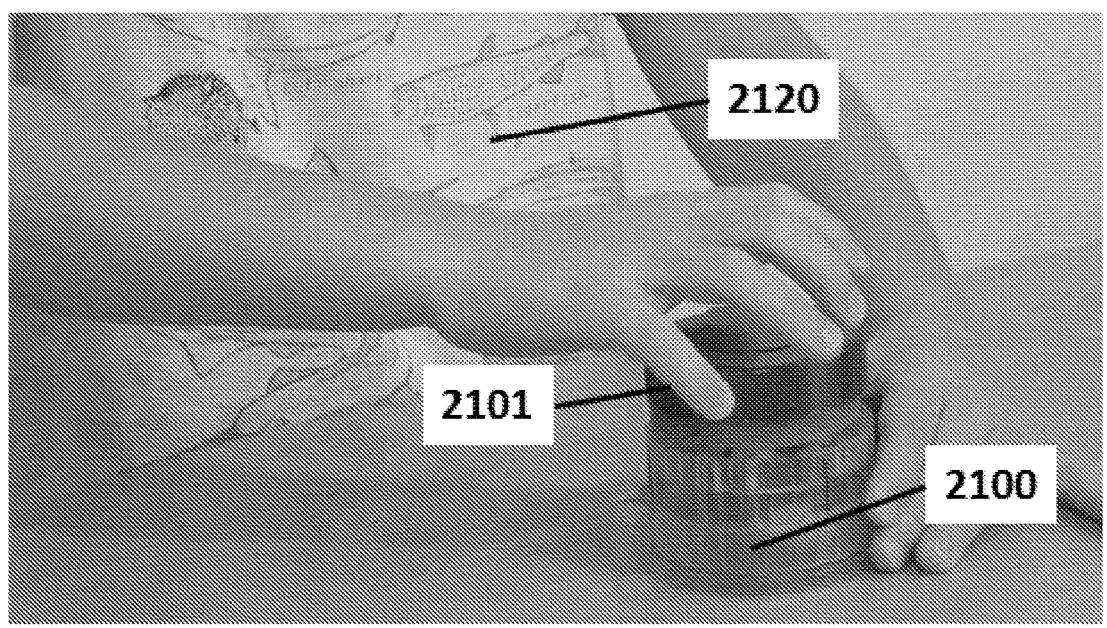
FIG. 21E shows a user rotating a cap into an elution position on an exemplary sample preparation device.
Figure 21F:
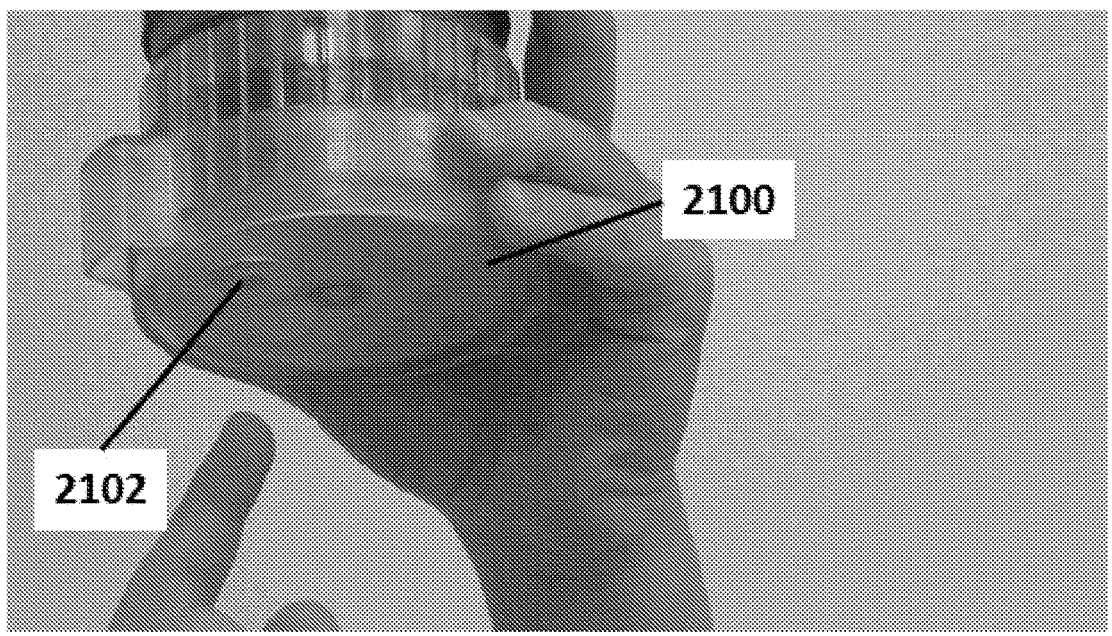
FIG. 21F shows a sample elution port on an exemplary sample preparation device.

Firstly (FIG. 21A), with the use of pipette or other sample handling tool 2110, a nucleic acid containing sample is loaded into the device 2100 by a user 2120. The device is provided preloaded with all reagents including lysis buffer, washing buffer, and elution buffer. After the completion of sample loading, the cap 2101 of the device is closed and locked (FIG. 21B). Next, the cap is further rotated to the lysis position (FIG. 21C). By rotating the cap, the center post/screw 2001 can pull the cap down and apply positive pressure (FIG. 20). The sample is then broken apart by the lysis buffer to release the nucleic acid. The positive pressure drives the lysed sample through the matrix, and the air can pass through the matrix to dry the matrix then. After the sample lysis, the cap is rotated to the next position (i.e., washing position) and the matrix is aligned with washing buffer well (FIG. 21D). The center post/screw can further pull the cap down and apply positive pressure. The positive pressure drives the washing buffer through the matrix, and the air can pass through the matrix to dry the matrix. Subsequently, the cap is further rotated to drive the device to its next position, i.e., elution position (FIG. 21E). Elution buffer is released and elutes nucleic acid from the matrix. Finally (FIG. 21F), purified nucleic acid is eluted and collected in the collection well 2102.

Example 8

Autonomous Control of Rotational Device

Figure 35:
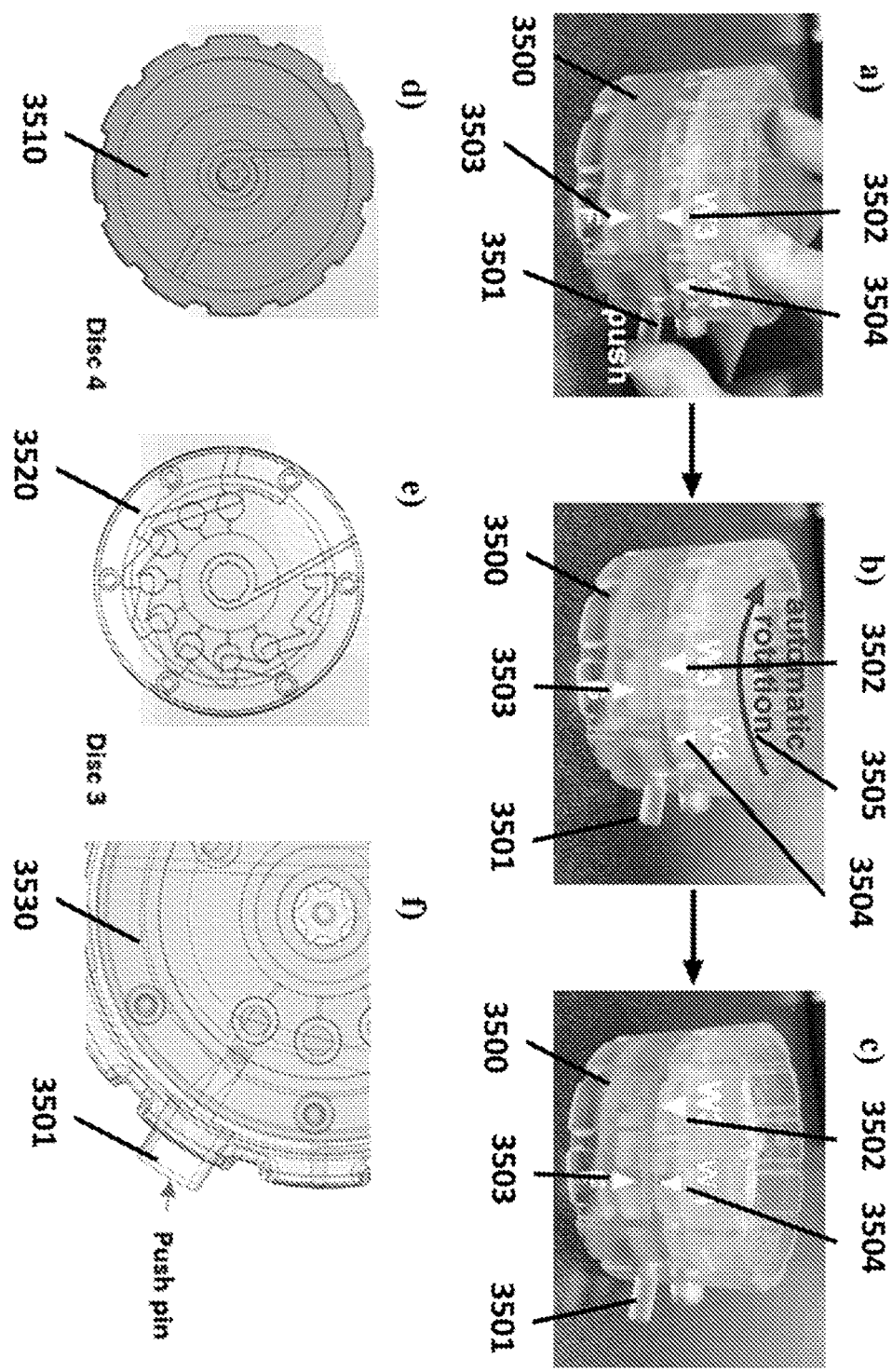

FIG. 35 shows an exemplary rotational device 3500 driven by an internal spring for autonomous control of the operation and manipulation of the device. This design can improve robustness of device operations and can provide an easy user experience since the device is not required to be manually rotated to precise positions. A spring is place at the center of the device to provide force for automatic rotation. A grove is designed to guide the rotation to desired position. The device can wound up before use or can be stored in a wound-up state.

By pushing a button or pin on the side 3501, the device's filter layer rotates 30 degree each time to align with reagent wells on the top layer and receiving wells on the bottom layer. At the starting position (e.g., FIG. 35A), marker-W3 3502 on the top layer is aligned with marker-F 3503 on the bottom layer. When the button is pressed, internal force in the device automatically rotates 3505 the top layer 30 degrees clockwise relative to the bottom layer within seconds (e.g., FIG. 35B). After rotation, the marker-W4 3504 on the top layer is aligned with marker-F 3503 on the bottom layer (e.g., FIG. 35C). The speed of rotation can be controlled by increasing or decreasing the spring force, or by controlling the friction between rotating plates. Simultaneously, the rotation can pull down a cap to add air pressure to drive solution through the matrix, as disclosed herein.

FIG. 35D shows a schematic of a disc 3510 within the device. FIG. 35E shows a schematic of another disc 3520 within the device. FIG. 35F shows a schematic of the device bottom layer 3530 with the button or pin 3501 which can be pressed to initiate automatic actuation of the device.

Example 9

Controlled Sample Preparation with the Device and Results Output

Figure 37:
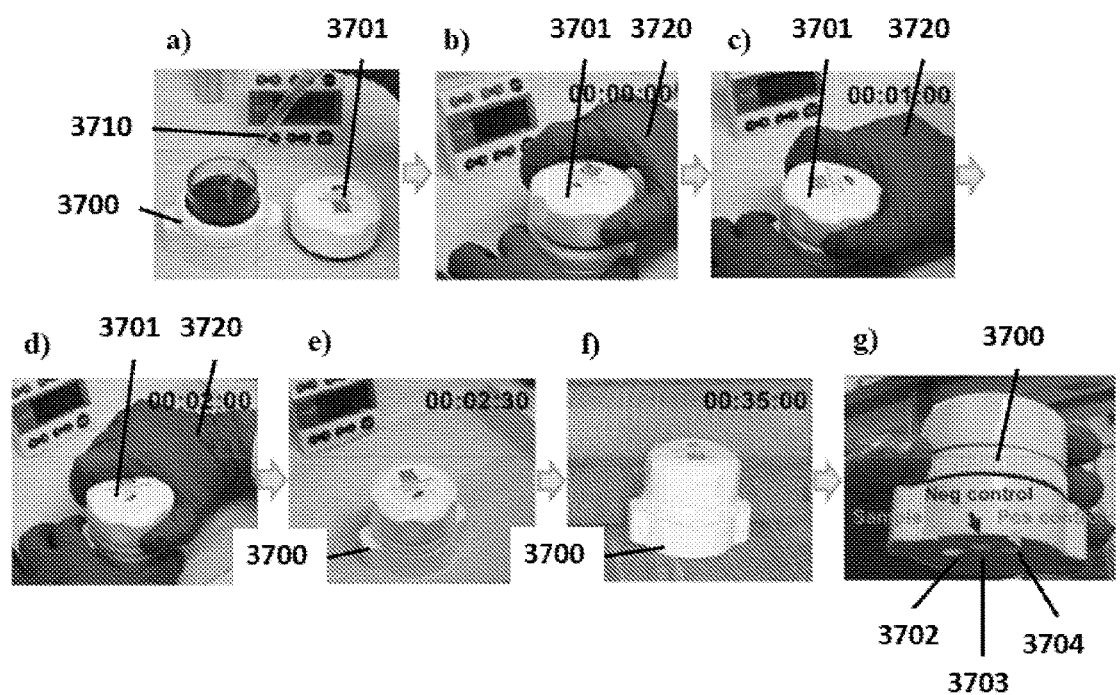

FIG. 37 shows an exemplary method for preparing a sample using a device within a short time period. 0.5 mL urine sample containing *Chlamydia trachomatis*, along with reagents needed for the sample preparation such as lysis buffer, washing buffer, elution buffer are loaded in the device 3700 with pipettes (FIG. 37A). One the sample and reagents are loaded, the cap 3701 of the device is closed and rotated to the lock position by the user 3720 at time 00:00:00 (hour:minute:second). Next, the cap is rotated to the next position (i.e., lysis position) to release the lysis buffer and start the reaction (FIG. 37B). The sample is lysed to release the nucleic acid with the presence of the lysis buffer. The cap is further rotated to a third position (or washing position) at time 00:01:00 to displace the washing buffer (FIG. 37C). The washing buffer passes through the matrix and removes inhibitors from the lysed sample. The cap is rotated to the next position for elution at time 00:02:00 (FIG. 37D). Elution buffer is released elutes nucleic acid from the matrix. After this step, at time 00:02:30, sample preparation is complete (FIG. 37E). The purified nucleic acid can then be incubated within the device to conduct an amplification reaction of the purified sample (FIG. 37F). The amplification reaction is complete at time 00:35:00 and the results can be observed and imaged (e.g., by fluorescence signal) (FIG. 37G). The device can provide a signal from the sample 3702, as well as signal from a negative control 3703 and signal from a positive control 3704. These signals can indicate the presence of a target analyte (e.g., *C. trachomatis*) in the sample. Rotation, incubation, and imaging of the device can also be performed by an automated base station.

Amplified samples with different concentrations of *C. trachomatis* elementary bodies (EB) were characterized in a device 3800 and compared to a negative control 3801, as shown in FIG. 38A and FIG. 38B. There is no detectable signal of fluorescence for the control sample, while for samples that contain 20 EB/mL 3802 and 50 EB/mL 3803 of *C. trachomatis*, signals are quite discernable after 40 cycles of reaction.

Figure 36:
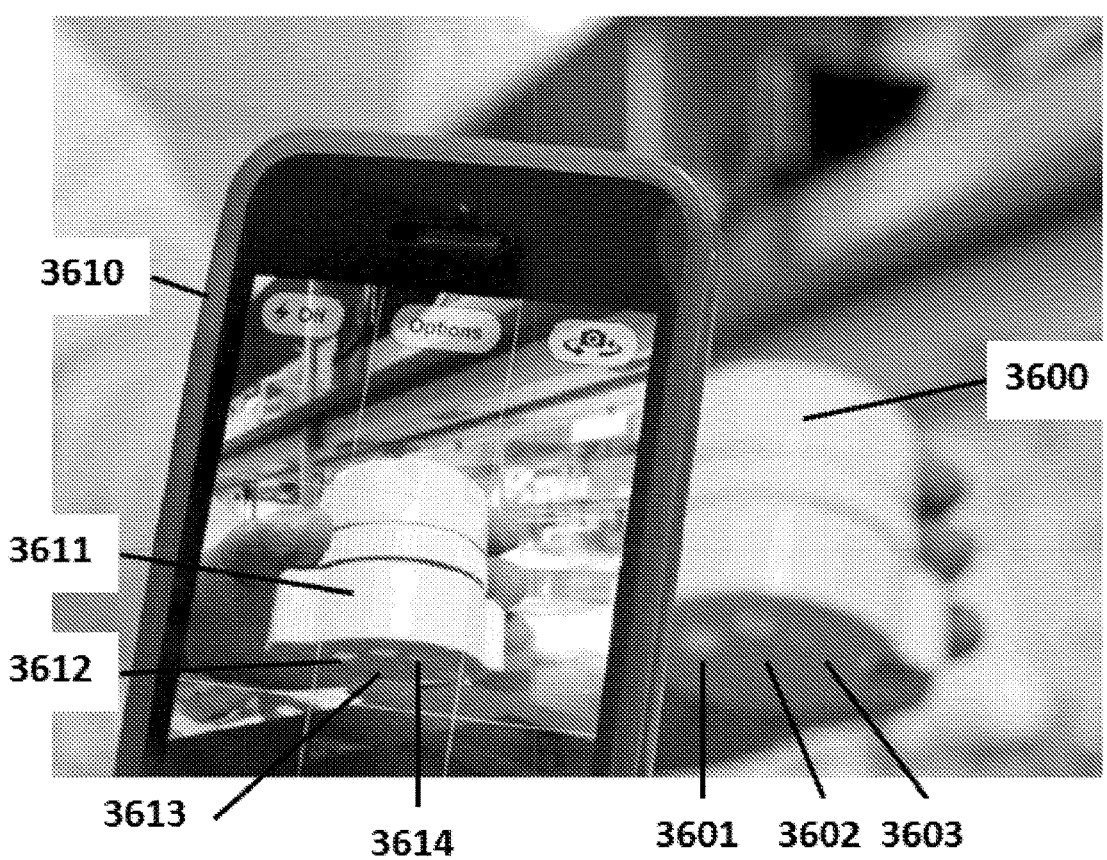

Once the results are obtained, they can be outputted and provided to a recipient immediately. An exemplary method of providing the results via an electronic device is shown in FIG. 36. A device 3600 with signal from a sample 3601, a negative control 3602, and a positive control 3603 is imaged with a mobile device (e.g., an iPhone) 3610. An image of the device 3611 with signal conveying results for a sample 3612, a negative control 3613 and a positive control 3614 is taken and can be sent out to a recipient.

Example 10

Integrated Device

Devices provided in the present disclosure are highly compatible with and can integrate a variety of sample preparation methods from different vendors and manufactures. Two exemplary integrated devices are shown in FIGS. 39A and 39B. In FIG. 39A, device 3900 is mounted in a base station 3910 which is battery-powered and capable of heating and imaging the device. This type of device can find useful in various fields and applications, for example, point-of-care (POC) or limited-resource settings (e.g., FIG. 40A). Another exemplary integrated device as depicted in FIG. 39B has a disposable base layer 3920 instead of the base station. This battery-free, disposable base layer is capable of operating (e.g., by spring force) and heating (e.g., by chemical reaction) the device; Imaging and detection of results can be performed using a separate device, such as a cell phone, wireless device, or other mobile electronic device. Once the reaction is done within the device, the results can be imaged and output to a recipient via, for example, a cell phone. Integrated devices equipped with disposable layers can be utilized in applications such as pathogen detection (blood and urine), pandemic response (e.g., FIG. 40B), digital PCR (e.g., FIG. 40C), viral load, genotyping, and antibiotic susceptibility (e.g., FIG. 40D).

Example 11

Temperature Control

FIG. 41 shows an example of a rotational sample preparation device 4100 with an integrated electric temperature control module (e.g., FIG. 41A). The temperature control module comprises a well 4101, constructed from thermally conductive polycarbonate and with a foil heater and a control thermistor placed on the outside wall of the well (e.g., FIG. 41B). The well is directly attached on the reagent layer of a rotational sample preparation device. The temperature control module is controlled by an electronic control unit 4110, and the performance is measured with a thermal probe (Thorlabs) 4102, which is placed directly in the well surrounded by the testing solution. The data are recorded by using Thorlabs temperature sensor probe TSP 01 software at an interval of 1 second.

First, the device was evaluated with 800 µL of water with a plug-in power supply at a voltage of 4.58 volts at room temperature (the desired temperature is 63±2° C.). The device was tested three times, and the solution could be heated to the desired temperature within 140 seconds, with the standard deviation less than 0.3° C. during the testing period (e.g., FIG. 42A). Table 1 shows results from the three test runs.

TABLE 1

In-device heating results with 800 µL water, 4.58 V power supply

| 4.58 V PWR | Run1 | Run2 | Run 3 |
|---|---|---|---|
| Max | 63.17 | 63 | 63.14 |
| Min | 62.08 | 62.55 | 62.78 |
| Average | 62.87 | 62.83 | 62.96 |
| Std Dev | 0.27 | 0.08 | 0.08 |
| Time to 61° C. (sec) | 136 | 128 | 123 |

Second, the device was evaluated with 800 µL of water, using four AA batteries as the power supply at room temperature (the desired temperature is 63±2° C.). The device was tested three times, and the solution could be heated up to the desired temperature within 150 seconds, with the standard deviation less than 0.1° C. during the testing period (e.g., FIG. 42B). Table 2 shows results from the three test runs.

TABLE 2

In-device heating results with 800 µL water, 4 AA batteries as the power supply

| 4AA Batteries | Run1 | Run2 | Run 3 |
|---|---|---|---|
| Max | 63.83 | 63.17 | 61.88 |
| Min | 63.69 | 62.77 | 61.49 |
| Average | 63.73 | 63.07 | 61.71 |
| Std Dev | 0.05 | 0.10 | 0.09 |
| Time to 61° C. (sec) | 95 | 117 | 147 |

Third, the device was evaluated with 200 µL of human plasma and 600 µL of lysis buffer (e.g., from Zymo viral RNA kit) with a plug-in power supply at a voltage of 4.58 volts at room temperature (the desired temperature is 63±2° C.). The thermal property of the lysed sample can be different from water. The device was tested three times, and the solution could be heated up to the desired temperature within around 180 seconds, with the standard deviation less than 0.3° C. during the testing (e.g., FIG. 42C). Table 3 shows results from the three test runs.

TABLE 3

In-device heating results with 800 µL of sample and lysis solution, 4.58 V power supply

| 4.58 V PWR | Run1 | Run2 | Run 3 |
|---|---|---|---|
| Max | 62.19 | 61.77 | 62.40 |
| Min | 61.47 | 61.16 | 61.22 |
| Average | 61.17 | 61.37 | 61.55 |
| Std Dev | 0.14 | 0.12 | 0.30 |
| Time to 61° C. (sec) | 155 | 173 | 151 |

Fourth, the device was evaluated with 200 µL of human plasma and 600 µL of lysis buffer (Zymo viral RNA kit) with four AA batteries as a power supply at room temperature (the desired temperature is 63±2° C.). The device was tested three times, and the solution could be heated up to the desired temperature within 130 seconds, with the standard deviation less than 0.12° C. during the testing period (e.g., FIG. 42D). Table 4 shows results from the three test runs.

TABLE 4

In-device heating results with 800 µL of sample and lysis solution, 4 AA batteries as the power supply

| 4AA Batteries | Run1 | Run2 | Run 3 |
|---|---|---|---|
| Max | 62.27 | 62.52 | 62.65 |
| Min | 61.76 | 61.89 | 62.01 |
| Average | 61.96 | 62.14 | 62.28 |
| Std Dev | 0.11 | 0.12 | 0.12 |
| Time to 61° C. (sec) | 126 | 122 | 123 |

This demonstrates that a device with an integrated electric temperature control module can heat a water solution or sample (plasma and lysis buffer) from room temperature to a desired temperature of 63±2° C. by either a plug-in power supply (4.58 V) or AA batteries. The performance of the module is highly reproducible and fluctuation of temperature can be tightly controlled over the incubation period.

DEFINITIONS

As used herein, "about" means+/−10% of the recited value.

As used herein, "or" includes "and/or."

By "above" is meant a relative position in which a first structure is in a higher position than a second structure. For instance, in a device including a first substrate, a second substrate above the first substrate, and a third substrate above the second substrate, the term "above" provides the relative positional relationship of the first, second, and third substrates and in no way signifies that the third substrate must necessarily be the top or uppermost substrate in the device. For instance, if the device is turned over, then the third substrate would be the lowest substrate in the device. Thus, it is understood that all relative positions described herein (e.g., above, beneath, between, etc.) are intended to encompass different orientations of the device in use, in operation, or during manufacture.

By "beneath" is meant a relative position in which a first structure is in a lower position than a second structure. For instance, in a device including a first substrate, a second substrate beneath the first substrate, and a third substrate beneath the second substrate, the term "beneath" provides the relative positional relationship of the first, second, and third substrates and in no way signifies that the first substrate must necessarily be the top or uppermost substrate in the device.

By "between" is meant a relative position in which an intermediate structure separates a first and a second structure. For instance, in a device including an intermediate substrate disposed between a first and a second substrate, the term "between" provides the relative positional relationship of the first, second, and intermediate substrates and in no way signifies that the first substrate must necessarily be the top or uppermost substrate in the device.

By "chamber" is meant a volumetric portion of a substrate capable of containing one or more substances, e.g., reagents, samples, immiscible fluids, and/or lubricants. Such chambers can have any useful structure, such as a well, a channel (e.g., a microchannel), a hole, a duct, a bridge, or a cavity having any useful cross-section or dimension(s).

By "to connect" is meant to allow for fluidic communication between two or more structures. Such fluidic communication can be between two or more similar structures (e.g., between two or more substrates or between two or more chambers) or between two or more different structures (e.g., between one or more substrates and one or more chambers).

By "contact" is meant a physical interaction between two components or structures. This physical interaction can be direct (i.e., where a first component interacts with a second component) or indirect (i.e., where a first component interacts with an interleaving component, which in turn interacts with a second component).

By "fluidic communication" or "fluidically connected" is meant the state of being able to pass a liquid or gas in a substantially unrestricted chamber. Fluidic communication can occur by any physical process, including diffusion across a membrane, active transport, or passive transport. Fluidic communication does not include limited diffusion of a substance (e.g., a reagent, sample, or fluid, as described herein) into the bulk material making up a substrate.

By "immiscible fluid" is meant a first fluid (e.g., a gas or a liquid) that generally forms a different phase over certain ranges of temperature, pressure, and composition as compared to a second fluid. In some cases, the second fluid is an aqueous solution, a sample for storage, preservation, processing, or analysis, and/or a reagent for storing, preserving, processing, or analyzing the sample; and the first fluid is a fluid that is immiscible with one or more of the second fluids at certain ranges of temperature, pressure, and composition useful for storing, preserving, processing, or analyzing the sample.

By a "microfluidic" structure is meant a structure having at least one feature that is 1,000 µm or less in at least one dimension. Exemplary features include a substrate (e.g., the thickness of a substrate or the length, width, or height of a component embedded within a substrate), a chamber (e.g., a well, a channel, a hole, a duct, a bridge, or a cavity), a membrane (e.g., the thickness of a membrane or the length, width, or height of a component (e.g., one or more pores or other physical structures) embedded within a membrane), or a capture region. In some cases, the structure includes more than one, two, three, four, five, six, seven, eight, nine, ten, twenty, or more features that are 1,000 µm or less in at least one dimension (e.g., height, width, depth, or thickness).

By "process chamber" is meant a chamber, as described herein, for combining one or more fluids and/or one or more reagents; for containing one or more fluids and/or one or more reagents; for reacting one or more fluids and/or one or more reagents; for processing one or more fluids and/or one or more reagents; and/or for analyzing one or more fluids and/or one or more reagents. In some examples, the process chamber includes a sample that is combined with one or more fluids and/or one or more reagents. In other examples, the process chamber includes a sample that is reacted (e.g., such as a lysis reaction) with one or more fluids and/or one or more reagents. In yet other examples, the process chambers include a sample that is processed (e.g., using a capture region and/or a capture agent, as described herein, including filtered and/or extracted). In particular cases, the process chamber includes a sample and/or relative movement causes a sample to enter the process chamber. A device can include any number of useful process chambers (e.g., one, two, three, four, five, six, seven, eight, nine, ten, fifteen, twenty, or more process chambers).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A reagent dispensing device comprising:
    (a) a first substrate having a first surface, wherein the first substrate comprises one or more first chambers situated within the first substrate;
    (b) a first resistant unit disposed adjacent to the first surface of the first substrate and fluidically connected to at least one of the one or more first chambers, wherein the first resistant unit comprises a first reagent; and
    (c) a first pushing unit configured to move along a circular path within a plane parallel or about parallel to the first surface of the first substrate, wherein a movement of the first pushing unit along the circular path within the plane parallel or about parallel to the first surface of the first substrate causes the first reagent to enter at least one of the one or more first chambers, and wherein the first pushing unit is configured to slidably engage along the first surface or slidably engage with the first resistant unit disposed above the first substrate along the first surface.

2. The reagent dispensing device of claim 1,
    wherein the first pushing unit comprises at least one protrusion, wherein the movement of the first pushing unit in a direction parallel or about parallel to the first surface of the first substrate causes at least one protrusion to contact the first resistant unit, thereby releasing the first reagent in the first resistant unit into at least one of the one or more first chambers.

3. The reagent dispensing device of claim 1, wherein the movement of the first pushing unit is not powered electrically.

4. The reagent dispensing device of claim 1, wherein the device further comprises a second resistant unit disposed adjacent to the first surface of the first substrate and fluidically connected to at least one of the one or more first chambers, wherein the second resistant unit comprises a second reagent, wherein the first and second resistant units are radially aligned along the circular path, wherein the movement of the first pushing unit along the circular path causes the second reagent to enter at least one of the one or more first chambers, wherein the volume, shape, or length of the first resistant unit relative to the second resistant unit is configured to affect relative timing of release of the first reagent relative to the second reagent into at least one of the one or more first chambers.

5. The reagent dispensing device of claim 1, wherein the device further comprises a second resistant unit disposed adjacent to the first surface of the first substrate and fluidically connected to at least one of the one or more first chambers, wherein the second resistant unit comprises a second reagent, wherein the first and second resistant units are radially aligned along the circular path, wherein the movement of the first pushing unit along the circular path causes the second reagent to enter at least one of the one or more first chambers, and wherein the distance between the first resistant unit and the second resistant unit is configured to affect relative timing of release of the first reagent relative to the second reagent into the one or more first chambers.

6. The reagent dispensing device of claim 1, wherein the device further comprises a second resistant unit disposed adjacent to the first surface of the first substrate and fluidically connected to at least one of the one or more first chambers, wherein the second resistant unit comprises a second reagent, wherein the first and second resistant units are radially aligned along the circular path, wherein the movement of the first pushing unit along the circular path causes the second reagent to enter at least one of the one or more first chambers, wherein viscosity of the first reagent is configured to affect relative timing of release of the first reagent relative to the second reagent into at least one of the one or more first chambers.

7. The reagent dispensing device of claim 1, wherein the first reagent comprises a lysis buffer, a wash buffer, or an elution buffer.

8. The reagent dispensing device of claim 1, wherein at least one of the one or more first chambers comprises a fluid and the first resistant unit comprises an immiscible fluid relative to the fluid in the first chamber.

9. The reagent dispensing device of claim 1, wherein the first pushing unit and the first resistant unit are configured to provide feedback for the movement of the first pushing unit along the circular path that results in decelerating, accelerating, or stopping of the movement.

10. The reagent dispensing device of claim 1, wherein the first resistant unit comprises a deformable substrate or a blister.

11. The reagent dispensing device of claim 1, wherein the first resistant unit comprises a first wall bordering an aperture within the first surface, wherein the aperture is in fluid communication with one or more of the one or more first chambers.

12. The reagent dispensing device of claim 11, wherein the movement of the first pushing unit along the circular path causes the first wall to rupture, thereby causing the first reagent in the first resistant unit to enter at least one of the one or more first chambers.

13. The reagent dispensing device of claim 1, wherein the device is a microfluidic device.

14. The reagent dispensing device of claim 1, wherein the device further comprises one or more air vents fluidically connected to the one or more first chambers.

15. The reagent dispensing device of claim 1, further comprising a sample inlet port or sample input well.

16. The reagent dispensing device of claim 1, further comprising a controller to control the movement of the first pushing unit.

17. The reagent dispensing device of claim 1, wherein the first reagent comprises a liquid, a powder, or a gel.

18. The reagent dispensing device of claim 1, wherein the first reagent comprises microbeads, probes, primers, nucleic acids, DNA, RNA, polypeptides, antibodies, or any combination thereof.

* * * * *